United States Patent
Bates et al.

(10) Patent No.: US 11,352,371 B2
(45) Date of Patent: Jun. 7, 2022

(54) THIENOPYRIMIDINE DERIVATIVES AS ACC INHIBITORS AND USES THEREOF

(71) Applicant: Gilead Sciences, Inc., Foster City, CA (US)

(72) Inventors: Jamie G. Bates, Burlingame, CA (US); Ana Z. Gonzalez Buenrostro, San Mateo, CA (US); Hongyan Guo, San Mateo, CA (US); Xiaochun Han, San Jose, CA (US); Brian J. Kirby, Redwood City, CA (US); Yurong Lai, Dublin, CA (US); Michael L. Mitchell, Castro Valley, CA (US); Gregg M. Schwarzwalder, Redwood City, CA (US); James G. Taylor, Burlingame, CA (US); Ting Wang, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 55 days.

(21) Appl. No.: 16/986,909

(22) Filed: Aug. 6, 2020

(65) Prior Publication Data

US 2021/0053990 A1 Feb. 25, 2021

Related U.S. Application Data

(60) Provisional application No. 62/885,038, filed on Aug. 9, 2019.

(51) Int. Cl.
*C07D 519/00* (2006.01)

(52) U.S. Cl.
CPC .................. *C07D 519/00* (2013.01)

(58) Field of Classification Search
CPC .................................................. C07D 519/00
USPC ...................................................... 514/260.1
See application file for complete search history.

(56) References Cited

U.S. PATENT DOCUMENTS

| | | |
|---|---|---|
| 8,969,557 B2 | 3/2015 | Harriman et al. |
| 9,453,026 B2 | 9/2016 | Harriman et al. |
| 9,765,089 B2 | 9/2017 | Greenwood et al. |
| 9,944,655 B2 | 4/2018 | Harriman et al. |
| 9,988,399 B2 | 6/2018 | Greenwood et al. |
| 10,179,793 B2 | 1/2019 | Ghosh et al. |
| 10,183,951 B2 | 1/2019 | Amedio, Jr. et al. |
| 10,208,044 B2 | 2/2019 | Greenwood et al. |
| 10,208,063 B2 | 2/2019 | Greenwood et al. |
| 10,472,374 B2 | 11/2019 | Bhat et al. |
| 10,487,090 B2 | 11/2019 | Calimsiz et al. |
| 10,519,165 B2 | 12/2019 | Geier et al. |
| 10,745,412 B2 | 8/2020 | Humphreys et al. |
| 2017/0166582 A1 | 6/2017 | Ghosh et al. |
| 2018/0021341 A1 | 1/2018 | Harriman et al. |
| 2018/0280394 A1 | 10/2018 | Bates et al. |
| 2019/0040078 A1 | 2/2019 | Bennett et al. |
| 2019/0134041 A1 | 5/2019 | Bates et al. |

FOREIGN PATENT DOCUMENTS

| | | |
|---|---|---|
| WO | WO-2013071169 A1 | 5/2013 |
| WO | WO-2017091602 A1 | 6/2017 |
| WO | WO-2017091617 A1 | 6/2017 |
| WO | WO-2018133858 A1 | 7/2018 |
| WO | WO-2018161008 A1 | 9/2018 |
| WO | WO-2019015583 A1 | 1/2019 |
| WO | WO-2019072478 A1 | 4/2019 |

OTHER PUBLICATIONS

Goedeke, L. et al. (2018) "Acetyl-CoA Carboxylase Inhibition Reverses NAFLD and Hepatic Insulin Resistance but Promotes Hypertriglyceridemia in Rodents" Hepatology 68(6): 2197-2211.
Bates, J. et al. (2020) "Acetyl-CoA carboxylase inhibition disrupts metabolic reprogramming during hepatic stellate cell activation" Journal of Hepatology 73: 896-905.
International Search Report and Written Opinion dated Oct. 7, 2020 for Intl. Appl. No. PCT/US2020/045192.

*Primary Examiner* — Kahsay Habte

(57) ABSTRACT

The present disclosure relates generally to thienopyrimidine compounds that bind to Acetyl-CoA Carboxylase (ACC) and act as inhibitors of ACC. The disclosure further relates to the use of the thienopyrimidine compounds for the preparation of a medicament for the treatment of diseases and/or conditions through binding of ACC, including liver diseases such as non-alcoholic fatty liver disease (NAFLD) and non-alcoholic steatohepatitis (NASH).

37 Claims, 1 Drawing Sheet

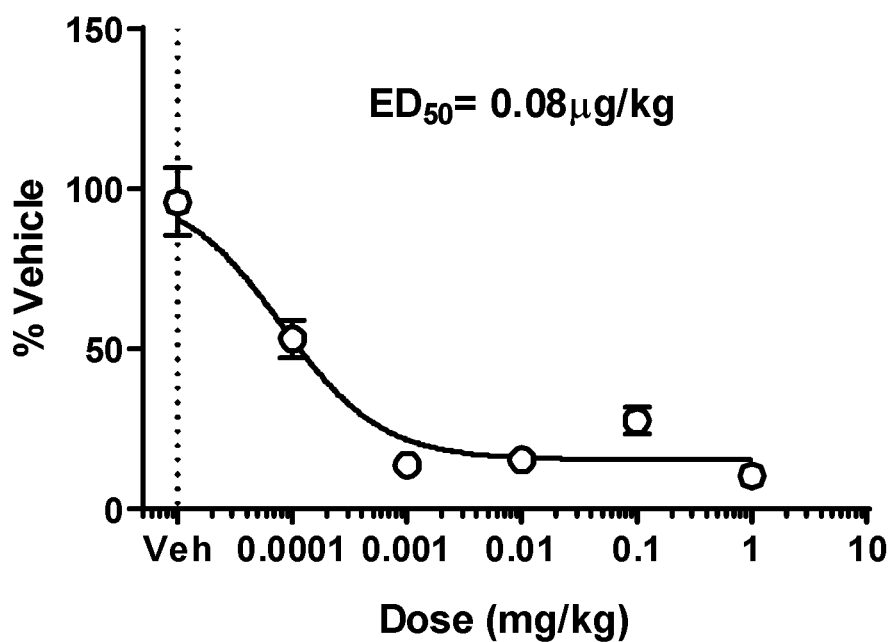

THIENOPYRIMIDINE DERIVATIVES AS ACC INHIBITORS AND USES THEREOF

CROSS REFERENCE TO RELATED APPLICATIONS

This application claims the benefit under 35 U.S.C. § 119(e) of U.S. provisional application No. 62/885,038, filed on Aug. 9, 2019, which is hereby incorporated herein by reference in its entirety for all purposes.

FIELD

The present disclosure relates to compounds that bind to and act as inhibitors of Acetyl-CoA Carboxylase (ACC). The disclosure further relates to the use of the compounds for the treatment and/or prophylaxis of ACC-mediated diseases and/or conditions.

BACKGROUND

Acetyl-CoA carboxylase (ACC) catalyzes the ATP-dependent carboxylation of acetyl-CoA to form malonyl-CoA. Malonyl-CoA is considered both a building block for fatty acid (FA) biosynthesis and a regulator of mitochondrial FA oxidation. Due to its role in malonyl-CoA formation ACC is positioned at the metabolic intersection between lipid synthesis and oxidation pathways. Here ACC is believed to help control the switch between carbohydrate and fat utilization in lipogenic tissues (liver, adipose) and oxidative tissues (liver, heart, skeletal muscle). As such ACC has been a target of interest for the development of therapies for a variety of metabolic disorders.

For example, ACC inhibitors have been explored as treatments for diabetes, obesity and other manifestations of metabolic syndrome. More recently, ACC inhibitors have been clinically studied in connection with specific liver diseases such as non-alcoholic fatty liver disease (NAFLD) and non-alcoholic steatohepatitis (NASH).

A need remains for ACC inhibitors with desirable potency, selectivity, and reduced detrimental effects.

SUMMARY

The present disclosure provides compounds useful as inhibitors of Acetyl-CoA Carboxylase (ACC). The disclosure further relates to the use of the compounds for the treatment and/or prophylaxis of diseases and/or conditions through binding of ACC by said compounds.

In one embodiment, provided herein is a compound of Formula I,

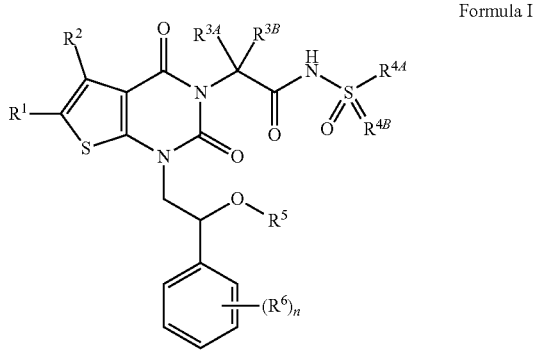

Formula I or a pharmaceutically acceptable salt thereof, wherein:
$R^1$ is cyano, halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, or a cyclic group selected from a 4-8 membered monocyclic heterocycle having 1-2 heteroatoms independently selected from nitrogen, oxygen, or sulfur, a 5-6 membered monocyclic heteroaryl having 1-4 heteroatoms independently selected from nitrogen, oxygen, or sulfur, or a 8-10 membered bicyclic heteroaryl having 1-5 heteroatoms independently selected from nitrogen, oxygen, or sulfur, wherein each cyclic group is independently optionally substituted with 1-4 substituents independently selected from halogen, cyano, $C_{1-3}$ alkyl, and $C_{1-3}$ alkoxy;

$R^2$ is hydrogen or $C_{1-4}$ alkyl, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;

each R is independently hydrogen or a group selected from $C_{1-6}$ alkyl, 3-8 membered monocyclic cycloalkyl, phenyl, 8-10 membered bicyclic aryl; 4-8 membered monocyclic heteroaryl having 1-2 heteroatoms independently selected from nitrogen, oxygen, or sulfur, 5-6 membered monocyclic heteroaryl having 1-4 heteroatoms independently selected from nitrogen, oxygen, or sulfur, and 8-10 membered bicyclic heteroaryl having 1-5 heteroatoms independently selected from nitrogen, oxygen, or sulfur, wherein each group is optionally substituted with 1-4 substituents independently selected from halogen, cyano, $C_{1-3}$ alkyl, and $C_{1-3}$ alkoxy;

$R^{3A}$ and $R^{3B}$ are each independently hydrogen or a $C_{1-3}$ alkyl optionally substituted with 1 to 3 substituents independently selected from halogen, cyano, $C_{1-3}$ alkyl, or $C_{1-3}$ alkoxy; or $R^{3A}$ and $R^{3B}$ together with the carbon to which they are attached form cyclopropylenyl, cyclobutylenyl, oxetanyl, or tetrahydrofuranyl, each optionally substituted with 1 to 3 substituents independently selected from halogen, cyano, $C_{1-3}$ alkyl, or $C_{1-3}$ alkoxy;

$R^{4A}$ is $C_{1-6}$ alkyl, $C_{1-6}$ alkoxy, $C_{3-6}$ cycloalkyl, $C_{3-6}$ cycloalkoxy, phenyl or phenoxy, each optionally substituted with 1 to 3 substituents independently selected from halogen, cyano, $C_{1-3}$ alkyl, $C_{1-6}$ alkoxy, $C_{3-6}$ cycloalkyl, or $C_{3-6}$ cycloalkoxy, wherein each $C_{1-3}$ alkyl, $C_{1-6}$ alkoxy, $C_{3-6}$ cycloalkyl, or $C_{3-6}$ cycloalkoxy is optionally substituted with one $C_{1-3}$ alkoxy or 1 to 3 halogens; or $R^{4A}$ is —OR$^{41}$, wherein $R^4$ is a 5-6 membered heteroaryl having 1-2 heteroatoms independently selected from nitrogen, oxygen, or sulfur, optionally substituted with 1 to 3 substituents independently selected from halogen, cyano, or $C_{1-3}$ alkyl; or $R^{4A}$ is —N(R$^{42}$), wherein each $R^{42}$ is independently selected from hydrogen, $C_{1-6}$ alkyl, or $C_{3-6}$ cycloalkyl; or two $R^{42}$ together with the nitrogen to which they are attached to form a 4-6 membered heterocycle, optionally substituted with one $C_{1-3}$ alkoxy or 1 to 3 halogens;

$R^{4B}$ is oxo or =NR$^{43}$, wherein $R^{43}$ is $C_{1-6}$ alkyl, $C_{3-6}$ cycloalkyl, $C_{4-6}$ heterocyclyl, $C_{3-6}$ cycloalkoxy, phenyl, or 5-6 membered heteroaryl having 1-2 heteroatoms independently selected from nitrogen, oxygen, or sulfur, wherein each $R^{43}$ is optionally substituted with 1 to 3 substituents independently selected from halogen, cyano, or $C_{1-3}$ alkyl;

$R^5$ is an 6-12 membered fused, bridged, or spiro heterocycle having 1 or 2 heteroatoms independently selected from oxygen, sulfur, or nitrogen, wherein the fused, bridged, or spiro heterocycle is optionally substituted with 1 to 4 substituents independently selected from halogen, hydroxyl, oxo, amino, cyano, —$OR^{51}$, —$SR^{51}$, —$N(R^{51})_2$, —$N(R)C(O)R^{51}$, —$C(O)N(R^{51})_2$, —$N(R^{51})C(O)N(R^{51})_2$, —$N(R^{51})C(O)OR^{51}$, —$OC(O)N(R^{51})_2$, —$N(R^{51})SO_2R^{51}$, —$SO_2N(R^{51})_2$, —$C(O)R^{51}$, —$C(O)OR^{51}$, —$OC(O)R^{51}$, —$S(O)R^{51}$, or —$SO_2R$, $C_{1-3}$ alkyl, $C_{1-3}$ alkoxy, wherein each $R^5$ is independently hydrogen or $C_{1-3}$ alkyl;

$R^6$ is hydrogen, halogen $C_{1-3}$ alkyl, $C_{1-6}$ alkoxy, $C_{3-6}$ cycloalkyl, or $C_{3-6}$ cycloalkoxy, wherein the $C_{1-3}$ alkyl, $C_{1-6}$ alkoxy, $C_{3-6}$ cycloalkyl, or $C_{3-6}$ cycloalkoxy is optionally substituted with one —O—$CH_3$ or 1 to 3 halogens; and n is 1, 2, or 3.

In some embodiments, provided herein are pharmaceutical compositions comprising a compound provided herein, or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof. In some embodiments, the pharmaceutical compositions further comprise a therapeutically effective amount of the one or more (e.g., one, two, three, four, one or two, one to three, or one to four) additional therapeutic agents, or a pharmaceutically acceptable salt thereof.

In some embodiments, the present disclosure provides methods of inhibiting ACC activity in a subject in need thereof, comprising administering to the subject a therapeutically effective amount of a compound provided herein (e.g., a compound of Formula I, II, IIa, III, IIIa, IV, or IVa), or a pharmaceutically acceptable salt thereof, or a pharmaceutical composition provided herein.

In some embodiments, the present disclosure provides methods of treating a patient having an ACC mediated condition, comprising administering to the patient a therapeutically effective amount of a compound provided herein (e.g., a compound of Formula I, II, IIa, III, IIIa, IV, or IVa), or a pharmaceutically acceptable salt thereof, or a pharmaceutical composition provided herein.

BRIEF DESCRIPTION OF THE DRAWINGS

FIG. 1 shows a graph depicting the results of an in vivo De Novo Lipogenesis (DNL) study for the compound of Example 1.

DETAILED DESCRIPTION

The present disclosure relates to ACC inhibitors. The disclosure also relates to compositions and methods relating to ACC inhibitors and the use of such compounds for treatment and/or prophylaxis of ACC-mediated diseases and conditions. The disclosure also relates to compositions and methods of treating and/or preventing liver disease including an ACC inhibitor in combination with one or more additional therapeutic agents.

It is commonly believed that patients with certain ACC-mediated diseases, such as obesity, diabetes, or liver diseases including non-alcoholic fatty liver disease (NAFLD) and non-alcoholic steatohepatitis (NASH) can benefit from the treatment with an ACC inhibitor and optionally one or more additional therapeutic agents. Such therapies can benefit from the inclusion of ACC inhibitors with improved potency resulting in efficacy at lower doses.

Moreover, it is further believed that ACC inhibitors with improved liver targeting properties and liver-selective efficacy can help reduce systemic drug exposure and related toxicities or adverse events. Liver targeted ACC inhibitors are therefore believed to be especially desirable for the treatment or prevention of liver diseases, such as NAFLD, NASH, and related conditions, such as liver fibrosis, cirrhosis, or hepatocellular carcinoma.

The present disclosure is based, at least in part, on the recognition that the ACC inhibitors provided herein can be useful for the treatment or prevention of ACC-mediated diseases and/or conditions as single-agents or as components of a combination therapy.

ACC inhibitors can be useful in treating and preventing a variety of conditions, including liver disease. Liver diseases can include acute or chronic damages to the liver, for example, by infection, injury, abnormal build-up of normal substances in the blood, or other causes. Although many ACC inhibitors and related analogues are known, such ACC inhibitors can suffer from drawbacks including poor efficacy, metabolism issues, and/or adverse events.

Disclosed herein are ACC inhibitors and related compositions and methods. ACC inhibitors disclosed herein can surprisingly maintain good therapeutic effect while minimizing the risk of adverse effects and adverse metabolism issues.

In some embodiments, ACC inhibitors described herein can have desirable cellular potency. For example, in some embodiments high cellular potency could provide higher ACC inhibition with lower doses of administered drug relative to compounds having lower cellular potency.

In some embodiments, the present disclosure provides ACC inhibitors that can demonstrate high levels of ACC inhibition in the liver with reduced systemic ACC inhibition. Reduced systemic ACC inhibition can be advantageous, for example by reducing and/or limiting the possibility of systemic adverse reactions or by reducing risks of potential drug-drug interactions with systemic drugs.

Definitions and General Parameters

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present specification, the following terms and phrases are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group.

Unless chemically or structurally required, no directionality is indicated or implied by the order in which a chemical group is written or named. A solid line coming out of the center of a ring indicates that the point of attachment for a substituent on the ring can be at any ring atom. For example, Ra in the below structure can be attached to any of the five carbon ring atoms or RV can replace the hydrogen attached to the nitrogen ring atom:

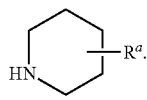

The prefix "C$_{u-v}$" indicates that the following group has from u to v carbon atoms. For example, "C$_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula I, II, IIa, II, IIIa, IV, or IVa. Also included are the specific compounds of Examples 1 to 32.

Reference to "about" a value or parameter herein includes (and describes) embodiments that are directed to that value or parameter per se. In certain embodiments, the term "about" includes the indicated amount 10%. In other embodiments, the term "about" includes the indicated amount 5%. In certain other embodiments, the term "about" includes the indicated amount 1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms (i.e., C$_{1-8}$ alkyl), 1 to 6 carbon atoms (i.e., C$_{1-6}$ alkyl), 1 to 4 carbon atoms (i.e., C$_{1-4}$ alkyl), or 1 to 3 carbon atoms (i.e., C$_{1-3}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amino" refers to the group —NR$^y$R$^z$ wherein R$^y$ and R$^z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

The term "fused" refers to a ring which is bound to an adjacent ring.

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems. In some embodiments the bridged ring fusion is

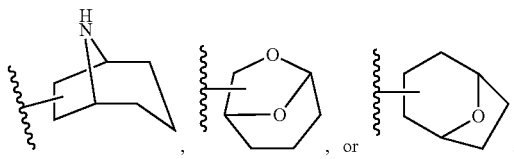

In some embodiments the bridged ring fusion is is

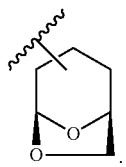

In some embodiments the bridged ring fusion is

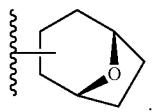

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., $C_{1-20}$ heteroaryl), 3 to 12 carbon ring atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_{2-20}$ heterocyclyl), 2 to 12 carbon ring atoms (i.e., $C_{2-12}$ heterocyclyl), 2 to 10 carbon ring atoms (i.e., $C_{2-10}$ heterocyclyl), 2 to 8 carbon ring atoms (i.e., $C_{2-8}$ heterocyclyl), 3 to 12 carbon ring atoms (i.e., $C_{3-12}$ heterocyclyl), 3 to 8 carbon ring atoms (i.e., $C_{3-8}$ heterocyclyl), or 3 to 6 carbon ring atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. As used herein, the terms "heterocycle", "heterocyclyl", and "heterocyclic ring" are used interchangeably. In some embodiments, the "Heterocyclyl" or "heterocyclic ring" or "heterocycle" is a bridged heterocycloalkyl. In some embodiments, the bridged heterocycloalkyl has one or more oxygens. In some embodiments, the bridged heterocycloalkyl is a bridged tetrahydrofuran.

"Hydroxy" or "hydroxyl" refers to the group —OH.

"Oxo" refers to the group (=O) or (O).

"Sulfonyl" refers to the group —S(O)$_2$R$^c$, where R$^c$ is alkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms).

Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

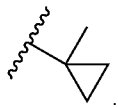

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine, amino acids, or other bases known to persons skilled in the art. The compounds of the present disclosure which contain one or more basic groups, i.e., groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to persons skilled in the art.

If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts.

The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources.

Furthermore, compounds disclosed herein may be subject to tautomerism. Where tautomerism, e.g., keto-enol tautomerism, of compounds or their prodrugs may occur, the individual forms, like e.g., the keto and enol form, are each within the scope of the disclosure as well as their mixtures in any ratio. The same applies for stereoisomers, like e.g., enantiomers, cis/trans isomers, diastereomers, conformers and the like.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. The term "deprotecting" refers to removing the protecting group.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof of the compounds described herein or a pharmaceutically acceptable salt or a mixture thereof. If desired, isomers can be separated by methods well known in the art, e.g., by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high-pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other.

Compounds disclosed herein and their pharmaceutically acceptable salts may, in some embodiments, include an asymmetric center and may thus give rise to enantiomers, diastereomers, and other stereoisomeric forms that may be defined, in terms of absolute stereochemistry, as (R)- or (S)- or, as (D)- or (L)- for amino acids. Some embodiments include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/solation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphoros, fluorine and chlorine, such as, but not limited to $^{2}$H (deuterium, D), $^{3}$H (tritium), $^{11}$C, $^{13}$C, $^{14}$C, $^{15}$N, $^{18}$F, $^{31}$P, $^{32}$P, $^{3}$S, $^{36}$Cl and $^{125}$I. Various isotopically labeled compounds of the present disclosure, for example those into which radioactive isotopes such as $^{3}$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds disclosed herein, in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g., a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have beneficial DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising a compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure can encompass any composition made by admixing at least one compound of the present disclosure and a pharmaceutically acceptable carrier.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

"$IC_{50}$" or "$EC_{50}$" refers to the inhibitory concentration required to achieve 50% of the maximum desired effect, which in many cases here is the inhibition of ACC enzymatic activity or inhibition of de novo lipogenesis (DNL). This term is obtained using an in vitro assay or an in vivo study evaluating the concentration-dependent inhibition of ACC enzymatic activity or de novo lipogenesis.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. In some embodiments, the term "treatment" or "treating" means administering a compound or pharmaceutically acceptable salt of Formula (I), (II), (IIa), (III), (IIIa), (IV) or (IVa) for the purpose of: (i) delaying the onset of a disease, that is, causing the clinical symptoms of the disease not to develop or delaying the development thereof, (ii) inhibiting the disease, that is, arresting the development of clinical symptoms; and/or (iii) relieving the disease, that is, causing the regression of clinical symptoms or the severity thereof.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to ACC inhibition. The therapeutically effective amount may vary depending on the subject, and disease or condition being treated, the weight and age of the subject, the severity of the disease or condition, and the manner of administering, which can readily be determined by one or ordinary skill in the art.

| List of Abbreviations and Acronyms | |
|---|---|
| Abbreviation | Meaning |
| (±)-BINAP | (±)-2,2'-Bis(diphenylphosphino)-1,1'-binaphthalene |
| 2-MeTHF | 2-Methyltetrahydrofuran |
| ACN or MeCN | Acetonitrile |
| aq. | Aqueous |
| AUC | Area under the concentration-time curve |
| Bn | Benzyl |
| BOC or Boc | t-Butyloxycarbonyl |
| BSA | Bovine serum albumin |
| BSS | Balanced Salt Solution |
| calcd | Calculated |
| $C_{max}$ | Maximum observed concentration measured after dosing |
| CL/F | Apparent oral clearance |
| DAST | (diethylamino)sulfur trifluoride |
| DCM | Dichloromethane |
| DIBAL-H | Diisobutylaluminum hydride |
| DMF | N,N-Dimethylformamide |
| DMSO | Dimethylsulfoxide |
| DNL | De novo lipogenesis |
| EA | Ethyl acetate |
| EDTA | Ethylenediaminetetraacetic acid |
| ESI | Electrospray Ionization |
| Et | Ethyl |
| $Et_2O$ | Diethyl ether |
| EtOAc | Ethyl acetate |
| FBS | Fetal bovine serum |
| h or hr(s) | Hour(s) |
| HATU | 1-[Bis(dimethylamino)methylene]-1H-1,2,3-triazolo[4,5-b]pyridinium 3-oxid hexafluorophosphate |
| HCC | Hepatocellular carcinoma |
| HPLC | High performance liquid chromatography |
| IPA | Isopropyl alcohol |
| IPTG | Isopropyl β-D-1-thiogalactopyranoside |
| LCMS or LC/MS | Liquid Chromatography Mass Spectrometry |
| Me | Methyl |
| MEM | Minimum Essential Medium |
| MeOH | Methanol |
| MSA | Methanesulfonic acid |
| min | Minute(s) |
| MS | Mass Spectrometry |
| m/z | Mass-to-charge ratio |
| NADPH | Dihydronicotinamide-adenine dinucleotide phosphate |
| NAFLD | Non-alcoholic fattyl liver disease |
| NASH | Non-alcoholic steatohepatitis |
| NMP | N-Methylpyrrolidone |
| NMR | Nuclear Magnetic Resonance spectroscopy |
| n-BuLi | n-Butyllithium |
| PBC | Primary Biliary Cirrhosis |
| PE | Petroleum ether |
| PSC | Primary Sclerosing Cholangitis |
| rpm | Revolutions per minute |
| RT or rt | Room temperature |
| sat. | Saturated |
| SCF | Supercritical Fluid Chromatography |
| TBAF | Tetrabutylammonium fluoride |
| TBDMS | tert-Butyldimethylsilyl |
| TBS | tert-Butyldimethylsilyl |
| TEMPO | 2,2,6,6-Tetramethylpiperidine 1-oxyl |
| TFA | Trifluoroacetic acid |
| THF | Tetrahydrofuran |
| TLC | Thin Layer Chromatography |
| TMS | Trimethylsilyl |
| $V_z/F$ | Apparent volume of distribution |

As used herein, an "ACC inhibitor" refers to any agent that is capable of binding and inhibiting Acetyl-CoA carboxylase (ACC). ACC inhibitors may act as inhibitors or partial inhibitors of ACC. The agent may be a chemical compound or biological molecule (e.g., a protein or antibody). The activity of an ACC inhibitor may be measured by methods known in the art, such as those described and cited in U.S. Pat. No. 8,969,557 and/or in U.S. Pat. No. 10,208,063, both of which are incorporated herein by reference in their entirety.

As referred to herein, an "ASK1 inhibitor" may be any agent that is capable of inactivating an apoptosis signal regulating kinase 1 (ASK1) protein. The agent may be a chemical compound or biological molecule (e.g., a protein or antibody). The ASK1 protein activity may be measured by several different methods. For example, the activity of an ASK1 protein may be determined based on the ability of the ASK1 protein to phosphorylate a substrate protein. Methods for identifying an ASK1 inhibitor are known (see, e.g., U.S. 2007/0276050). Exemplary ASK1 substrate proteins include MAPKK3, MAPKK4, MAPKK6, MAPKK7, or fragments thereof. The ASK1 protein activity may also be measured by the phosphorylation level of the ASK1 protein, for example, the phosphorylation level of a threonine residue in the ASK1 protein corresponding to threonine 838 (T838) of a human full-length ASK1 protein or threonine 845 (T845) of a mouse full-length ASK1 protein. For example, where the ASK1 protein comprises a full-length human ASK1 protein sequence, an ASK1 inhibitor may attenuate phosphorylation of T838 in the full-length human ASK1 protein sequence. A site-specific antibody against human ASK1 T838 or mouse ASK1 T845 may be used to detect the phosphohorylation level.

As used herein, a "FXR agonist" refers to any agent that is capable of binding and activating farnesoid X receptor (FXR) which may be referred to as bile acid receptor (BAR) or NR1H4 (nuclear receptor subfamily 1, group H, member 4) receptor. FXR agonist may act as agonists or partial agonists of FXR. The agent may be a chemical compound or biological molecule (e.g., a protein or antibody). The activity of a FXR agonist may be measured by several different methods, e.g., in an in vitro assay using the fluorescence resonance energy transfer (FRET) cell free assay as described in Pellicciari, et al. Journal of Medicinal Chemistry, 2002 vol. 15, No. 45:3569-72.

Compounds

In one embodiment, provided herein is a compound of Formula I,

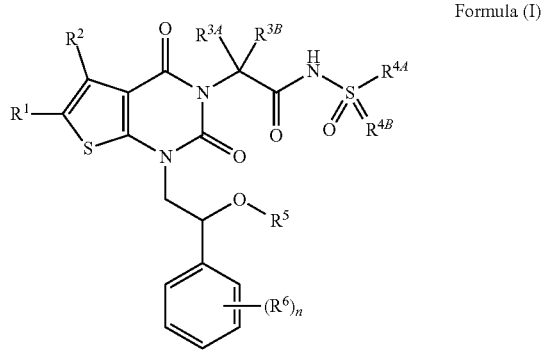

Formula (I)

or a pharmaceutically acceptable salt thereof,
wherein:
$R^1$ is cyano, halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, or a cyclic group selected from a 4-8 membered monocyclic heterocycle having 1-2 heteroatoms independently selected from nitrogen, oxygen, or sulfur, a 5-6 membered monocyclic heteroaryl having 1-4 heteroatoms independently selected from nitrogen, oxygen, or sulfur, or a 8-10 membered bicyclic heteroaryl having 1-5 heteroatoms independently selected from nitrogen, oxygen, or sulfur, wherein each cyclic group is independently optionally substituted with 1-4 substituents independently selected from halogen, cyano, $C_{1-3}$ alkyl, and $C_{1-3}$ alkoxy;
$R^2$ is hydrogen or $C_{1-4}$ alkyl, optionally substituted with one or more halogens, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;
each R is independently hydrogen or a group selected from $C_{1-6}$ alkyl, 3-8 membered monocyclic cycloalkyl, phenyl, 8-10 membered bicyclic aryl; 4-8 membered monocyclic heteroaryl having 1-2 heteroatoms independently selected from nitrogen, oxygen, or sulfur, 5-6 membered monocyclic heteroaryl having 1-4 heteroatoms independently selected from nitrogen, oxygen, or sulfur, and 8-10 membered bicyclic heteroaryl having 1-5 heteroatoms independently selected from nitrogen, oxygen, or sulfur, wherein each group is optionally substituted with 1-4 substituents independently selected from halogen, cyano, $C_{1-3}$ alkyl, and $C_{1-3}$ alkoxy;
$R^{3A}$ and $R^{3B}$ are each independently hydrogen or a $C_{1-3}$ alkyl optionally substituted with 1 to 3 substituents independently selected from halogen, cyano, $C_{1-3}$ alkyl, or $C_{1-3}$ alkoxy; or $R^{3A}$ and $R^{3B}$ together with the carbon to which they are attached form cyclopropylenyl cyclobutylenyl, oxetanyl, or tetrahydrofuranyl, each optionally substituted with 1 to 3 substituents independently selected from halogen, cyano, $C_{1-3}$ alkyl, or $C_{1-3}$ alkoxy;
$R^{4A}$ is $C_{1-6}$ alkyl, $C_{1-6}$ alkoxy, $C_{3-6}$ cycloalkyl, $C_{3-6}$ cycloalkoxy, phenyl or phenoxy, each optionally substituted with 1 to 3 substituents independently selected from halogen, cyano, $C_{1-3}$ alkyl, $C_{1-6}$ alkoxy, $C_{3-6}$ cycloalkyl, or $C_{3-6}$ cycloalkoxy, wherein each $C_{1-3}$ alkyl, $C_{1-6}$ alkoxy, $C_{3-6}$ cycloalkyl, or $C_{3-6}$ cycloalkoxy is optionally substituted with one $C_{1-3}$ alkoxy or 1 to 3 halogens; or
$R^{4A}$ is —OR$^{41}$, wherein $R^{41}$ is a 5-6 membered heteroaryl having 1-2 heteroatoms independently selected from nitrogen, oxygen, or sulfur, optionally substituted with 1 to 3 substituents independently selected from halogen, cyano, or $C_{1-3}$ alkyl; or
$R^{4A}$ is —N(R$^{42}$)$_2$, wherein each $R^{42}$ is independently selected from hydrogen or $C_{1-6}$ alkyl, or $C_{3-6}$ cycloalkyl; or two $R^{42}$ together with the nitrogen to which they are attached form a 4-6 membered heterocycle, optionally substituted with one $C_{1-3}$ alkoxy or 1 to 3 halogens;
$R^{4B}$ is oxo or =NR$^{43}$, wherein $R^{43}$ is selected from $C_{1-6}$ alkyl, $C_{3-6}$ cycloalkyl, $C_{4-6}$ heterocyclyl, $C_{3-6}$ cycloalkoxy, phenyl, or 5-6 membered heteroaryl having 1-2 heteroatoms independently selected from nitrogen, oxygen, or sulfur, wherein each $R^{43}$ is optionally substituted with 1 to 3 substituents independently selected from halogen, cyano, or $C_{1-3}$ alkyl;
$R^5$ is a 6-12 membered fused, bridged, or spiro heterocycle having 1 or 2 heteroatoms independently selected from oxygen, sulfur, or nitrogen, wherein the fused, bridged, or spiro heterocycle is optionally substituted with 1 to 4 substituents independently selected from halogen, hydroxyl, oxo, amino, cyano, —OR$^{51}$, —SR$^{51}$, —N(R$^{51}$)$_2$, —N(R$^{51}$)C(O)R$^{51}$, —C(O)N(R$^{51}$)$_2$, —N(R$^{51}$)C(O)N(R$^{51}$)$_2$, —N(R$^{51}$)C(O)OR$^{51}$, —OC(O)N(R$^{51}$)$_2$, —N(R$^{51}$)SO$_2$R$^{51}$, —SO$_2$N(R$^{51}$)$_2$, —C(O)R$^{51}$, —C(O)OR$^{51}$, —OC(O)R$^{51}$, —S(O)R$^{51}$, or —SO$_2$R, C$_{1-3}$ alkyl, C$_{1-3}$ alkoxy, wherein each R$^{51}$ is independently hydrogen or C$_{1-6}$ alkyl;

R$^6$ is independently hydrogen, C$_{1-3}$ alkyl, halogen, C$_{1-6}$ alkoxy, C$_{3-6}$ cycloalkyl, or C$_{3-6}$ cycloalkoxy, wherein the C$_{1-6}$ alkoxy, C$_{3-6}$ cycloalkyl, or C$_{3-6}$ cycloalkoxy is optionally substituted with one —O—CH$_3$ or 1 to 3 halogen, wherein the C$_{1-3}$ alkyl, or C$_{1-6}$ alkoxy, C$_{3-6}$ cycloalkyl, or C$_{3-6}$ cycloalkoxy is optionally substituted with 1 to 3 substituents independently selected from halogen, cyano, C$_{1-3}$ alkyl, or C$_{1-3}$ alkoxy; and n is 1, 2, or 3.

In some embodiments of the compound of Formula (I), or a pharmaceutically acceptable salt thereof, R$^1$ is cyano or a 5 membered heteroaryl having 2 to 3 heteroatoms independently selected from nitrogen, oxygen, or sulfur, wherein the heteroaryl is optionally substituted with 1 to 4 substituents independently selected from halogen, cyano, C$_{1-3}$ alkyl, and C$_{1-3}$ alkoxy.

In some embodiments of the compound of Formula (I), or a pharmaceutically acceptable salt thereof, R$^2$ is C$_{1-3}$ alkyl optionally substituted with 1 to 3 substituents independently selected from the group consisting of halogen, cyano, C$_{1-3}$ alkyl, and C$_{1-3}$ alkoxy.

In some embodiments of the compound of Formula (I), or a pharmaceutically acceptable salt thereof, R$^{4A}$ is C$_{1-6}$ alkyl, C$_{1-6}$ alkoxy, C$_{3-6}$ cycloalkyl, C$_{1-6}$ cycloalkoxy, phenyl, or phenoxy, each optionally substituted with 1 to 3 substituents independently selected from halogen, cyano, or C$_{1-3}$ alkyl, wherein each C$_{1-3}$ alkyl is optionally substituted with one C$_{1-3}$ alkoxy or 1 to 3 halogens. In some embodiments, the halogen is F.

In some embodiments of the compound of Formula (I), or a pharmaceutically acceptable salt thereof, R$^{3A}$ and R$^{3B}$ are each independently hydrogen or a C$_{1-3}$ alkyl optionally substituted with 1 to 3 substituents independently selected from halogen, cyano, C$_{1-3}$ alkyl, or C$_{1-3}$ alkoxy. In some embodiments the halogen is F.

In some embodiments of the compound of Formula (I), or a pharmaceutically acceptable salt thereof, R$^{3A}$ and R$^{3B}$ together with the carbon to which they are attached form cyclopropylenyl cyclobutylenyl, oxetanyl, or tetrahydrofuranyl, each optionally substituted with 1 to 3 substituents independently selected from halogen, cyano, C$_{1-3}$ alkyl, or C$_{1-3}$ alkoxy. In some embodiments, the halogen is F.

In some embodiments of the compound of Formula (I), or a pharmaceutically acceptable salt thereof, R$^{4A}$ is C$_{1-6}$ alkyl, C$_{1-6}$ alkoxy, C$_{3-6}$ cycloalkyl, C$_{3-6}$ cycloalkoxy, phenyl or phenoxy, each optionally substituted with 1 to 3 substituents independently selected from halogen, cyano, C$_{1-3}$ alkyl, C$_{1-6}$ alkoxy, C$_{3-6}$ cycloalkyl, or C$_{3-6}$ cycloalkoxy, wherein each C$_{1-3}$ alkyl, C$_{1-6}$ alkoxy, C$_{3-6}$ cycloalkyl, or C$_{3-6}$ cycloalkoxy is optionally substituted with one C$_{1-3}$ alkoxy or 1 to 3 halogens, and R$^{4B}$ is oxo. In some embodiments of the compound of Formula (I), or a pharmaceutically acceptable salt thereof, R$^{4A}$ is C$_{1-6}$ alkyl, C$_{1-6}$ alkoxy, C$_{3-6}$ cycloalkyl, C$_{3-6}$ cycloalkoxy, phenyl or phenoxy, each optionally substituted with 1 to 3 substituents independently selected from halogen, cyano, C$_{1-3}$ alkyl, C$_{1-6}$ alkoxy, C$_{3-6}$ cycloalkyl, or C$_{3-6}$ cycloalkoxy, and R$^{4B}$ is oxo. In some embodiments of the compound of Formula (I), or a pharmaceutically acceptable salt thereof, R$^{4A}$ is C$_{1-6}$ alkyl, C$_{1-6}$ alkoxy, C$_{3-6}$ cycloalkyl, C$_{3-6}$ cycloalkoxy, phenyl or phenoxy, and R$^{4B}$ is oxo. In some embodiments, the halogen is F.

In some embodiments of the compound of Formula (I), or a pharmaceutically acceptable salt thereof, R$^{4A}$ is C$_{1-6}$ alkyl, C$_{1-6}$ alkoxy, C$_{3-6}$ cycloalkyl, C$_{3-6}$ cycloalkoxy, phenyl or phenoxy, each optionally substituted with 1 to 3 substituents independently selected from halogen, cyano, C$_{1-3}$ alkyl, C$_{1-6}$ alkoxy, C$_{3-6}$ cycloalkyl, or C$_{3-6}$ cycloalkoxy, wherein each C$_{1-3}$ alkyl, C$_{1-6}$ alkoxy, C$_{3-6}$ cycloalkyl, or C$_{3-6}$ cycloalkoxy is optionally substituted with one C$_{1-3}$ alkoxy or 1 to 3 halogens, and R$^{4B}$ is =NR$^{43}$, wherein R$^{43}$ is C$_{1-6}$ alkyl, C$_{3-6}$ cycloalkyl, C$_{4-6}$ heterocyclyl, C$_{3-6}$ cycloalkoxy, phenyl, or 5-6 membered heteroaryl having 1-2 heteroatoms independently selected from nitrogen, oxygen, or sulfur, wherein each R$^{43}$ is optionally substituted with 1 to 3 substituents independently selected from halogen, cyano, or C$_{1-3}$ alkyl. In some embodiments of the compound of Formula (I), or a pharmaceutically acceptable salt thereof, R$^{4A}$ is C$_{1-6}$ alkyl, C$_{1-6}$ alkoxy, C$_{3-6}$ cycloalkyl, C$_{3-6}$ cycloalkoxy, phenyl or phenoxy, each optionally substituted with 1 to 3 substituents independently selected from halogen, cyano, C$_{1-3}$ alkyl, C$_{1-6}$ alkoxy, C$_{3-6}$ cycloalkyl, or C$_{3-6}$ cycloalkoxy, and R$^{4B}$ is =NR$^{43}$, wherein R$^{43}$ is C$_{1-6}$ alkyl, C$_{3-6}$ cycloalkyl, C$_{4-6}$ heterocyclyl, C$_{3-6}$ cycloalkoxy, phenyl, or 5-6 membered heteroaryl having 1-2 heteroatoms independently selected from nitrogen, oxygen, or sulfur, wherein each R$^{43}$ is optionally substituted with 1 to 3 substituents independently selected from halogen, cyano, or C$_{1-3}$ alkyl. In some embodiments of the compound of Formula (I), or a pharmaceutically acceptable salt thereof, R$^{4A}$ is C$_{1-6}$ alkyl, C$_{1-6}$ alkoxy, C$_{3-6}$ cycloalkyl, C$_{3-6}$ cycloalkoxy, phenyl or phenoxy, and R$^{4B}$ is =NR$^{43}$, wherein R$^{43}$ is C$_{1-6}$ alkyl, C$_{3-6}$ cycloalkyl, C$_{4-6}$ heterocyclyl, C$_{3-6}$ cycloalkoxy, phenyl, or 5-6 membered heteroaryl having 1-2 heteroatoms independently selected from nitrogen, oxygen, or sulfur. In some embodiments, the halogen is F.

In some embodiments of the compound of Formula (I), or a pharmaceutically acceptable salt thereof, R$^{4A}$ is —OR$^{41}$, wherein R$^{41}$ is a 5-6 membered heteroaryl having 1-2 heteroatoms independently selected from nitrogen, oxygen, or sulfur.

In some embodiments of the compound of Formula (I), or a pharmaceutically acceptable salt thereof, R$^{4A}$ is —N(R$^{42}$)$_2$, wherein each R$^{42}$ is independently selected from hydrogen or C$_{1-6}$ alkyl, or C$_{3-6}$ cycloalkyl; or two R$^{42}$ together with the nitrogen to which they are attached form a 4-6 membered heterocycle, optionally substituted with one C$_{1-3}$ alkoxy or 1 to 3 halogens.

In some embodiments of the compound of Formula (I), or a pharmaceutically acceptable salt thereof, R$^5$ is a 6-12 membered fused heterocycle having 1 or 2 heteroatoms independently selected from oxygen, sulfur, or nitrogen, wherein the fused heterocycle is optionally substituted with 1 to 4 substituents independently selected from halogen, hydroxyl, oxo, amino, cyano, —OR$^{51}$, —SR$^{51}$, —N(R$^{51}$)$_2$, —N(R$^{51}$)C(O)R$^{51}$, —C(O)N(R$^{51}$)$_2$, —N(R$^{51}$)C(O)N(R$^{51}$)$_2$, —N(R$^{51}$)C(O)OR$^{51}$, —OC(O)N(R$^{51}$)$_2$, —N(R$^{51}$)SO$_2$R$^{51}$, —SO$_2$N(R$^{51}$)$_2$, —C(O)R$^{51}$, —C(O)OR$^{51}$, —OC(O)R$^{51}$, —S(O)R$^{51}$, or —SO$_2$R, C$_{1-3}$ alkyl, C$_{1-3}$ alkoxy, wherein each R$^{51}$ is independently hydrogen or C$_{1-6}$ alkyl. In some embodiments, each halogen can independently be F. In some embodiments of the compound of Formula (I), or a pharmaceutically acceptable salt thereof, R$^5$ is an 8-10 membered fused heterocycle having 1 or 2 heteroatoms independently selected from oxygen or nitrogen. In some embodiments of the compound of Formula (I), or a pharmaceutically acceptable salt thereof, R⁵ is selected from

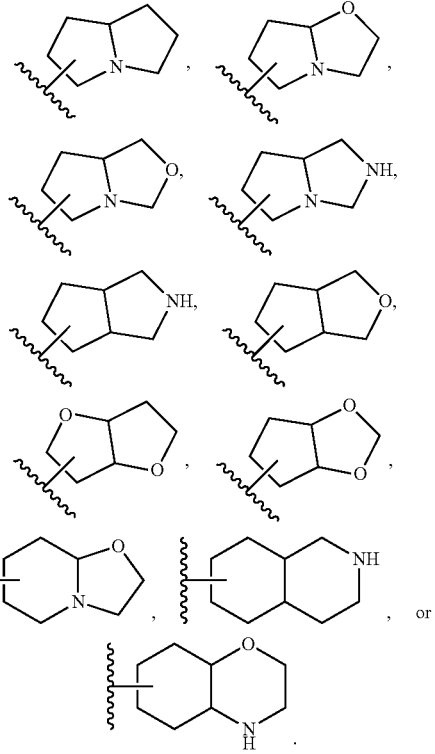

In some embodiments of the compound of Formula (I), or a pharmaceutically acceptable salt thereof, R⁵ is a 6-12 membered bridged heterocycle having 1 or 2 heteroatoms independently selected from oxygen, sulfur, or nitrogen, wherein the bridged heterocycle is optionally substituted with 1 to 4 substituents independently selected from halogen, hydroxyl, oxo, amino, cyano, —OR⁵¹, —SR⁵¹, —N(R⁵¹)₂, —N(R⁵¹)C(O)R⁴¹, —C(O)N(R⁵¹)₂, —N(R⁵¹)C(O)N(R⁵¹)₂, —N(R⁵¹)C(O)OR⁵¹, —OC(O)N(R⁵¹)₂, —N(R⁵¹)SO₂R⁵¹, —SO₂N(R⁵¹)₂, —C(O)R⁵¹, —C(O)OR⁵¹, —OC(O)R⁵¹, —S(O)R⁵¹, or —SO₂R, C₁₋₃ alkyl, C₁₋₃ alkoxy, wherein each R⁵¹ is independently hydrogen or C₁₋₆ alkyl. In some embodiments, each halogen can independently be F. In some embodiments of the compound of Formula (I), or a pharmaceutically acceptable salt thereof, R⁵ is an 8-10 membered bridged heterocycle having 1 or 2 heteroatoms independently selected from oxygen or nitrogen. In some embodiments of the compound of Formula (I), or a pharmaceutically acceptable salt thereof, R⁵ is selected from

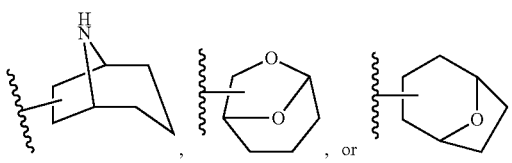

In some embodiments of the compound of Formula (I), or a pharmaceutically acceptable salt thereof, R⁵ is

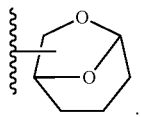

In some embodiments of the compound of Formula (I), or a pharmaceutically acceptable salt thereof, R⁵ is

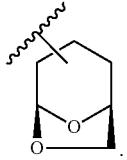

In some embodiments of the compound of Formula (I), or a pharmaceutically acceptable salt thereof, R⁵ is

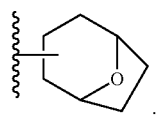

In some embodiments of the compound of Formula (I), or a pharmaceutically acceptable salt thereof, R⁵ is

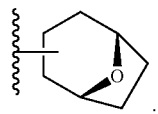

In some embodiments of the compound of Formula (I), or a pharmaceutically acceptable salt thereof, R⁵ is is a 6-12 membered spiro heterocycle having 1 or 2 heteroatoms independently selected from oxygen, sulfur, or nitrogen, wherein the spiro heterocycle is optionally substituted with 1 to 4 substituents independently selected from halogen, hydroxyl, oxo, amino, cyano, —OR⁵¹, —SR⁵¹, —N(R⁵¹)₂, —N(R⁵¹)C(O)R⁵¹, —C(O)N(R⁵¹)₂, —N(R⁵¹)C(O)N(R⁵¹)₂, —N(R⁵¹)C(O)OR⁵¹, —OC(O)N(R⁵¹)₂, —N(R⁵¹)SO₂R⁵¹, —SO₂N(R⁵¹)₂, —C(O)R⁵¹, —C(O)OR⁵¹, —OC(O)R⁵¹, —S(O)R⁵¹, or —SO₂R, C₁₋₃ alkyl, C₁₋₃ alkoxy, wherein each R⁵¹ is independently hydrogen or C₁₋₆ alkyl. In some embodiments, each halogen can independently be F. In some embodiments of the compound of Formula (I), or a pharmaceutically acceptable salt thereof, R⁵ is an 8-10 membered spiro heterocycle having 1 or 2 heteroatoms independently selected from oxygen or nitrogen. In some embodiments of the compound of Formula (I), or a pharmaceutically acceptable salt thereof, R⁵ is selected from

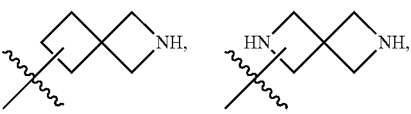

-continued

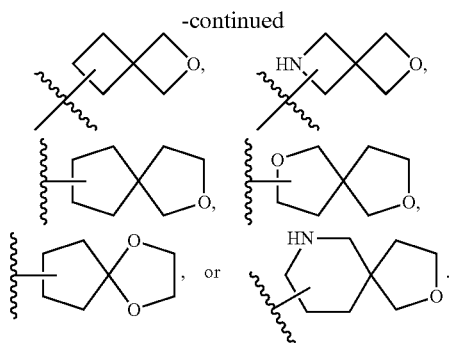

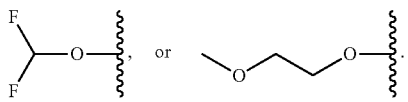

In some embodiments of the compound of Formula (I), or a pharmaceutically acceptable salt thereof, n is 1. In some embodiments of the compound of Formula (I), or a pharmaceutically acceptable salt thereof, n is 2. In some embodiments of the compound of Formula (I), or a pharmaceutically acceptable salt thereof, the two $R^6$ together with the phenyl group to which they are attached form a 8-10 membered bicyclic aryl or a bicyclic heteroaryl having one or two substituents selected from oxygen, nitrogen, and sulfur. In some embodiments of the compound of Formula (I), or a pharmaceutically acceptable salt thereof, the two $R^6$ together with the phenyl group to which they are attached form a naphtyl, indolyl, benzothiasoly, or benzodioxolyl. In some embodiments of the compound of Formula (I), or a pharmaceutically acceptable salt thereof, n is 3.

In some embodiments of the compound of Formula (I), or a pharmaceutically acceptable salt thereof, each $R^6$ is independently hydrogen, halogen, or $C_{1-3}$ alkoxy optionally substituted with one —O—$CH_3$ or 1 to 3 halogens. In some embodiments of the compound of Formula (I), or a pharmaceutically acceptable salt thereof, one or more $R^6$ is $C_{1-3}$ alkoxy optionally substituted with 1 to 3 F.

In some embodiments of the compound of Formula (I), or a pharmaceutically acceptable salt thereof, one or more $R^6$ is halogen. In some embodiments of the compound of Formula (I), or a pharmaceutically acceptable salt thereof, one or more $R^6$ is F. In some embodiments of the compound of Formula (I), or a pharmaceutically acceptable salt thereof, one or more $R^6$ is $C_{1-3}$ alkoxy. In some embodiments of the compound of Formula (I), or a pharmaceutically acceptable salt thereof, one or more $R^6$ is $C_{1-3}$ alkoxy substituted with one O—$CH_3$ or 1 to 3 halogens. In some embodiments of the compound of Formula (I), or a pharmaceutically acceptable salt thereof, one or more $R^6$ is $C_{1-3}$ alkoxy optionally substituted with 1 to 3 F. In some embodiments of the compound of Formula (I), or a pharmaceutically acceptable salt thereof, one or more $R^6$ is $C_2$ alkoxy substituted with one —O—$CH_3$. In some embodiments of the compound of Formula (I), or a pharmaceutically acceptable salt thereof, one or more $R^6$ is $C_1$ alkoxy substituted with one 1 to 3 halogens. In some embodiments of the compound of Formula (I), or a pharmaceutically acceptable salt thereof, one or more $R^6$ is $C_1$ alkoxy substituted with one 1 to 3 F. In some embodiments of the compound of Formula (I), or a pharmaceutically acceptable salt thereof, one or more $R^6$ is $C_1$ alkoxy substituted with 2 halogens. In some embodiments of the compound of Formula (I), or a pharmaceutically acceptable salt thereof, one or more $R^6$ is $C_1$ alkoxy substituted with 2 F.

In some embodiments of the compound of Formula (I), or a pharmaceutically acceptable salt thereof, each $R^6$ is independently H, F, —O—$CH_3$, In some embodiments of the compound of Formula (I), or a pharmaceutically acceptable salt thereof, each $R^6$ is independently hydrogen, F, or $C_{1-2}$ alkoxy optionally substituted with one —O—$CH_3$ or 1 to 2 F.

In some embodiments of the compound of Formula (I), or a pharmaceutically acceptable salt thereof, each $R^6$ is independently hydrogen, F, or $C_{1-2}$ alkoxy optionally substituted with one —O—$CH_3$ or 1 to 2 F, and n is 2.

In some embodiments, of the compound of Formula (I), or a pharmaceutically acceptable salt thereof, has two $R^6$ (n=2). In some embodiments the two $R^6$ are H and $C_1$ alkoxy. In some embodiments the two $R^6$ are F and $C_1$ alkoxy. In some embodiments the two $R^6$ are H and $C_1$ alkoxy substituted with 1 or 2 F. In some embodiments the two $R^6$ are H and $C_1$ alkoxy substituted with 1 F. In some embodiments the two $R^6$ are H and $C_1$ alkoxy substituted with 2 F. In some embodiments the two $R^6$ are F and $C_1$ alkoxy substituted with 1 or 2 F. In some embodiments the two $R^6$ are F and $C_1$ alkoxy substituted with 1 F. In some embodiments the two $R^6$ are F and $C_1$ alkoxy substituted with 2 F. In some embodiments the two $R^6$ are hydrogen and $C_2$ alkoxy. In some embodiments the two $R^6$ are F and $C_2$ alkoxy. In some embodiments the two $R^6$ are hydrogen and $C_2$ alkoxy substituted with one —O—$CH_3$. In some embodiments the two $R^6$ are F and $C_2$ alkoxy substituted with one —O—$CH_3$.

In some embodiments, the compound of Formula (I), or pharmaceutically acceptable salt thereof, is a compound of Formula (II), Formula (II)

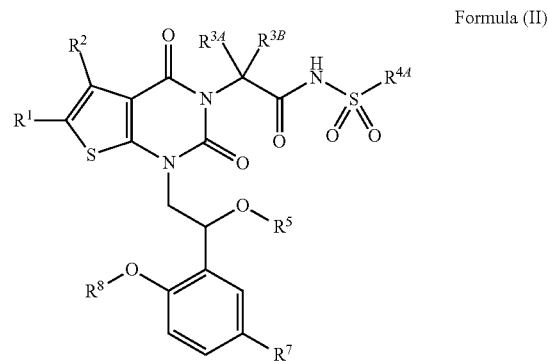

or a pharmaceutically acceptable salt thereof,
wherein:
$R^1$ is cyano or a 5 membered heteroaryl having 2 to 3 heteroatoms independently selected from the group consisting of nitrogen, oxygen, and sulfur;
$R^2$ is $C_{1-3}$ alkyl optionally substituted with 1 to 3 F;
$R^{3a}$ and $R^{3b}$ are each independently hydrogen or $CH_3$ optionally substituted with 1 to 3 F; or
$R^{3a}$ and $R^{3b}$ together with the carbon to which they are attached form cyclopropylenyl or cyclobutylenyl, each optionally substituted with 1 to 3 F;
$R^{4A}$ is $C_{1-6}$ alkyl, $C_{3-6}$ cycloalkyl, phenyl or pyridyl, each optionally substituted with 1 to 3 substituents independently selected from halogen (e.g., F), cyano, or $C_{1-3}$ alkyl, wherein each $C_{1-3}$ alkyl is optionally substituted with one $C_{1-3}$ alkoxy or 1 to 3 halogens (e.g., F);

$R^5$ is an 8-10 membered bridged heterocycloalkyl having one or two oxygens;
$R^7$ is hydrogen or halogen (e.g., F); and
$R^8$ is $C_{1-3}$ alkyl optionally substituted with one —O—$CH_3$ or 1 to 3 halogens (e.g., F).

In some embodiments, the compound of Formula (I) or (II), or a pharmaceutically acceptable salt thereof, is a compound of Formula (IIa),

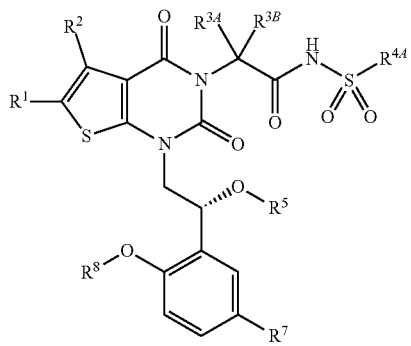

Formula (IIa)

or a pharmaceutically acceptable salt thereof, wherein the variables are as defined in Formula (II).

In some embodiments of the compound of Formula (I), (II), or (IIa), or a pharmaceutically acceptable salt thereof, $R^5$ is an 8 membered bridged heterocycloalkyl having one or two oxygens. In some embodiments of the compound of Formula (I), (II), or (IIa), or a pharmaceutically acceptable salt thereof, $R^5$ is an 8 membered bridged heterocycloalkyl having one oxygen. In some embodiments of the compound of Formula (I), (II), or (IIa), or a pharmaceutically acceptable salt thereof, $R^5$ is selected from

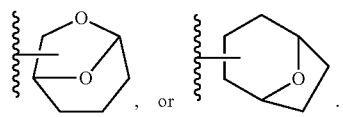

In some embodiments of the compound of Formula (I), (II), or (IIa), or a pharmaceutically acceptable salt thereof, $R^5$ is

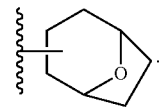

In some embodiments of the compound of Formula (I), (II), or (IIa), or a pharmaceutically acceptable salt thereof, $R^5$ is

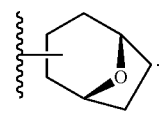

In some embodiments, the compound of Formula (I) or (II), or a therapeutically acceptable salt thereof, is a compound of Formula (III),

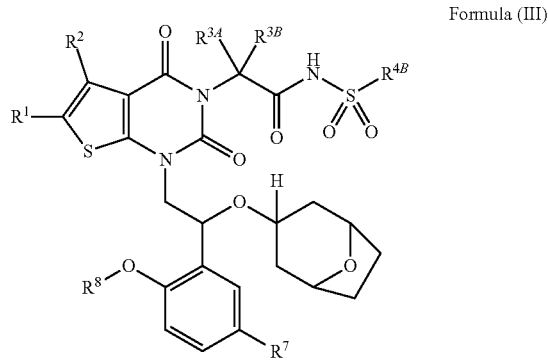

Formula (III)

or a pharmaceutically acceptable salt thereof,
wherein:
$R^1$ is cyano or a 5 membered heteroaryl having 2 to 3 heteroatoms independently selected from the group consisting of nitrogen, oxygen, and sulfur;
$R^2$ is $C_{1-3}$ alkyl optionally substituted with 1 to 3 F;
$R^{3A}$ and $R^{3B}$ are each independently hydrogen or $CH_3$ optionally substituted with 1 to 3 F; or
$R^{3A}$ and $R^{3B}$ together with the carbon to which they are attached form cyclopropylenyl or cyclobutylenyl, each optionally substituted with 1 to 3 F;
$R^{4A}$ is $C_{1-6}$ alkyl, $C_{3-6}$ cycloalkyl, phenyl or pyridyl, each optionally substituted with 1 to 3 substituents independently selected from halogen, cyano, or
$C_{1-3}$ alkyl, wherein each $C_{1-3}$ alkyl is optionally substituted with one $C_{1-3}$ alkoxy or 1 to 3 halogens;
$R^7$ is hydrogen or halogen; and
$R^8$ is $C_{1-3}$ alkyl optionally substituted with one —O—$CH_3$ or 1 to 3 halogens.

In some embodiments, the compound of Formula (I), (II), (IIa), or (III), or a pharmaceutically acceptable salt thereof, is a compound of Formula (IIIa),

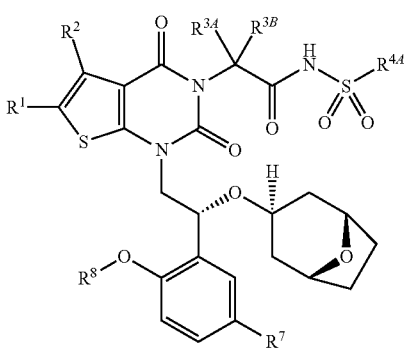

Formula (IIIa)

or a pharmaceutically acceptable salt thereof, wherein the variables are as defined in Formula (III).

In some embodiments of the compound of Formula (I), (II), (IIa), (III), or (IIIa), or a pharmaceutically acceptable salt thereof, $R^{3A}$ and $R^{3B}$ are each independently hydrogen or $CH_3$, wherein at least one of $R^{3A}$ and $R^{3B}$ is $CH_3$. In some embodiments of the compound of Formula (I), (II), (IIa), (III), or (IIIa), or a pharmaceutically acceptable salt thereof, one of $R^{3A}$ or $R^{3B}$ is hydrogen and one of $R^{3A}$ or $R^{3B}$ is $CH_3$. In some embodiments of the compound of Formula (I), (II), (IIa), (III), or (IIIa), or a pharmaceutically acceptable salt thereof, the compound has an S-configuration with respect to the carbon to which $R^{3A}$ and $R^{3B}$ are attached. In some embodiments of the compound of Formula (I), (II), (IIa), (III), or (IIIa), or a pharmaceutically acceptable salt thereof, the compound has an R-configuration with respect to the carbon to which $R^{3A}$ and $R^{3B}$ are attached.

In some embodiments of the compound of Formula (I), (II), (IIa), (III), or (IIIa), or a pharmaceutically acceptable salt thereof, $R^{3A}$ and $R^{3B}$ are each independently hydrogen or $CH_3$. In some embodiments of the compound of Formula (I), (II), (IIa), (III), or (IIIa), or a pharmaceutically acceptable salt thereof, at least one of $R^{3A}$ and $R^{3B}$ is $CH_3$. In some embodiments of the compound of Formula (I), (II), (IIa), (III), or (IIIa), or a pharmaceutically acceptable salt thereof, $R^{3A}$ and $R^{3B}$ are each hydrogen. In some embodiments of the compound of Formula (I), (II), (IIa), (III), or (IIIa), or a pharmaceutically acceptable salt thereof, $R^{3A}$ and $R^{3B}$ are each $CH_3$.

In some embodiments of the compound of Formula (I), (II), (IIa), (III), or (IIIa), or a pharmaceutically acceptable salt thereof, $R^{3A}$ and $R^{3B}$ together with the carbon to which they are attached form cyclopropylenyl or cyclobutylenyl. In some embodiments of the compound of Formula (I), (II), (IIa), (III), or (IIIa), or a pharmaceutically acceptable salt thereof, $R^{3A}$ and $R^{3B}$ together with the carbon to which they are attached form cyclopropylenyl. In some embodiments of the compound of Formula (I), (II), (IIa), (III), or (IIIa), or a pharmaceutically acceptable salt thereof, $R^{3A}$ and $R^{3B}$ together with the carbon to which they are attached form cyclobutylenyl.

In some embodiments of the compound of Formula (I), (II), (IIa), (III), or (IIIa), or a pharmaceutically acceptable salt thereof, $R^{4A}$ is $C_{1-6}$ alkyl optionally substituted with 1 to 3 substituents independently selected from halogen, cyano, or $C_{1-3}$ alkyl, wherein each $C_{1-3}$ alkyl is optionally substituted with one $C_{1-3}$ alkoxy or 1 to 3 halogens. In some embodiments of the compound of Formula (I), (II), (IIa), (III), or (IIIa), or a pharmaceutically acceptable salt thereof, $R^{4A}$ is $C_{1-6}$ alkyl. In some embodiments of the compound of Formula (I), (II), (IIa), (III), or (IIIa), or a pharmaceutically acceptable salt thereof, $R^{4A}$ is $C_{1-4}$ alkyl optionally substituted with 1 to 3 substituents independently selected from halogen, cyano, or $C_{1-3}$ alkyl, wherein each $C_{1-3}$ alkyl is optionally substituted with one $C_{1-3}$ alkoxy or 1 to 3 halogens. In some embodiments of the compound of Formula (I), (II), (IIa), (III), or (IIIa), or a pharmaceutically acceptable salt thereof, $R^{4A}$ is $C_{1-4}$ alkyl. In some embodiments of the compound of Formula (I), (II), (IIa), (III), or (IIIa), or a pharmaceutically acceptable salt thereof, $R^{4A}$ is t-butyl.

In some embodiments of the compound of Formula (I), (II), (IIa), (III), or (IIIa), or a pharmaceutically acceptable salt thereof, $R^{4A}$ is $C_{3-6}$ cycloalkyl optionally substituted with 1 to 3 substituents independently selected from halogen, cyano, or $C_{1-3}$ alkyl, wherein each $C_{1-3}$ alkyl is optionally substituted with one $C_{1-3}$ alkoxy or 1 to 3 halogens. In some embodiments of the compound of Formula (I), (II), (IIa), (III), or (IIIa), or a pharmaceutically acceptable salt thereof, $R^{4A}$ is $C_{3-6}$ cycloalkyl optionally substituted with one halogen or one $C_{1-3}$ alkyl, wherein each $C_{1-3}$ alkyl is optionally substituted with one $C_{1-3}$ alkoxy or 1 to 3 halogens. In some embodiments of the compound of Formula (I), (II), (IIa), (III), or (IIIa), or a pharmaceutically acceptable salt thereof, $R^{4A}$ is a $C_{3-6}$ cycloalkyl optionally substituted with one $CH_3$ or one F, wherein the $CH_3$ is optionally substituted with one —O—$CH_3$ or 1 to 2 F. In some embodiments of the compound of Formula (I), (II), (IIa), (III), or (IIIa), or a pharmaceutically acceptable salt thereof, $R^{4A}$ is $C_3$ cycloalkyl (cyclopropyl) optionally substituted with one F or one —$CH_3$, wherein the —$CH_3$ is optionally substituted with one —O—$CH_3$ or one or two F. In some embodiments of the compound of Formula (I), (II), (IIa), (III), or (IIIa), or a pharmaceutically acceptable salt thereof, $R^{4A}$ is $C_4$ cycloalkyl (cyclobutyl). In some embodiments of the compound of Formula (I), (II), (IIa), (III), or (IIIa), or a pharmaceutically acceptable salt thereof, $R^{4A}$ is

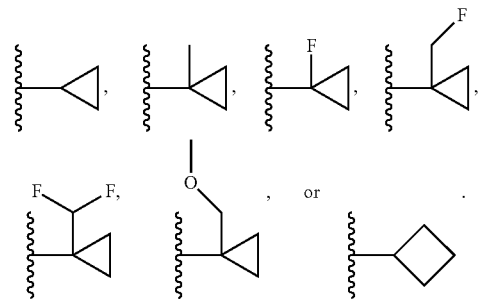

In some embodiments of the compound of Formula (I), (II), (IIa), (III), or (IIIa), or a pharmaceutically acceptable salt thereof, $R^{4A}$ is

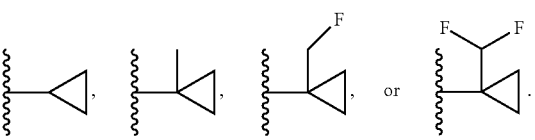

In some embodiments of the compound of Formula (I), (II), (IIa), (III), or (IIIa), or a pharmaceutically acceptable salt thereof, $R^{4A}$ is phenyl or pyridyl. In some embodiments of the compound of Formula (I), (II), (IIa), (III), or (IIIa), or a pharmaceutically acceptable salt thereof, $R^{4A}$ is pyridyl. In some embodiments of the compound of Formula (I), (II), (IIa), (III), or (IIIa), or a pharmaceutically acceptable salt thereof, $R^{4A}$ is

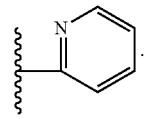

In some embodiments, the compound of Formula (I), (II), or (III), or a pharmaceutically acceptable salt thereof, is a compound of Formula (IV), Formula (IV)

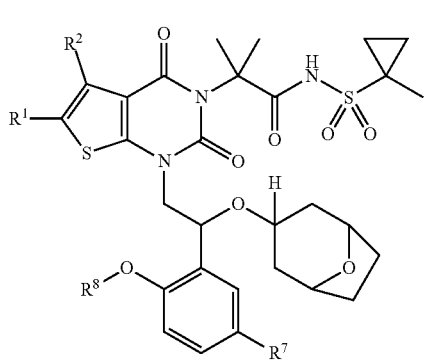

or a pharmaceutically acceptable salt thereof, wherein:

R¹ is cyano or a 5 membered heteroaryl having 2 to 3 heteroatoms independently selected from the group consisting of nitrogen, oxygen, and sulfur;

R² is $C_{1-3}$ alkyl optionally substituted with 1 to 3 F;

R⁷ is hydrogen or halogen (e.g., F); and

R⁸ is $C_{1-3}$ alkyl optionally substituted with one —O—CH₃ or 1 to 3 halogens (e.g., F).

In some embodiments, the compound of Formula (I), (II), (IIa), or (III), or a pharmaceutically acceptable salt thereof, is of Formula (IIIa), Formula (IVa)

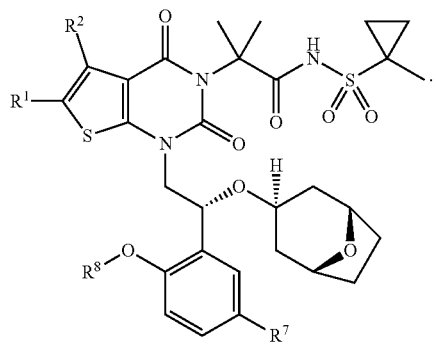

or a pharmaceutically acceptable salt thereof, wherein the variables are as defined in Formula (IV).

In some embodiments of the compound of Formula (I), (II), (IIa), (III), (IIIa), (IV) or (IVa), or a pharmaceutically acceptable salt thereof, R¹ is cyano.

In some embodiments of the compound of Formula (I), (II), (IIa), (III), (IIIa), (IV) or (IVa), or a pharmaceutically acceptable salt thereof, R¹ is a 5 membered heteroaryl having 2 to 3 heteroatoms independently selected from the group consisting of nitrogen, oxygen, and sulfur. In some embodiments of the compound of Formula (I), (II), (IIa), (III), (IIIa), (IV) or (IVa), or a pharmaceutically acceptable salt thereof, R¹ is oxazol, thiadiazolyl, and triazol. In some embodiments of the compound of Formula (I), (II), (IIa), (III), (IIIa), (IV) or (IVa), or a pharmaceutically acceptable salt thereof, R¹ is

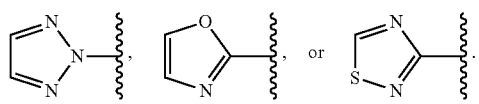

In some embodiments of the compound of Formula (I), (II), (IIa), (III), (IIIa), (IV) or (IVa), or a pharmaceutically acceptable salt thereof, R¹ is

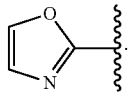

In some embodiments of the compound of Formula (I), (II), (IIa), (III), (IIIa), (IV) or (IVa), or a pharmaceutically acceptable salt thereof, R¹ is

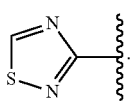

In some embodiments of the compound of Formula (I), (II), (IIa), (III), (IIIa), (IV) or (IVa), or a pharmaceutically acceptable salt thereof, R¹ is In some embodiments of the compound of Formula (I), (II), (IIa), (III), (IIIa), (IV) or (IVa), or a pharmaceutically acceptable salt thereof, R² is CH₃.

In some embodiments of the compound of Formula (II), (IIa), (III), (IIIa), (IV) or (IVa), or a pharmaceutically acceptable salt thereof, R⁷ is hydrogen. In some embodiments of the compound of Formula (II), (IIa), (III), (IIIa), (IV) or (IVa), or a pharmaceutically acceptable salt thereof, R⁷ is halogen. In some embodiments of the compound of Formula (II), (IIa), (III), (IIIa), (IV) or (IVa), or a pharmaceutically acceptable salt thereof, R⁷ is hydrogen or F.

In some embodiments of the compound of Formula (II), (IIa), (III), (IIIa), (IV) or (IVa), or a pharmaceutically acceptable salt thereof, R⁸ is $C_{1-3}$ alkyl. In some embodiments of the compound of Formula (II), (IIa), (III), (IIIa), (IV) or (IVa), or a pharmaceutically acceptable salt thereof, R⁸ is $C_1$ alkyl (—CH₃). In some embodiments of the compound of Formula (II), (IIa), (III), (IIIa), (IV) or (IVa), or a pharmaceutically acceptable salt thereof, R⁸ is $C_1$ alkyl substituted with 1 to 3 halogens. In some embodiments of the compound of Formula (II), (IIa), (III), (IIIa), (IV) or (IVa), or a pharmaceutically acceptable salt thereof, R⁸ is $C_1$ alkyl substituted with 1 to 3 F. In some embodiments of the compound of Formula (II), (IIa), (III), (IIIa), (IV) or (IVa), or a pharmaceutically acceptable salt thereof, R⁸ is

In some embodiments of the compound of Formula (II), (IIa), (III), (IIIa), (IV) or (IVa), or a pharmaceutically acceptable salt thereof, R⁸ is $C_{1-3}$ alkyl optionally substituted with one —O—CH₃. In some embodiments of the compound of Formula (II), (IIa), (III), (IIIa), (IV) or (IVa), or a pharmaceutically acceptable salt thereof, R⁸ is $C_2$ alkyl substituted with one —O—CH₃. In some embodiments of the compound of Formula (II), (IIa), (III), (IIIa), (IV) or (IVa), or a pharmaceutically acceptable salt thereof, R⁸ is

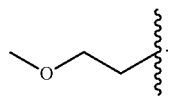 [SMILES: *CCOC]

In some embodiments, the compound of Formula (II), (IIa), (III), (IIIa), (IV) or (IVa), or a pharmaceutically acceptable salt thereof, is selected from the group consisting of:

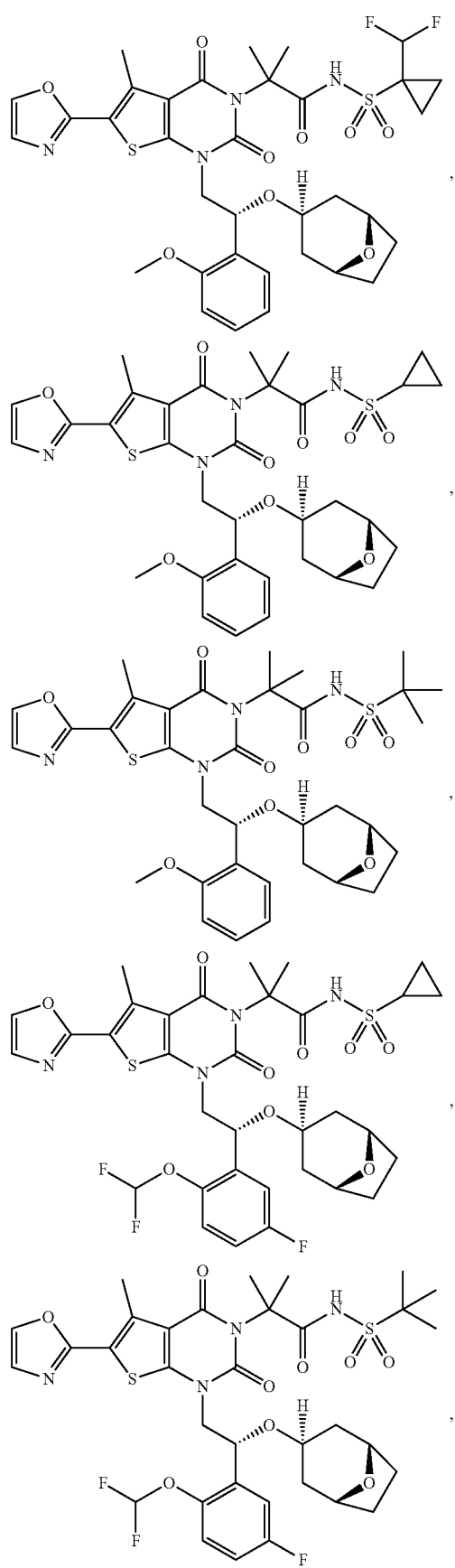
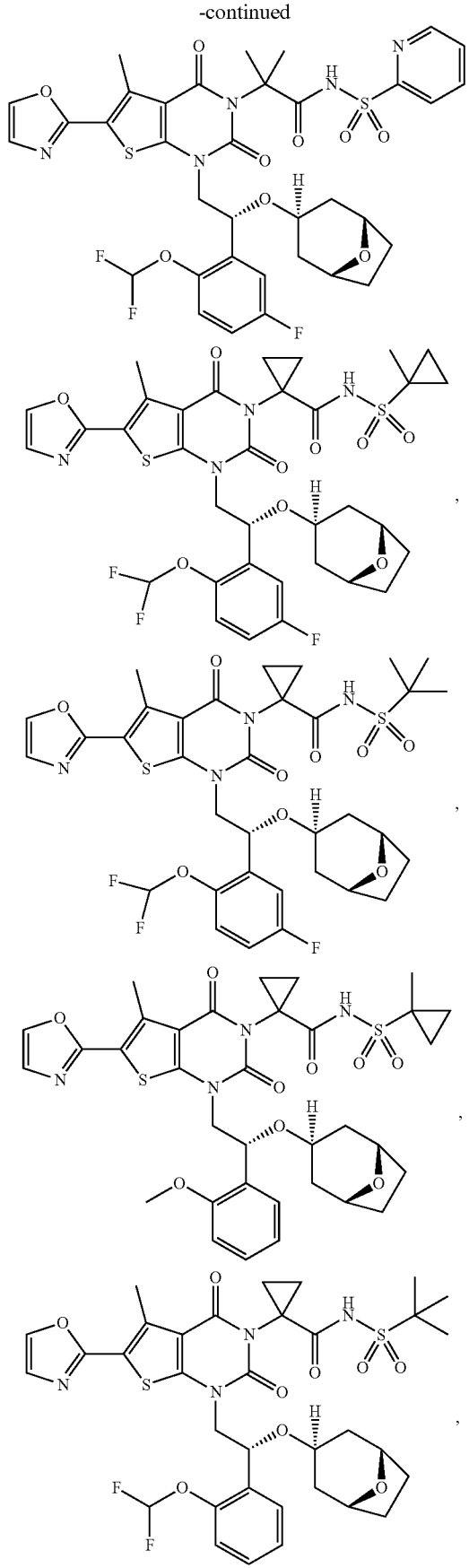

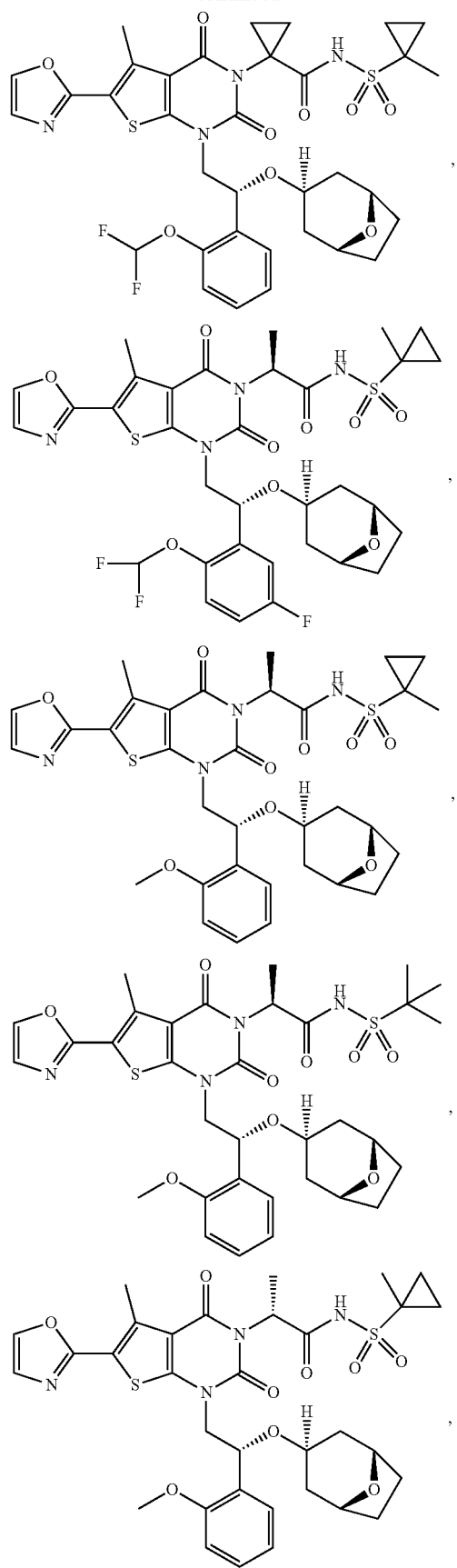
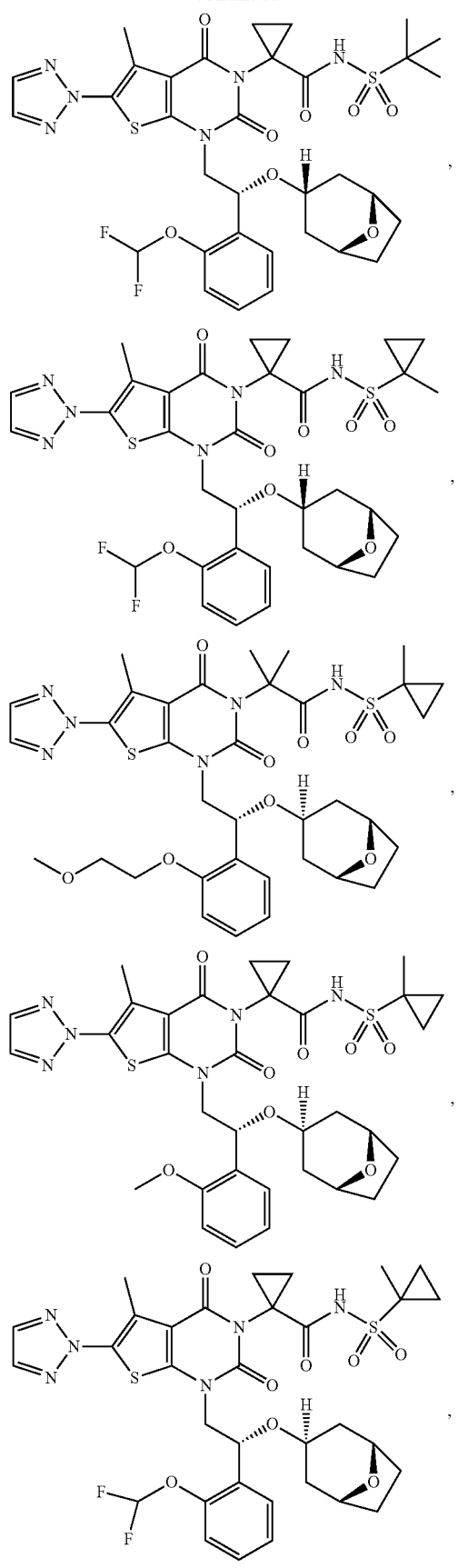

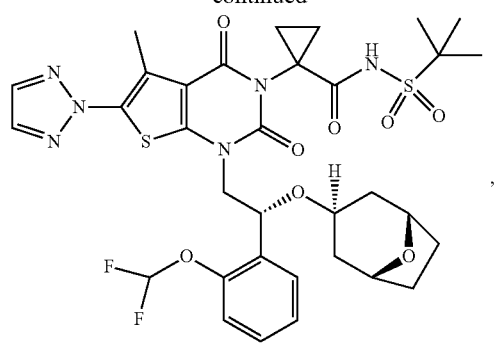
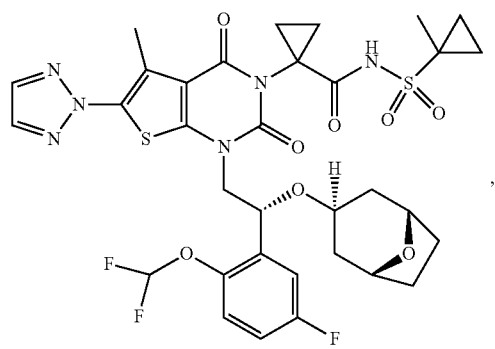
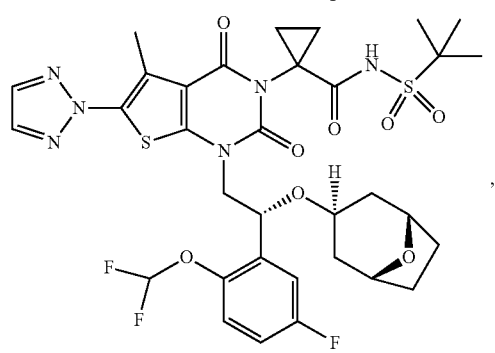
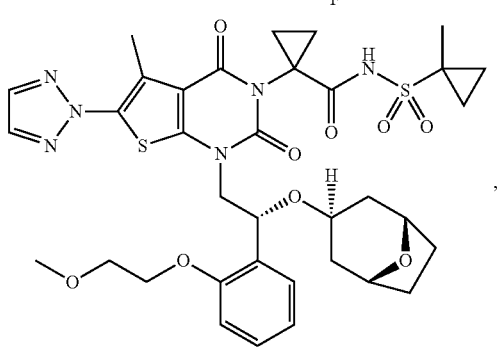
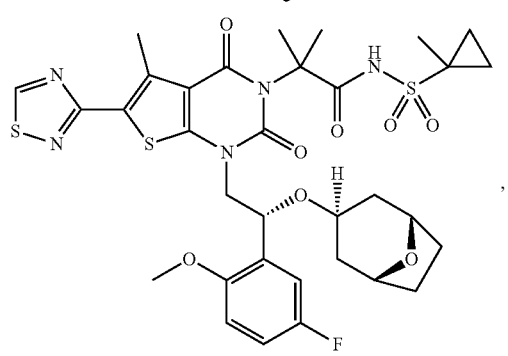
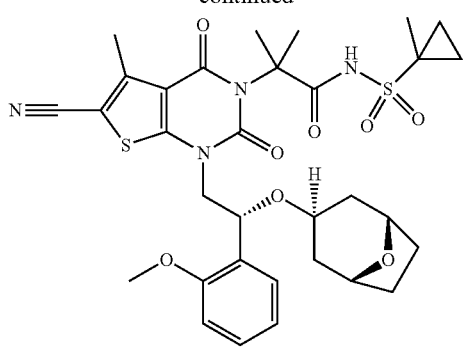
or a pharmaceutically acceptable salt thereof.
In some embodiments, the compound of Formula (II), (IIa), (III), (IIIa), (IV) or (IVa), or a pharmaceutically acceptable salt thereof, is selected from the group consisting of:
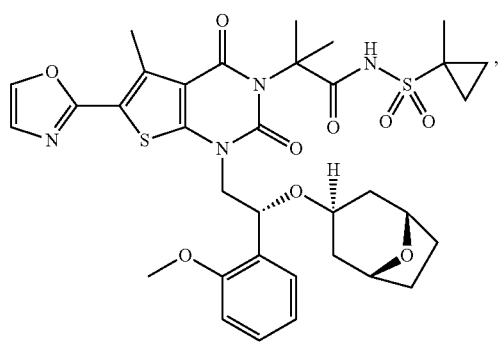
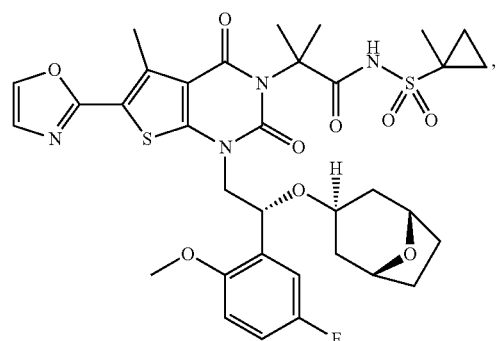
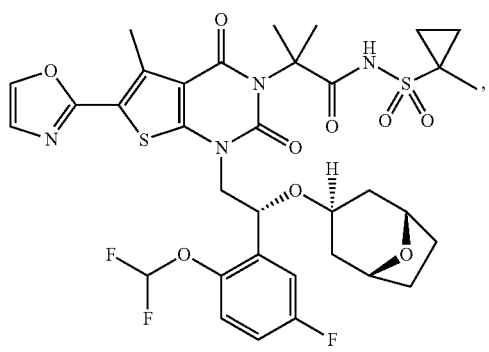
, and

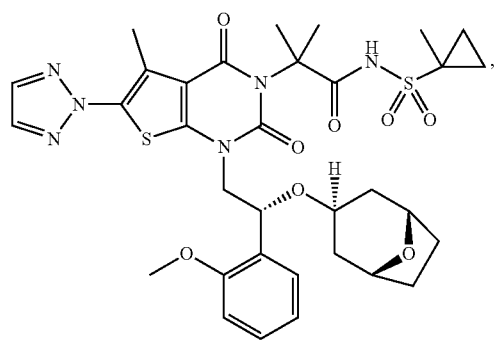

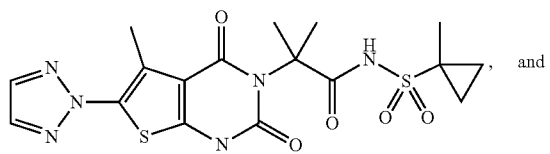

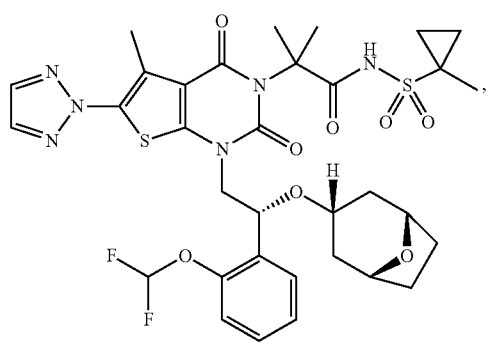 [SMILES: Cc1c(-n2nccn2)sc2c1c(=O)n(C(C)(C)C(=O)NS(=O)(=O)C1(C)CC1)c(=O)n2C[C@H](O[C@H]1C[C@H]2CC[C@@H](C1)O2)c1ccccc1OC(F)F]

or a pharmaceutically acceptable salt thereof.

In some embodiments, the compound of Formula (II), (IIa), (III), (IIIa), (IV) or (IVa), or a pharmaceutically acceptable salt thereof, is:

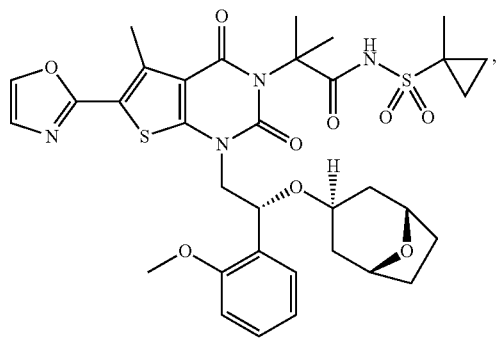 [SMILES: COc1ccccc1[C@H](Cn1c(=O)n(C(C)(C)C(=O)NS(=O)(=O)C2(C)CC2)c(=O)c2c(C)c(-c3ncco3)sc21)O[C@@H]1C[C@H]2CC[C@@H](C1)O2]

or a pharmaceutically acceptable salt thereof.

In some embodiments, the compound of Formula (II), (IIa), (III), (IIIa), (IV) or (IVa), or a pharmaceutically acceptable salt thereof, is:

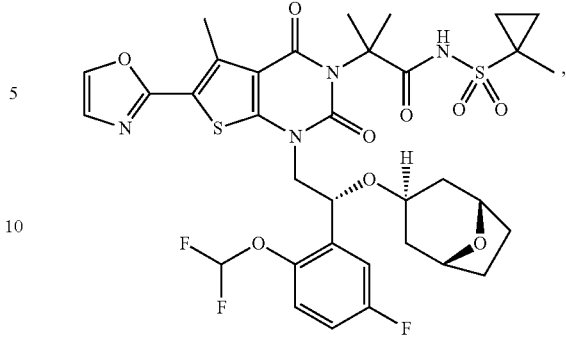

or a pharmaceutically acceptable salt thereof.

In some embodiments, the compound of Formula (II), (IIa), (III), (IIIa), (IV) or (IVa), or a pharmaceutically acceptable salt thereof, is:

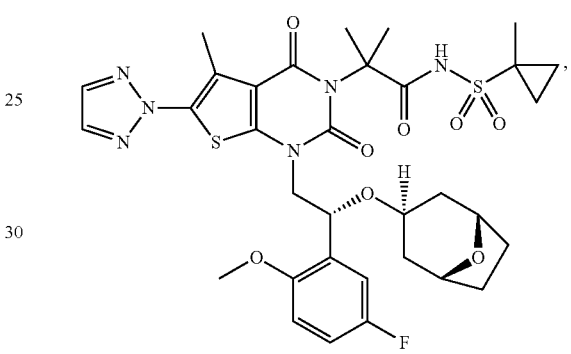

or a pharmaceutically acceptable salt thereof.

Pharmaceutical Compositions and Modes of Administration

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

The pharmaceutical composition of the present disclosure may additionally comprise one or more other compounds as active ingredients like a prodrug compound or other enzyme inhibitors.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

In some embodiments, the compounds of the present disclosure may also be used as salts with various counter-cations to yield an orally available formulation.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Treatment Methods and Uses

The disclosure further relates to the use of compounds disclosed herein for the treatment and/or prophylaxis of diseases and/or conditions through binding of ACC by said compounds. Further the present disclosure relates to the use of said compounds for the preparation of a medicament for the treatment and/or prophylaxis of diseases and/or conditions through binding of ACC by said compounds.

Medicaments as referred to herein may be prepared by conventional processes, including the combination of a compound according to the present disclosure and a pharmaceutically acceptable carrier.

In some embodiments, provided herein is a method of treating and/or preventing an ACC-mediated disease or condition in a patient in need thereof, comprising administering to the patient a therapeutically effective amount of a compound of Formula (I), (II), (IIa), (III), (IIIa), (IV) or (IVa), or a therapeutically acceptable salt thereof, or a composition comprising a compound of Formula (I), (II), (IIa), (III), (IIIa), (IV) or (IVa), or a therapeutically acceptable salt thereof.

In some embodiments, the ACC-mediated disease or condition is a metabolic disorder or a liver disease.

In some embodiments, the metabolic disorder includes metabolic syndrome, diabetes or a diabetes related disorder, obesity or an obesity comorbidity. In some embodiments, diabetes or a diabetes-related disorder includes Type 1 diabetes (insulin-dependent diabetes mellitus, IDDM), Type 2 diabetes (non-insulin-dependent diabetes mellitus, NIDDM), impaired glucose tolerance, insulin resistance, hyperglycemia, and a diabetic complication. In some embodiments, the diabetic complication includes atherosclerosis, coronary heart disease, stroke, peripheral vascular disease, nephropathy, hypertension, neuropathy and nephropathy. In some embodiments, the obesity comorbidity includes metabolic syndrome, dyslipidemia, hypertension, insulin resistance, diabetes (including Type 1 and Type 2 diabetes), coronary artery disease, and heart failure. In some embodiments, the metabolic disorder includes non-alcoholic fatty liver disease (MELD) or hepatic insulin resistance.

In some embodiments, the liver disease is hepatitis C, liver cancer, familial combined hyperlipidemia, non-alcoholic fatty liver disease (NAFLD), liver fibrosis, liver cirrhosis, or a cholestatic liver disease. In some embodiments, the liver disease is liver fibrosis. In some embodiment, the liver disease is liver cirrhosis. In some embodiments, the liver disease is progressive familial intrahepatic cholestasis, congenital hepatic fibrosis, primary biliary cirrhosis (PBC), or primary sclerosing cholangitis (PSC). In some embodiments, the liver disease is progressive familial intrahepatic cholestasis. In some embodiments, the liver disease is congenital hepatic fibrosis. In some embodiments, the liver disease is PBC. In some embodiments, the liver disease is PSC. In some embodiments, liver cancer comprises hepatocellular carcinoma (HCC), cholangiocarcinoma, angiosarcoma, or hemangiosarcoma. In some embodiments, liver cancer comprises HCC. In some embodiments, NAFLD comprises steatosis. In some embodiments, NAFLD comprises NASH. In some embodiments, NAFLD or NASH comprises liver fibrosis. In some embodiments, NAFLD or NASH comprises liver cirrhosis. In some embodiments, the NAFLD or NASH comprises compensated liver cirrhosis. In some embodiments, the NAFLD or NASH comprises decompensated liver fibrosis. In some embodiments, the NAFLD comprises HCC. In some embodiments, the liver disease is NASH.

In some embodiments, provided herein is a method of treating and/or preventing NAFLD or NASH in a patient in need thereof, comprising administering to the patient a therapeutically effective amount of a compound of Formula (I), (II), (IIa), (III), (IIIa), (IV) or (IVa), or a therapeutically acceptable salt thereof, or a composition comprising a compound of Formula (I), (II), (IIa), (III), (IIIa), (IV) or (IVa), or a therapeutically acceptable salt thereof. In some embodiments, NAFLD or NASH comprise liver fibrosis. In some embodiments, NAFLD or NASH comprise liver cirrhosis. In some embodiments, liver cirrhosis is compensated liver cirrhosis. In some embodiments, liver cirrhosis is decompensated liver cirrhosis. In some embodiments NAFLD or NASH comprise HCC. In some embodiments, the compound of Formula (I), (II), (IIa), (III), (IIIa), (IV) or (IVa), or a therapeutically acceptable salt thereof, is the compound of Example 1.

In some embodiments, provided herein is a method of preventing a liver disease or condition in a patient in need thereof, comprising administering to the patient a therapeutically effective amount of a compound of Formula (I), (II), (IIa), (III), (IIIa), (IV) or (IVa), or a therapeutically acceptable salt thereof, or a composition comprising a compound of Formula (I), (II), (IIa), (III), (IIIa), (IV) or (IVa), or a therapeutically acceptable salt thereof. In some embodiments, the liver disease or condition is liver fibrosis. In some embodiments, the liver disease or condition is liver cirrhosis. In some embodiments, liver cirrhosis is compensated liver cirrhosis. In some embodiments, liver cirrhosis is decompensated liver cirrhosis. In some embodiments, the liver disease or condition is HCC. In some embodiments, the compound of Formula (I), (II), (IIa), (III), (IIIa), (IV) or (IVa), or a therapeutically acceptable salt thereof, is the compound of Example 1.

In some embodiments, the present disclosure relates to the use of compounds according to Formula (I), (II), (IIa), (III), (IIIa), (IV) or (IVa) in the preparation of a medicament for the prophylaxis and/or treatment of an ACC-mediated disease or condition disclosed herein.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing ACC mediated disease or condition for which compounds of the present disclosure are indicated, generally satisfactory results are obtained when the compounds of the present disclosure are administered at a daily dosage of from about 0.1 milligram to about 300 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 0.1 milligrams to about 200 milligrams. This dosage regimen may be adjusted to provide the optimal therapeutic response. In some embodiments, the total daily dosage is from about 1 milligram to about 900 milligrams, about 1 milligram to about 800 milligrams, about 1 milligram to about 700 milligrams, about 1 milligram to about 600 milligrams, about 1 milligram to about 400 milligrams, about 1 milligram to about 300 milligrams, about 1 milligram to about 200 milligrams, about 1 milligram to about 100 milligrams, about 1 milligram to about 50 milligrams, about 1 milligram to about 20 milligram, or about 1 milligram to about 10 milligrams. In some embodiments, the total daily dosage is from about 1 milligram to about 5 milligrams, about 4 milligrams, about 3 milligrams, or about 2 milligrams. In some embodiments, the total daily dosage is from about 1 milligram to about 2 milligrams. In some embodiments, the total daily dosage is from about 1.0 milligram to about 1.5 milligrams. In some embodiments, the total daily dosage is about 1.2 milligrams. In some embodiments, the compound or pharmaceutically acceptable salt thereof is administered at a dose in the range of about 0.5 mg to about 20 mg per dose. In some embodiments, the compound or pharmaceutically acceptable salt thereof is administered at a dose in the range of about 0.5 mg to about 10 mg per dose. In some embodiments, the compound or pharmaceutically acceptable salt thereof is administered at a dose in the range of about 0.5 mg to about 5 mg per dose. In some embodiments, the compound or pharmaceutically acceptable salt thereof is administered at a dose in the range of about 1.0 mg to about 2 mg per dose. In some embodiments, the compound or pharmaceutically acceptable salt thereof is administered at a dose of about 1.2 mg per dose.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are frequently alternated with resting periods of about 1 to 28 days, commonly about 7 days or about 14 days, between cycles. The treatment cycles, in other embodiments, may also be continuous.

In some embodiments, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combinations

In some embodiments, a compound of Formula (I), (II), (IIa), (III), (IIIa), (IV) or (IVa) provided herein or a pharmaceutically acceptable salt, a stereoisomer, a mixture of stereoisomers, or a tautomer thereof, is administered in combination with one or more additional therapeutic agents to treat or prevent a disease or condition disclosed herein. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the pharmaceutical compositions provided herein have a compound of Formula (I) (II), (IIa), (III), (IIIa), (IV) or (IVa) provided herein or a pharmaceutically acceptable salt, a stereoisomer, a mixture of stereoisomers, or a tautomer thereof, and one or more additional therapeutic agents. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the one or more additional therapeutic agents are selected from a(n) angiotensin converting enzyme (ACE) inhibitor, Adenosine A3 receptor agonist, Adiponectin receptor agonist, AKT protein kinase inhibitor, AMP kinase activator, AMP-activated protein kinase (AMPK) activator, Amylin receptor agonist, Angiotensin II AT-1 receptor antagonist, Androgen receptor agonist, Apoptosis signal-regulating kinase 1 (ASK1) inhibitor, ATP citrate lyase inhibitor, Apolipoprotein $C_3$ (APOC3) antagonist, Autophagy protein modulator, Autotaxin inhibitors, Axl tyrosine kinase receptor inhibitor, Bax protein stimulator, Bioactive lipid, Calcitonin agonist, Cannabinoid receptor modulator, Caspase inhibitor, Caspase-3 stimulator, Cathepsin inhibitor (e.g., cathepsin B inhibitor), Caveolin 1 inhibitor, CCR2 chemokine antagonist, CCR3 chemokine antagonist, CCR5 chemokine antagonist, CD3 antagonist, Chloride channel stimulator, cholesterol solubilizer, CNR1 inhibitor, Cyclin D1 inhibitor, Cytochrome P450 7A1 inhibitor, Cytochrome P450 2E1 (CYP2E1) inhibitor, Diacylglycerol O acyltransferase 1 inhibitor (DGAT1) inhibitor, Diacylglycerol O acyltransferase 1 inhibitor (DGAT2) inhibitor, CXCR4 chemokine antagonist, Dipeptidyl peptidase IV inhibitor, Endosialin modulator, Endothelial nitric oxide synthase stimulator, Eotaxin ligand inhibitor, Extracellular matrix protein modulator, Farnesoid X receptor agonist, Fatty acid synthase inhibitors, FGF1 receptor agonist, Fibroblast activation protein (FAP) inhibitor, Fibroblast growth factor receptor ligands (e.g., FGF-15, FGF-19, FGF-21), Fish oil, Galectin-3 inhibitor, Glucagon receptor agonist, Glucagon-like peptide 1 receptor agonist, Glucocorticoid receptor antagonist, Glucose 6-phosphate 1-dehydrogenase inhibitor, Glutaminase inhibitor, Glutathione precursor, G-protein coupled bile acid receptor 1 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, HMG CoA reductase inhibitor, 11β-Hydroxysteroid dehydrogenase (11β-HSD1) inhibitor, Hypoxia inducible factor-2 alpha inhibitor, IL-1 antagonist, IL-6 receptor agonist, IL-10 agonist, IL-11 antagonist, IL-17 antagonist, Ileal sodium bile acid cotransporter inhibitor, Insulin sensitizer, Insulin ligand agonist, Insulin receptor agonist, integrin modulator, Integrin antagonist intereukin-1 receptor-associated kinase 4 (IRAK4) inhibitor, Jak2 tyrosine kinase inhibitor, Ketohexokinase (KHK) inhibitors, Klotho beta stimulator, leptin, leptin analog, 5-Lipoxygenase inhibitor, Lipoprotein lipase inhibitor, Liver X receptor, LPL gene stimulator, Lysophosphatidate-1 receptor (LPAR-1) antagonist, Lysyl oxidase homolog 2 (LOXL2) inhibitor, LXR inverse agonist, Macrophage mannose receptor 1 modulator, Matrix metalloproteinase (MMPs) inhibitor, MCH receptor-1 antagonist, MEKK-5 protein kinase inhibitor, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21(miR-21) inhibitor, Mitochondrial uncoupler, Mixed lineage kinase-3 inhibitor, Myelin basic protein stimulator, NACHT LRR PYD domain protein 3 (NLRP3) inhibitor, NAD-dependent deacetylase sirtuin-1 stimulator, NADPH oxidase inhibitor (NOX), Nicotinic acid receptor 1 agonist, P2X7 purinoceptor modulator, P2Y13 purinoceptor stimulator, PDE 3 inhibitor, PDE 4 inhibitor, PDE 5 inhibitor, PDGF receptor beta modulator, Peptidyl-prolyl cis-trans isomerase A inhibitor, Phenylalanine hydroxylase stimulator, Phospholipase C inhibitor, PPAR alpha agonist, PPAR gamma agonist, PPAR delta agonist, PPAR gamma modulator, PPAR alpha/delta agonist, PPAR alpha/gamma/delta agonist, Protease-activated receptor-2 antagonist, Protein kinase modulator, Rho associated protein kinase 2 (ROCK2) inhibitor, Snitrosoglutathione reductase (GSNOR) enzyme inhibitor, Sodium glucose transporter-2 (SGLT2) inhibitor, SREBP transcription factor inhibitor, STAT-1 inhibitor, STAT-3 modulator, Stearoyl CoA desaturase-1 inhibitor, Snitrosoglutathione reductase (GSNOR) enzyme inhibitor, Suppressor of cytokine signalling-1 stimulator, Suppressor of cytokine signalling-3 stimulator, Spleen tyorosine kinase (SYK) inhibitor, Transforming growth factor β (TGF-β), TGF-β antagonist (e.g., TGF-β1 antagonist, TGF-β2 antagonist, TGF-β3 antagonist, latent TGF 0 complex modulator), TGF-β receptor antagonist, Transforming growth factor β activated Kinase 1 (TAK1), Thyroid hormone receptor beta agonist, Toll-like receptor (TLR)-4 antagonist, Transglutaminase inhibitor, Tumor necrosis factor alpha (TNFα) ligand inhibitor, Tumor Progression Locus 2 (Tpl2) kinase inhibitor, Tyrosine kinase receptor modulator, GPCR modulator, nuclear hormone receptor modulator, WNT modulators, YAP/TAZ modulator, and Zonulin inhibitor.

Non-limiting examples of the one or more additional therapeutic agents include:

ACE inhibitors, such as enalapril;

Acetyl CoA carboxylase (ACC) inhibitors, such as NDI-010976 (firsocostat), DRM-01, gemcabene, PF-05175157, QLT-091382 or PF-05221304;

Acetyl CoA carboxylase/Diacylglycerol O acyltransferase 2 inhibitors, such as PF-07055341;

Acetaldehyde dehydrogenase inhibitors, such as ADX-629;

Adenosine receptor agonists, such as CF-102 (namodenoson), CF-101, CF-502, or CGS21680;

Adiponectin receptor agonists, such as ADP-355 or ADP-399;

Amylin/calcitonin receptor agonists, such as KBP-042 or KBP-089;

AMP activated protein kinase stimulators, such as PXL-770 or O-304;

AMP kinase activators/ATP citrate lyase inhibitors, such as as bempedoic acid (ETC-1002, ESP-55016);

AMP activated protein kinase/Endothelial nitric oxide synthase/NAD-dependent deacetylase sirtuin-1 stimulators, such as NS-0200 (leucine+metformin+sildenafil);
Androgen receptor agonists, such as LPCN-1144;
Angiotensin II AT-1 receptor antagonists, such as irbesartan;
Angiopoietin-related protein-3 inhibitors, such as IONIS-ANGPTL3-LRx;
Autotaxin inhibitors, such as PAT-505, PAT-048, GLPG-1690, X-165, PF-8380, AM-063, or BBT-877;
Axl tyrosine kinase receptor inhibitors, such as bemcentinib (BGB-324, R-428);
Bax protein stimulators, such as CBL-514;
Bioactive lipids, such as DS-102;
Cannabinoid receptor type 1 (CNR1) inhibitors, such as namacizumab, GWP-42004, REV-200, or CRB-4001;
Caspase inhibitors, such as emricasan;
Pan cathepsin B inhibitors, such as VBY-376;
Pan cathepsin inhibitors, such as VBY-825;
CCR2/CCR5 chemokine antagonists, such as cenivriviroc, maraviroc, CCX-872, or WXSH-0213;
CCR2 chemokine antagonists, such as propagermanium;
CCR2 chemokine/Angiotensin II AT-1 receptor antagonists, such as DMX-200, or DMX-250;
CCR2/CCR5 chemokine antagonists and FXR agonists, such as LJC-242 (tropifexor+cenivriviroc); CCR3 chemokine antagonists, such as bertilimumab;
Chloride channel stimulators, such as cobiprostone, or lubiprostone;
CD3 antagonists, such as NI-0401 (foralumab);
CXCR4 chemokine antagonists, such as AD-214;
Diglyceride acyltransferase 1 (DGAT1) inhibitors, such as GSK-3008356;
Diacylglycerol O acyltransferase 1 (DGAT1)/Cytochrome P450 2E1 inhibitors (CYP2E1), such as SNP-610;
Diglyceride acyltransferase 2 (DGAT2) inhibitors, such as IONIS-DGAT2Rx, or PF-06865571;
Dipeptidyl peptidase IV inhibitors, such as linagliptin or evogliptin;
Eotaxin ligand inhibitors, such as bertilimumab or CM-101;
Extracellular matrix protein modulators, such as CNX-024;
Farnesoid X receptor (FXR) agonists, such as AGN-242266, AGN-242256, EP-024297, RDX-023, BWL-200, AKN-083, EDP-305, GNF-5120, GS-9674, LMB-763, obeticholic acid, Px-102, Px-103, M790, M780, M450, M-480, MET-409, PX20606, EYP-001, TERN-101, TC-100, INT-2228;
Farnesoid X receptor (FXR)/G-protein coupled bile acid receptor 1(TGR5) agonists, such as INT-767;
Fatty acid synthase inhibitors, such as TVB-2640;
FGF receptor agonists/Klotho beta stimulators, such as BFKB-8488A (RG-7992);
Fibroblast growth factor 19 (rhFGF19)/cytochrome P450 (CYP)7A1 inhibitors, such as NGM-282;
Fibroblast growth factor 21(FGF-21) ligand, such as BMS-986171, BIO89-100, B-1344, or BMS-986036;
Fibroblast growth factor 21(FGF-21)/glucagon like peptide 1 (GLP-1) agonists, such as YH-25723 (YH-25724; YH-22241) or AKR-001;
Fish oil compositions, such as icosapent ethyl (Vascepa);
Galectin-3 inhibitors, such as GR-MD-02, GB-1107 (Gal-300), or GB1211 (Gal-400);
Glucagon-like peptide 1 receptor (GLP1R) agonists, such as AC-3174, liraglutide, cotadutide (MEDI-0382), exenatide, SAR-425899, LY-3305677, HM-15211, YH-25723, YH-GLP1, RPC-8844, PB-718, or semaglutide;
Glucocorticoid receptor antagonists, such as CORT-118335 (miricorilant);

Glucose 6-phosphate 1-dehydrogenase inhibitors, such as ST001;
G-protein coupled bile acid receptor 1(TGR5) agonists, such as RDX-009 or INT-777;
Heat shock protein 47 (HSP47) inhibitors, such as ND-L02-s0201;
HMG CoA reductase inhibitors, such as atorvastatin, fluvastatin, pitavastatin, pravastatin, rosuvastatin, or simvastatin;
Hypoxia inducible factor-2 alpha inhibitors, such as PT-2567;
IL-10 agonists, such as peg-ilodecakin;
Ileal sodium bile acid cotransporter inhibitors, such as odevixibat (A-4250), volixibat potassium ethanolate hydrate (SHP-262), GSK2330672, CJ-14199, or elobixibat (A-3309);
Insulin sensitizers, such as, KBP-042, MSDC-0602K, MSDC-5514, Px-102, RG-125 (AZD4076), VVP-100X, CB-4211, or ETI-101;
Insulin ligand/dsInsulin receptor agonists, such as ORMD-0801;
Integrin antagonists, such as IDL-2965;
IL-6 receptor agonists, such as KM-2702;
Ketohexokinase (KHK) inhibitors, such as PF-06835919;
beta Klotho (KLB)-FGF1c agonist, such as MK-3655 (NGM-313);
5-Lipoxygenase inhibitors, such as tipelukast (MN-001), DS-102 (AF-102);
Lipoprotein lipase inhibitors, such as CAT-2003;
LPL gene stimulators, such as alipogene tiparvovec;
Liver X receptor (LXR) modulators, such as PX-L603, PX-L493, BMS-852927, T-0901317, GW-3965, or SR-9238;
Lysophosphatidate-1 receptor antagonists, such as BMT-053011, UD-009 (CP-2090), AR-479, ITMN-10534, BMS-986020, or KI-16198;
Lysyl oxidase homolog 2 inhibitors, such as simtuzumab or PXS-5382A (PXS-5338);
Macrophage mannose receptor 1 modulators, such as tilmanocept-Cy3 (technetium Tc 99m tilmanocept);
Membrane copper amine oxidase (VAP-1) inhibitors, such as TERN-201;
MEKK-5 protein kinase (ASK-1) inhibitors, such as GS-4997, SRT-015, or GS-444217, GST-HG-151;
MCH receptor-1 antagonists, such as CSTI-100 (ALB-127158);
Methionine aminopeptidase-2 inhibitors, such as ZGN-839, ZGN-839, or ZN-1345;
Methyl CpG binding protein 2 modulators, such as mercaptamine;
Mitochondrial uncouplers, such as 2,4-dinitrophenol or HU6;
Mixed lineage kinase-3 inhibitors, such as URMC-099-C;
Myelin basic protein stimulators, such as olesoxime;
NADPH oxidase 1/4 inhibitors, such as GKT-831 or APX-311;
Nicotinic acid receptor 1 agonists, such as ARI-3037M0;
Nitazoxinide;
NACHT LRR PYD domain protein 3 (NLRP3) inhibitors, such as KDDF-201406-03, NBC-6, IFM-514, or JT-194 (JT-349);
Nuclear receptor modulators, such as DUR-928 (DV-928);
P2X7 purinoceptor modulators, such as SGM-1019;
P2Y13 purinoceptor stimulators, such as CER-209;
PDE 3/4 inhibitors, such as tipelukast (MN-001);
PDE 5 inhibitors, such as sildenafil or MS™-102;

PDGF receptor beta modulators, such as BOT-191 or BOT-509;
Peptidyl-prolyl cis-trans isomerase inhibitors, such as CRV-431 (CPI-432-32), NVP-018, or NV-556 (NVP-025);
Phenylalanine hydroxylase stimulators, such as HepaStem;
PPAR agonists (including PPAR alpha agonists, PPAR alpha/delta agonists, PPAR alpha/delta/gamma agonists, PPAR delta agonists), such as elafibranor (GFT-505), MBX-8025, deuterated pioglitazone R-enantiomer, pioglitazone, DRX-065, saroglitazar, or IVA-337; PPAR alpha agonists, such as aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (fish oil, e.g., icosapent ethyl (Vascepa; ethyl eicosapentaenoic acid), or docosahexaenoic acid), pirinixic acid, GW409544, AZ 242, LY518674, NS-220, AVE8134, BMS-711939, aleglitazar, muraglitzar, or saroglitazar;
PPAR alpha/delta agonists such as elafibranor;
PPAR alpha/delta/gamma agonists such as lanifibranor;
PPAR delta agonists such as seladelpar;
Protease-activated receptor-2 antagonists, such as PZ-235;
Protein kinase modulators, such as CNX-014;
Rho associated protein kinase (ROCK) inhibitors, such as REDX-10178 (REDX-10325) or KD-025;
Semicarbazide-Sensitive Amine Oxidase/Vascular Adhesion Protein-1 (SSAO/VAP-1) Inhibitors, such as PXS-4728A;
S-nitrosoglutathione reductase (GSNOR) enzyme inhibitors, such as SL-891;
Sodium glucose transporter-2(SGLT2) inhibitors, such as ipragliflozin, remogliflozin etabonate, ertugliflozin, dapagliflozin, tofogliflozin, or sotagliflozin;
SREBP transcription factor inhibitors, such as CAT-2003 or MDV-4463;
Stearoyl CoA desaturase-1 inhibitors, such as aramchol;
Thyroid hormone receptor (THR) beta agonists, such as resmetriom (MGL-3196), MGL-3745, or VK-2809;
TLR-2/TLR-4 antagonists, such as VB-201 (CI-201);
TLR-4 antagonists, such as JKB-121;
Tyrosine kinase receptor modulators, such as CNX-025 or GFE-2137 (repurposed nitazoxanide);
GPCR modulators, such as CNX-023;
Nuclear hormone receptor modulators, such as Px-102;
Xanthine oxidase/Urate anion exchanger 1 (URAT1) inhibitors, such as RLBN-1001, RLBN-1127; and
Zonulin Inhibitors, such as lorazotide acetate (INN-202).

In some embodiments, the one or more additional therapeutic agents are selected from A-4250, AC-3174, acetylsalicylic acid, AK-20, alipogene tiparvovec, AMX-342, AN-3015, aramchol, ARI-3037M0, ASP-8232, AZD-2693, bertilimumab, Betaine anhydrous, BI-1467335, BMS-986036, BMS-986171, BMT-053011, BOT-191, BTT-1023, CAT-2003, cenicriviroc, CBW-511, CER-209, CF-102, CGS21680, CNX-014, CNX-023, CNX-024, CNX-025, cobiprostone, colesevelam, dapagliflozin, DCR-LIV1, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, fluasterone (ST-002), FT-4101, GKT-831, GNF-5120, GRI-0621, GR-MD-02, GS-300, GS-4997, GS-9674, HTD-1801, HST-202, HST-201, hydrochlorothiazide, icosabutate (PRC-4016), icosapent ethyl ester, IMM-124-E, INT-767, INV-240, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452 (tropifexor), LM-011, LM-002 (CVI-LM-002), LMB-763, LYN-100, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-160, norursodeoxycholic acid, NVP-022, O-304, obeticholic acid (OCA), 25HC3S, olesoxime, PAT-505, PAT-048, PBI-4547, pegilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), RPI-500, saroglitazar, semaglutide, simtuzumab, solithromycin, sotagliflozin, statins (atorvastatin, fluvastatin, pitavastatin, pravastatin, rosuvastatin, simvastatin), symbiotic, TCM-606F, TEV-45478, TQA-3526, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, XRx-117, ZGN-839, ZG-5216, ZSYM-008, and ZYSM-007.

In some embodiments, the methods and pharmaceutical compositions provided herein include a therapeutically effective amount of an Apoptosis Signal-Regulating Kinase 1 (ASK1) inhibitor and a therapeutically effective amount of an Acetyl-CoA Carboxylase (ACC) inhibitor, wherein the ACC inhibitor is a compound of Formula (I) (II), (IIa), (III), (IIIa), (IV) or (IVa) provided herein or a pharmaceutically acceptable salt thereof.

In some embodiments of the methods and pharmaceutical compositions disclosed herein, the ASK1 inhibitor is GS-4997 (selonsertib, SEL).

ASK1 inhibitors, such as the compound of Formula (V), can be synthesized and characterized using methods known to those of skill in the art, such as those described in U.S. 2007/0276050, U.S. 2011/0009410, and U.S. 2013/0197037.

In some embodiments, the ACC inhibitor is the compound of Example 1 and the ASK1 inhibitor is GS-4997 (selonsertib, SEL).

In some embodiments, the methods and compositions provided herein include a therapeutically effective amount of a Farnesoid X Receptor (FXR) agonist and a therapeutically effective amount of an Acetyl CoA Carboxylase (ACC) inhibitor, wherein the ACC inhibitor is a compound of Formula (I), (II), (IIa), (III), (IIIa), (IV) or (IVa) provided herein or a pharmaceutically acceptable salt thereof.

In some embodiments of the methods and pharmaceutical compositions disclosed herein, the FXR agonist is GS-9674 (cilofexor, CILO).

In some embodiments of the methods and pharmaceutical compositions disclosed herein, the FXR agonist is a compound having the structure:

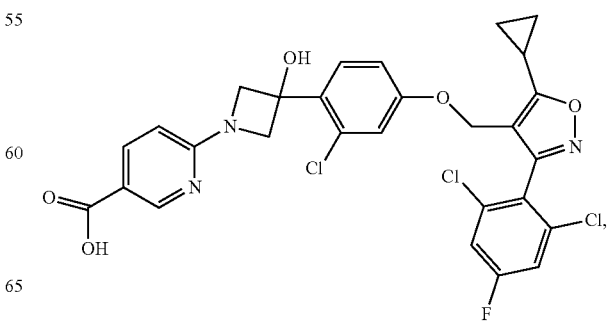

-continued

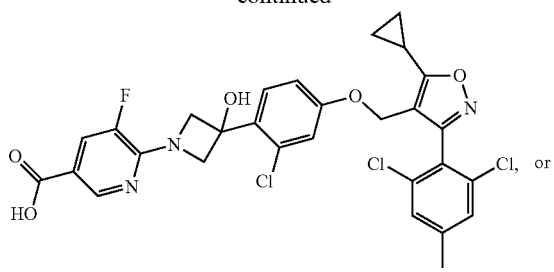

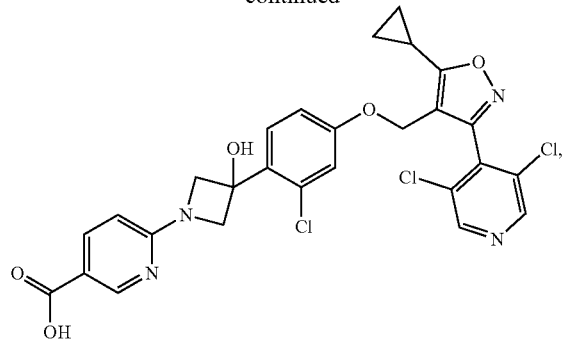

or a pharmaceutically acceptable salt thereof.

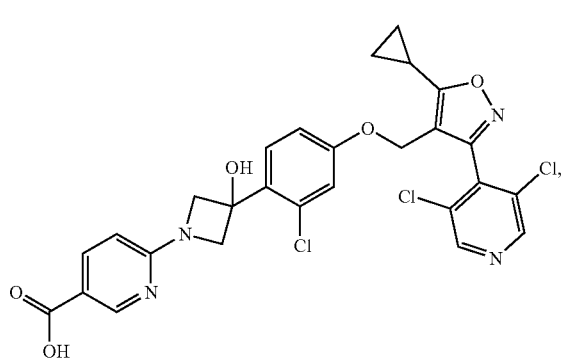

or a pharmaceutically acceptable salt thereof.

In some embodiments, the ACC inhibitor is the compound of Example 1 and the FXR agonist is GS-9674 (cilofexor, CILO).

In some embodiments, the ACC inhibitor is the compound of Example 1 and the FXR agonist is a compound having the structure:

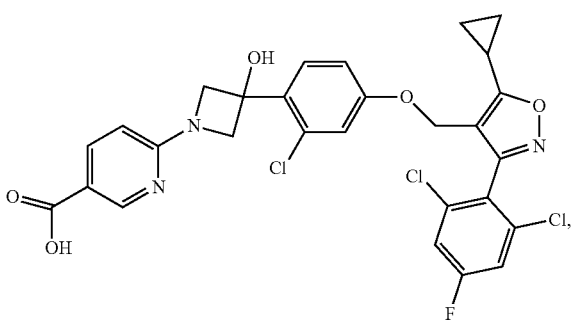

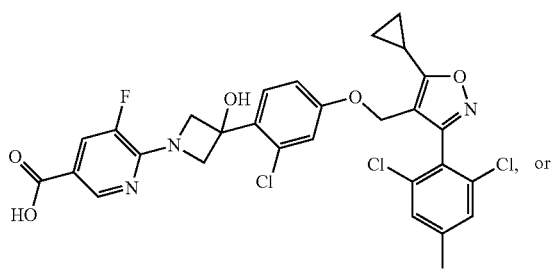

or a pharmaceutically acceptable salt thereof.

In some embodiments, the methods and compositions provided herein include a therapeutically effective amount of a PPAR agonist (e.g., PPAR alpha agonist, PPAR alpha/delta agonist, PPARalpha/delta/gamma agonist, PPAR delta agonist) or fish oil and a therapeutically effective amount of an Acetyl CoA Carboxylase (ACC) inhibitor, wherein the ACC inhibitor is a compound of Formula (I), (II), (IIa), (III), (IIIa), (IV) or (IVa) provided herein or a pharmaceutically acceptable salt thereof. In some embodiments, the PPAR agonist is a PPAR alpha agonist. In some embodiments, the PPAR alpha agonist is selected from aluminum clofibrate, bezafibrate, ciprofibrate, choline fenofibrate, clinofibrate, clofibrate, clofibride, fenofibrate, gemfibrozil, pemafibrate, ronifibrate, simfibrate, pirinixic acid, GW409544, AZ 242, LY518674, NS-220, AVE8134, BMS-711939, aleglitazar, muraglitzar, and saroglitazar. In some embodiments, the PPAR agonist (e.g., PPAR alpha agonist) is a fibrate. In some embodiments, the PPAR agonist (e.g., PPAR alpha agonist) is fenofibrate. In some embodiments, the PPAR agonist is a PPAR alpha/delta agonist (e.g., elafibranor). In some embodiments, the PPAR agonist is a PPAR alpha/delta/gamma agonist (e.g., lanifibranor). In some embodiments, the PPAR agonist is a PPAR delta agonist (e.g., seladelpar). In some embodiments, the ACC inhibitor is the compound of Example 1 and the PPAR agonist is fenofibrate. In some embodiments the fish oil is an omega-3 fatty acid or docosahexaenoic acid. In some embodiments, the fish oil is icosapent ethyl (e.g., Vascepa). In some embodiments, the ACC inhibitor is the compound of Example 1 and the fish oil is icosapent ethyl.

In some embodiments, the methods and compositions provided herein include a therapeutically effective amount of a GLP-1 receptor agonist and a therapeutically effective amount of an Acetyl CoA Carboxylase (ACC) inhibitor, wherein the ACC inhibitor is a compound of Formula (I), (II), (IIa), (III), (IIIa), (IV) or (IVa) provided herein or a pharmaceutically acceptable salt thereof. In some embodiments, the GLP-1 receptor agonist is liraglutide or semaglutide. In some embodiments, the GLP-1 receptor agonist is semaglutide. In some embodiments, the ACC inhibitor is the compound of Example 1 and the GLP-1 receptor agonist is semaglutide.

In some embodiments, the methods and compositions provided herein include a therapeutically effective amount of a TGFβ antagonist and a therapeutically effective amount of an Acetyl CoA Carboxylase (ACC) inhibitor, wherein the ACC inhibitor is a compound of Formula (I), (II), (IIa), (III), (IIIa), (IV) or (IVa) provided herein or a pharmaceutically acceptable salt thereof. In some embodiments, the TGFβ antagonist is a TGFβ1-specific antibody. TGFβ1-specific antibodies can be prepared and characterized using methods known to those of skill in the art, such as those described in PCT International Application Publication No. WO 2018/129329 and in U.S. Pat. No. 9,518,112. In some embodiments, the TGFβ antagonist binds to a TGFβ latency-associated peptide (LAP), e.g., TGFβ1-LAP. TGFβ1-LAP-specific antibodies can be prepared and characterized using methods known to those of skill in the art, such as those described in U.S. Pat. No. 8,198,412 or 10,017,567. In some embodiments, the TGFβ antagonist binds to TGFβ (e.g., TGFβ1) in a context independent manner (e.g., independent of the location of TGFβ in a specific tissue or organ). In some embodiments, the TGFβ antagonist binds to TGFβ (TGFβ1) in a context-dependent manner. In some embodiments, the TGFβ antagonist blocks activation of latent TGFβ (e.g., latent TGFβ1) that is localized in the extracellular matrix, e.g., in connective tissue. In some embodiments, the TGFβ antagonist blocks activation of latent TGFβ (e.g., latent TGFβ1) that is localized in the thymus, a lymph node, or in a tumor microenvironment (e.g., in a patient having liver cancer). In some embodiments, the TGFβ antagonist blocks activation of latent TGFβ (e.g., latent TGFβ1) by Latent TGFβ Binding Protein (LTBP). In some embodiments, the TGFβ antagonist blocks activation of latent TGFβ (e.g., latent TGFβ1) by Glycoprotein-A Repetitions Predominant protein (GARP), as described, e.g., in U.S. Pat. No. 10,000,572. In some embodiments, the TGFβ antagonist is ARGX-115. In some embodiments, the TGFβ antagonist is an anti-latency-associated peptide (LAP) antibody that specifically binds to a LAP-TGFβ1 complex. In some embodiments, the anti-LAP antibody specifically binds to LAP-TGFβ1 complexes in the extracellular matrix (ECM), e.g., of connective tissue in the liver. In some embodiments, the anti-LAP antibody specifically binds to LAP-TGFβ1 complexes on the surfaces of certain immunosuppressive cell types, such as regulatory T cells (Tregs), tumor-associated macrophages, or myeloid-derived suppressor cells, e.g., in a tumor microenvironment. In some embodiments, the anti-LAP antibody is a TLS-01 antibody. In some embodiments, the anti-LAP antibody specifically binds to LAP-TGFβ1 complexes in any context. In some embodiments, the anti-LAP antibody is a TLS-02 antibody. In some embodiments, the TGFβ antagonist comprises a TGFβ receptor. In some embodiments, the TGFβ antagonist is a TGFβ receptor-Fc fusion protein. In some embodiments, the TGFβ antagonist is an antibody comprising a TGFβ receptor. TGFβ antagonists comprising a TGFβ receptor that can be useful in connection with the compositions and methods provided herein have been described, e.g., in PCT International Publication Nos. WO 2019/113123 A1 and WO 2019/113464 A1. In some embodiments, the ACC inhibitor is the compound of Example 1.

In some embodiments, the methods and compositions provided herein include a therapeutically effective amount of an Apoptosis Signal-Regulating Kinase 1 (ASK1) inhibitor, a therapeutically effective amount of a Farnesoid X Receptor (FXR) agonist and a therapeutically effective amount of an Acetyl CoA Carboxylase (ACC) inhibitor, wherein the ACC inhibitor is a compound of Formula (I), (II), (IIa), (III), (IIIa), (IV) or (IVa) provided herein or a pharmaceutically acceptable salt thereof. In some embodiments, the ASK1 inhibitor is GS-4997 (selonsertib, SEL) and the FXR agonist is GS-9674 (cilofexor, CILO). In some embodiments, the ASK1 inhibitor is GS-4997 (selonsertib, SEL) and the FXR agonist is a compound having the structure:

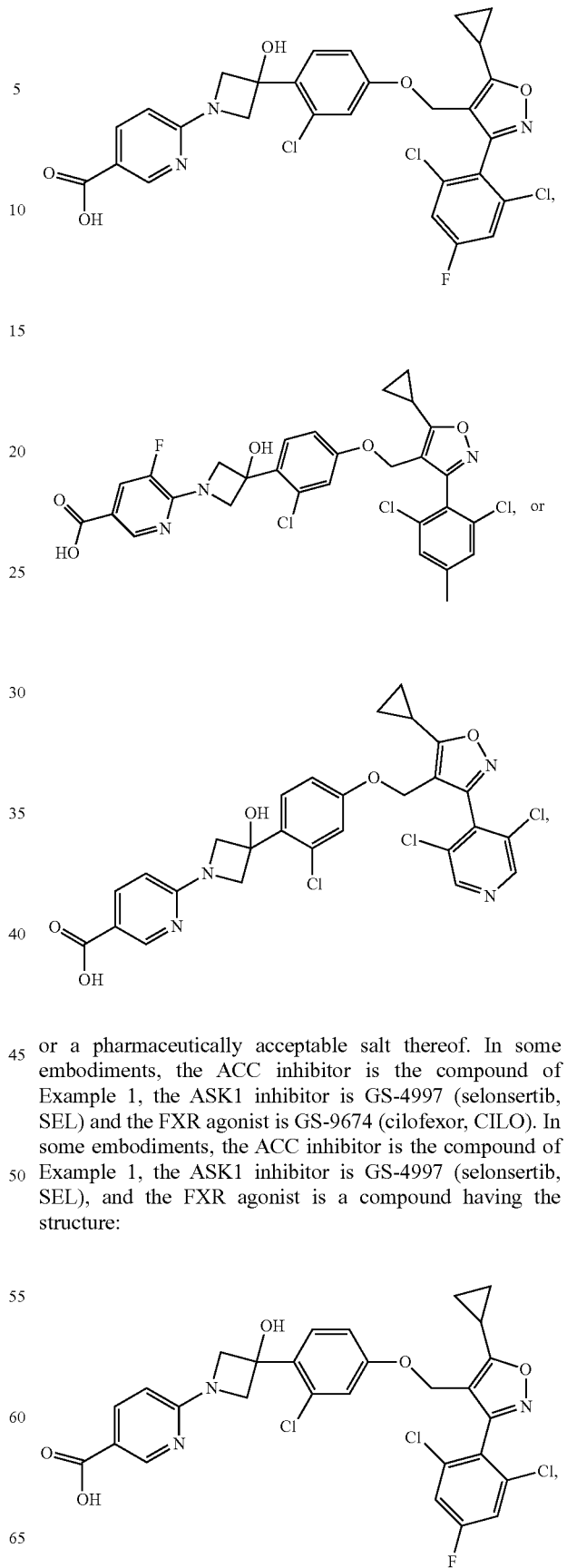

or a pharmaceutically acceptable salt thereof. In some embodiments, the ACC inhibitor is the compound of Example 1, the ASK1 inhibitor is GS-4997 (selonsertib, SEL) and the FXR agonist is GS-9674 (cilofexor, CILO). In some embodiments, the ACC inhibitor is the compound of Example 1, the ASK1 inhibitor is GS-4997 (selonsertib, SEL), and the FXR agonist is a compound having the structure:

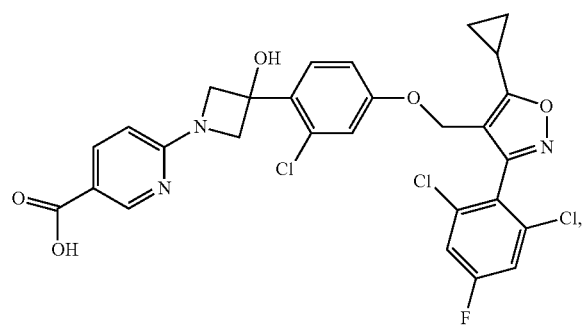

51
-continued

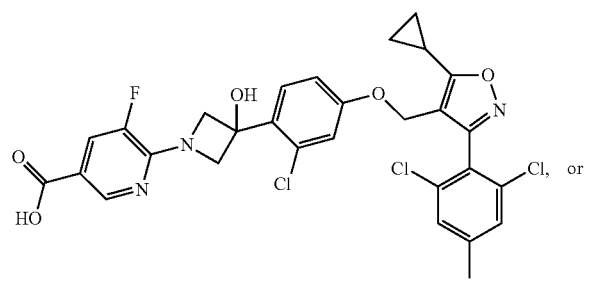

52
-continued

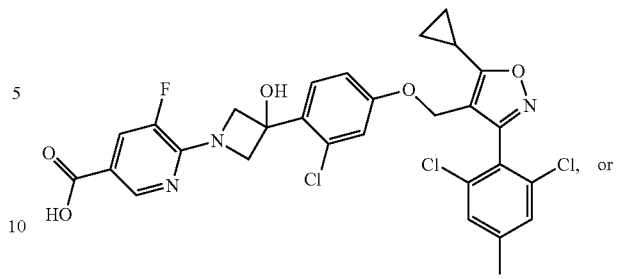

or a pharmaceutically acceptable salt thereof.

In some embodiments, the methods and compositions provided herein include a therapeutically effective amount of a GLP-1 receptor agonist, a therapeutically effective amount of a Farnesoid X Receptor (FXR) agonist, and a therapeutically effective amount of an Acetyl CoA Carboxylase (ACC) inhibitor, wherein the ACC inhibitor is a compound of Formula (I), (II), (IIa), (III), (IIIa), (IV) or (IVa) provided herein or a pharmaceutically acceptable salt thereof. In some embodiments, the GLP-1 receptor agonist is semaglutide and the FXR agonist is GS-9674 (Cilofexor, CILO). In some embodiments, the ACC inhibitor is the compound of Example 1, the GLP-1 receptor agonist is semaglutide and the FXR agonist is GS-9674 (Cilofexor, CILO). In some embodiments, the GLP-1 receptor agonist is semaglutide and the FXR agonist is a compound having the structure:

or a pharmaceutically acceptable salt thereof. In some embodiments, the ACC inhibitor is the compound of Example 1, the GLP-1 receptor agonist is semaglutide and the FXR agonist is a compound having the structure:

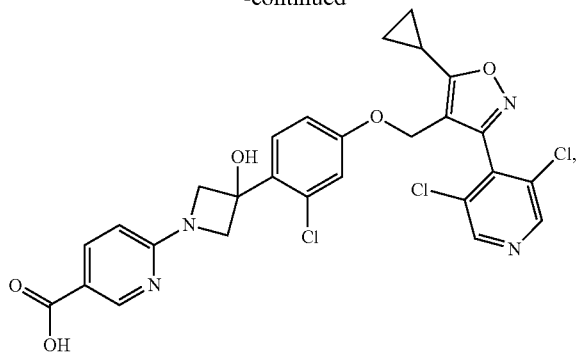

or a pharmaceutically acceptable salt thereof.

In some embodiments, the one or more additional therapeutic agents comprise a(n) anti-obesity agent (including an appetite suppressant), anti-diabetic agent, anti-hyperglycemic agent, lipid lowering agents, anti-hypertensive agent, or anti-cancer agent.

In some embodiments, the lipid lowering agent comprises a(n) bile acid sequestrant, HMG-CoA reductase inhibitor, HMG-CoA synthase inhibitor, cholesterol absorption inhibitor, acyl coenzyme A-cholesterol acyl transferase (ACAT) inhibitor, CETP inhibitor, squalene synthetase inhibitors, PPARalpha agonist, Pa receptor modulator, Da receptor modulator, lipoprotein synthesis inhibitor, renin-angiotensin system inhibitor, PPARdelta partial agonist, bile acid reabsorption inhibitor, PPARgamma agonist, triglyceride synthesis inhibitor, microsomal triglyceride transport inhibitor, transcription modulator, squalene epoxidase inhibitor, low density lipoprotein receptor inducer, platelet aggregation inhibitor, 5-lipoxygenase (5-LO) inhibitor, 5-lipoxygenase activating protein (FLAP) inhibitor, niacin, or niacin-bound chromium.

In some embodiments, the anti-hypertensive agent comprises a(n) diuretic, beta-adrenergic blocker, calcium channel blocker, angiotensin converting enzyme (ACE) inhibitor, neutral endopeptidase inhibitor, endothelin antagonist, vasodilator, angiotensin ii receptor antagonist, alpha/beta adrenergic blocker, alpha 1 blocker, alpha 2 agonist, aldosterone inhibitor, mineralocorticoid receptor inhibitor, renin inhibitors, and angiopoietin 2 binding agent.

In some embodiments, the anti-diabetic agent comprises a(n) acetyl-CoA carboxylase (ACC) inhibitor, DGAT-1 inhibitor, AZD7687, LCQ908, DGAT-2 inhibitor, monoacylglycerol O-acyltransferase inhibitor, PDE-10 inhibitor, AMPK activator, sulfonylureas (e.g., acetohexamide, chlorpropamide, diabinese, glibenclamide, glipizide, glyburide, blimipiride, gliclazide, glipentide, gliquidone, glisolamide, tolazamide, tolbutamide), meglitinide, alpha-amylase inhibitor (e.g., tendamistat, treastatin, AL-3688), alpha-glucoside hydrolase inhibitor (e.g., acarbose), alpha-glucosidase inhibitor (e.g., adiposine, camiglibose, emiglitate, miglitol, voglibose, pradimicin-Q, sarbostatin), PPAR-gamma agonist (e.g., balaglitazone, ciglitazone, darglitazone, englitazone, isaglitazone, pioglitazone, rosiglitazone, troglitazone), PPARalpha/gamma agonist (e.g., CLX-0940, GW-1536, GW-1929, GW-2433, KRP-297, L-796449, LR-90, MK-0767, SB-219994), biguanide (e.g., metformin, buformin), GLP-1 modulator (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitor (e.g., resveratrol, GSK2245840, GSK184072), DPP-IV inhibitors (e.g., sitagliptin, vildagliptin, alogliptin, dutogliptin, linagliptin, saxagliptin), insulin secretagogues, fatty acid oxidation inhibitor, A2 antagonists, JNK inhibitors, glucokinase activators (e.g., TTP-399, TTP-355, TTP-547, AZD1656, ARRY403, MK-0599, TAK-329, AZD5658, GKM-001), insulin, insulin mimetics, glycogen phosphorylase inhibitors (e.g., GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulator (e.g., MBX-2982, GSK1292263, APD597, PSN821), FGF21 derivatives, TGR5 (GPBAR1) receptor agonists (e.g., INT777), GPR40 agonists (e.g., TAK-875), GPR120 agonists, nicotinic acid receptor (HM74A) activator, SGLT1 inhibitor (e.g., GSK1614235), carnitine palmitoyl transferase enzyme inhibitor, fructose 1,6-diphosphatase inhibitor, aldose reductase inhibitor, mineralocorticoid receptor inhibitor, TORC2 inhibitor, CCR2 inhibitor, CCR5 inhibitor, PKC (e.g., PKCalpha, PKCbeta, PKCgamma) inhibitor, fatty acid synthetase inhibitor, serine palmitoyl transferase inhibitor, GPR81 modulator, GPR39 modulator, GPR43 modulator, GPR41 modulator, GPR105 modulator, Kv1 0.3 inhibitor, retinol binding protein 4 inhibitor, glucocorticoid receptor modulator, somatostatin receptor (e.g., SSTR1, SSTR2, SSTR3, SSTR5) inhibitor, PDHK2 inhibitor, PDHK4 inhibitor, MAP4K4 inhibitor, IL1-beta modulator, or RXR-alpha modulator.

In some embodiments, the anti-obesity agent comprises a(n) 11-beta-hydroxysteroid dehydrogenase 1 inhibitor, stearoyl-CoA desaturase (SCD-1) inhibitor, MCR-4 agonist, CCK-A agonist, monoamine reuptake inhibitor (e.g., sibutramine), sympathomimetic agent, beta-3-adrenergic receptor agonist, dopamine receptor agonist (e.g., bromocriptine), melanocyte-stimulating hormone or analogs thereof, 5-Eff2c agonist (e.g., lorcaserin/Belviq), melanin concentrating hormone antagonist, leptin, leptin analog, leptin agonist, galanin antagonist, lipase inhibitors (e.g., tetrahydrolipstatin/Orlista anorectic agent (e.g., bombesin agonist), NPY antagonists e.g., velneperit), $PYY_{3\text{-}36}$ (or analogs thereof), BRS3 modulator, opioid receptor mixed antagonist, thyromimetic agent, dehydroepiandrosterone, glucocorticoid agonist or antagonist, orexin antagonist, CLP-1 receptor agonist, ciliary neurotrophic factors (e.g., Axokine), human agouti-related protein (AGRP) inhibitor, H3 antagonist or inverse agonist, neuromedin U agonist, MTP/ApoB inhibitor (e.g., gut-selective MTP inhibitor such as dirlotapide, JTT130, Usistapide, SLX4090), MetAp2 inhibitor (e.g., ZGN-433), agent with mixed modulatory activity at two or more of glucagon, GIP, and GLP1 receptors (e.g., MAR-701, ZP2929), norepinephrine reuptake inhibitor, opioid antagonist (e.g., naltrexone), CBI receptor antagonist or inverse agonist, ghrelin agonist or antagonist, oxyntomodulin or analogs thereof, monoamine uptake inhibitor (e.g., tesofensine), or combination agents (e.g., buprorion plus zonisamide (Empatic), pramlintide plus metreleptin, buprorion plus naltrexone (Contrave), phentermine plus topiramate (Qsymia).

In some embodiments, the anti-cancer agent comprises metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-retinoic acid, 2-CdA, 2-chlorodeoxyadenosine, 5-azacitidine, 5-fluorouracil (5-FU), 6-mercaptopurine (6-MP), 6-Thioguanine (6-717G), Abraxane®, Accutane®, actinomycin-D, Adriamycin®, Adrucil®, Afinitor®, Agrylin®, Ala-Cort®, aldesleukin, alemtuzumab, ALIMTA®, alitretinoin, Alkaban-AQ®, Alkeran®, all-transretinoic acid, alpha interferon, altretamine, amethopterin, amifostine, aminoglutethimide, anagrelide, Anandron®, anastrozole, arabinosylcytosine, Ara-C, Aranesp®, Aredia®, Arimidex®, Aromasin®, Arranon®, Arsenic Trioxide, Arzerra™, asparaginase, ATRA, Avastin®, azacitidine, BCG, BCNU, bendamustine, bevacizumab, bexarotene, BEXXAR®, bicalutamide, BiCNU, Blenoxane®, bleomycin, bortezomib, busulfan, Busulfex®, $C_{225}$, calcium leucovorin, Campath®, Camptosar®, camptothecin-11, capecitabine, Carac™, carboplatin, carmustine, carmustine wafer, Casodex®, CC-5013, CCI-779, CCNU, CDDP, CeeNU, Cerubidine®, cetuximab, chlorambucil, citrovorum factor, cladribine, cortisone, Cosmegen®, CPT-11, Cytadren®, Cytosar-U®, Cytoxan®, dacarbazine, dacogen, dactinomycin, darbepoetin alfa, dasatinib, daunomycin, daunorubicin hydrochloride, daunorubicin liposomal, DaunoXome®, decadron, decitabine, Delta-Cortef®, Deltasone®, denileukin, diftitox, DepoCyt™, dexamethasone, dexamethasone acetate, dexamethasone sodium phosphate, dexasone, dexrazoxane, DHAD, DIC, diodex, docetaxel, Doxil®, doxorubicin, doxorubicin liposomal, Droxia™, DTIC, DTIC-Dome®, Duralone®, Efudex®, Eligard™, Ellence™, Eloxatin™, Elspar®, Emcyt®, epirubicin, epoetin alfa, erbitux, erlotinib, erwinial-asparaginase, estramustine, ethyol, Etopophos®, etoposide, etoposide phosphate, Eulexin®, Everolimus, Evista®, exemestane, Fareston®, Faslodex®, Ferrara®, filgrastim, floxuridine; Fludara®, fludarabine, Fluoroplex®, fluorouracil, fluorouracil (cream), fluoxymesterone, flutamide, folinic acid, FUDR®, fulvestrant, get gemcitabine, gemtuzumab, ozogamicin, gemzar, Gleevec™, Gliadel® Wafer, GM-CSF, goserelin, granulocyte—colony stimulating factor (GCSF), granulocyte macrophage colony stimulating factor (GMCST), Halotestin®, Herceptin®, hexadrol, Hexalen®, hexamethylmelamine, HMM, Hycamtin®, Hydrea®, Hydrocort Acetate®, hydrocortisone, hydrocortisone sodium phosphate, hydrocortisone sodium succinate hydrocortone phosphate, hydroxyurea, ibritumomab, ibritumomab, tiuxetan, Idamycin®, idarubicin Ifex®, ifosfamide, imatinib mesylate, imidazole carboxamide, interferon alfa, interferon alfa-2b (PEG Conjugate), interleukin-2; interleukin-11, intron A® (interferon alfa-2b), Iressa®, irinotecan, isotretinoin, ixabepilone, Ixempra™, Kidrolase®, Lanacort®, lapatinib, L-asparaginase, LCR, lenalidomide, letrozole, leucovorin, leukeran, Leukine™, leuprolide, leurocristine, Leustatin™, liposomal ara-C, Liquid Pred®, lomustine, L-PAM, L-sarcolysin, Lupron®, Lupron Depot®, Matulane®; maxidex, mechlorethamine, mechlorethamine hydrochloride, Medralone®, Medrol®, Megace®, megestrol, megestrol acetate, melphalan, mercaptopurine, mesna, Mesnex™, methotrexate, methotrexate sodium, methylprednisolone, Meticorten®, mitomycin, mitomycin-C, mitoxantrone, M-Prednisol®, MTC, MTX, Mustargen®, mustine, Mutamycin®, Myleran®, Mylocel™, Mylotarg®, Navelbine®, nelarabine, Neosar®, Neulasta™, Neumega®, Neupogen®, Nexavar®, Nilandron®, nilotinib, nilutamide, Nipent®, nitrogen mustard, Novaldex®, Novantrone®, nplate, octreotide, octreotide acetate, ofatumumab, Oncospar®, Oncovin®, Ontak®, Onxal™, oprelvekin, Oraped®, Orasone®, oxaliplatin, paclitaxel, paclitaxel protein-bound, pamidronate, panitumumab, Panretin®, Paraplatin®, pazopanib, Pediapred®, PEG interferon, pegaspargase, pegfilgrastim, PEG-INTRON™, PEG-L-asparaginase, PEMETREXED, pentostatin, phenylalanine mustard, Platinol Platinol-AQ®, prednisolone, prednisone, Prelone®, procarbazine, PROCRIT®, Proleuking®, prolifeprospan 20 with carmustine implant, Purinethol®, raloxifene, Revlimid®, Rheumatrex®, Rituxan®, Rituxima®, Roferon-A® (Interferon Alfa-2a), romiplostim, Rubex®, rubidomycin hydrochloride, Sandostatin®, Sandostatin LAR®, sargramostim, Solu-Cortef®, Solu-Medrol®, sorafenib, SPRYCEL™, STI-571, streptozocin, SU11248, sunitinib, Sutent®, tamoxifen, Tarceva®, Targretin®, Tasigna®, Taxol®, Taxotere®, Temodar®, temozolomide, temsirolimus, teniposide, TESPA, thalidomide, Thalomid®, TheraCys®, thioguanine, Thioguanine Tabloid®, thiophosphoamide, Thioplex®, thiotepa, TICE®, Toposar®, topotecan, toremifene, Torisel®, tositumomab, trastuzutnab, Treanda®, tretinoin, Trexall™, Trisenox®, TSPA, TYKERB®, VCR, Vectibix™, Velban®, Velcade®, VePesid®, Vesanoid®, Viadur™, Vidaza®, vinblastine, Vinblastine Sulfate, Vincasar Pfs®, vincristine, vinoreibine, vinorelbine tartrate, VLB, VM-26, vorinostat, votrient, VP-16, Vumon®, Xeloda®, Zanosar®, Zevalin™, Zinecard®, Zoladex®, zoledronic acid, zolinza, or Zometak®.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that these examples are exemplary and not exhaustive. Many changes can be made in the specific embodiments which are disclosed and still obtain a like or similar result without departing from the spirit and scope of the disclosure.

Compounds disclosed herein can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. In some cases, the identity of the final product can render apparent the identity of the necessary starting materials by a process of inspection, given the examples herein. Compounds can be isolated in the form of their pharmaceutically acceptable salts, such as those described above. Compounds described herein are typically stable and isolatable at room temperature and pressure.

An illustration of the preparation of compounds disclosed herein is shown below. Unless otherwise indicated, variables have the same meaning as described above. The examples presented below are intended to illustrate particular embodiments of the disclosure. Suitable starting materials, building blocks and reagents employed in the synthesis as described below are commercially available from Sigma-Aldrich or Acros Organics, for example, or can be routinely prepared by procedures described in the literature, for example in "March's Advanced Organic Chemistry: Reactions, Mechanisms, and Structure", 5$^{th}$ Edition; John Wiley & Sons or T. Eicher, S. Hauptmann "The Chemistry of Heterocycles; Structures, Reactions, Synthesis and Application", 2$^{nd}$ edition, Wiley-VCH 2003; Fieser et al. "Fiesers' Reagents for organic Synthesis" John Wiley & Sons 2000.

General Schemes

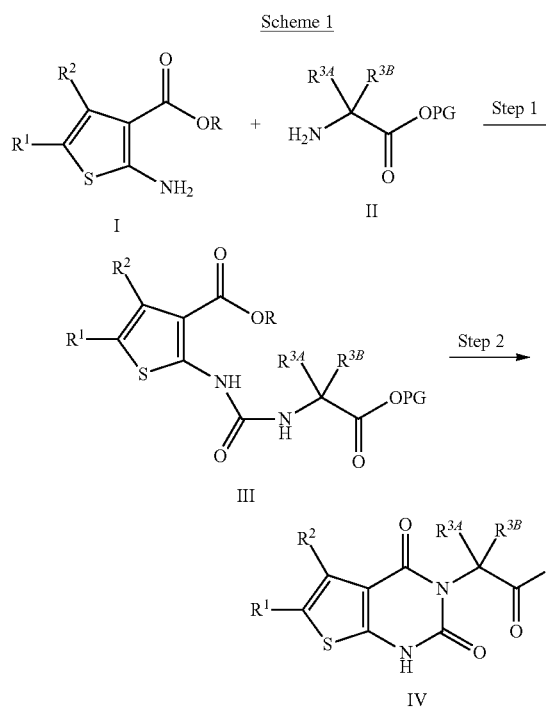

Scheme 1 shows a general synthesis of intermediate IV. To one skilled in the art, an appropriately substituted 2-aminothiophene I and protected amino ester II, where the protecting group can be, for example, tert-butyl, tert-butyldimethylsilyl, or tert-butyldiphenylsilyl, are condensed with triphosgene, for example, to provide urea III. Cyclization of urea III to thienopyrimidine-2,4dione IV can be achieved under a variety of conditions, including basic conditions using cesium carbonate or tert-butoxide, for example.

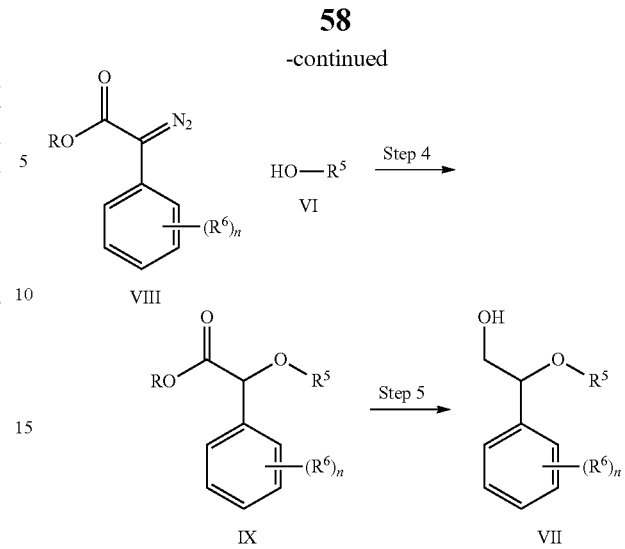

Scheme 2 shows a general synthesis of intermediate VII. Epoxide V can undergo reaction with an appropriate nucleophile such as alcohol VI, under conditions known to those skilled in the art, such as Lewis acid catalysis using copper tetrafluoroborate hydrate or erbium(III) trifluoromethanesulfonate, for instance, to give primary alcohol VII. Alternatively, primary alcohol VII can be prepared through reaction of diazoester VIII with primary alcohol VII using a catalyst such as rhodium(II) triphenylacetate dimer, for example to give ester IX. Ester IX can be reduced by reducing agents known to those skilled in the art, such as lithium borohydride, for example.

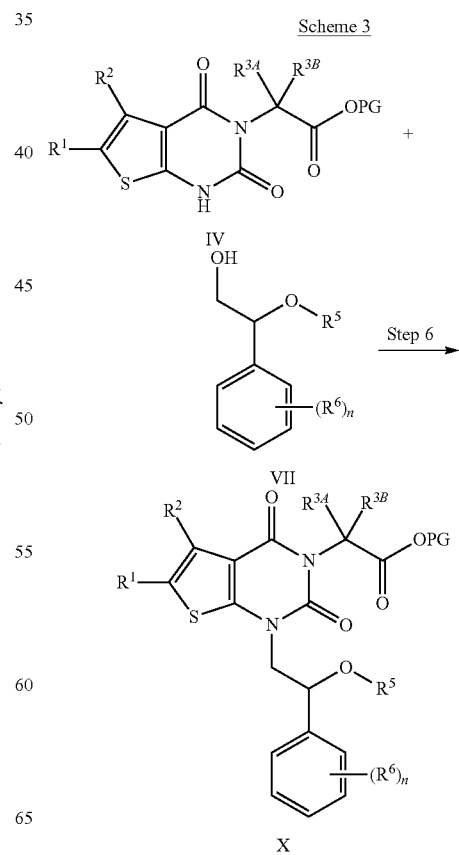

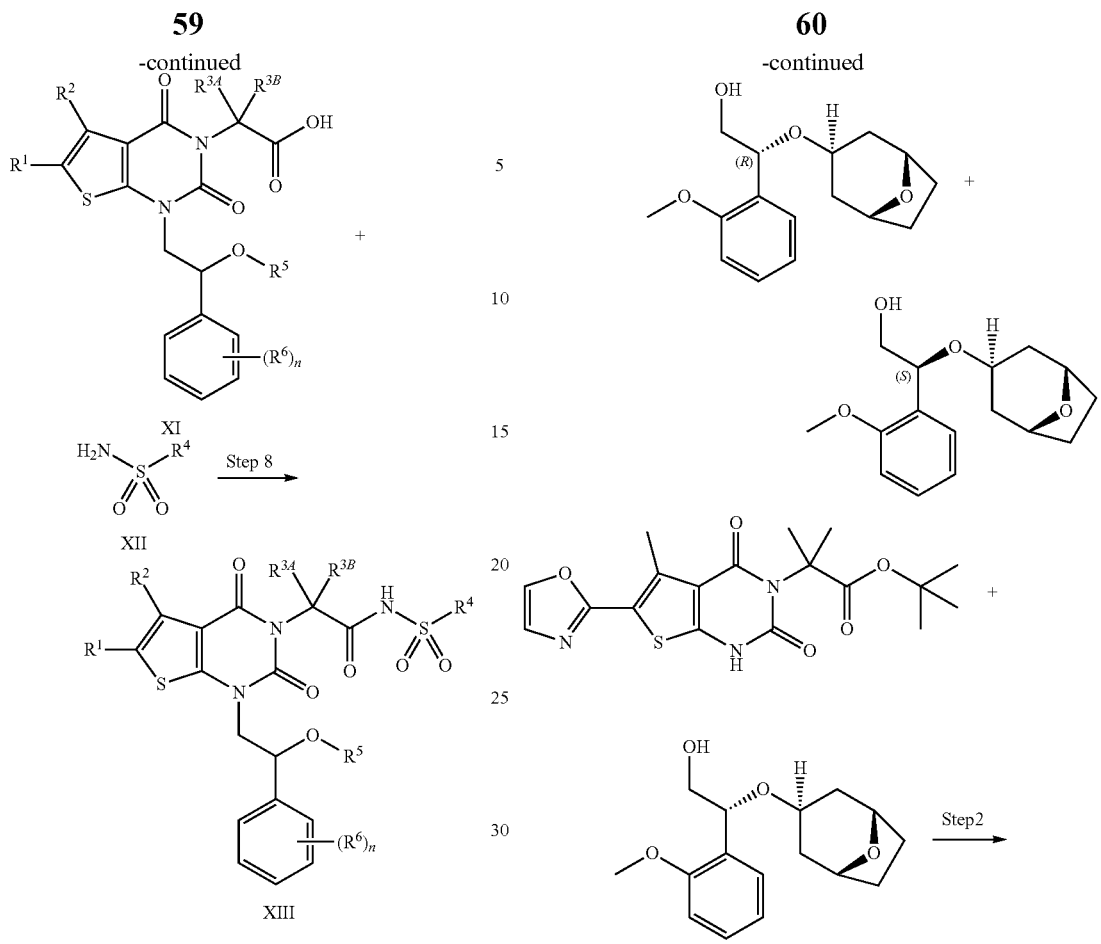

Scheme 3 shows a general synthesis of compound XIII Alcohol VII can be activated and coupled with thienopyrimidine-2,4dione IV using conditions known to those skilled in the art, such as Mitsunobu reaction conditions such as triphenylphosphine and diisopropyl azodicarboxylate, for example, to give substituted thienopyrimidine-2,4dione X. The ester protecting group can be removed under appropriate conditions known to those skilled in the art, such as, for example, sulfuric acid, hydrochloric acid or trifluoroacetic acid for the deprotected of a tert-butyl protecting group, to give carboxylic acid XI. Carboxylic acid XI can be coupled with sulfonamide XII using conditions known to those skilled in the art, such as a coupling reagent such as HATU for instance, and bases such as diisopropylethylamine and sodium hydride, to give compound XIII.

Example 1: Preparation of 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methyl-N-((1-methylcyclopropyl)sulfonyl)propanamide

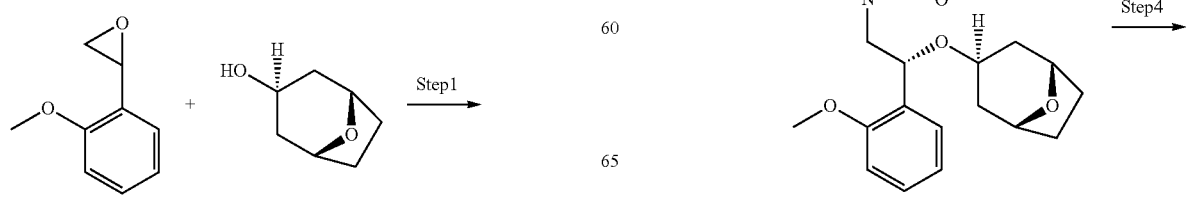

-continued

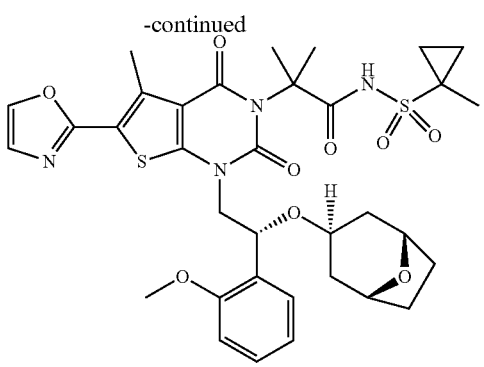

Step 1: 2-(((1R,3s,5S)-8-oxabicyclo[3.2.1]octan-3-yl)oxy)-2-(2-methoxyphenyl)ethan-1-ol Racemate

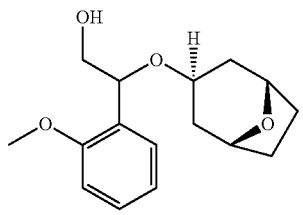 [SMILES: COc1ccccc1C(CO)O[C@@H]1C[C@H]2CC[C@@H](C1)O2]

To a suspension of copper tetrafluoroborate hydrate (0.05 mmol) in DCM (3 mL) at room temperature was added exo-8-oxabicyclo[3.2.1]octan-3-ol (5 mmol) and 2-(2-methoxyphenyl)oxirane (6 mmol). The suspension was stirred rapidly overnight. Reaction mixture was concentrated and purified by silica gel column (0-75% EtOAc/Hex) to provide the racemic product. (R)-2-(((1R,3s,5S)-8-oxabicyclo[3.2.1]octan-3-yl)oxy)-2-(2-methoxyphenyl)ethan-1-ol was obtained as second peak from further separation by chiral SFC separation (IG SFC 5 µm 21×250 mm, EtOH as co-solvent) MS (m/z) 279.21 [M+H]$^+$.

Step 2: tert-butyl 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-cl]pyrimidin-3(2H)-yl)-2-methylpropanoate

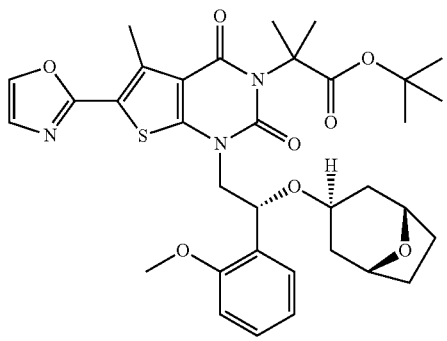 [SMILES: COc1ccccc1[C@H](Cn1c(=O)n(C(C)(C)C(=O)OC(C)(C)C)c(=O)c2c(C)c(-c3ncco3)sc21)O[C@@H]1C[C@H]2CC[C@@H](C1)O2]

tert-Butyl 2-methyl-2-(5-methyl-6-(oxazol-2-yl)-2,4-dioxo-1,4-dihydrothieno[2,3-d]pyrimidin-3(2H)-yl)propanoate was prepared according to WO 2013/071169 tert-Butyl 2-methyl-2-(5-methyl-6-(oxazol-2-yl)-2,4-dioxo-1,4-dihydrothieno[2,3-d]pyrimidin-3(2H)-yl)propanoate were (0.23 mmol) and (R)-2-(((1R,3s,5S)-8-oxabicyclo[3.2.1]octan-3-yl)oxy)-2-(2-methoxyphenyl)ethan-1-ol (0.299 mmol) were dissolved in THF (2 mL). Diisopropyl azodicarboxylate (0.345 mmol) and triphenylphosphine (0.345 mmol) were added sequentially. The reaction mixture was stirred at room temperature in sealed tube for 17 hours. The reaction mixture was loaded onto silica gel column and purified by silica gel chromatography (0-100% EtOAc/Hex) to afford a mixture of N-alkylated and O-alkylated products. The two regioisomers were separated with HPLC (Gemini, 5-100% ACN/H$_2$O+0.1% TFA) to afford tert-butyl 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropanoate (first peak). MS (m/z) 651.91 [M+H]$^+$.

Step 3: 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropanoic acid

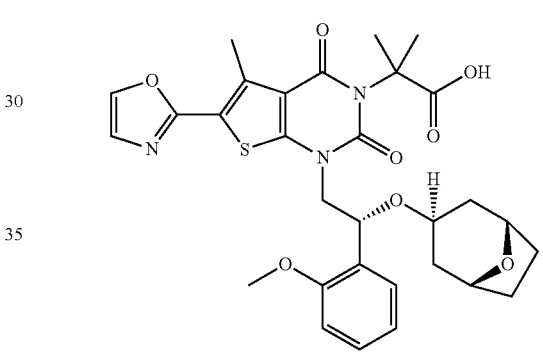

Concentrated sulfuric acid (3 mL) was added to water (3 mL) with vigorous stirring at 0° C. and isopropanol (6 mL) was added. tert-Butyl 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropanoate (0.092 mmol) was treated with 0.5 mL of the above sulfuric acid solution at 0° C. The reaction mixture was allowed to warm to room temperature with stirring and kept at room temperature for 8 hours. The reaction mixture was diluted with water (5 mL), extracted with EtOAc (5 mL) and organic phase was separated, washed with water and concentrated. The residue was purified with HPLC (Gemini, 5-100% ACN/H$_2$O+0.1% TFA) and lyophilized from ACN/H$_2$O to afford 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropanoic acid. MS (m/z) 594.72 [M−H]$^−$.

Step 4: 2-(1-((R)-2-(((1R,3s,5S)-8-oxabicyclo[3.2.1]
octan-3-yl)oxy)-2-(2-methoxyphenyl)ethyl)-5-
methyl-6-(oxazol-2-yl)-2,4-dioxo-1,4-dihydrothieno
[2,3-d]pyrimidin-3(2H)-yl)-2-methyl-N-((1-
methylcyclopropyl)sulfonyl)propanamide Example 2: Preparation of 2-(1-((R)-2-(((1R,3s,5S)-
8-oxabicyclo[3.2.1]octan-3-yl)oxy)-2-(2-methoxy-
phenyl)ethyl)-5-methyl-6-(oxazol-2-yl)-2,4-dioxo-1,
4-dihydrothieno[2,3-d]pyrimidin-3(2H)-yl)-N-((1-
(difluoromethyl)cyclopropyl)sulfonyl)-2-
methylpropanamide

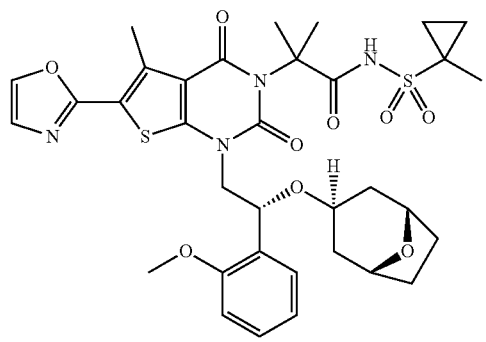 [SMILES: COc1ccccc1[C@H](Cn1c(=O)n(C(C)(C)C(=O)NS(=O)(=O)C2(C)CC2)c(=O)c2c(C)c(-c3ncco3)sc21)O[C@@H]1C[C@H]2CC[C@@H](C1)O2]

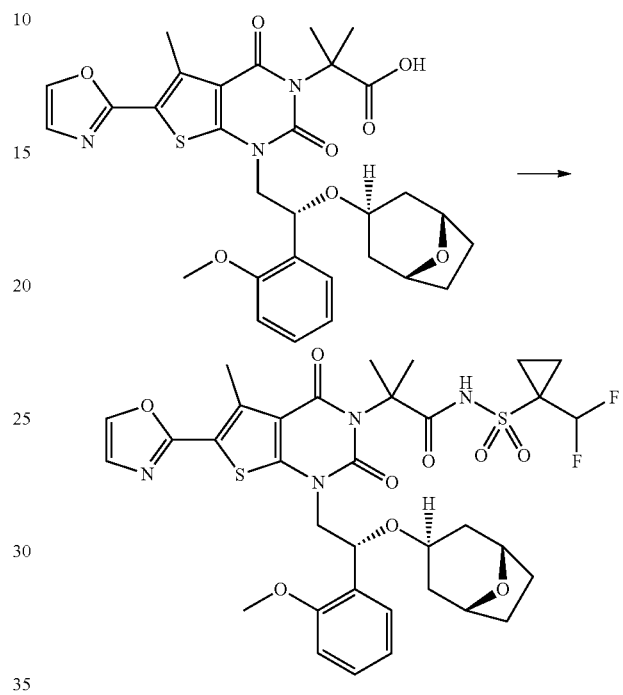

2-(1-((R)-2-(((1R,3 s,5S)-8-oxabicyclo[3.2.1]octan-3-yl)
oxy)-2-(2-methoxyphenyl)ethyl)-5-methyl-6-(oxazol-2-yl)-
2,4-dioxo-1,4-dihydrothieno[2,3-d]pyrimidin-3(2H)-yl)-2-
methylpropanoic acid (0.044 mmol) was dissolved in DMF
(0.5 mL) at room temperature under argon. Diisopropyleth-
ylamine (0.087 mmol) and HATU (0.052 mmol) were added
sequentially. The reaction mixture was stirred under argon at
room temperature for 20 hours. Sodium hydride (60% in
mineral oil) (0.175 mmol) was added at room temperature to
a solution of methyl cyclopropyl sulfonamide (0.2 mmol) in
DMF (1 mL). The reaction mixture was stirred at room
temperature for one hour to afford a slurry. The above
pre-formed HATU adduct was added dropwise to the slurry
over 5 minutes. The resulting reaction mixture was stirred at
room temperature for 15 minutes. The reaction mixture was
diluted with EtOAc (3 mL) and was partitioned between 1N
HCl and EtOAc. The organic phase was separated and
concentrated. The resulting residue was dissolved in a
minimal amount of dichloromethane, adsorbed onto silica
gel prep-TLC plates and purified (1/1 EtOAc/Heptane) to
afford 2-(1-((R)-2-(((1R,3s,5S)-8-oxabicyclo[3.2.1]octan-3-
yl)oxy)-2-(2-methoxyphenyl)ethyl)-5-methyl-6-(oxazol-2-
yl)-2,4-dioxo-1,4-dihydrothieno[2,3-d]pyrimidin-3(2H)-
yl)-2-methyl-N-((1-methylcyclopropyl)sulfonyl)
propanamide. MS (m/z) 711.81 [M−H]⁻. $^1$H NMR (400
MHz, Acetonitrile-d3) δ 8.82 (s, 1H), 7.89 (d, J=0.9 Hz, 1H),
7.52 (dd, J=7.6, 1.8 Hz, 1H), 7.32 (ddd, J=8.2, 7.4, 1.8 Hz,
1H), 7.27 (d, J=0.9 Hz, 1H), 7.04 (td, J=7.5, 1.0 Hz, 1H),
6.97 (dd, J=8.3, 1.0 Hz, 1H), 5.32 (dd, J=8.9, 4.5 Hz, 1H),
4.28-4.13 (m, 3H), 4.00-3.89 (m, 1H), 3.84 (s, 3H), 3.58 (tt,
J=10.8, 5.7 Hz, 1H), 2.82 (s, 3H), 1.80 (s, 3H), 1.75 (s, 3H),
1.86-1.64 (m, 5H), 1.59-1.46 (m, 3H), 1.55 (s, 3H), 1.46-
1.37 (m, 1H), 1.32-1.21 (m, 1H), 0.93 (tt, J=4.2, 1.8 Hz, 2H).

2-(1-((R)-2-(((1R,3s,5S)-8-oxabicyclo[3.2.1]octan-3-yl)
oxy)-2-(2-methoxyphenyl)ethyl)-5-methyl-6-(oxazol-2-yl)-
2,4-dioxo-1,4-dihydrothieno[2,3-d]pyrimidin-3(2H)-yl)-2-
methylpropanoic acid (7.5 μmol) was dissolved in DMF (1
mL) at room temperature under argon. Diisopropylethylam-
ine (38 μmol) and HATU (18.8 μmol) were added sequen-
tially. The reaction mixture was stirred under argon at room
temperature for 20 hours. To a solution of 1-(difluorom-
ethyl)cyclopropane-1-sulfonamide (63 μmol) in DMF (1
mL), was added sodium hydride (60% in mineral oil) (57
μmol) at room temperature. The reaction mixture was stirred
for one hour to afford a slurry. The above pre-formed HATU
adduct was added dropwise to this slurry over 5 minutes.
The resulting reaction mixture was stirred at room tempera-
ture for 20 minutes. The reaction mixture was diluted with
EtOAc (3 mL) and partitioned between 1N HCl and EtOAc.
The organic phase was separated and concentrated. The
resulting residue was dissolved in a minimal amount of
dichloromethane, and adsorbed onto and purified on silica
gel prep-TLC plates (1/1 EtOAc/Heptane) to afford 2-(1-
((R)-2-(((1R,3s,5S)-8-oxabicyclo[3.2.1]octan-3-yl)oxy)-2-
(2-methoxyphenyl)ethyl)-5-methyl-6-(oxazol-2-yl)-2,4-di-
oxo-1,4-dihydrothieno[2,3-d]pyrimidin-3(2H)-yl)-N-((1-
(difluoromethyl)cyclopropyl)sulfonyl)-2-
methylpropanamide. MS (m/z) 747.63 [M−H]⁻. $^1$H NMR
(400 MHz, Acetonitrile-d3) δ 7.88 (d, J=0.8 Hz, 1H), 7.52
(dd, J=7.6, 1.7 Hz, 1H), 7.31 (ddd, J=8.2, 7.4, 1.8 Hz, 1H),
7.26 (d, J=0.9 Hz, 1H), 7.03 (td, J=7.5, 1.0 Hz, 1H), 6.97
(dd, J=8.3, 1.0 Hz, 1H), 6.63 (t, J=57.2 Hz, 1H), 5.34-5.26
(m, 1H), 4.25 (dq, J=9.6, 3.4 Hz, 2H), 4.07 (dd, J=13.0, 6.8
Hz, 2H), 3.85 (s, 3H), 3.58 (tt, J=10.9, 5.7 Hz, 1H), 2.81 (s, 3H), 1.84-1.63 (m, 4H), 1.75 (s, 3H), 1.72 (s, 3H), 1.55-1.37 (m, 2H), 1.37-1.15 (m, 4H), 1.29 (s, 3H), 0.96-0.85 (m, 2H).

Example 3: Preparation of 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3 (2H)-yl)-N-(tert-butylsulfonyl)-2-methylpropanamide

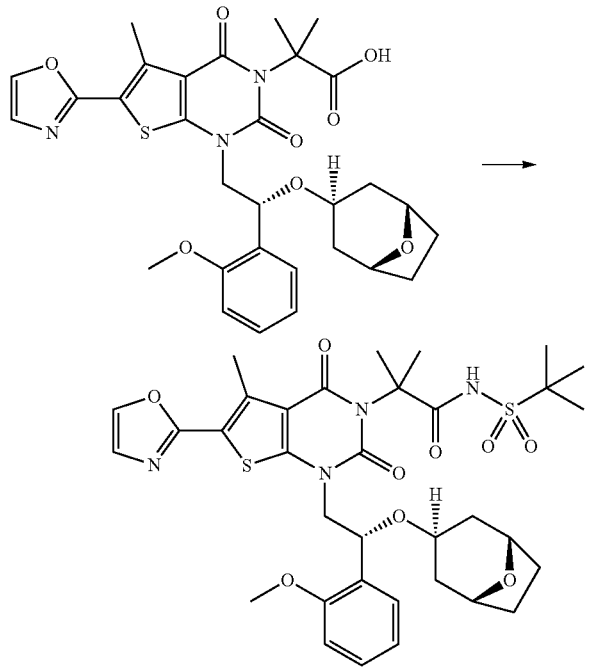

2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropanoic acid (0.022 mmol) was dissolved in DMF (1 mL) at room temperature under argon. Diisopropylethylamine (0.044 mmol) and HATU (0.026 mmol) were added sequentially. The reaction mixture was stirred under argon at room temperature for 20 hours. To a solution of tert-butylsulfonamide (0.134 mmol) in DMF (1 mL) was added sodium hydride (60% in mineral oil) (0.087 mmol) at room temperature. The reaction mixture was stirred at room temperature for one hour to afford a slurry. The above pre-formed HATU adduct was added dropwise to the slurry over 5 minutes. The resulting reaction mixture was stirred at room temperature for 15 minutes. The reaction mixture was diluted with EtOAc (3 mL) and partitioned between 1N HCl and EtOAc. The organic phase was separated and concentrated. The resulting residue was purified with HPLC (Gemini, 5-100% ACN/H$_2$O+0.1% TFA) and lyophilized from ACN/H$_2$O to afford 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-(tert-butylsulfonyl)-2-methylpropanamide. MS (m/z) 713.69 [M−H]⁻. ¹H NMR (400 MHz, Acetonitrile-d3) δ 8.56 (s, 1H), 7.89 (d, J=0.8 Hz, 1H), 7.52 (dd, J=7.6, 1.7 Hz, 1H), 7.32 (ddd, J=8.2, 7.4, 1.8 Hz, 1H), 7.27 (d, J=0.9 Hz, 1H), 7.04 (td, J=7.4, 1.0 Hz, 1H), 6.97 (dd, J=8.2, 1.0 Hz, 1H), 5.32 (dd, J=8.7, 4.5 Hz, 1H), 4.31-4.11 (m, 3H), 3.95 (dd, J=14.2, 8.8 Hz, 1H), 3.84 (s, 3H), 3.59 (tt, J=10.9, 5.7 Hz, 1H), 2.82 (s, 3H), 1.84-1.62 (m, 3H), 1.79 (s, 3H), 1.75 (s, 3H), 1.55-1.34 (m, 4H), 1.43 (s, 9H), 1.33-1.19 (m, 1H).

Example 4: Preparation of 2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3 (2H)-yl)-N-(cyclopropylsulfonyl)-2-methylpropanamide

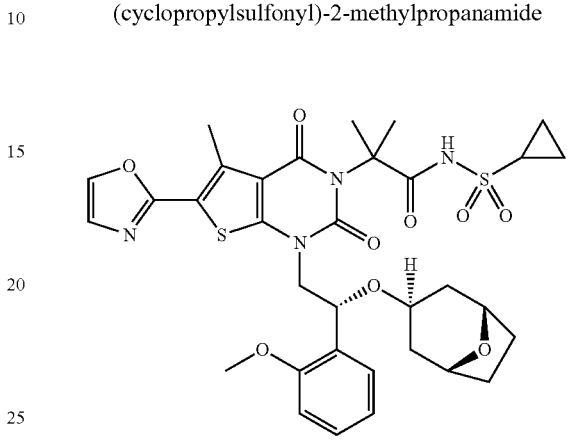

2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-(cyclopropylsulfonyl)-2-methylpropanamide was prepared in a manner similar to Example 3 except using cyclopropylsulfonamide instead of tert-butylsulfonamide. MS (m/z) 697.56 [M−H]⁻. ¹H NMR (400 MHz, Methanol-d4) δ 8.00-7.93 (m, 1H), 7.48 (dd, J=7.5, 1.5 Hz, 1H), 7.33-7.23 (m, 2H), 7.01 (t, J=7.4 Hz, 1H), 6.93 (d, J=8.1 Hz, 1H), 5.41-5.31 (m, 1H), 4.29 (d, J=18.8 Hz, 2H), 4.19-3.95 (m, 2H), 3.81 (s, 3H), 3.61 (tt, J=11.0, 5.9 Hz, 1H), 3.02 (ddd, J=13.0, 8.1, 4.9 Hz, 1H), 2.80 (s, 3H), 1.89-1.66 (m, 10H), 1.56-1.44 (m, 3H), 1.39-1.29 (m, 1H), 1.22 (h, J=6.4, 5.7 Hz, 2H), 1.17-1.08 (m, 2H).

Example 5: Preparation of 2-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide

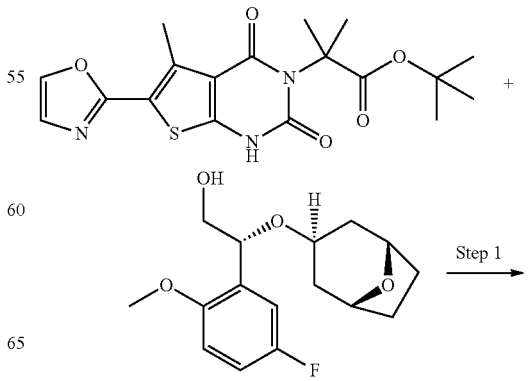

Step 1

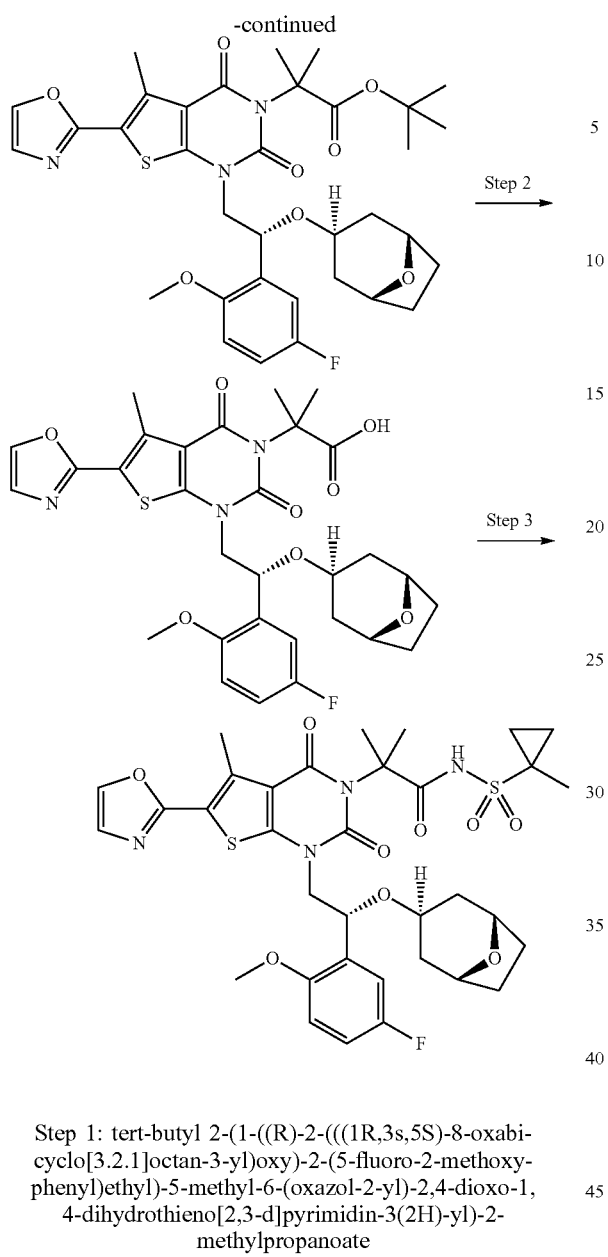

Step 1: tert-butyl 2-(1-((R)-2-(((1R,3s,5S)-8-oxabi-cyclo[3.2.1]octan-3-yl)oxy)-2-(5-fluoro-2-methoxy-phenyl)ethyl)-5-methyl-6-(oxazol-2-yl)-2,4-dioxo-1,4-dihydrothieno[2,3-d]pyrimidin-3(2H)-yl)-2-methylpropanoate Triphenylphosphine (2 mmol) was dissolved in vial in 2-MeTHF (6 mL) and cooled to 0° C. Diisopropyl azodicarboxylate (2 mmol) was added and the reaction mixture was stirred at 0° C. for 30 minutes, then stirred at room temperature for an additional 20 minutes to give a suspension.

In a separate flask, tert-butyl 2-methyl-2-(5-methyl-6-(oxazol-2-yl)-2,4-dioxo-1,4-dihydrothieno[2,3-d]pyrimidin-3(2H)-yl)propanoate, prepared according to WO 2017/091617 (0.332 mmol), and (R)-2-(((1R,3s,5S)-8-oxabicyclo[3.2.1]octan-3-yl)oxy)-2-(5-fluoro-2-methoxyphenyl)ethan-1-ol (0.332 mmol) were dissolved in 2-MeTHF (3.0 mL). The mixture from the vial above was added dropwise, giving a solution that was stirred at room temperature for 14 hours. The reaction mixture was concentrated, dissolved in a minimal amount of DCM/Hex and purified twice by normal phase chromatography (0-40% EtOAC/Hex), followed by HPLC (Gemini, 5-100% ACN/H₂O+0.1% TFA) to give tert-butyl 2-(1-((R)-2-(((1R,3s,5S)-8-oxabicyclo[3.2.1]octan-3-yl)oxy)-2-(5-fluoro-2-methoxyphenyl)ethyl)-5-methyl-6-(oxazol-2-yl)-2,4-dioxo-1,4-dihydrothieno[2,3-d]pyrimidin-3(2H)-yl)-2-methylpropanoate (the more polar product). MS (m/z) 669.83 [M+H]⁺.

Step 2: 2-(1-((R)-2-(((1R,3s,5S)-8-oxabicyclo[3.2.1]octan-3-yl)oxy)-2-(5-fluoro-2-methoxyphenyl)ethyl)-5-methyl-6-(oxazol-2-yl)-2,4-dioxo-1,4-dihydrothieno[2,3-d]pyrimidin-3(2H)-yl)-2-methylpropanoic acid

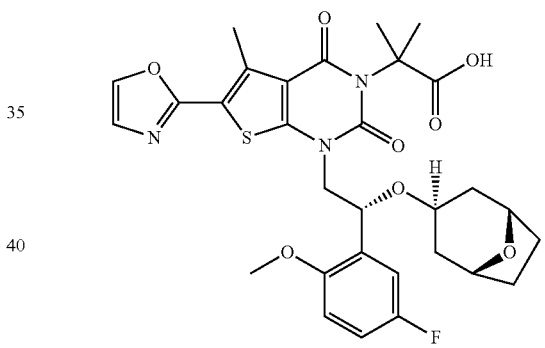

Trifluoroacetic acid (1 mL) was added to a solution of tert-butyl 2-(1-((R)-2-(((1R,3s,5S)-8-oxabicyclo[3.2.1]octan-3-yl)oxy)-2-(5-fluoro-2-methoxyphenyl)ethyl)-5-methyl-6-(oxazol-2-yl)-2,4-dioxo-1,4-dihydrothieno[2,3-d]pyrimidin-3(2H)-yl)-2-methylpropanoate (0.07 mmol) in dichloromethane (2 mL). The reaction mixture was stirred for one hour. The reaction mixture was concentrated, dissolved in DMF and purified by HPLC (Gemini, 5-100% ACN/H₂O+0.1% TFA). The product was lyophilized to give 2-(1-((R)-2-(((1R,3s,5S)-8-oxabicyclo[3.2.1]octan-3-yl)oxy)-2-(5-fluoro-2-methoxyphenyl)ethyl)-5-methyl-6-(oxazol-2-yl)-2,4-dioxo-1,4-dihydrothieno[2,3-d]pyrimidin-3(2H)-yl)-2-methylpropanoic acid. MS (m/z) 613.90 [M+H]⁺.

Step 3: 2-(1-((R)-2-(((1R,3s,5S)-8-oxabicyclo[3.2.1]octan-3-yl)oxy)-2-(5-fluoro-2-methoxyphenyl)ethyl)-5-methyl-6-(oxazol-2-yl)-2,4-dioxo-1,4-dihydrothieno[2,3-d]pyrimidin-3(2H)-yl)-2-methyl-N-((1-methylcyclopropyl)sulfonyl)propanamide

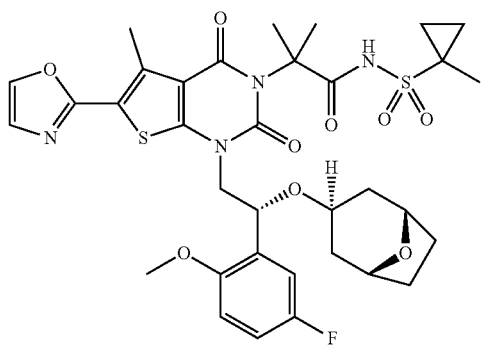 [SMILES: COc1ccc(F)cc1[C@H](Cn1c(=O)n(C(C)(C)C(=O)NS(=O)(=O)C2(C)CC2)c(=O)c2c(C)c(-c3ncco3)sc21)O[C@@H]1C[C@H]2CC[C@@H](C1)O2]

Diisopropylethylamine (0.085 mmol) was added to a solution of 2-(1-((R)-2-(((1R,3s,5S)-8-oxabicyclo[3.2.1]octan-3-yl)oxy)-2-(5-fluoro-2-methoxyphenyl)ethyl)-5-methyl-6-(oxazol-2-yl)-2,4-dioxo-1,4-dihydrothieno[2,3-d]pyrimidin-3(2H)-yl)-2-methylpropanoic acid (0.042 mmol) in DMF (1.0 mL), followed by the addition of HATU (0.051 mmol). The resulting solution was stirred at room temperature for 4 hours.

In a separate flask, 1-methylcyclopropane-1-sulfonamide (0.042 mmol) was dissolved in DMF (2 mL) and cooled to 0° C. in an ice bath. Sodium hydride (60% in mineral oil) (0.17 mmol) was added and the reaction mixture was stirred for 35 minutes at 0° C. The ice bath was removed and stirring continued for 90 minutes. The resulting mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by HPLC (Gemini, 5-100% ACN/H$_2$O+0.1% TFA) to give 2-(1-((R)-2-(((1R,3s,5S)-8-oxabicyclo[3.2.1]octan-3-yl)oxy)-2-(5-fluoro-2-methoxyphenyl)ethyl)-5-methyl-6-(oxazol-2-yl)-2,4-dioxo-1,4-dihydrothieno[2,3-d]pyrimidin-3(2H)-yl)-2-methyl-N-((1-methylcyclopropyl)sulfonyl)propanamide after lyophilization. MS (m/z) 730.90 [M+H]$^+$.
$^1$H NMR (400 MHz, Methanol-d4) δ 8.02 (dd, J=12.6, 0.9 Hz, 1H), 7.31 (dd, J=8.1, 0.9 Hz, 1H), 7.27-7.09 (m, 1H), 7.03 (td, J=8.7, 3.9 Hz, 1H), 7.00-6.86 (m, 1H), 5.44-5.23 (m, 1H), 4.34 (d, J=15.1 Hz, 2H), 4.11 (dd, J=49.7, 11.5 Hz, 2H), 3.87 (d, J=47.1 Hz, 3H), 3.66 (tq, J=10.4, 5.3 Hz, 1H), 2.81 (d, J=20.9 Hz, 3H), 2.00-1.68 (m, 9H), 1.68-1.43 (m, 8H), 1.43-1.25 (m, 2H), 0.98-0.78 (m, 2H).

Example 6: Preparation of 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methyl-N-((1-methylcyclopropyl)sulfonyl)propenamide

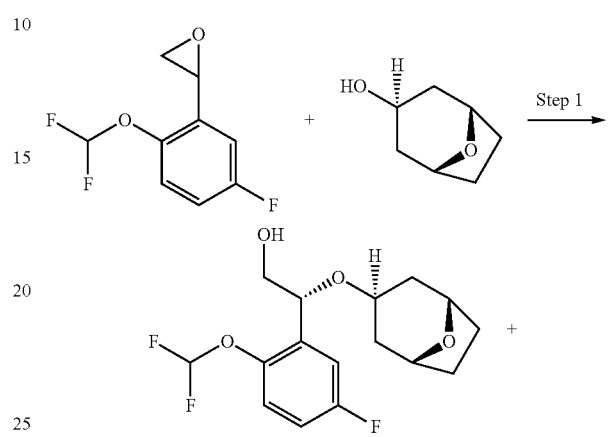

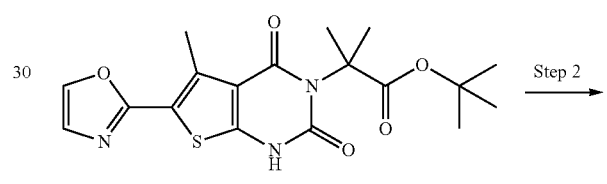

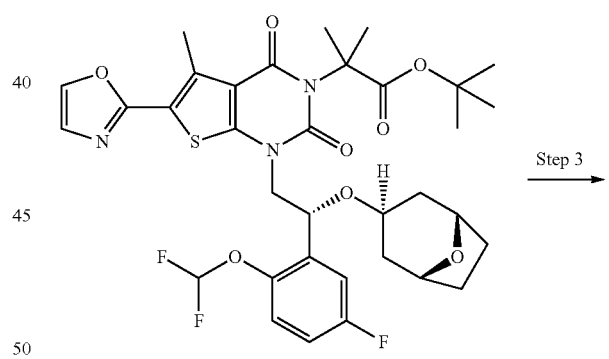

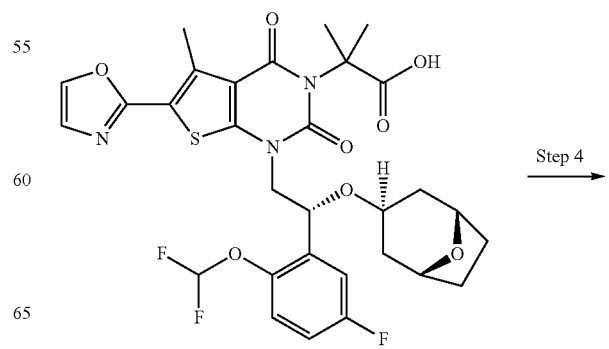

-continued

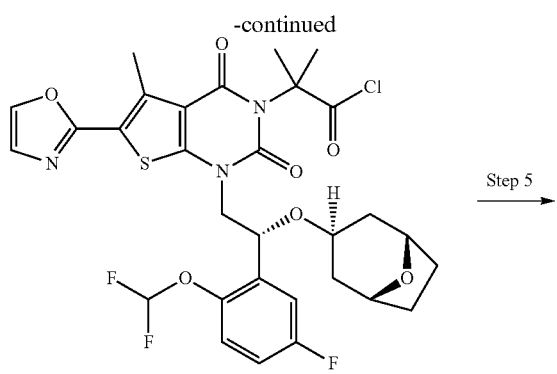

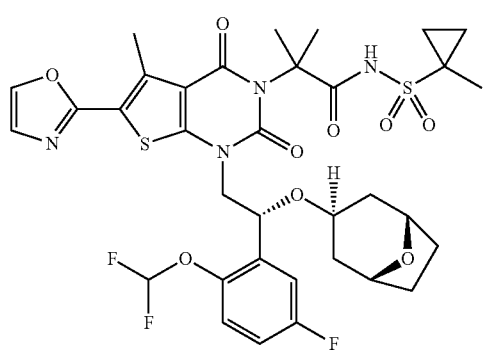

Step 1: (R)-2-(((1R,3s,5S)-8-oxabicyclo[3.2.1]octan-3-yl)oxy)-2-(2-(difluoromethoxy)-5-fluorophenyl)ethan-1-ol

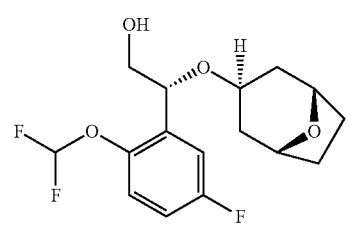 [SMILES: OC[C@H](O[C@@H]1C[C@H]2CC[C@@H](C1)O2)c1cc(F)ccc1OC(F)F]

2-(2-(Difluoromethoxy)-5-fluorophenyl)oxirane (4.90 mmol) and exo-8-oxabicyclo[3.2.1]octan-3-ol (5.88 mmol) were added at room temperature to a suspension of copper tetrafluoroborate hydrate (0.010 mmol) in dichloromethane (10 mL). The resulting suspension was stirred rapidly overnight and concentrated. The residue was purified by column chromatography (0-75% ethyl acetate/hexane), re-purified by column chromatography (0-10% methanol/DCM), and re-purified again by column chromatography (50% ethyl acetate/hexane). The resulting racemate was resolved by chiral SFC separation (IF, 10% EtOH) to give (R)-2-(((1R,3s,5S)-8-oxabicyclo[3.2.1]octan-3-yl)oxy)-2-(2-(difluoromethoxy)-5-fluorophenyl)ethan-1-ol. MS (m/z) 332.68 [M+H]+.

Step 2: tert-butyl 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoate

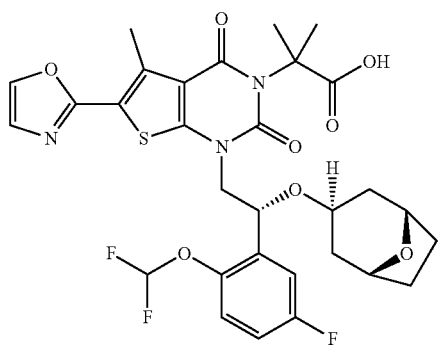

Diisopropylazodicarboxylate (1.93 mmol) was added dropwise at 0° C. to a solution of triphenylphosphine (1.93 mmol) in THF (7.0 mL). The resulting solution was then warmed to room temperature and became a suspension.

In a separate vial, tert-butyl 2-methyl-2-(5-methyl-6-(oxazol-2-yl)-2,4-dioxo-1,4-dihydrothieno[2,3-d]pyrimidin-3(2H)-yl)propanoate (0.475 mmol) and (R)-2-(((1R,3s,5S)-8-oxabicyclo[3.2.1]octan-3-yl)oxy)-2-(2-(difluoromethoxy)-5-fluorophenyl)ethan-1-ol (0.570 mmol) were combined and dissolved in THF (2.30 mL). At 0° C., the above suspension (7.0 mL) was added to this solution. The reaction mixture was allowed to warm to room temperature and stirred for 4 hours. The reaction was quenched with brine, extracted with ethyl acetate (3×), dried over Na$_2$SO$_4$, filtered and concentrated. The residue was purified by HPLC (Gemini, 5-100% ACN/H$_2$O+0.1% TFA) to give tert-butyl 2-(1-((R)-2-(((1R,3 s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoate after concentration. MS (m/z) 705.99 [M+H]+.

Step 3: 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoic acid A premixed solution of H₂SO₄ (0.655 mL), isopropanol (1.19 mL), and H₂O (0.73 mL) was added at room temperature to a flask containing tert-butyl 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoate (0.194 mmol). The reaction mixture was stirred for 4 hours. Water and ethyl acetate were added and the aqueous phase was extracted with ethyl acetate (2×). The combined organic phases were dried over Na₂SO₄, filtered and concentrated to give 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoate acid. MS (m/z) 649.94 [M+H]⁺.

Step 4: 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoyl chloride

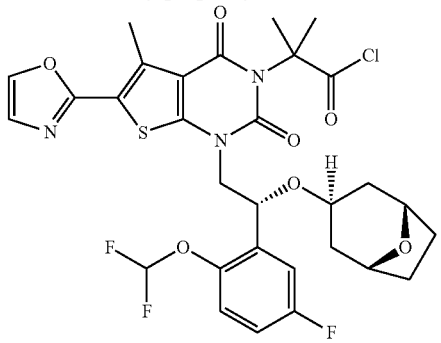

Oxalyl chloride (0.182 mmol) was added at 0° C. to a solution of 2-(1-((R)-2-(((1R,3 s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoic acid (0.122 mmol) in DCM (1.1 mL). DMF (0.02 mmol) was then added and the reaction mixture was stirred at 0° C. for 2 hours. The resulting reaction mixture was concentrated to yield 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoyl chloride, which was used directly in the next step.

Step 5: 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methyl-N-((1-methylcyclopropyl)sulfonyl)propanamide

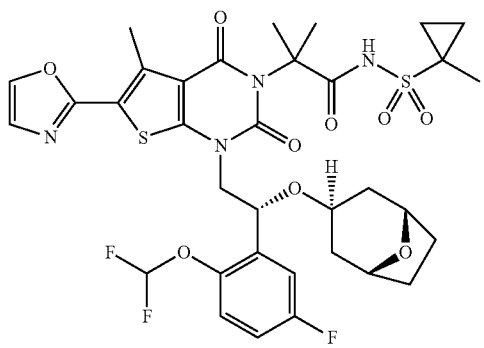 [SMILES: Cc1c(-c2ncco2)sc2c1c(=O)n(C(C)(C)C(=O)NS(=O)(=O)C1(C)CC1)c(=O)n2C[C@H](O[C@@H]1C[C@H]2CC[C@@H](C1)O2)c1cc(F)ccc1OC(F)F]

Crude 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoyl chloride (0.121 mmol) was dissolved in DCM (1 mL) and triethylamine (0.727 mmol) was added. The resulting suspension was stirred at room temperature for 5 minutes and 1-methylcyclopropanesulfonamide (0.242 mmol) was added. The suspension was stirred overnight and concentrated. The residue was dissolved in 1:1 methanol/acetonitrile, filtered, and purified by HPLC (Gemini, 5-100% ACN/H₂O+0.1% TFA). After lyophilization, the product was dissolved in a minimal amount of dichloromethane, and adsorbed onto and purified by preparative TLC (silica gel, 80% ethyl acetate/hexane) and concentrated to give 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methyl-N-((1-methylcyclopropyl)sulfonyl)propanamide. MS (m/z) 765.39 [M−H]⁻. ¹H NMR (400 MHz, Acetonitrile-d3) δ 8.80 (s, 1H), 7.87 (d, J=0.9 Hz, 1H), 7.36 (dd, J=9.2, 3.1 Hz, 1H), 7.25 (d, J=0.8 Hz, 1H), 7.18 (dd, J=9.0, 4.6 Hz, 1H), 7.11 (ddd, J=9.0, 7.9, 3.2 Hz, 1H), 6.78 (t, J=73.6 Hz, 1H), 5.23 (dd, J=8.2, 4.3 Hz, 1H), 4.32-4.11 (m, 3H), 3.92 (dd, J=14.4, 8.3 Hz, 1H), 3.61 (tt, J=10.9, 5.7 Hz, 1H), 2.79 (s, 3H), 1.87-1.79 (m, 1H), 1.75 (s, 3H), 1.74-1.63 (m, 6H), 1.58-1.45 (m, 7H), 1.44-1.36 (m, 1H), 1.35-1.29 (m, 1H), 0.92-0.86 (m, 2H).

Example 7: Preparation of 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-(cyclopropylsulfonyl)-2-methylpropanamide

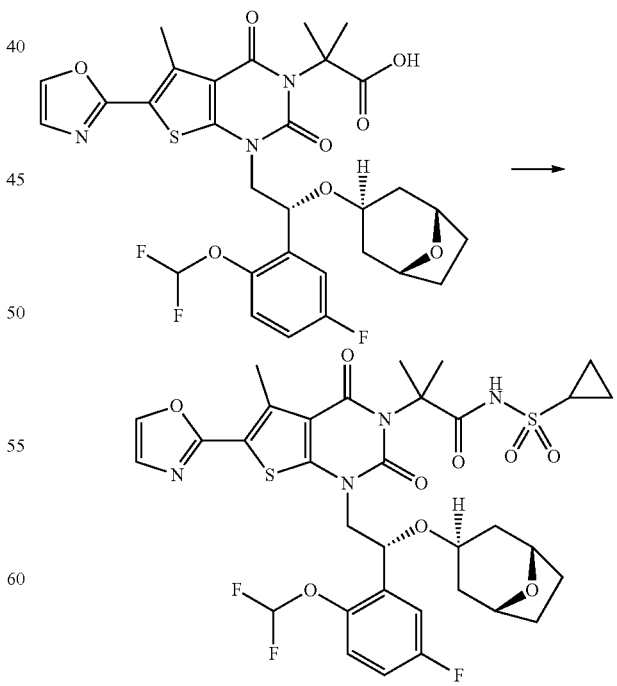

DMF (0.30 mL) was added under argon to a mixture of 2-(1-((R)-2-(((1R,3s,5S)-8-oxabicyclo[3.2.1]octan-3-yl)

oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoic acid (0.097 mmol) and HATU (0.116 mmol). Diisopropylethylamine (0.194 mmol) was added and the resulting solution was stirred overnight at room temperature.

In a separate vessel, sodium hydride (60% in mineral oil) (0.388 mmol) and cyclopropanesulfonamide (0.388 mmol) were combined and placed under argon. DMF (0.75 mL) was added and the suspension was stirred for 1 hour at room temperature. The above carboxylic acid/HATU solution was added to this suspension and the resulting mixture was stirred for 15 minutes. The reaction mixture was quenched with 1M HCl and extracted with ethyl acetate (2×). The combined organic phases were dried over $Na_2SO_4$, filtered, concentrated, and purified by HPLC (Gemini, 5-100% ACN/$H_2O$+0.1% TFA). After lyophilization, the residue was dissolved in a minimal amount of dichloromethane, and adsorbed onto and purified by preparative TLC (silica gel, 50% ethyl acetate/DCM) to give 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-(cyclopropylsulfonyl)-2-methylpropanamide. MS (m/z) 751.55 [M–H]⁻. ¹H NMR (400 MHz, Acetonitrile-d3) δ 8.94 (s, 1H), 7.88 (d, J=0.9 Hz, 1H), 7.36 (dd, J=9.2, 3.1 Hz, 1H), 7.25 (d, J=0.8 Hz, 1H), 7.18 (dd, J=9.0, 4.5 Hz, 1H), 7.11 (ddd, J=9.0, 7.9, 3.2 Hz, 1H), 6.78 (t, J=74.0, 73.4 Hz, 1H), 5.23 (dd, J=8.3, 4.3 Hz, 1H), 4.26 (s, 1H), 4.21 (s, 1H), 4.16 (dd, J=14.5, 4.1 Hz, 1H), 3.92 (dd, J=14.4, 8.5 Hz, 1H), 3.60 (tt, J=10.9, 5.8 Hz, 1H), 2.97-2.86 (m, 1H), 2.80 (s, 3H), 1.87-1.79 (m, 1H), 1.77-1.63 (m, 9H), 1.55-1.45 (m, 2H), 1.40 (td, J=11.4, 3.5 Hz, 1H), 1.33-1.27 (m, 1H), 1.18-0.98 (m, 4H).

Example 8: Preparation of 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-(tert-butylsulfonyl)-2-methylpropanamide

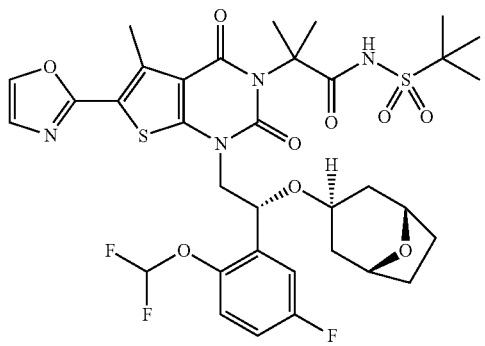 [SMILES: Cc1c(-c2ncco2)sc2c1c(=O)n(C(C)(C)C(=O)NS(=O)(=O)C(C)(C)C)c(=O)n2C[C@H](O[C@@H]1C[C@H]2CC[C@@H](C1)O2)c1cc(F)ccc1OC(F)F]

2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-(tert-butylsulfonyl)-2-methylpropanamide was prepared in a manner similar to Example 7 except using 2-methylpropane-2-sulfonamide instead of cyclopropanesulfonamide in Step 1. MS (m/z) 767.54 [M–H]⁻. ¹H NMR (400 MHz, Acetonitrile-d3) δ 8.57 (s, 1H), 7.87 (d, J=0.8 Hz, 1H), 7.36 (dd, J=9.2, 3.2 Hz, 1H), 7.25 (d, J=0.8 Hz, 1H), 7.18 (dd, J=9.0, 4.6 Hz, 1H), 7.11 (ddd, J=9.0, 7.9, 3.2 Hz, 1H), 6.76 (t, J=73.6 Hz, 1H), 5.24 (dd, J=8.2, 4.3 Hz, 1H), 4.30-4.11 (m, 3H), 3.93 (dd, J=14.5, 8.2 Hz, 1H), 3.63 (tt, J=10.9, 5.7 Hz, 1H), 2.79 (s, 3H), 1.81 (ddt, J=12.6, 6.2, 1.9 Hz, 1H), 1.77-1.62 (m, 9H), 1.54-1.45 (m, 2H), 1.44-1.31 (m, 10H), 1.32-1.24 (m, 1H).

Example 9: Preparation of 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methyl-N-(pyridin-2-ylsulfonyl)propanamide

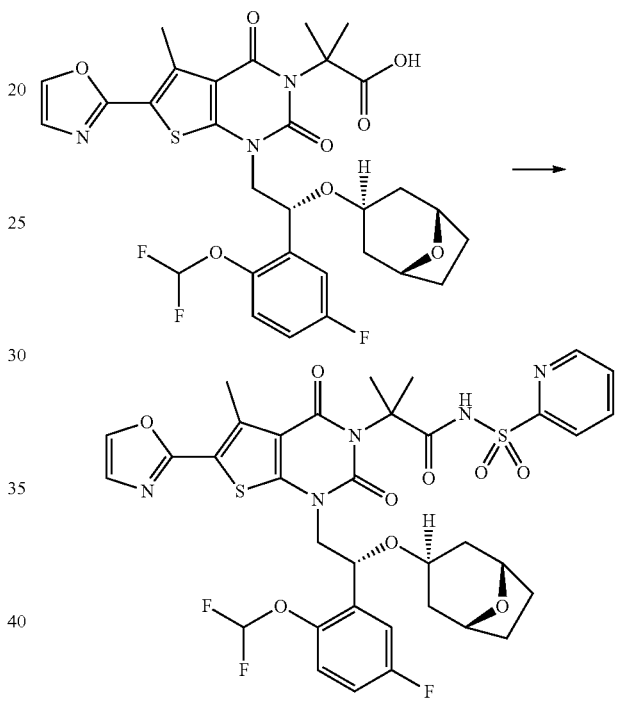

2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methylpropanoic acid (60 μmol) was dissolved in DMF (0.5 mL) at room temperature under argon. Diisopropylethylamine (120 μmol) and HATU (90 μmol) were added sequentially. The reaction mixture was stirred under argon at room temperature for 17 hours.

In a separate flask, sodium hydride (60% in mineral oil) (240 μmol) was added to a solution of pyridine-2-sulfonamide (240 μmol) in DMF (1 mL). The reaction mixture was stirred at room temperature for one hour to afford a slurry. The above solution was added dropwise to this slurry over 5 minutes. The resulting reaction mixture was stirred at room temperature for 72 hours. The reaction mixture was diluted with EtOAc (5 mL) and partitioned between 1N HCl and EtOAc. The organic phase was separated and concentrated. The residue was dissolved in a minimal amount of dichloromethane, and adsorbed onto and purified by preparative TLC (silica gel, 3/1 EtOAc/Heptane) to afford crude product. Further purification with HPLC (Gemini, 5-100% ACN/$H_2O$+0.1% TFA) and lyophilization from ACN/$H_2O$ afforded 2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-2-methyl-N-(pyridin-2-ylsulfonyl)propanamide. MS (m/z) 788.61 [M−H]⁻. ¹H NMR (400 MHz, Acetonitrile-d3) δ 9.53 (br, 1H), 8.71 (ddd, J=4.7, 1.7, 0.9 Hz, 1H), 8.17 (dt, J=7.9, 1.1 Hz, 1H), 8.07 (td, J=7.8, 1.7 Hz, 1H), 7.91 (d, J=0.8 Hz, 1H), 7.65 (ddd, J=7.6, 4.7, 1.2 Hz, 1H), 7.38 (dd, J=9.2, 3.2 Hz, 1H), 7.28 (d, J=0.9 Hz, 1H), 7.22 (dd, J=9.0, 4.6 Hz, 1H), 7.14 (ddd, J=9.0, 7.9, 3.2 Hz, 1H), 6.79 (dd, J=74.4, 72.8 Hz, 1H), 5.24 (dd, J=8.4, 4.1 Hz, 1H), 4.34-4.21 (m, 2H), 4.18 (dd, J=14.5, 4.1 Hz, 1H), 3.92 (dd, J=14.5, 8.4 Hz, 1H), 3.63 (tt, J=10.9, 5.7 Hz, 1H), 2.78 (s, 3H), 1.93-1.85 (m, 1H), 1.77-1.65 (m, 3H), 1.70 (s, 3H), 1.62 (s, 3H), 1.56-1.48 (m, 2H), 1.42 (ddd, J=12.4, 10.7, 3.6 Hz, 1H), 1.32 (ddd, J=12.9, 10.5, 3.6 Hz, 1H).

Example 10: Preparation of 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)cyclopropane-1-carboxamide

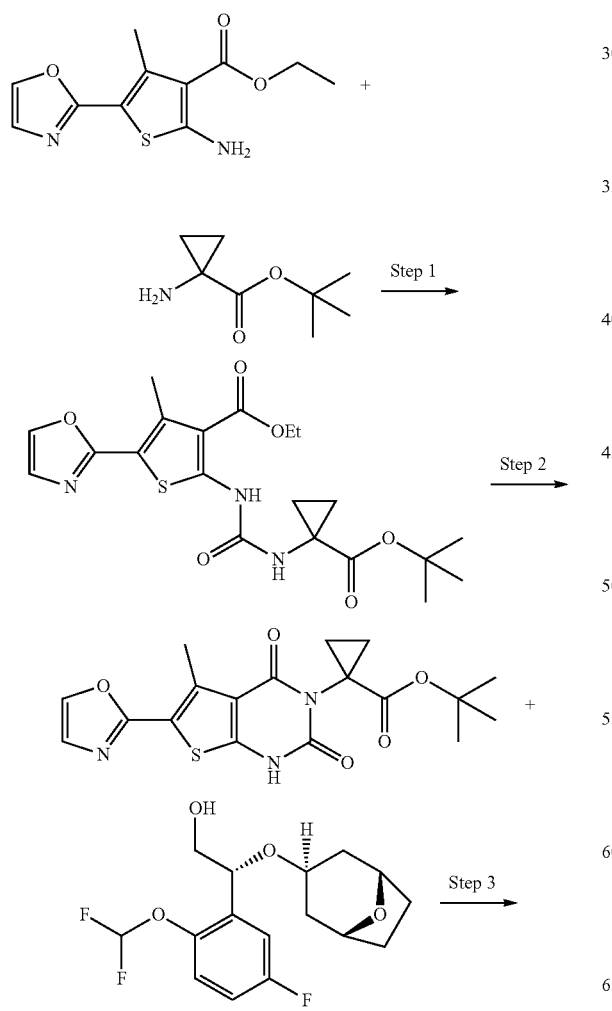

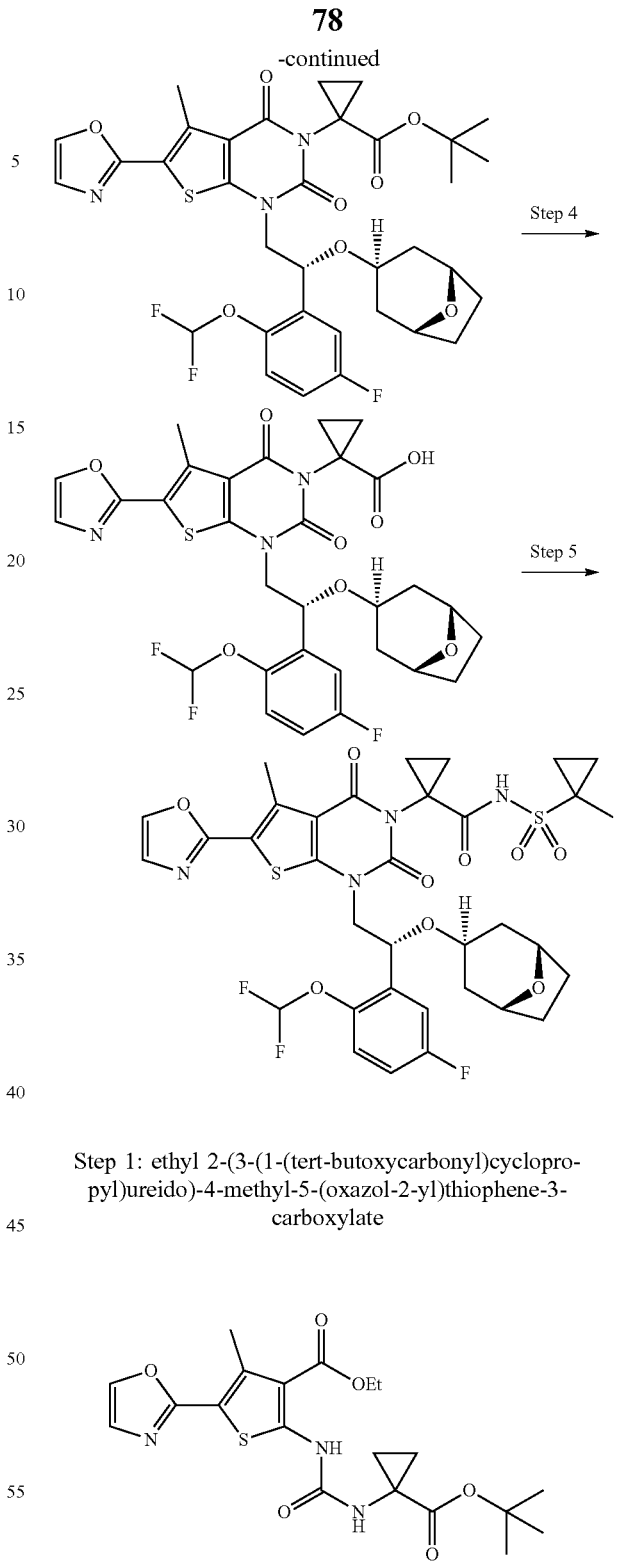

Step 1: ethyl 2-(3-(1-(tert-butoxycarbonyl)cyclopropyl)ureido)-4-methyl-5-(oxazol-2-yl)thiophene-3-carboxylate Triphosgene (2 mmol) was added at 0° C. to a mixture of ethyl 2-amino-4-methyl-5-oxazol-2-yl-thiophene-3-carboxylate, prepared according to WO 2017/075056 (5.5 mmol), in dichloromethane (100 mL), followed by a slow addition of triethylamine (17 mmol). The reaction mixture was stirred for 1 hour at 0° C., then at room temperature for two hours. tert-Butyl 1-aminocyclopropane-1-carboxylate (6 mmol) was added and the resulting reaction mixture was stirred at room temperature overnight. The reaction mixture was filtered, concentrated and purified by normal phase chromatography (0-100% EtOAc/Hex) to give ethyl 2-(3-(1-(tert-butoxycarbonyl)cyclopropyl)ureido)-4-methyl-5-(oxazol-2-yl)thiophene-3-carboxylate. MS (m/z) 436.11 [M+H]⁺.

Step 2: tert-butyl 1-(5-methyl-6-(oxazol-2-yl)-2,4-dioxo-1,4-dihydrothieno[2,3-d]pyrimidin-3(2H)-yl)cyclopropane-1-carboxylate

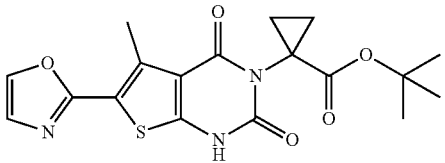 [SMILES: Cc1c(-c2ncco2)sc2[nH]c(=O)n(C3(C(=O)OC(C)(C)C)CC3)c(=O)c12]

A mixture of ethyl 2-(3-(1-(tert-butoxycarbonyl)cyclopropyl)ureido)-4-methyl-5-(oxazol-2-yl)thiophene-3-carboxylate (4.59 mmol) and cesium carbonate (18 mmol) was stirred in dioxane/tert-butanol mixture (8 mL/8 mL) at 90° C. for 3 hours. The reaction mixture was concentrated, dissolved in ethyl acetate and washed with 1N HCl solution. The aqueous layer was back extracted with ethyl acetate (2×) and combined organic layers were washed with brine, dried (MgSO₄), filtered and purified by normal phase chromatography (0-100% EtOAc/Hex) to give tert-butyl 1-(5-methyl-6-(oxazol-2-yl)-2,4-dioxo-1,4-dihydrothieno[2,3-d]pyrimidin-3(2H)-yl)cyclopropane-1-carboxylate. MS (m/z) 390.09 [M+H]⁺.

Step 3: tert-butyl 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)cyclopropane-1-carboxylate

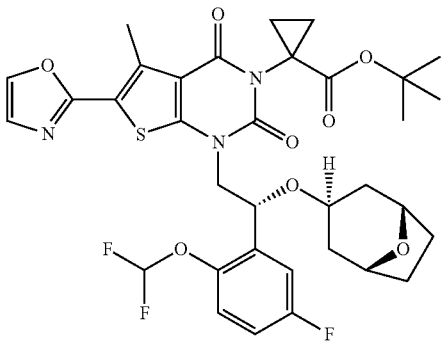 [SMILES: Cc1c(-c2ncco2)sc2c1c(=O)n(C1(C(=O)OC(C)(C)C)CC1)c(=O)n2C[C@H](O[C@@H]1C[C@H]2CC[C@@H](C1)O2)c1cc(F)ccc1OC(F)F]

In a vial, triphenylphosphine (0.27 mmol) was dissolved in 2-MeTHF (2 mL) and cooled to ° C. Diisopropyl azodicarboxylate (0.27 mmol) was added and the reaction mixture was stirred at 0° C. for 30 minutes, then stirred at room temperature for additional 20 minutes to give a suspension.

In a separate flask, tert-butyl 1-(5-methyl-6-(oxazol-2-yl)-2,4-dioxo-1,4-dihydrothieno[2,3-d]pyrimidin-3(2H)-yl)cyclopropane-1-carboxylate (0.09 mmol) and (R)-2-(((1R,3s,5S)-8-oxabicyclo[3.2.1]octan-3-yl)oxy)-2-(2-(difluoromethoxy)-5-fluorophenyl)ethan-1-ol (0.09 mmol) were dissolved in 2-MeTHF (1.0 mL). The mixture from above was added dropwise, giving a solution that was stirred at room temperature for 14 hours. The reaction mixture was concentrated, dissolved in a minimal amount of DCM/Hex and purified twice by normal phase chromatography (0-40% EtOAC/Hex) to give tert-butyl 1-(1-((R)-2-(((1R,3 s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3 (2H)-yl)cyclopropane-1-carboxylate. MS (m/z) 703.73 [M+H]⁺.

Step 4: 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)cyclopropane-1-carboxylic acid

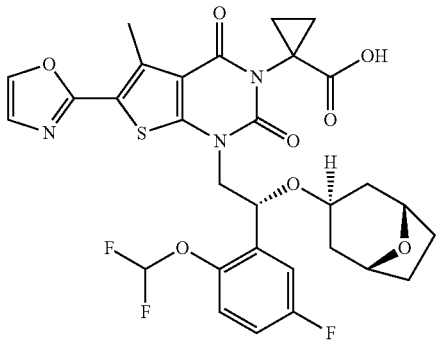 [SMILES: Cc1c(-c2ncco2)sc2c1c(=O)n(C1(C(=O)O)CC1)c(=O)n2C[C@H](O[C@@H]1C[C@H]2CC[C@@H](C1)O2)c1cc(F)ccc1OC(F)F]

Trifluoroacetic acid (0.5 mL) was added to a solution of tert-butyl 1-(1-((R)-2-(((1R,3 s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)cyclopropane-1-carboxylate (0.024 mmol) in dichloromethane (1 mL). The reaction mixture was stirred for one hour. The reaction mixture was concentrated, dissolved in DMF and purified by HPLC (Gemini, 5-100% ACN/H₂O+0.1% TFA). Product was lyophilized to give 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)cyclopropane-1-carboxylic acid. MS (m/z) 648.00 [M+H]⁺.

Step 5: 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)cyclopropane-1-carboxamide

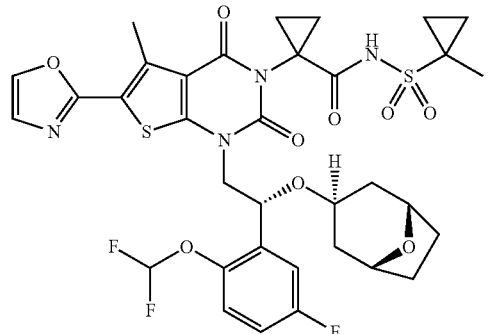

Diisopropylethylamine (0.018 mmol) was added to a solution of 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)cyclopropane-1-carboxylic acid (0.009 mmol) in DMF (1.0 mL), followed by addition of HATU (0.011 mmol). The resulting solution was stirred at room temperature for 4 hours.

In a separate flask, 1-methylcyclopropane-1-sulfonamide (0.041 mmol) was dissolved in DMF (0.7 mL) and cooled to 0° C. Sodium hydride (60% in mineral oil) (0.037 mmol) was added and reaction mixture was stirred for 35 minutes at 0° C. in an ice bath. The ice bath was removed and stirring continued for 90 minutes. This mixture was added to the above solution and stirring was continued for 2 hours. The reaction mixture was diluted with ethyl acetate, acidified with 1N HCl and extracted with EtOAc (2×). Combined organic layers were washed with 5% lithium chloride solution (3×), brine, and concentrated under reduced pressure. The obtained crude material was purified by HPLC (Gemini, 5-100% ACN/H$_2$O+0.1% TFA) to give the desired product 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)cyclopropane-1-carboxamide after lyophilization. MS (m/z) 764.87 [M+H]$^+$. $^1$H NMR (400 MHz, Methanol-d4) δ 8.01 (s, 1H), 7.23 (d, J=63.1 Hz, 4H), 6.83 (d, J=73.3 Hz, 1H), 5.34 (s, 1H), 4.61 (s, 1H), 4.36 (d, J=20.9 Hz, 2H), 3.81 (d, J=76.9 Hz, 2H), 2.86 (s, 3H), 2.15-1.66 (m, 6H), 1.66-1.45 (m, 8H), 1.45-1.08 (m, 3H), 0.91 (d, J=2.0 Hz, 2H).

Diisopropylethylamine (0.018 mmol) was added to a solution of 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)cyclopropane-1-carboxylic acid (0.009 mmol) in DMF (1.0 mL), followed by addition of HATU (0.011 mmol). The resulting solution was stirred at room temperature for 4 hours.

In a separate flask, 2-methylpropane-2-sulfonamide (0.041 mmol) was dissolved in DMF (0.7 mL) and cooled to 0° C. Sodium hydride (60% in mineral oil, 0.037 mmol) was added and the reaction mixture was stirred for 35 minutes at 0° C. in an ice bath. The ice bath was removed and stirring continued for 90 minutes. This mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by HPLC (Gemini, 5-100% ACN/H$_2$O+0.1% TFA) to give the desired product 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-(tert-butylsulfonyl)cyclopropane-1-carboxamide after lyophilization. MS (m/z) 766.85 [M+H]$^+$. $^1$H NMR (400 MHz, Methanol-d4) δ 8.01 (s, 1H), 7.23 (d, J=62.0 Hz, 4H), 6.93 (t, J=73.9 Hz, 1H), 5.33 (s, 1H), 4.62 (s, 1H), 4.36 (d, J=19.8 Hz, 2H), 3.80 (d, J=74.5 Hz, 2H), 2.86 (s, 3H), 2.08-1.70 (m, 6H), 1.57 (d, J=11.9 Hz, 3H), 1.42 (m, 12H).

Example 11: Preparation of 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-(tert-butylsulfonyl)cyclopropane-1-carboxamide Example 12: Preparation of 1-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)cyclopropane-1-carboxamide

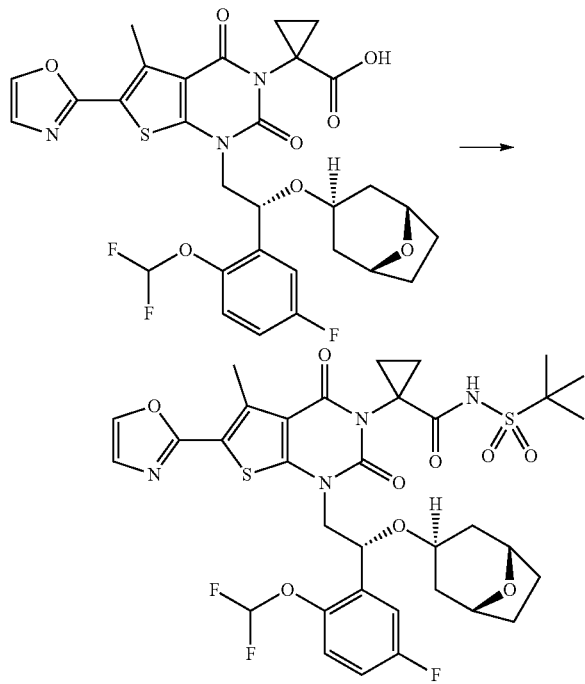

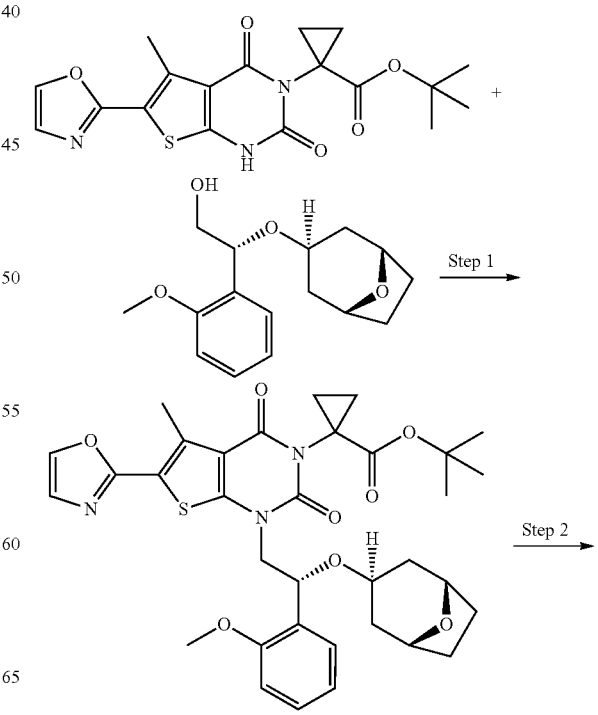

83

-continued

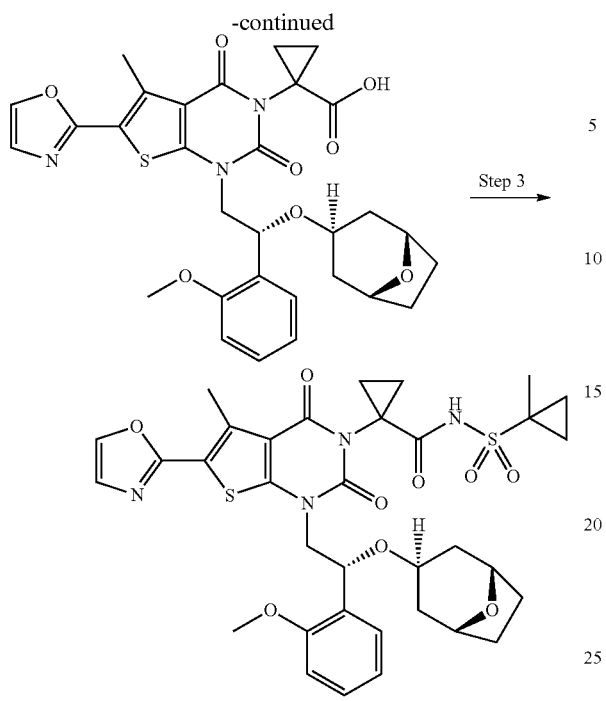

Step 1: tert-butyl 1-(1-((R)-2-(((1R,3s,5S)-8-oxabi-cyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)cyclopropane-1-carboxylate

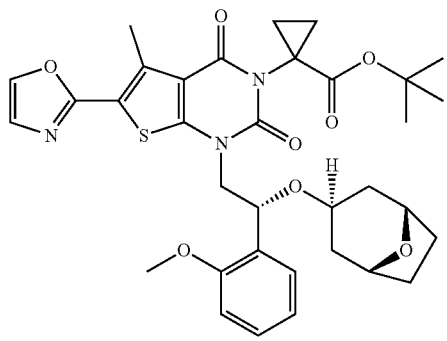 [SMILES: COc1ccccc1[C@H](Cn1c(=O)n(C2(C(=O)OC(C)(C)C)CC2)c(=O)c2c(C)c(-c3ncco3)sc21)O[C@@H]1C[C@H]2CC[C@@H](C1)O2]

tert-Butyl 1-(5-methyl-6-(oxazol-2-yl)-2,4-dioxo-1,4-dihydrothieno[2,3-d]pyrimidin-3(2H)-yl)cyclopropane-1-carboxylate (0.231 mmol) and (R)-2-(((1S,5S)-8-oxabicyclo[3.2.1]octan-3-yl)oxy)-2-(2-methoxyphenyl)ethan-1-ol (0.279 mmol) were dissolved in THF (2 mL) at room temperature. Diisopropyl azodicarboxylate (0.347 mmol) and triphenylphosphine (0.347 mmol) were added sequentially. The reaction mixture was stirred at room temperature in a sealed tube for 17 hours. The reaction mixture was purified by silica gel column (0-100% EtOAc/Hex) to afford a mixture of tert-butyl 1-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)cyclopropane-1-carboxylate and tert-butyl 1-(2-((R)-2-(((1R,3s,5S)-8-oxabicyclo[3.2.1]octan-3-yl)oxy)-2-(2-methoxyphenyl)ethoxy)-5-methyl-6-(oxazol-

84

2-yl)-4-oxothieno[2,3-d]pyrimidin-3(4H)-yl)cyclopropane-1-carboxylate. MS (m/z) 650.26 [M+H]$^+$.

Step 2: tert-butyl 1-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)cyclopropane-1-carboxylate

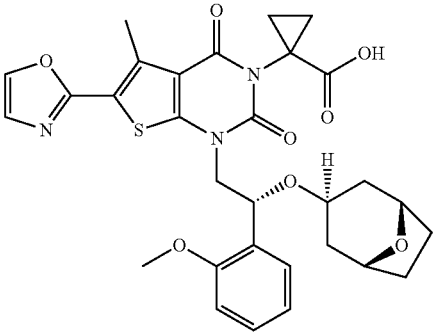 [SMILES: COc1ccccc1[C@H](Cn1c(=O)n(C2(C(=O)O)CC2)c(=O)c2c(C)c(-c3ncco3)sc21)O[C@@H]1C[C@H]2CC[C@@H](C1)O2]

Concentrated sulfuric acid (3 mL) was added to water (3 mL) with vigorous stirring at 0° C., followed by addition of isopropanol (6 mL). A mixture of tert-butyl 1-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)cyclopropane-1-carboxylate and tert-butyl 1-(2-((R)-2-(((1R,3s,5S)-8-oxabicyclo[3.2.1]octan-3-yl)oxy)-2-(2-methoxyphenyl)ethoxy)-5-methyl-6-(oxazol-2-yl)-4-oxothieno[2,3-d]pyrimidin-3(4H)-yl)cyclopropane-1-carboxylate (0.216 mmol) was treated with 5 mL of the above sulfuric acid solution at 0° C. The reaction mixture was allowed to warm to room temperature with stirring and kept at room temperature for 3 hours. The reaction mixture was diluted with water (10 mL) and extracted with EtOAc (10 mL). The organic phase was separated, washed with water and concentrated. The residue was purified with HPLC (Gemini, 5-100% ACN/H$_2$O+0.1% TFA) and lyophilized from ACN/H$_2$O to afford 1-(1-((R)-2-(((1R,3s,5S)-8-oxabicyclo[3.2.1]octan-3-yl)oxy)-2-(2-m ethoxyphenyl)ethyl)-5-methyl-6-(oxazol-2-yl)-2,4-dioxo-1,4-dihydrothieno[2,3-d]pyrimidin-3(2H)-yl)cyclopropane-1-carb oxylic acid. MS (m/z) 592.22 [M−H]$^−$.

Step 3: 1-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)cyclopropane-1-carboxamide

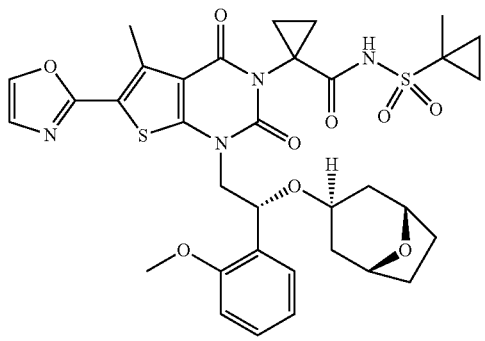 [SMILES: COc1ccccc1[C@H](Cn1c(=O)n(C2(C(=O)NS(=O)(=O)C3(C)CC3)CC2)c(=O)c2c(C)c(-c3ncco3)sc21)O[C@@H]1C[C@H]2CC[C@@H](C1)O2]

1-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)cyclopropane-1-carboxylic acid (34 µmol) was dissolved in DMF (0.5 mL) at room temperature under argon. Diisopropylethylamine (67 µmol) and HATU (40 µmol) were added sequentially. The reaction mixture was stirred under argon at room temperature for 17 hours. Sodium hydride (60% in mineral oil) (135 µmol) was added at room temperature to a solution of 1-methylcyclopropane-1-sulfonamide (152 µmol) in DMF (0.5 mL). The reaction mixture was stirred at room temperature for one hour to afford a slurry. The pre-formed HATU adduct was added dropwise over 5 minutes to the slurry. The resulting reaction mixture was stirred at room temperature for 20 minutes. The reaction mixture was then diluted with EtOAc (5 mL) and partitioned between 1N HCl and EtOAc. The organic phase was separated and concentrated. The residue was dissolved in a minimal amount of dichloromethane, adsorbed onto and purified by preparative TLC (silica gel, 1/1 EtOAc/Heptane to afford 1-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)cyclopropane-1-carboxamide. MS (m/z) 709.69 [M−H]⁻. ¹H NMR (400 MHz, Acetonitrile-d3) δ 8.97 (d, J=12.7 Hz, 1H), 7.91 (d, J=0.8 Hz, 1H), 7.63-7.41 (m, 1H), 7.40-7.30 (m, 1H), 7.28 (d, J=0.8 Hz, 1H), 7.08-6.97 (m, 2H), 5.36-5.30 (m, 1H), 4.59-4.39 (m, 1H), 4.28-4.19 (m, 2H), 4.01-3.76 (m, 4H), 3.74-3.52 (m, 1H), 2.86 (s, 3H), 1.95-1.60 (m, 8H), 1.61-1.08 (m, 9H), 0.98-0.85 (m, 2H).

Example 13: Preparation of 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)-N-(tert-butylsulfonyl)cyclopropane-1-carboxamide

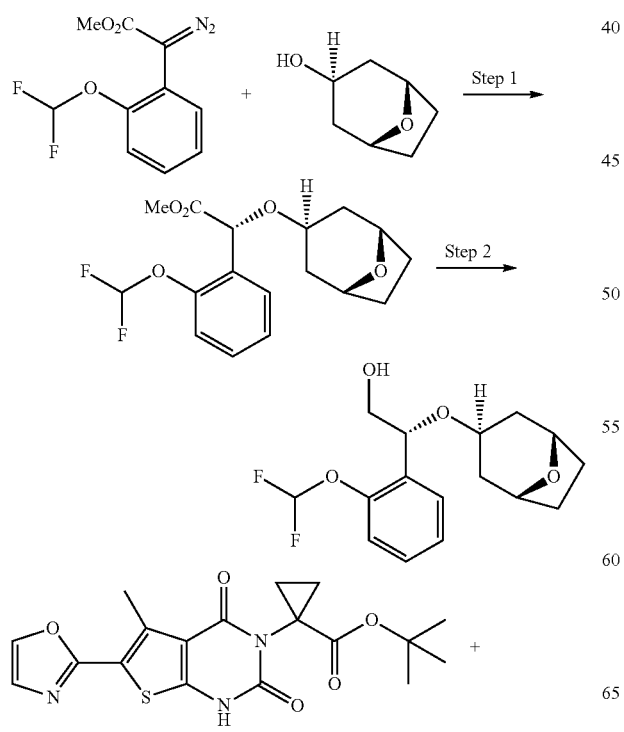

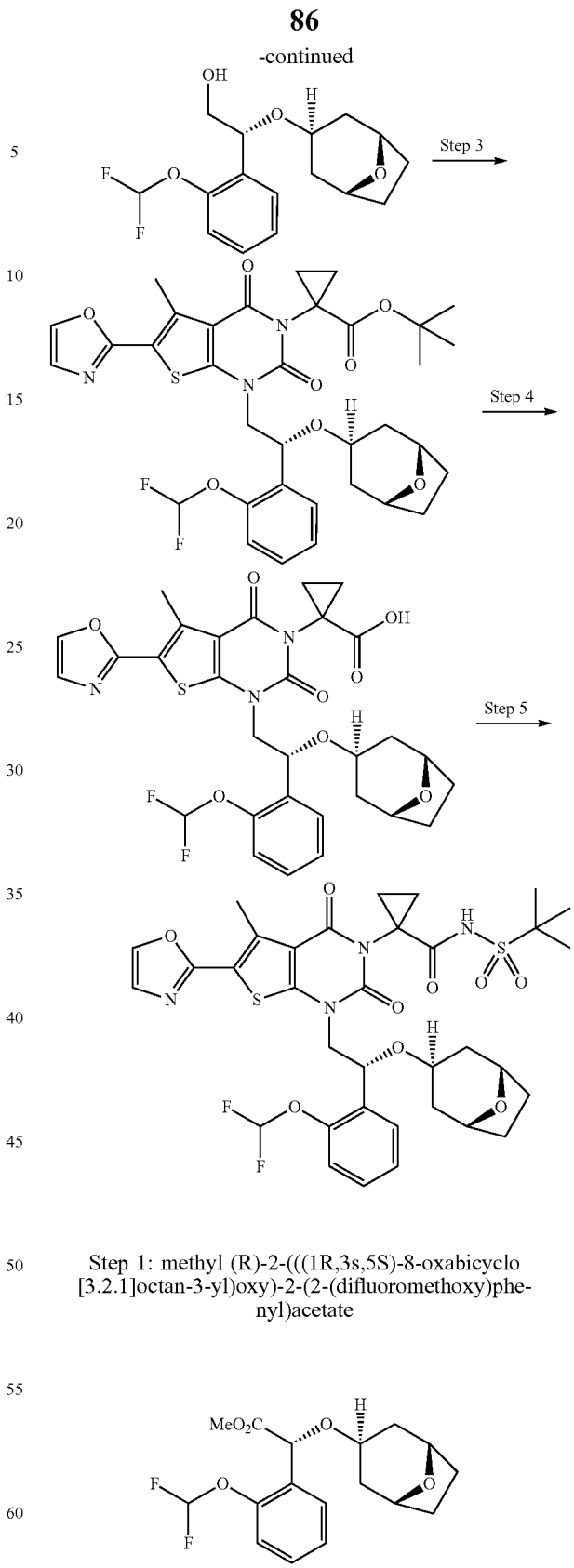

Step 1: methyl (R)-2-(((1R,3s,5S)-8-oxabicyclo[3.2.1]octan-3-yl)oxy)-2-(2-(difluoromethoxy)phenyl)acetate Under argon, a mixture of exo-8-oxabicyclo[3.2.1]octan-3-ol (4.08 mmol), Rh₂(TPA)₄ (0.017 mmol), and 1,10-di(anthracen-9-yl)-12-hydroxy-4,5,6,7-tetrahydrodiindeno[7,1-de:1',7'-fg][1,3,2]dioxaphosphocine 12-oxide (0.017 mmol) was dissolved in DCM (48 mL) and heated to 40° C. A solution of methyl 2-diazo-2-(2-(difluoromethoxy)phenyl)acetate (0.823 g, 3.40 mmol) in DCM (10 mL) was added dropwise and the solution bubbled. After 1 hour, the reaction mixture was concentrated and purified by column chromatography (0-100% ethyl acetate/hexane). After concentration, the residue was re-purified by column chromatography (0-40% ethyl acetate/hexane) and concentrated. The racemate was resolved by chiral SFC separation (IC, 5% EtOH—NH$_3$) to give methyl (R)-2-(((1R,3s,5S)-8-oxabicyclo[3.2.1]octan-3-yl)oxy)-2-(2-(difluoromethoxy)phenyl)acetate. MS (m/z) 342.82 [M+H]$^+$.

Step 2: (R)-2-(((1R,3s,5S)-8-oxabicyclo[3.2.1]octan-3-yl)oxy)-2-(2-(difluoromethoxy)phenyl)ethan-1-ol

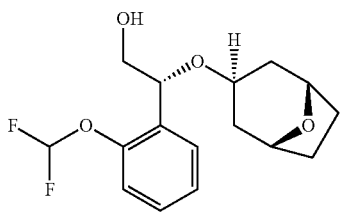 [SMILES: OC[C@H](O[C@@H]1C[C@H]2CC[C@@H](C1)O2)c1ccccc1OC(F)F]

A 2.0 M solution of lithium borohydride in THF (3.15 mmol) was added to a solution of methyl (R)-2-(((1R,3s,5S)-8-oxabicyclo[3.2.1]octan-3-yl)oxy)-2-(2-(difluoromethoxy)phenyl)acetate (0.789 mmol) in THF (8 mL). The reaction mixture was heated to 40° C. After 1 hour, the reaction was cooled to room temperature and quenched carefully by dropwise addition of aqueous NH$_4$Cl. The phases were separated and the aqueous phase was extracted with ethyl acetate (3×). The combined organic extracts were dried over Na$_2$SO$_4$, filtered, concentrated, and purified by column chromatography (0-100% ethyl acetate/hexane) to give (R)-2-(((1R,3s,5S)-8-oxabicyclo[3.2.1]octan-3-yl)oxy)-2-(2-(difluoromethoxy)phenyl)ethan-1-ol. MS (m/z) 314.74 [M+H]$^+$.

Step 3: tert-butyl 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)cyclopropane-1-carboxylate

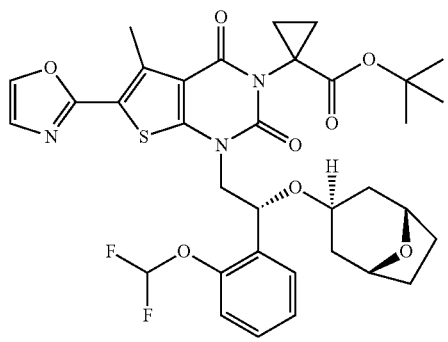 [SMILES: Cc1c(-c2ncco2)sc2c1c(=O)n(C1(C(=O)OC(C)(C)C)CC1)c(=O)n2C[C@H](O[C@@H]1C[C@H]2CC[C@@H](C1)O2)c1ccccc1OC(F)F]

Diisopropylazodicarboxylate (1.95 mmol) was added dropwise to a solution of triphenylphosphine (1.95 mmol) in THF (6.80 mL) at 0° C. The solution was warmed to room temperature and became a suspension.

In a separate vial, tert-butyl 1-(5-methyl-6-(oxazol-2-yl)-2,4-dioxo-1,4-dihydrothieno[2,3-d]pyrimidin-3 (2H)-yl)cyclopropane-1-carboxylate, (0.390 mmol) and (R)-2-(((1R,3s,5S)-8-oxabicyclo[3.2.1]octan-3-yl)oxy)-2-(2-(difluoromethoxy)phenyl)ethan-1-ol (0.468 mmol) were combined and dissolved in THF (2.2 mL). At 0° C., the above suspension (2.17 mL) was added to this suspension. The reaction mixture was allowed to warm to room temperature and stirred for 4 hours. The reaction was quenched with brine, extracted with ethyl acetate (3×), dried over Na$_2$SO$_4$, filtered and concentrated. The residue was purified by HPLC (Gemini, 5-100% ACN/H$_2$O+0.1% TFA) to give tert-butyl 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)cyclopropane-1-carboxylate after concentration. MS (m/z) 685.74 [M+H]$^+$.

Step 4: 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)cyclopropane-1-carboxylic acid

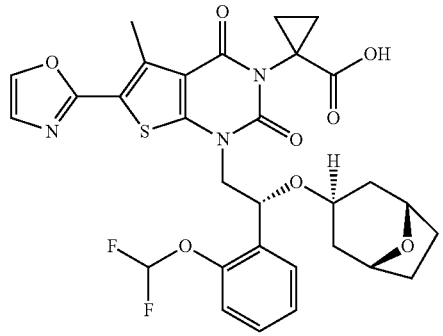 [SMILES: Cc1c(-c2ncco2)sc2c1c(=O)n(C1(C(=O)O)CC1)c(=O)n2C[C@H](O[C@@H]1C[C@H]2CC[C@@H](C1)O2)c1ccccc1OC(F)F]

A premixed solution of H$_2$SO$_4$ (0.492 mL), isopropanol (0.90 mL), and H$_2$O (0.56 mL) was added at room temperature to a flask containing tert-butyl 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)cyclopropane-1-carboxylate (0.146 mmol). The reaction mixture was stirred for 4 hours. Water and ethyl acetate were added and the aqueous phase was extracted with ethyl acetate (2×). Combined organic phases were dried over Na$_2$SO$_4$, filtered and concentrated to give 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)cyclopropane-1-carboxylic acid. MS (m/z) 629.97 [M+H]$^+$.

Step 5: 1-(1-((R)-2-(((1R,3s,5S)-8-oxabicyclo[3.2.1]
octan-3-yl)oxy)-2-(2-(difluoromethoxy)phenyl)
ethyl)-5-methyl-6-(oxazol-2-yl)-2,4-dioxo-1,4-dihy-
drothieno[2,3-d]pyrimidin-3(2H)-yl)-N-(tert-
butylsulfonyl)cyclopropane-1-carboxamide

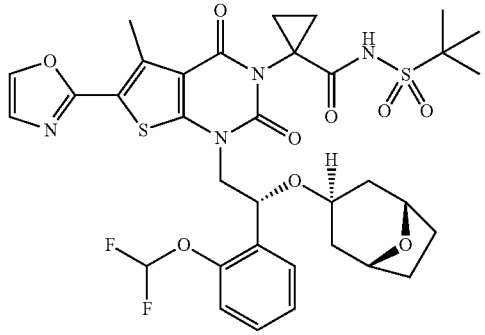 [SMILES: Cc1c(-c2ncco2)sc2c1c(=O)n(C1(C(=O)NS(=O)(=O)C(C)(C)C)CC1)c(=O)n2C[C@H](O[C@@H]1C[C@H]2CC[C@@H](C1)O2)c1ccccc1OC(F)F]

DMF (0.10 mL) was added under argon to a mixture of 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)cyclopropane-1-carboxylic acid (0.018 mmol) and HATU (0.021 mmol). Diisopropylethylamine (0.035 mmol) was added and the resulting solution was stirred overnight at room temperature.

In a separate vessel, 60% sodium hydride (0.070 mmol) and 2-methylpropane-2-sulfonamide (0.070 mmol) were combined and placed under argon. DMF (0.50 mL) was added and the suspension was stirred for 1 hour at room temperature. The carboxylic acid/HATU solution was added to this suspension and the resulting mixture was stirred for 15 minutes. The reaction mixture was quenched with H$_2$O, filtered, and purified by HPLC (Gemini, 5-100% ACN/H$_2$O+0.1% TFA) to give 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)-N-(tert-butylsulfonyl)cyclopropane-1-carboxamide after lyophilization. MS (m/z) 747.71 [M−H]$^−$. $^1$H NMR (400 MHz, Acetonitrile-d3) δ 8.69 (d, J=28.0 Hz, 1H), 7.88 (s, 1H), 7.60 (d, J=47.9 Hz, 1H), 7.48-7.27 (m, 2H), 7.26 (s, 1H), 7.23-7.08 (m, 1H), 6.84 (t, J=74.0 Hz, 1H), 5.28 (d, J=17.0 Hz, 1H), 4.50 (d, J=13.2 Hz, 1H), 4.24 (d, J=18.3 Hz, 2H), 3.96-3.49 (m, 2H), 2.83 (s, 3H), 1.90-1.75 (m, 3H), 1.74-1.62 (m, 3H), 1.53-1.38 (m, 3H), 1.36 (s, 9H), 1.33-0.94 (m, 3H).

Example 14: Preparation of 1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)cyclopropane-1-carboxamide

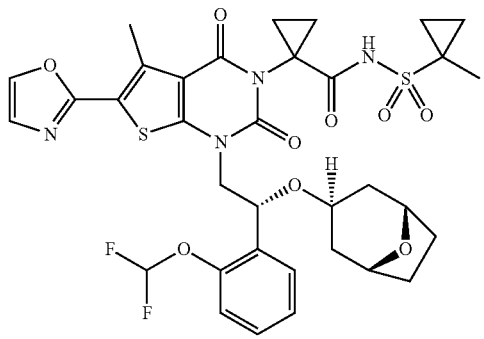 [SMILES: Cc1c(-c2ncco2)sc2c1c(=O)n(C1(C(=O)NS(=O)(=O)C3(C)CC3)CC1)c(=O)n2C[C@H](O[C@@H]1C[C@H]2CC[C@@H](C1)O2)c1ccccc1OC(F)F]

1-(1-((R)-2-(((1R,3s,5S)-8-oxabicyclo[3.2.1]octan-3-yl)oxy)-2-(2-(difluoromethoxy)phenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)cyclopropane-1-carboxamide was prepared in a manner similar to Example 13 except using 1-methylcyclopropane-1-sulfonamide instead of 2-methylpropane-2-sulfonamide in Step 5. MS (m/z) 745.65 [M−H]$^−$. $^1$H NMR (400 MHz, Acetonitrile-d3) δ 8.93 (d, J=35.8 Hz, 1H), 7.88 (s, 1H), 7.73-7.48 (m, 1H), 7.48-7.27 (m, 2H), 7.26 (s, 1H), 7.17 (t, J=10.1 Hz, 1H), 6.84 (t, J=74.0 Hz, 1H), 5.29 (d, J=19.3 Hz, 1H), 4.49 (d, J=14.3 Hz, 1H), 4.25 (d, J=23.1 Hz, 2H), 3.99-3.64 (m, 1H), 3.58 (dd, J=10.8, 5.3 Hz, 1H), 2.84 (s, 3H), 1.90-1.75 (m, 3H), 1.74-1.61 (m, 3H), 1.53-1.24 (m, 10H), 1.20-0.99 (m, 1H), 0.89 (d, J=1.8 Hz, 2H).

Example 15: Preparation of (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide

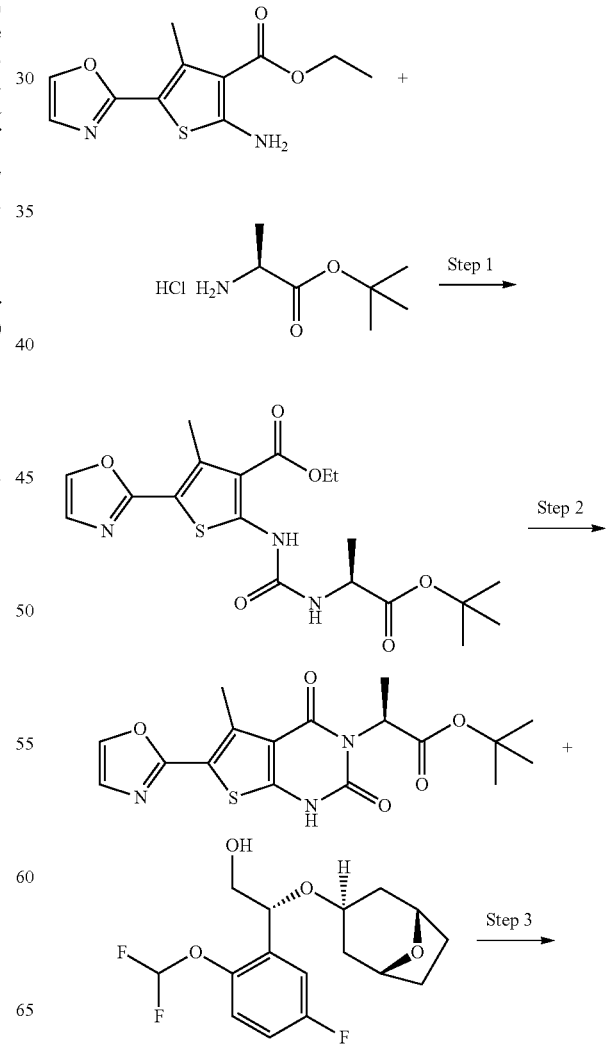

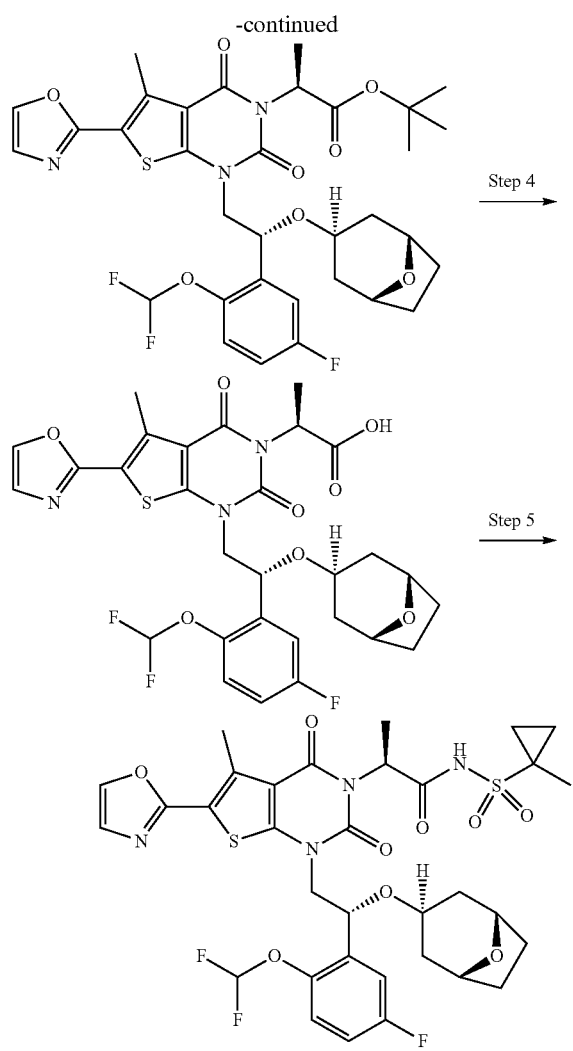

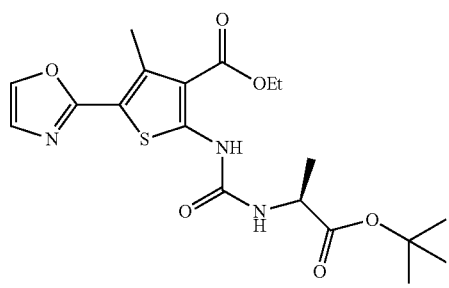 [SMILES: CCOC(=O)c1c(NC(=O)N[C@@H](C)C(=O)OC(C)(C)C)sc(-c2ncco2)c1C]

Step 1: ethyl (S)-2-(3-(1-(tert-butoxy)-1-oxopropan-2-yl)ureido)-4-methyl-5-(oxazol-2-yl)thiophene-3-carboxylate Triphosgene (4.65 mmol) was added at 0° C. to a mixture of ethyl 2-amino-4-methyl-5-oxazol-2-yl-thiophene-3-carboxylate, prepared according to WO 2017/075056 (13.9 mmol), in dichloromethane (100 mL), followed by a slow addition of triethylamine (69 mmol). The reaction mixture was stirred for 1 hour at 0° C., then at room temperature for two hours. tert-Butyl L-alaninate hydrochloride (20.8 mmol) was added and the reaction mixture was stirred at room temperature overnight. The reaction mixture was filtered to remove solid materials, concentrated and purified by normal phase chromatography (0-100% EtOAc/Hex) to give ethyl (S)-2-(3-(1-(tert-butoxy)-1-oxopropan-2-yl)ureido)-4-methyl-5-(oxazol-2-yl)thiophene-3-carboxylate.

Step 2: tert-butyl (S)-2-(5-methyl-6-(oxazol-2-yl)-2,4-dioxo-1,4-dihydrothieno[2,3-d]pyrimidin-3(2H)-yl)propanoate

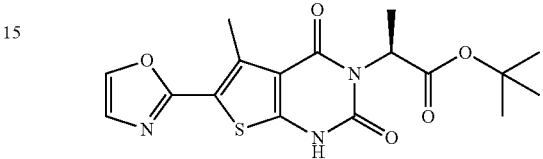

A mixture of ethyl (S)-2-(3-(1-(tert-butoxy)-1-oxopropan-2-yl)ureido)-4-methyl-5-(oxazol-2-yl)thiophene-3-carboxylate (2.60 mmol) and cesium carbonate (33.5 mmol) in tert-butanol (100 mL) was stirred at 80° C. for 3 hours. The reaction mixture was concentrated, dissolved in ethyl acetate and washed with 1N HCl solution. Aqueous layer was back extracted with ethyl acetate (2×) and combined organic layers were washed with brine, dried (MgSO$_4$), filtered and purified by normal phase chromatography (0-100% EtOAc/Hex) to give tert-butyl (S)-2-(5-methyl-6-(oxazol-2-yl)-2,4-dioxo-1,4-dihydrothieno[2,3-d]pyrimidin-3(2H)-yl)propanoate. MS (m/z) 378.09 [M+H]$^+$.

Step 3: tert-butyl (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)propanoate

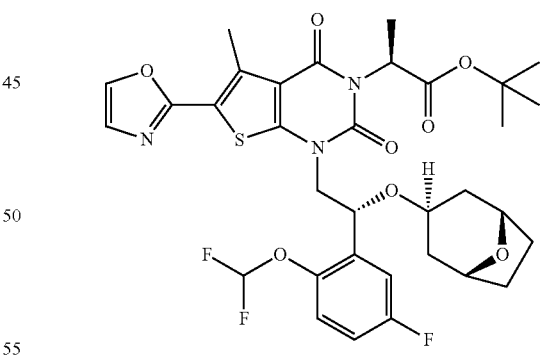

In a vial, triphenylphosphine (0.636 mmol) was dissolved in 2-MeTHF (6 mL) and cooled to 0° C. Diisopropyl azodicarboxylate (0.636 mmol) was added and the reaction mixture was stirred at 0° C. for 30 minutes, then stirred at room temperature for an additional 20 minutes to give a suspension.

In a separate flask, tert-butyl (S)-2-(5-methyl-6-(oxazol-2-yl)-2,4-dioxo-1,4-dihydrothieno[2,3-d]pyrimidin-3(2H)-yl)propanoate (0.212 mmol) and (R)-2-(((1R,3s,5S)-8-oxabicyclo[3.2.1]octan-3-yl)oxy)-2-(2-(difluoromethoxy)-5-fluorophenyl)ethan-1-ol (0.212 mmol) were dissolved in 2-MeTHF (3.0 mL). The mixture from above was added dropwise, giving a solution that was stirred at room temperature for 14 hours. The reaction mixture was concentrated, dissolved in a minimal amount of DCM/Hex and purified twice by normal phase chromatography (0-40% EtOAC/Hex), followed by preparative HPLC (Gemini, 5-100% ACN/H₂O+0.1% TFA) to give tert-butyl (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)propanoate (the more polar product). MS (m/z) 691.82 [M+H]⁺.

Step 4: (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl) propanoic acid

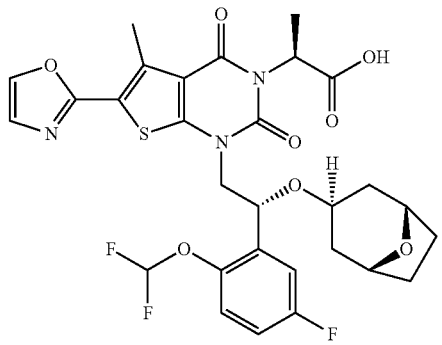 [SMILES: Cc1c(-c2ncco2)sc2c1c(=O)n([C@@H](C)C(=O)O)c(=O)n2C[C@H](O[C@@H]1C[C@H]2CC[C@@H](C1)O2)c1cc(F)ccc1OC(F)F]

Trifluoroacetic acid (1 mL) was added to a solution of tert-butyl (S)-2-(1-((R)-2-(((1R,3 s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)propanoate (0.066 mmol) in dichloromethane (2 mL). The reaction mixture was stirred for one hour. The reaction mixture was concentrated, dissolved in DMF and purified by HPLC (Gemini, 5-100% ACN/H₂O+0.1% TFA) to give (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl) propanoic acid after lyophilization. MS (m/z) 635.96 [M+H]⁺.

Step 5: (S)-2-(1-((R)-2-(01R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide

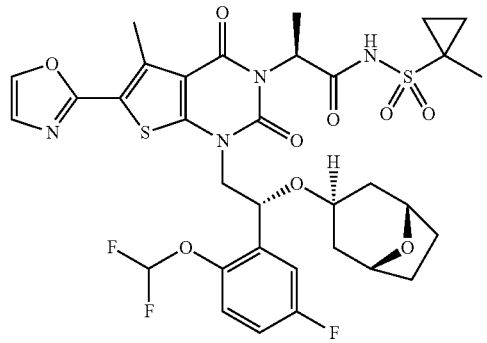 [SMILES: Cc1c(-c2ncco2)sc2c1c(=O)n([C@@H](C)C(=O)NS(=O)(=O)C1(C)CC1)c(=O)n2C[C@H](O[C@@H]1C[C@H]2CC[C@@H](C1)O2)c1cc(F)ccc1OC(F)F]

Diisopropylethylamine (0.112 mmol) was added to a solution of (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)propanoic acid (0.057 mmol) in DMF (1.0 mL), followed by the addition of HATU (0.068 mmol). The resulting solution was stirred at room temperature for 4 hours.

In a separate flask, 1-methylcyclopropane-1-sulfonamide (0.255 mmol) was dissolved in DMF (2 mL) and cooled to 0° C. Sodium hydride (60% in mineral oil, 0.23 mmol) was added and the reaction mixture was stirred for 35 minutes at 0° C. in an ice bath. The ice bath was removed and stirring continued for 90 minutes. The resulting mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by HPLC (Gemini, 5-100% ACN/H₂O+0.1% TFA) to give desired product (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide after lyophilization. MS (m/z) 751.59 [M–H]⁻. ¹H NMR (400 MHz, Methanol-d4) δ 8.01 (d, J=0.9 Hz, 1H), 7.38 (dd, J=9.0, 3.1 Hz, 1H), 7.31 (d, J=0.9 Hz, 1H), 7.23 (dd, J=9.0, 4.5 Hz, 1H), 7.14 (ddd, J=9.0, 7.7, 3.2 Hz, 1H), 7.10-6.71 (m, 1H), 5.49 (q, J=6.8 Hz, 1H), 5.38 (t, J=6.4 Hz, 1H), 4.35 (d, J=17.6 Hz, 2H), 4.20 (d, J=6.0 Hz, 1H), 3.70 (tt, J=11.0, 5.7 Hz, 2H), 2.86 (s, 3H), 2.00-1.89 (m, 1H), 1.89-1.71 (m, 3H), 1.66 (dt, J=10.9, 5.8 Hz, 2H), 1.59 (m, 1H), 1.58-1.51 (m, 7H), 1.51-1.29 (m, 2H), 1.03-0.80 (m, 2H).

Example 16: Preparation of (S)-2-(1-((R)-2-(((1R, 3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide

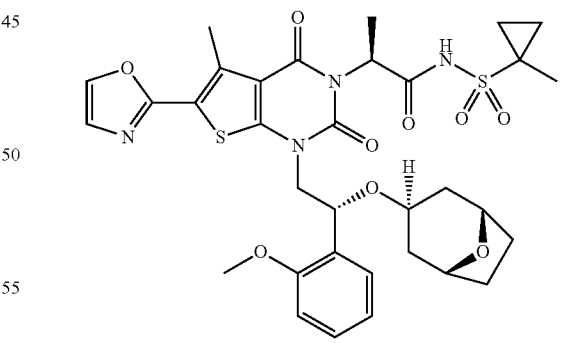

(S)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide prepared in a similar manner as (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide, except using (R)-2-(((1R,3s,5S)-8-oxabicyclo[3.2.1]octan-3-yl)oxy)-2-(2-methoxyphenyl)ethan-1-ol instead of (R)-2-(((1R,3s,5S)-8-oxabicyclo[3.2.1]octan-3-yl)oxy)-2-(2-(difluoromethoxy)-5-fluorophenyl)ethan-1-ol in step 3. MS (m/z) 697.68 [M–H]⁻. ¹H NMR (400 MHz, Methanol-d4) δ 7.98 (s, 1H), 7.49 (dd, J=7.5, 1.5 Hz, 1H), 7.34-7.25 (m, 2H), 7.05-6.93 (m, 2H), 5.49 (q, J=6.8 Hz, 1H), 5.37 (dd, J=9.1, 4.3 Hz, 1H), 4.34-4.19 (m, 3H), 4.05-3.94 (m, 1H), 3.86 (s, 3H), 3.59 (tt, J=10.7, 5.9 Hz, 1H), 2.85 (s, 3H), 1.88-1.59 (m, 5H), 1.56-1.43 (m, 10H), 1.32-1.21 (m, 1H), 0.98-0.82 (m, 2H).

Example 17: Preparation of (S)-2-(1-((R)-2-(((1R, 3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-(tert-butylsulfonyl)propanamide

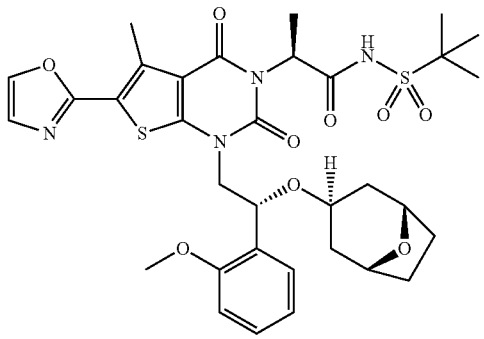 [SMILES: COc1ccccc1[C@H](Cn1c(=O)n([C@@H](C)C(=O)NS(=O)(=O)C(C)(C)C)c(=O)c2c(C)c(-c3ncco3)sc21)O[C@@H]1C[C@H]2CC[C@@H](C1)O2]

(S)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-(tert-butylsulfonyl)propanamide prepared in a manner similar to (S)-2-(1-((R)-2-(((1R,3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide, except using (R)-2-(((1R,3s,5S)-8-oxabicyclo[3.2.1]octan-3-yl)oxy)-2-(2-methoxyphenyl)ethan-1-ol instead of (R)-2-(((1R,3s,5S)-8-oxabicyclo[3.2.1]octan-3-yl)oxy)-2-(2-(difluoromethoxy)-5-fluorophenyl)ethan-1-ol in step 3 and 2-methylpropane-2-sulfonamide instead of 1-methylcyclopropane-1-sulfonamide in step 5. MS (m/z) 699.71 [M–H]⁻. ¹H NMR (400 MHz, Methanol-d4) δ 7.99 (s, 1H), 7.50 (dd, J=7.5, 1.4 Hz, 1H), 7.34-7.25 (m, 2H), 7.06-6.93 (m, 2H), 5.47 (q, J=6.7 Hz, 1H), 5.37 (dd, J=8.9, 4.4 Hz, 1H), 4.34-4.20 (m, 3H), 3.99 (dd, J=14.3, 9.2 Hz, 1H), 3.86 (s, 3H), 3.60 (tt, J=11.3, 6.0 Hz, 1H), 2.85 (s, 3H), 1.85-1.66 (m, 4H), 1.60-1.44 (m, 6H), 1.42 (d, J=3.8 Hz, 9H), 1.32-1.22 (m, 1H).

Example 18: Preparation of (R)-2-(1-((R)-2-(((1R, 3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propenamide

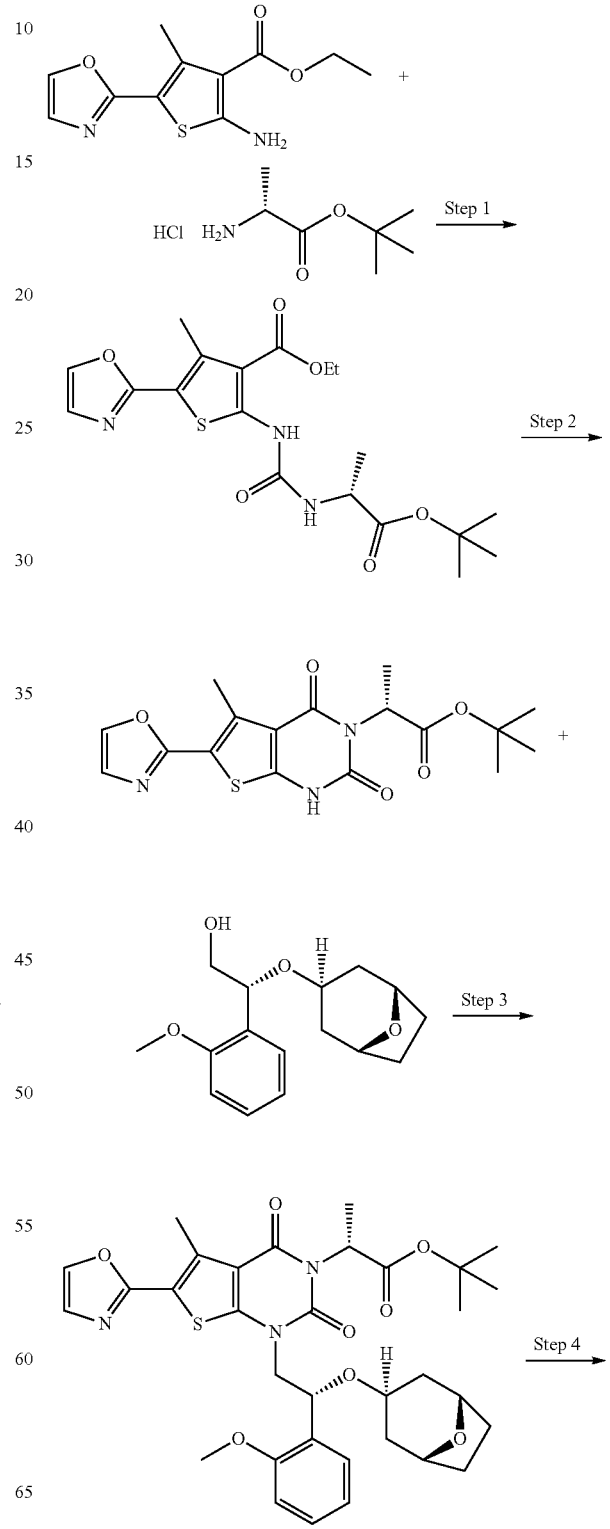

-continued

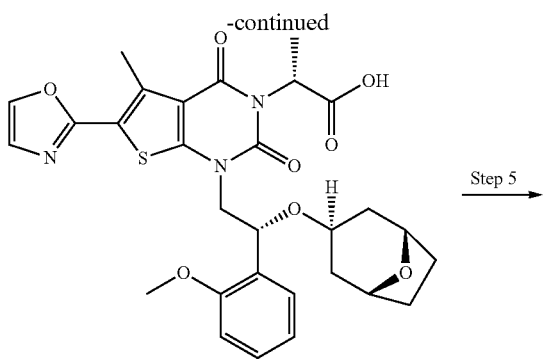

Step 2: tert-butyl (R)-2-(5-methyl-6-(oxazol-2-yl)-2,4-dioxo-1,4-dihydrothieno[2,3-c]pyrimidin-3(2H)-yl)propanoate

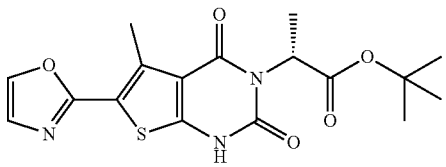

A mixture of ethyl (R)-2-(3-(1-(tert-butoxy)-1-oxopropan-2-yl)ureido)-4-methyl-5-(oxazol-2-yl)thiophene-3-carboxylate (2.60 mmol) and cesium carbonate (33.5 mmol) in tert-butanol (100 mL) was stirred at 80° C. for 3 hours. The reaction mixture was concentrated, dissolved in ethyl acetate and washed with 1N HCl solution. Aqueous layer was back extracted with ethyl acetate (2×) and combined organic layers were washed with brine, dried (MgSO$_4$), filtered and purified by normal phase chromatography (0-100% EtOAc/Hex) to give tert-butyl (R)-2-(5-methyl-6-(oxazol-2-yl)-2,4-dioxo-1,4-dihydrothieno[2,3-d]pyrimidin-3(2H)-yl)propanoate. MS (m/z) 376.37 [M−H]$^-$.

Step 3: tert-butyl (R)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)propanoate

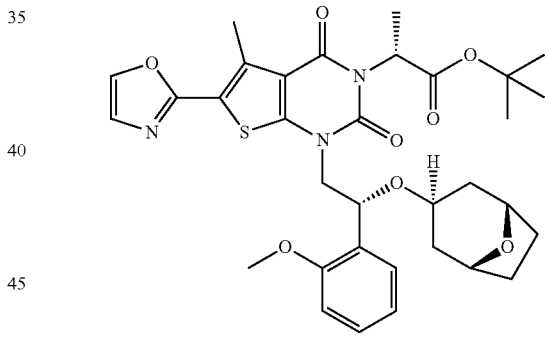

In a vial, triphenylphosphine (0.95 mmol) was dissolved in 2-MeTHF (6 mL) and cooled to 0° C. Diisopropyl azodicarboxylate (0.95 mmol) was added and the reaction mixture was stirred at 0° C. for 30 minutes, then stirred at room temperature for an additional 20 minutes to give a suspension.

In a separate flask, tert-butyl (R)-2-(5-methyl-6-(oxazol-2-yl)-2,4-dioxo-1,4-dihydrothieno[2,3-d]pyrimidin-3(2H)-yl)propanoate (0.318 mmol) and (R)-2-(((1R,3s,5S)-8-oxabicyclo[3.2.1]octan-3-yl)oxy)-2-(2-methoxyphenyl)ethan-1-ol (0.318 mmol) were dissolved in 2-MeTHF (3.0 mL). The mixture from above was added dropwise, giving a solution that was stirred at room temperature for 14 hours. The reaction mixture was concentrated, dissolved in a minimal amount of DCM/Hex and purified twice by normal phase chromatography (0-40% EtOAC/Hex), followed by preparative HPLC (Gemini, 5-100% ACN/H$_2$O+0.1% TFA) to tert-butyl (R)-2-(1-((R)-2-(((1R,3s,5S)-8-oxabicyclo[3.2.1]octan-3-yl)oxy)-2-(2-methoxyphenyl)ethyl)-5-

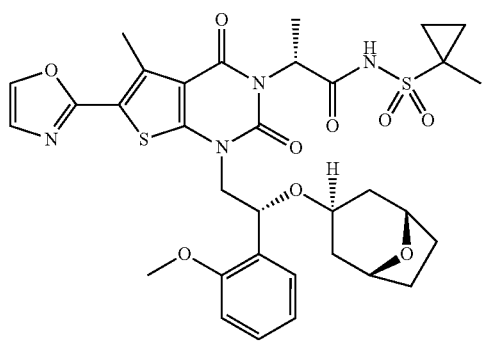

Step 1: ethyl (R)-2-(3-(1-(tert-butoxy)-1-oxopropan-2-yl)ureido)-4-methyl-5-(oxazol-2-yl)thiophene-3-carboxylate

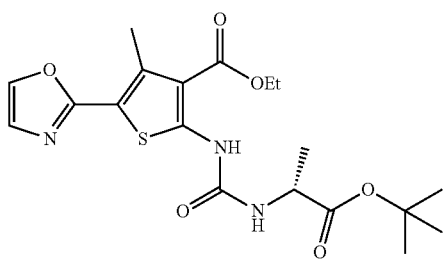 [SMILES: CCOC(=O)c1c(NC(=O)N[C@H](C)C(=O)OC(C)(C)C)sc(-c2ncco2)c1C]

Triphosgene (4.65 mmol) was added at 0° C. to a mixture of ethyl 2-amino-4-methyl-5-oxazol-2-yl-thiophene-3-carboxylate, prepared according to WO 2017/075056 (13.9 mmol) in dichloromethane (100 mL), followed by a slow addition of triethylamine (69 mmol). The reaction mixture was stirred for 1 hour at 0° C., then at room temperature for two hours. tert-Butyl D-alaninate hydrochloride (20.8 mmol) was added and the reaction mixture was stirred at room temperature overnight. The reaction mixture was filtered to remove solid materials, concentrated and purified by normal phase chromatography (0-100% EtOAc/Hex) to give ethyl (R)-2-(3-(1-(tert-butoxy)-1-oxopropan-2-yl)ureido)-4-methyl-5-(oxazol-2-yl)thiophene-3-carboxylate. MS (m/z) 424.13 [M+H]$^+$.

methyl-6-(oxazol-2-yl)-2,4-dioxo-1,4-dihydrothieno[2,3-d]pyrimidin-3(2H)-yl)propanoate (more polar product). MS (m/z) 637.90 [M+H]⁺.

Step 4: (R)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)propanoic acid

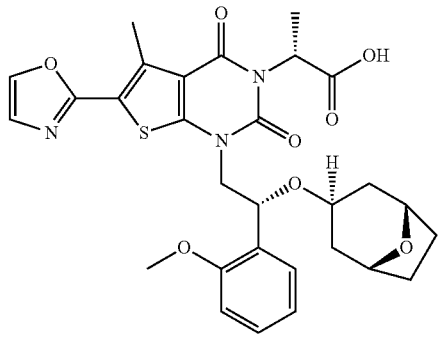 [SMILES: COc1ccccc1[C@H](Cn1c(=O)n([C@H](C)C(=O)O)c(=O)c2c(C)c(-c3ncco3)sc21)O[C@@H]1C[C@H]2CC[C@@H](C1)O2]

Trifluoroacetic acid (1 mL) was added to a solution of tert-butyl (R)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)propanoate (0.085 mmol) in dichloromethane (2 mL). The reaction mixture was stirred for 4 hours. The reaction mixture was then concentrated, dissolved in DMF and purified by HPLC (Gemini, 5-100% ACN/H₂O+0.1% TFA). Product was lyophilized to give (R)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)propanoic acid. MS (m/z) 581.81 [M+H]⁺.

Step 5: (R)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide

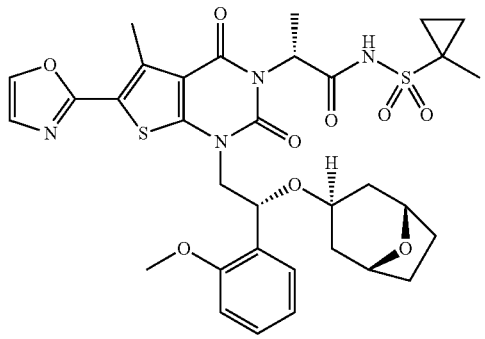 [SMILES: COc1ccccc1[C@H](Cn1c(=O)n([C@H](C)C(=O)NS(=O)(=O)C2(C)CC2)c(=O)c2c(C)c(-c3ncco3)sc21)O[C@@H]1C[C@H]2CC[C@@H](C1)O2]

Diisopropylethylamine (0.131 mmol) was added to a solution of (R)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)propanoic acid (0.065 mmol) in DMF (1.0 mL), followed by addition of HATU (0.078 mmol). The resulting solution was stirred at room temperature for 4 hours.

In a separate flask, 1-methylcyclopropane-1-sulfonamide (0.294 mmol) was dissolved in DMF (0.7 mL) and cooled to 0° C. Sodium hydride (60% in mineral oil, 0.261 mmol) was added and reaction mixture was stirred for 35 minutes at 0° C. in an ice bath. The ice bath was removed and stirring continued for 90 minutes. The resulting mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by normal phase chromatography (10-100% EtOAc/Hex) to give product that was re-purified by HPLC (Gemini, 5-100% ACN/H₂O+0.1% TFA) to give (R)-2-(1-((R)-2-(((1R,3s,5S)-8-oxabicyclo[3.2.1]octan-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide after lyophilization. MS (m/z) 697.66 [M−H]⁻. ¹H NMR (400 MHz, Methanol-d4) δ 8.01 (d, J=0.9 Hz, 1H), 7.52 (dd, J=7.5, 1.8 Hz, 1H), 7.40-7.29 (m, 2H), 7.09-6.92 (m, 2H), 5.46 (dq, J=39.9, 7.1 Hz, 1H), 4.41-4.24 (m, 2H), 4.17 (d, J=6.6 Hz, 2H), 3.88 (d, J=9.8 Hz, 3H), 3.64 (tt, J=10.8, 5.6 Hz, 2H), 2.88 (d, J=6.8 Hz, 3H), 1.93-1.62 (m, 5H), 1.55 (d, J=6.6 Hz, 9H), 1.43-1.26 (m, 2H), 0.93 (dddd, J=28.8, 9.2, 6.9, 5.1 Hz, 2H).

Example 19: Preparation of 2-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide

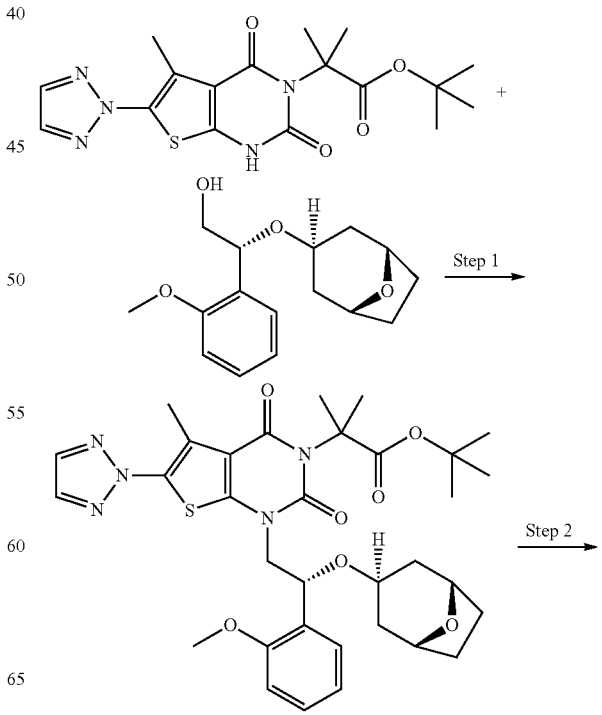

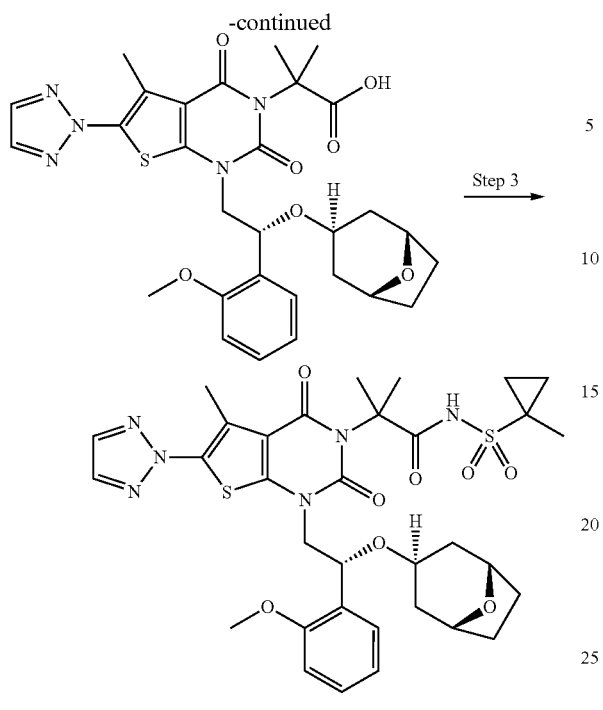

Step 1: tert-butyl 2-(1-((R)-2-(((1R,3s,5S)-8-oxabi-cyclo[3.2.1]oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-m ethylpropanoate

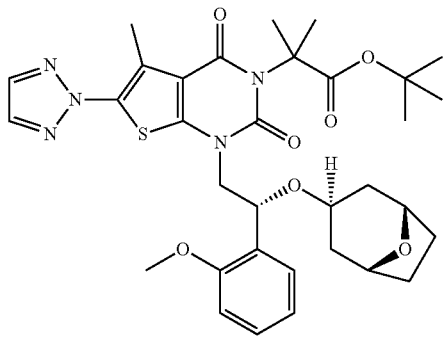 [SMILES: COc1ccccc1[C@H](Cn1c(=O)n(C(C)(C)C(=O)OC(C)(C)C)c(=O)c2c(C)c(-n3nccn3)sc21)O[C@@H]1C[C@H]2CC[C@@H](C1)O2]

In a vial, triphenylphosphine (3 mmol) was dissolved in 2-MeTHF (6 mL) and cooled to 0° C. Diisopropyl azodicarboxylate (3 mmol) was added and the reaction mixture was stirred at 0° C. for 30 minutes, then stirred at room temperature for an additional 20 minutes to give a suspension.

In a separate flask, tert-butyl 2-methyl-2-(5-methyl-2,4-dioxo-6-(2H-1,2,3-triazol-2-yl)-1,4-dihydrothieno[2,3-d]pyrimidin-3(2H)-yl)propanoate, prepared according to WO 2017/091617 (0.6 mmol) and (R)-2-(((1R,3s,5S)-8-oxabicyclo[3.2.1]octan-3-yl)oxy)-2-(2-methoxyphenyl)ethan-1-ol (0.72 mmol) were dissolved in 2-MeTHF (3.0 mL). The mixture from above was added dropwise, giving a solution that was stirred at room temperature for 14 hours. The reaction mixture was concentrated, dissolved in a minimal amount of DCM/Hex and purified twice by normal phase chromatography (0-40% EtOAC/Hex), followed by preparative HPLC (Gemini, 5-100% ACN/H₂O+0.1% TFA) to give tert-butyl 2-(1-((R)-2-(((1R,3s,5S)-8-oxabicyclo[3.2.1]octan-3-yl)oxy)-2-(2-m ethoxyphenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoate (the polar product). MS (m/z) 674.14 [M+Na]⁺.

Step 2: 2-(1-((R)-2-(((1R,3s,5S)-8-oxabicyclo[3.2.1] octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-m ethylpropanoic acid

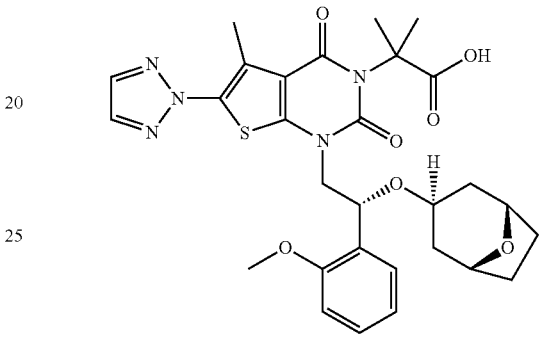

Trifluoroacetic acid (2 mL) was added to a solution of tert-butyl 2-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoate (0.391 g, 0.6 mmol) in dichloromethane (5 mL). The reaction mixture was stirred for one hour. The reaction mixture was concentrated, dissolved in DMF and purified by HPLC (Gemini, 5-100% ACN/H₂O+0.1% TFA). The product was lyophilized to give 2-(1-((R)-2-(((1R,3s,5S)-8-oxabicyclo[3.2.1]octan-3-yl) oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoic acid. MS (m/z) 595.87 [M+H]⁺.

Step 3: 2-(1-((R)-2-(((1R,3s,5S)-8-oxabicyclo[3.2.1] octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide

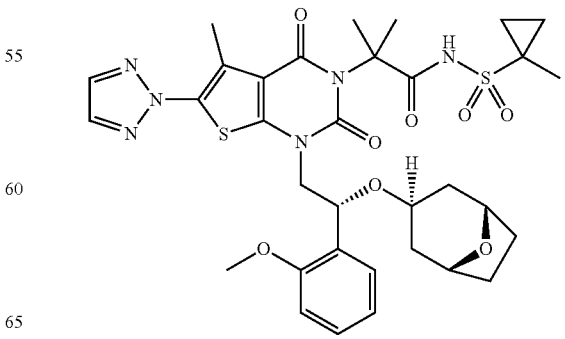

Diisopropylethylamine (0.29 mmol) was added to a solution of 2-(1-((R)-2-(((1R,3s,5S)-8-oxabicyclo[3.2.1]octan-3-yl)oxy)-2-(2-m ethoxyphenyl)ethyl)-5-methyl-2,4-dioxo-6-(2H-1,2,3-triazol-2-yl)-1,4-dihydrothieno[2,3-d]pyrimidin-3 (2H)-yl)-2-methylpropanoic acid (0.15 mmol) in DMF (1.0 mL), followed by the addition of HATU (0.178 mmol). The resulting solution was stirred at room temperature for 4 hours.

In a separate flask, 1-methylcyclopropane-1-sulfonamide (0.67 mmol) was dissolved in DMF (2 mL) and cooled to 0° C. Sodium hydride (60% in mineral oil, 0.59 mmol) was added and reaction mixture was stirred for 35 minutes at 0° C. in an ice bath. The ice bath was removed and stirring continued for 90 minutes. This mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by HPLC (Gemini, 5-100% ACN/H$_2$O+0.1% TFA) to give 2-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide after lyophilization. MS (m/z) 712.88 [M+H]$^+$. $^1$H NMR (400 MHz, Methanol-d4) δ 7.99 (d, J=7.4 Hz, 2H), 7.50 (dd, J=7.6, 1.7 Hz, 1H), 7.37-7.23 (m, 1H), 7.12-6.83 (m, 2H), 5.48-5.26 (m, 1H), 4.33 (d, J=19.7 Hz, 2H), 4.19-3.94 (m, 2H), 3.84 (s, 3H), 3.65 (dq, J=10.6, 5.5 Hz, 1H), 2.60 (d, J=5.1 Hz, 3H), 2.05-1.66 (m, 9H), 1.66-1.46 (m, 7H), 1.46-1.35 (m, 2H), 0.93 (t, J=4.0 Hz, 3H).

Example 20: Preparation of 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide

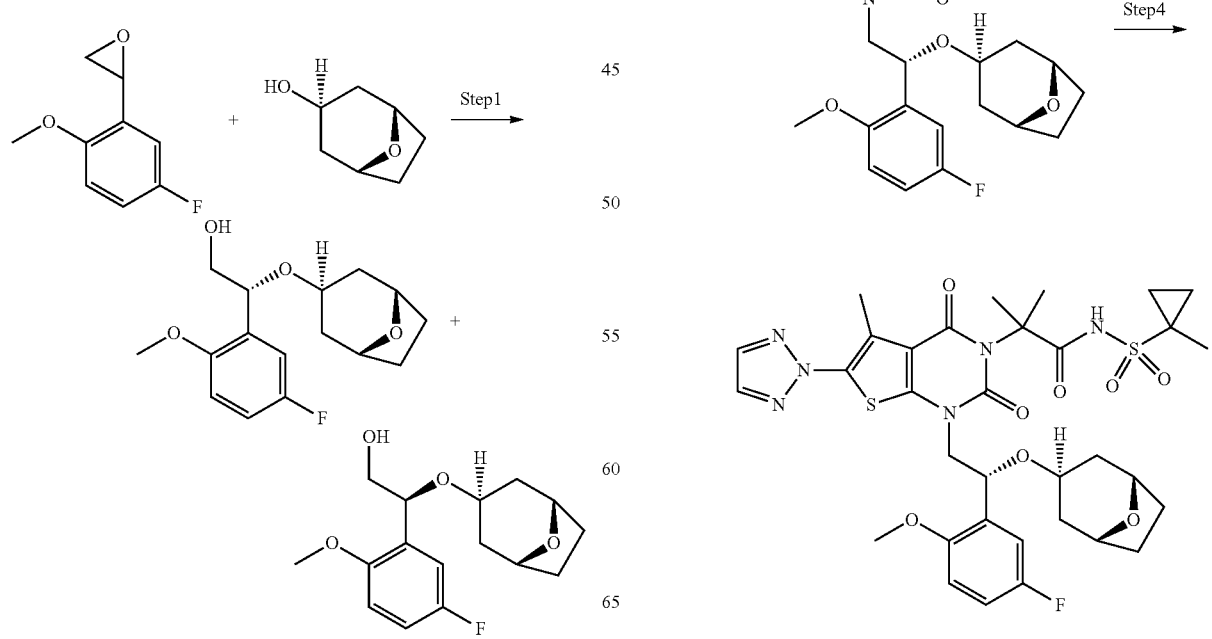

Step 1: (R)-2-(((1S,5S)-8-oxabicyclo[3.2.1]octan-3-yl)oxy)-2-(5-fluoro-2-methoxyphenyl)ethan-1-ol

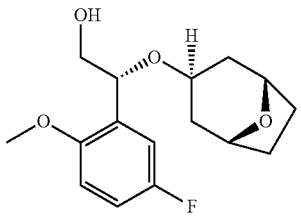 [SMILES: COc1ccc(F)cc1[C@H](CO)O[C@@H]1C[C@H]2CC[C@@H](C1)O2]

Exo-8-oxabicyclo[3.2.1]octan-3-ol (3 mmol) was dissolved in DCM (1 mL) at room temperature. Er(OTf)$_3$ (0.268 mmol) was added to one portion. The resulting reaction mixture was cooled to 0° C. under argon. A solution of 2-(5-fluoro-2-methoxyphenyl)oxirane (4 mmol) in DCM (1 mL) was added dropwise at 0° C. and the resulting reaction mixture was stirred for 2 hours. The reaction mixture was purified directly on silica gel column (0-100% EtOAc/Hex) to afford product as a racemic mixture. Resolution of this racemic mixture by SFC (IF, 5 μm 21×250 mm, EtOH—NH$_3$ co-solvent) afforded (R)-2-(((1S,5S)-8-oxabicyclo[3.2.1]octan-3-yl)oxy)-2-(5-fluoro-2-m ethoxyphenyl) ethan-1-ol (second peak). MS (m/z) 297.10 [M+H]$^+$.

Step 2: tert-butyl 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-m ethylpropanoate

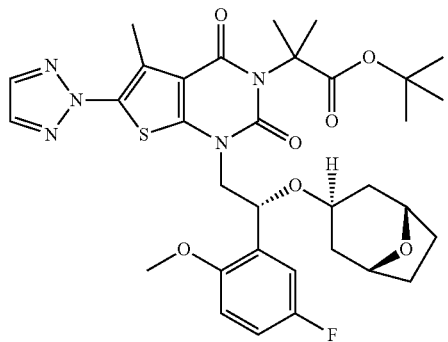 [SMILES: COc1ccc(F)cc1[C@H](Cn1c(=O)n(C(C)(C)C(=O)OC(C)(C)C)c(=O)c2c(C)c(-n3nccn3)sc21)O[C@@H]1C[C@H]2CC[C@@H](C1)O2]

tert-Butyl 2-methyl-2-(5-methyl-2,4-dioxo-6-(2H-1,2,3-triazol-2-yl)-1,4-dihydrothieno[2,3-d]pyrimidin-3(2H)-yl) propanoate was prepared as described in WO 2017/091617.

tert-Butyl 2-methyl-2-(5-methyl-2,4-dioxo-6-(2H-1,2,3-triazol-2-yl)-1,4-dihydrothieno[2,3-d]pyrimidin-3(2H)-yl) propanoate (0.204 mmol) and (R)-2-(((1S,5S)-8-oxabicyclo[3.2.1]octan-3-yl)oxy)-2-(5-fluoro-2-methoxyphenyl)ethan-1-ol (0.266 mmol) were mixed with THF (2 mL) at room temperature. Diisopropyl azodicarboxylate (0.307 mmol) and triphenylphosphine (0.307 mmol) were added sequentially. The reaction mixture was stirred at room temperature in a sealed tube for 17 hours. The reaction mixture was then purified directly on a silica gel column (0-100% EtOAc/Hex) to afford a mixture of N-alkylated and O-alkylated products. These two regioisomers were separated with HPLC (Gemini, 5-100% ACN/H$_2$O+0.1% TFA) to afford tert-butyl 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoate (first peak). MS (m/z): 668.30 [M−H]$^−$.

Step 3: 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoic acid

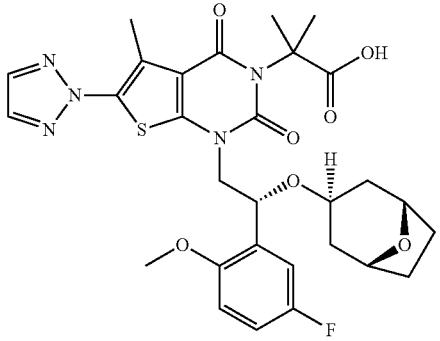 [SMILES: COc1ccc(F)cc1[C@H](Cn1c(=O)n(C(C)(C)C(=O)O)c(=O)c2c(C)c(-n3nccn3)sc21)O[C@@H]1C[C@H]2CC[C@@H](C1)O2]

Concentrated sulfuric acid (3 mL) was added to water (3 mL) with vigorous stirring at 0° C., followed by addition of isopropanol (6 mL). tert-Butyl 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoate (0.07 mmol) was treated with 3 mL of the above sulfuric acid solution at 0° C. The reaction mixture was allowed to warm to room temperature with stirring and kept at room temperature for 8 hours. The reaction mixture was diluted with water (5 mL), extracted with EtOAc (5 mL) and the organic phase was separated, washed with water and concentrated. The residue was purified with HPLC (Gemini, 5-100% ACN/H$_2$O+0.1% TFA) and lyophilized from ACN/H$_2$O to afford 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoic acid. MS (m/z) 612.22 [M−H]$^−$.

Step 4: 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide

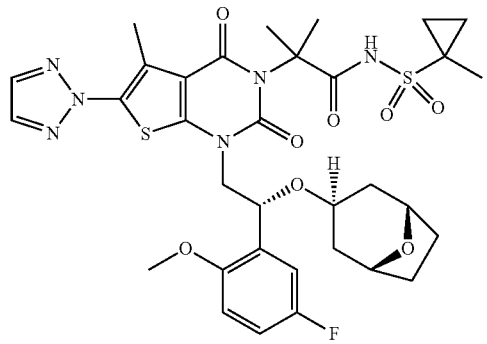 [SMILES: COc1ccc(F)cc1[C@H](Cn1c(=O)n(C(C)(C)C(=O)NS(=O)(=O)C2(C)CC2)c(=O)c2c(C)c(-n3nccn3)sc21)O[C@@H]1C[C@H]2CC[C@@H](C1)O2]

2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoic acid (0.06 mmol) was dissolved in DMF (1 mL) at room temperature under argon. Diisopropylethylamine (0.422 mmol) and HATU (0.072 mmol) were added sequentially. The reaction mixture was stirred under argon at room temperature for 17 hours.

Sodium hydride (60% in mineral oil, 0.64 mmol) was added at room temperature to a solution of 1-methylcyclopropane-1-sulfonamide (0.663 mmol) in DMF (1 mL). The reaction mixture was stirred for one hour to afford a slurry. The above solution was added dropwise over 5 minutes. The resulting reaction mixture was stirred at room temperature for 15 minutes. The reaction mixture was diluted with EtOAc (10 mL) and partitioned between 1N HCl and EtOAc. The organic phase was separated and concentrated. Residue was dissolved in a minimal amount of dichloromethane, and adsorbed onto and purified by preparative TLC (silica gel, 1/1 EtOAc/Heptane) to afford 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide. MS (m/z) 729.62 [M–H]⁻. $^1$H NMR (400 MHz, Acetonitrile-d3) δ 8.81 (s, 1H), 7.96 (s, 2H), 7.25 (dd, J=9.3, 3.2 Hz, 1H), 7.14-6.99 (m, 1H), 6.94 (dd, J=9.0, 4.4 Hz, 1H), 5.27 (dd, J=8.5, 4.6 Hz, 1H), 4.27 (d, J=15.3 Hz, 2H), 4.15 (d, J=14.4 Hz, 1H), 3.90 (d, J=11.1 Hz, 1H), 3.81 (s, 3H), 3.62 (tt, J=10.9, 5.7 Hz, 1H), 2.59 (s, 3H), 1.89-1.65 (m, 4H), 1.77 (s, 3H), 1.75 (s, 3H), 1.53 (s, 3H), 1.64-1.39 (m, 5H), 1.39-1.25 (m, 1H), 1.00-0.85 (m, 2H).

Example 21: Preparation of 2-(1-((R)-2-(((1R,3r,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide

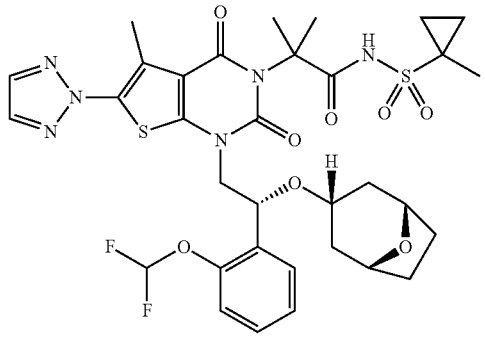 [SMILES: Cc1c(-n2nccn2)sc2c1c(=O)n(C(C)(C)C(=O)NS(=O)(=O)C1(C)CC1)c(=O)n2C[C@H](O[C@H]1C[C@H]2CC[C@@H](C1)O2)c1ccccc1OC(F)F]

2-(1-((R)-2-(((1R,3r,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide was prepared in a manner similar to Example 13 except using endo-8-oxabicyclo[3.2.1]octan-3-ol instead of exo-8-oxabicyclo[3.2.1]octan-3-ol in Step 1, tert-butyl 2-methyl-2-(5-methyl-2,4-dioxo-6-(2H-1,2,3-triazol-2-yl)-1,4-dihydrothieno[2,3-d]pyrimidin-3(2H)-yl)propanoate instead of tert-butyl 1-(5-methyl-6-(oxazol-2-yl)-2,4-dioxo-1,4-dihydrothieno[2,3-d]pyrimidin-3(2H)-yl)cyclopropane-1-carboxylate in Step 3, and 1-methylcyclopropane-1-sulfonamide instead of 2-methylpropane-2-sulfonamide in Step 5. Chiral separation of 24(1R,3r,5S)-8-oxabicyclo[3.2.1]octan-3-yl)oxy)-2-(2-(difluoromethoxy)phenyl)ethan-1-ol was carried out in Step 2 using SFC IF 5% IPA-NH₃ to give (R)-2-(((1R,3r,5S)-8-oxabicyclo[3.2.1]octan-3-yl)oxy)-2-(2-(difluoromethoxy)phenyl)ethan-1-ol as the second peak. MS (m/z) 747.70 [M–H]⁻. $^1$H NMR (400 MHz, Acetonitrile-d3) δ 8.81 (s, 1H), 7.97 (s, 2H), 7.65 (dd, J=7.6, 1.9 Hz, 1H), 7.42 (td, J=7.7, 1.9 Hz, 1H), 7.35 (td, J=7.5, 1.3 Hz, 1H), 7.18 (d, J=7.5 Hz, 1H), 6.84 (t, J=73.8 Hz, 1H), 5.40 (dd, J=9.0, 4.8 Hz, 1H), 4.26-4.09 (m, 3H), 4.09-3.91 (m, 1H), 3.46 (t, J=5.1 Hz, 1H), 2.60 (s, 3H), 1.90-1.83 (m, 2H), 1.80 (s, 3H), 1.77 (s, 3H), 1.74-1.62 (m, 5H), 1.61-1.54 (m, 3H), 1.53 (s, 3H), 0.95-0.88 (m, 2H).

Example 22: Preparation of 1-(1-((R)-2-(((1R,3r,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-(tert-butylsulfonyl)cyclopropane-1-carboxamide

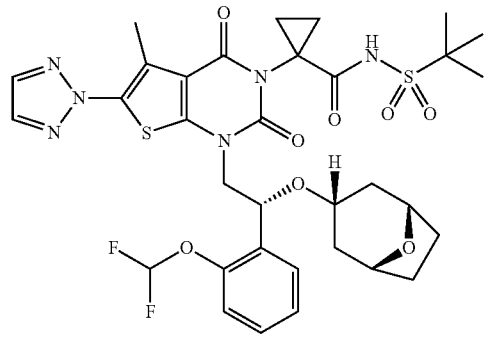 [SMILES: Cc1c(-n2nccn2)sc2c1c(=O)n(C1(C(=O)NS(=O)(=O)C(C)(C)C)CC1)c(=O)n2C[C@H](O[C@H]1C[C@H]2CC[C@@H](C1)O2)c1ccccc1OC(F)F]

1-(1-((R)-2-(((1R,3r,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-(tert-butylsulfonyl)cyclopropane-1-carboxamide was prepared in a manner similar to Example 13 except using endo-8-oxabicyclo[3.2.1]octan-3-ol instead of exo-8-oxabicyclo[3.2.1]octan-3-ol in Step 1 and tert-butyl 1-(5-methyl-2,4-dioxo-6-(2H-1,2,3-triazol-2-yl)-1,4-dihydrothieno[2,3-d]pyrimidin-3(2H)-yl)cyclopropane-1-carboxylate instead of tert-butyl 1-(5-methyl-6-(oxazol-2-yl)-2,4-dioxo-1,4-dihydrothieno[2,3-d]pyrimidin-3(2H)-yl)cyclopropane-1-carboxylate in Step 3. Chiral separation of 24(1R,3r,5S)-8-oxabicyclo[3.2.1]octan-3-yl)oxy)-2-(2-(difluoromethoxy)phenyl)ethan-1-ol was carried out in Step 2 using SFC IF 5% WA-NH₃ to give (R)-2-(((1R,3r,5S)-8-oxabicyclo[3.2.1]octan-3-yl)oxy)-2-(2-(difluoromethoxy)phenyl)ethan-1-ol as the second peak. MS (m/z) 747.69 [M–H]⁻. $^1$H NMR (400 MHz, Acetonitrile-d3) δ 8.68 (d, J=70.9 Hz, 1H), 7.95 (s, 2H), 7.69-7.52 (m, 1H), 7.47-7.24 (m, 2H), 7.24-7.03 (m, 1H), 6.81 (t, J=73.9 Hz, 1H), 5.35 (s, 1H), 4.65-4.40 (m, 1H), 4.26-4.01 (m, 2H), 3.89-3.57 (m, 1H), 3.54-3.35 (m, 1H), 2.61 (s, 3H), 1.91-1.79 (m, 3H), 1.79-1.68 (m, 3H), 1.69-1.45 (m, 4H), 1.37 (s, 9H), 1.32-1.19 (m, 2H).

Example 23: Preparation of 1-(1-((R)-2-(((1R,3r,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

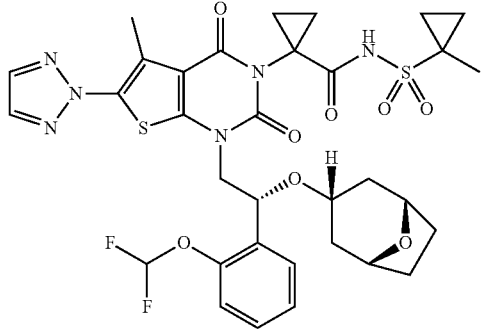 [SMILES: Cc1c(-n2nccn2)sc2c1c(=O)n(C1(C(=O)NS(=O)(=O)C3(C)CC3)CC1)c(=O)n2C[C@H](O[C@H]1C[C@H]2CC[C@@H](C1)O2)c1ccccc1OC(F)F]

1-(1-((R)-2-(((1R,3r,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide was prepared in a manner similar to Example 13 except using endo-8-oxabicyclo[3.2.1]octan-3-ol instead of exo-8-oxabicyclo[3.2.1]octan-3-ol in Step 1, tert-butyl 1-(5-methyl-2,4-dioxo-6-(2H-1,2,3-triazol-2-yl)-1,4-dihydrothieno[2,3-d]pyrimidin-3(2H)-yl)cyclopropane-1-carboxylate instead of tert-butyl 1-(5-methyl-6-(oxazol-2-yl)-2,4-dioxo-1,4-dihydrothieno[2,3-d]pyrimidin-3(2H)-yl)cyclopropane-1-carboxylate in Step 3, and 1-methylcyclopropane-1-sulfonamide instead of 2-methylpropane-2-sulfonamide in Step 5. Chiral separation of 2-(((1R,3r,5S)-8-oxabicyclo[3.2.1]octan-3-yl)oxy)-2-(2-(difluoromethoxy)phenyl)ethan-1-ol was carried out in Step 2 using SFC IF 5% WA-NH₃ to give (R)-2-(((1R,3r,5S)-8-oxabicyclo[3.2.1]octan-3-yl)oxy)-2-(2-(difluoromethoxy)phenyl)ethan-1-ol as the second peak. MS (m/z) 745.69 [M−H]⁻. 1H NMR (400 MHz, Acetonitrile-d3) δ 8.91 (d, J=84.5 Hz, 1H), 7.95 (s, 2H), 7.68-7.53 (m, 1H), 7.48-7.25 (m, 2H), 7.15 (dd, J=19.6, 8.1 Hz, 1H), 6.81 (t, J=73.9 Hz, 1H), 5.36 (s, 1H), 4.61-4.40 (m, 1H), 4.12 (d, J=21.2 Hz, 2H), 3.93-3.59 (m, 1H), 3.54-3.36 (m, 1H), 2.65-2.57 (m, 3H), 1.89-1.81 (m, 3H), 1.65 (d, J=54.3 Hz, 7H), 1.51-1.46 (m, 2H), 1.46 (s, 3H), 1.35-1.17 (m, 2H), 0.93-0.85 (m, 2H).

Example 24: Preparation of 2-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide

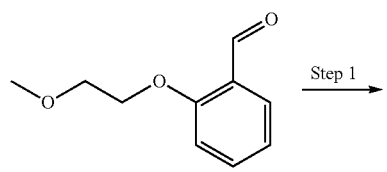

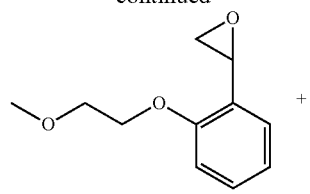

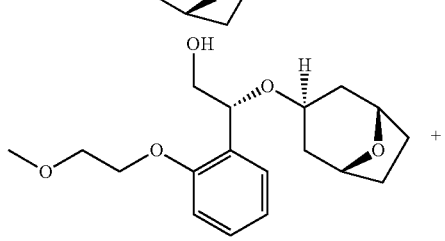

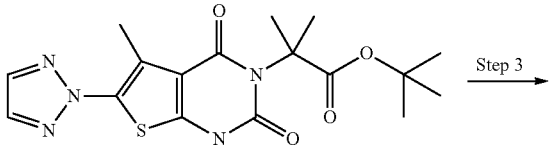

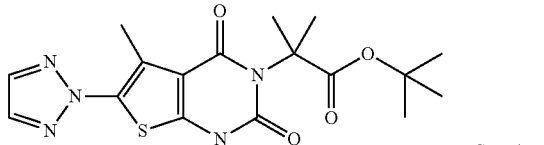

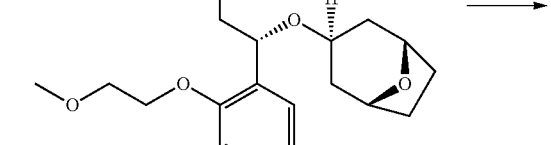

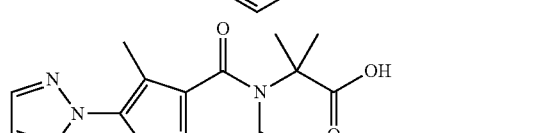

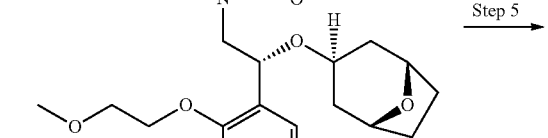

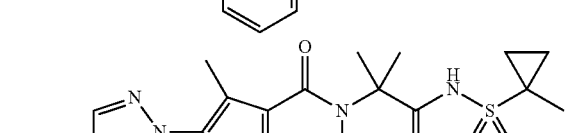

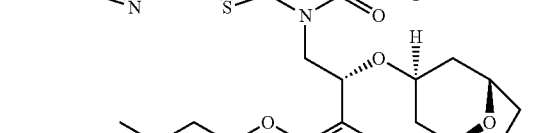

Step 1: 2-(2-(2-methoxyethoxy)phenyl)oxirane

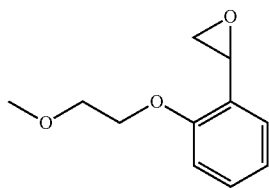

Trimethylsulfonium iodide (33 mmol) was dissolved in DMSO (10 mL) at room temperature under argon. Sodium hydride (60% in mineral oil) (33 mmol) was added and stirred at room temperature for one hour. A solution of 2-(2-methoxyethoxy)benzaldehyde (28 mmol) in DMSO (2 mL) was added dropwise and the reaction mixture was stirred for 17 hours. The reaction mixture was diluted with EtOAc (10 mL) and poured onto NH$_4$Cl/water (20 mL). The organic phase was separated and washed with water and brine, and concentrated. The residue was purified on silica gel column with 0-100% EtOAc/Hex to afford 2-(2-(2-methoxyethoxy)phenyl)oxirane. MS (m/z) 195.12 [M+H]$^+$.

Step 2: (R)-2-(((1R,3r,5S)-8-oxabicyclo[3.2.1]octan-3-yl)oxy)-2-(2-(2-methoxyethoxy)phenyl)ethan-1-ol

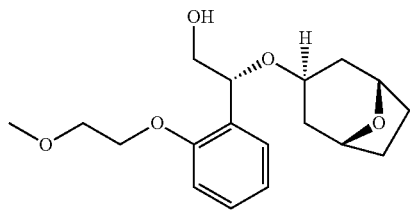 [SMILES: COCCOc1ccccc1[C@H](CO)O[C@@H]1C[C@H]2CC[C@@H](C1)O2]

Exo-8-oxabicyclo[3.2.1]octan-3-ol (693 mg, 5 mmol) was dissolved in DCM (2 mL) and Er(OTf)$_3$ (0.4 mmol) was added to one portion. The resulting reaction mixture was cooled to 0° C. under argon. A solution of 2-(2-(2-methoxyethoxy)phenyl)oxirane (4 mmol) in DCM (1 mL) was added dropwise and the resulting reaction mixture was stirred for 2 hours. The reaction mixture was purified directly on silica gel column (0-100% EtOAc/Hex) to afford a racemic mixture. Resolution of the racemic mixture by SFC (AD-H 5 µm 21×250 mm, MeOH co-solvent) afforded (R)-2-(((1R,3r,5S)-8-oxabicyclo[3.2.1]octan-3-yl)oxy)-2-(2-(2-methoxyethoxy)phenyl)ethan-1-ol (second peak). MS (m/z) 323.22 [M+H]$^+$.

Step 3: tert-butyl 2-(2-((R)-2-(((1R,3r,5S)-8-oxabicyclo[3.2.1]octan-3-yl)oxy)-2-(2-(2-methoxyethoxy)phenyl)ethoxy)-5-methyl-4-oxo-6-(2H-1,2,3-triazol-2-yl)thieno[2,3-c]pyrimidin-3(4H)-yl)-2-methylpropanoate

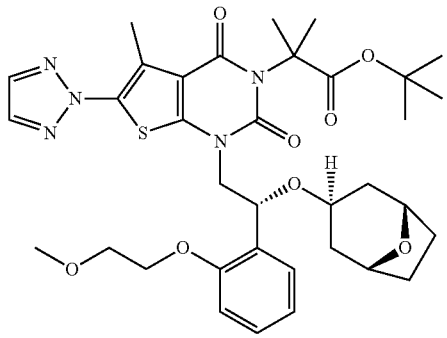 [SMILES: COCCOc1ccccc1[C@H](Cn1c(=O)n(C(C)(C)C(=O)OC(C)(C)C)c(=O)c2c(C)c(-n3nccn3)sc21)O[C@@H]1C[C@H]2CC[C@@H](C1)O2]

tert-Butyl 2-methyl-2-(5-methyl-2,4-dioxo-6-(2H-1,2,3-triazol-2-yl)-1,4-dihydrothieno[2,3-d]pyrimidin-3(2H)-yl)propanoate (0.204 mmol) and (R)-2-(((1R,3r,5S)-8-oxabicyclo[3.2.1]octan-3-yl)oxy)-2-(2-(2-methoxyethoxy)phenyl)ethan-1-ol (0.266 mmol) were dissolved in THF (2 mL). Diisopropyl azodicarboxylate (0.307 mmol) and triphenylphosphine (0.307 mmol) were added sequentially and the reaction mixture was stirred at room temperature in a sealed tube for 17 hours. The reaction mixture was purified directly on silica gel column (0-100% EtOAc/Hex) to afford a mixture of tert-butyl 2-methyl-2-(5-methyl-2,4-dioxo-6-(2H-1,2,3-triazol-2-yl)-1,4-dihydrothieno[2,3-d]pyrimidin-3(2H)-yl)propanoate and tert-butyl 2-(2-((R)-2-(((1R,3r,5S)-8-oxabicyclo[3.2.1]octan-3-yl)oxy)-2-(2-(2-methoxyethoxy)phenyl)ethoxy)-5-methyl-4-oxo-6-(2H-1,2,3-triazol-2-yl)thieno[2,3-d]pyrimidin-3(4H)-yl)-2-methylpropanoate. MS (m/z) 694.31 [M–H]$^-$.

Step 4: 2-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoic acid

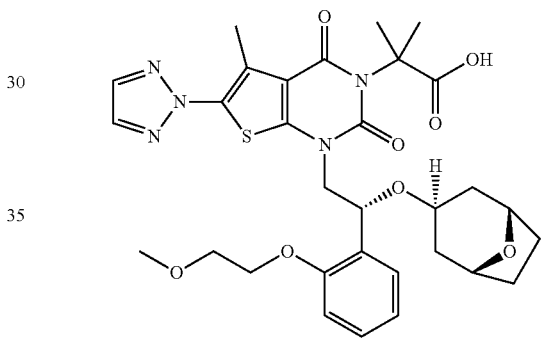

Concentrated sulfuric acid (3 mL) was added to water (3 mL) with vigorous stirring at 0° C., followed by an addition of isopropanol (6 mL). A mixture of tert-butyl 2-methyl-2-(5-methyl-2,4-dioxo-6-(2H-1,2,3-triazol-2-yl)-1,4-dihydrothieno[2,3-d]pyrimidin-3(2H)-yl)propanoate and tert-butyl 2-(2-((R)-2-(((1R,3r,5S)-8-oxabicyclo[3.2.1]octan-3-yl)oxy)-2-(2-(2-methoxyethoxy)phenyl)ethoxy)-5-methyl-4-oxo-6-(2H-1,2,3-triazol-2-yl)thieno[2,3-d]pyrimidin-3(4H)-yl)-2-methylpropanoate (0.23 mmol) was treated with 5 mL of the above sulfuric acid solution at 0° C. The reaction mixture was allowed to warm to room temperature with stirring and kept at room temperature for 8 hours. The reaction mixture was diluted with water (10 mL) and extracted with EtOAc (10 mL). The organic phase was separated, washed with water and concentrated. The residue was purified with HPLC (Gemini, 5-100% ACN/H$_2$O+0.1% TFA) and lyophilized from ACN/H$_2$O to afford 2-(1-((R)-2-(((1R,3s,5S)-8-oxabicyclo[3.2.1]octan-3-yl)oxy)-2-(2-(2-m ethoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoic acid (first peak). MS (m/z) 638.23 [M–H]$^-$.

Step 5: 2-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide

Example 25: Preparation of 1-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

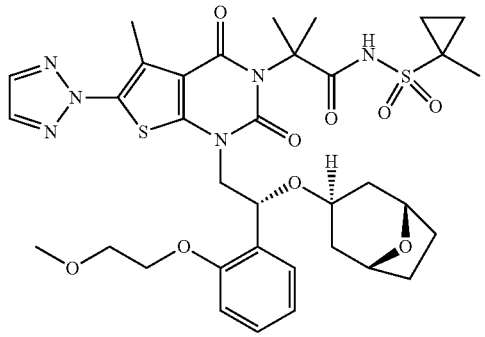 [SMILES: COCCOc1ccccc1[C@H](Cn1c(=O)n(C(C)(C)C(=O)NS(=O)(=O)C2(C)CC2)c(=O)c2c(C)c(-n3nccn3)sc21)O[C@@H]1C[C@H]2CC[C@@H](C1)O2]

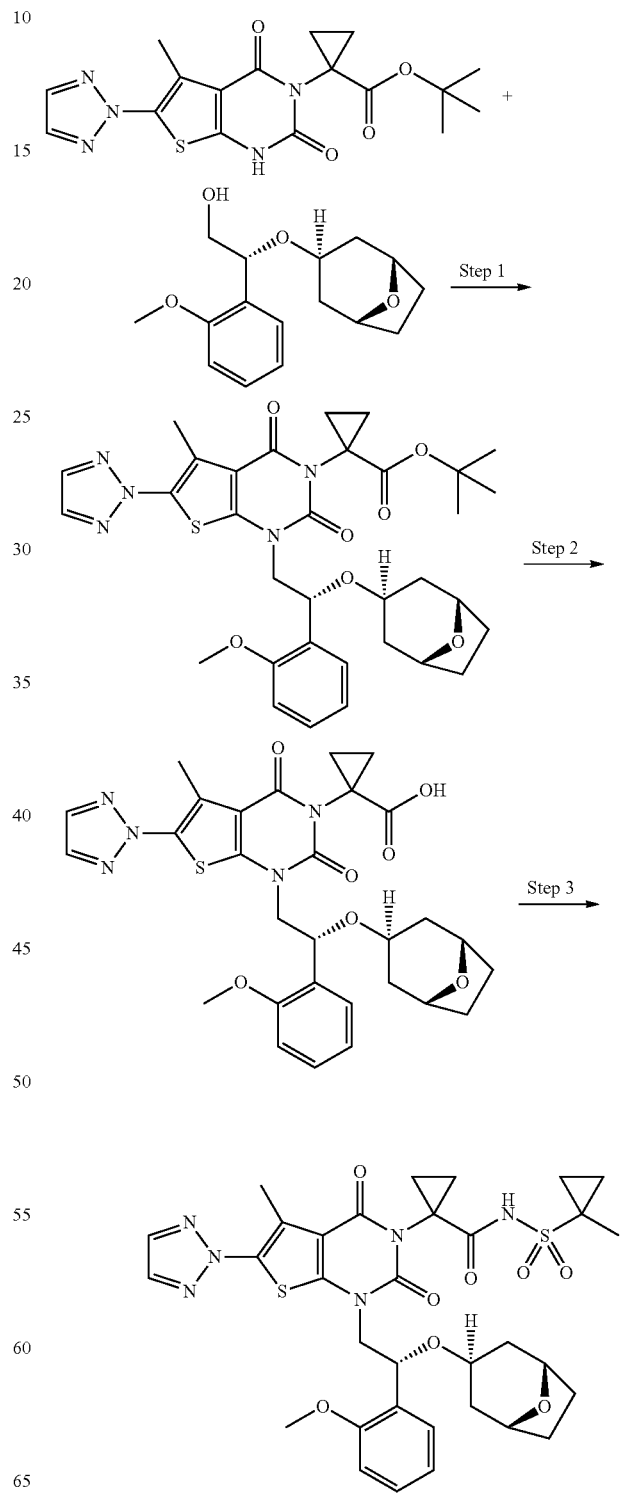

2-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-2-methylpropanoic acid (0.067 mmol) was dissolved in DMF (0.5 mL) at room temperature under argon. Diisopropylethylamine (0.133 mmol) and HATU (0.087 mmol) were added sequentially and the reaction mixture was stirred under argon at room temperature for 17 hours.

In a separate vessel, sodium hydride (60% in mineral oil, 0.334 mmol) was added to a solution of 1-methylcyclopropane-1-sulfonamide (0.4 mmol) in DMF (0.5 mL). The reaction mixture was stirred at room temperature for one hour to afford a slurry. The above solution was added dropwise over 5 minutes to this slurry. The resulting reaction mixture was stirred at room temperature for 15 minutes. The reaction mixture was diluted with EtOAc (5 mL) and partitioned between 1N HCl and EtOAc. The organic phase was separated and concentrated. Residue was dissolved in a minimal amount or dichloromethane, and adsorbed and purified by preparative TLC (silica gel, 1/1 EtOAc/Heptane) to afford 2-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-2-methyl-N-((1-methylcyclopropyl)sulfonyl)propanamide. MS (m/z) 755.78 [M−H]−. $^1$H NMR (400 MHz, Acetonitrile-d3) δ 8.82 (s, 1H), 7.97 (s, 2H), 7.48 (dd, J=7.6, 1.8 Hz, 1H), 7.31 (ddd, J=8.2, 7.4, 1.8 Hz, 1H), 7.17-6.84 (m, 2H), 5.33 (dd, J=9.0, 4.1 Hz, 1H), 4.32-4.12 (m, 6H), 3.95 (dd, J=14.3, 9.0 Hz, 1H), 3.75 (t, J=4.7 Hz, 2H), 3.57 (tt, J=10.9, 5.7 Hz, 1H), 3.32 (s, 3H), 2.60 (s, 3H), 1.87-1.61 (m, 3H), 1.79 (s, 3H), 1.74 (s, 3H), 1.59-1.35 (m, 6H), 1.53 (s. 3H), 1.33-1.20 (m, 1H), 0.97-0.88 (m, 2H).

Step 1: tert-butyl 1-(1-((R)-2-(((1R,3r,5S)-8-oxabi-cyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate

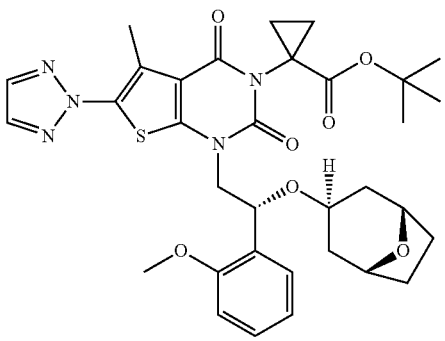 [SMILES: COc1ccccc1[C@H](Cn1c(=O)n(C2(C(=O)OC(C)(C)C)CC2)c(=O)c2c(C)c(-n3nccn3)sc21)O[C@@H]1C[C@H]2CC[C@@H](C1)O2]

tert-Butyl 1-(5-methyl-2,4-dioxo-6-(2H-1,2,3-triazol-2-yl)-1,4-dihydrothieno[2,3-d]pyrimidin-3(2H)-yl)cyclopropane-1-carboxylate (0.231 mmol) and (R)-2-(((1S,5S)-8-oxabicyclo[3.2.1]octan-3-yl)oxy)-2-(2-methoxyphenyl)ethan-1-ol (0.291 mmol) were dissolved in THF (2 mL). Diisopropyl azodicarboxylate (0.347 mmol) and triphenylphosphine (0.347 mmol) were added sequentially. The reaction mixture was stirred at room temperature in a sealed tube for 17 hours. The reaction mixture was purified directly on silica gel column (0-100% EtOAc/Hex) to afford a mixture of N-alkylated and O-alkylated products that was purified further by HPLC (Gemini, 5-100% ACN/H₂O+0.1% TFA) and lyophilized from ACN/H₂O to afford tert-butyl 1-(1-((R)-2-(((1R,3r,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate. MS (m/z) 650.26 [M+H]$^+$.

Step 2: 1-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid

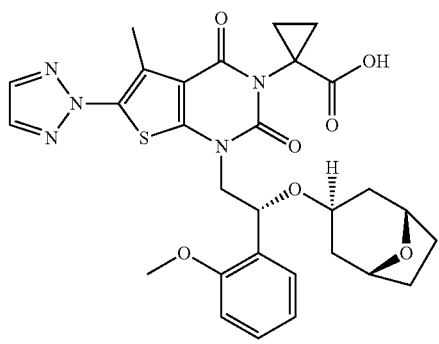

Concentrated sulfuric acid (3 mL) was added to water (3 mL) with vigorous stirring at 0° C., followed by addition of isopropanol (6 mL). tert-Butyl 1-(1-((R)-2-(((1R,3r,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate (0.066 mmol) was treated with 2 mL of the above sulfuric acid solution at 0° C. The reaction mixture was allowed to warm to room temperature with stirring and kept at room temperature for 3 hours. The reaction mixture was diluted with water (3 mL) and extracted with EtOAc (3 mL). The organic phase was separated, washed with water and concentrated. The residue was purified with HPLC (Gemini, 5-100% ACN/H₂O+0.1% TFA) and lyophilized from ACN/H₂O to afford the 1-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid. MS (m/z) 592.22 [M–H]$^-$.

Step 3: 1-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

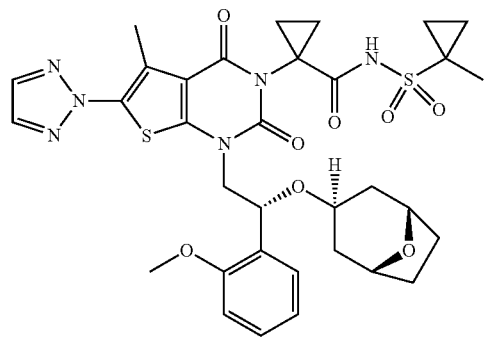 [SMILES: COc1ccccc1[C@H](Cn1c(=O)n(C2(C(=O)NS(=O)(=O)C3(C)CC3)CC2)c(=O)c2c(C)c(-n3nccn3)sc21)O[C@@H]1C[C@H]2CC[C@@H](C1)O2]

1-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid (23.6 µmol) was dissolved in DMF (0.5 mL) at room temperature under argon. Diisopropylethylamine (47 µmol) and HATU (28 µmol) were added sequentially. The reaction mixture was stirred under argon at room temperature for 17 hours.

In a separate vessel, sodium hydride (60% in mineral oil, 94 µmop was added at room temperature to a solution of 1-methylcyclopropane-1-sulfonamide (106 µmol) in DMF (0.5 mL). The reaction mixture was stirred for one hour to afford a slurry. The above solution was added dropwise over 5 minutes to this slurry. The resulting reaction mixture was stirred at room temperature for 20 minutes. The reaction mixture was diluted with EtOAc (5 mL) and partitioned between 1N HCl and EtOAc. The organic phase was separated and concentrated. Residue was dissolved in a minimal amount of dichloromethane, and adsorbed onto and purified by preparative TLC (silica gel, 1/1 EtOAc/Heptane) to afford 1-(1-((R)-2-(((1R,3s,5S)-8-oxabicyclo[3.2.1]octan-3-yl)oxy)-2-(2-methoxyphenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide. MS (m/z) 709.69 [M–H]$^-$. $^1$H NMR (400 MHz, Acetonitrile-d3) δ 8.97 (d, J=18.0 Hz, 1H), 7.97 (s, 2H), 7.49 (d, J=26.0 Hz, 1H), 7.40-7.24 (m, 1H), 7.09-6.97 (m, 2H), 5.37-5.28 (m, 1H), 4.64-4.36 (m, 1H), 4.31-4.2 (m, 2H), 3.93-3.76 (m, 4H), 3.68-3.52 (m, 1H), 2.64 (s, 3H), 1.93-1.64 (m, 7H), 1.49 (s, 3H), 1.58-1.34 (m, 5H), 1.33-1.12 (m, 2H), 0.97-0.88 (m, 2H).

Example 26: Preparation of 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

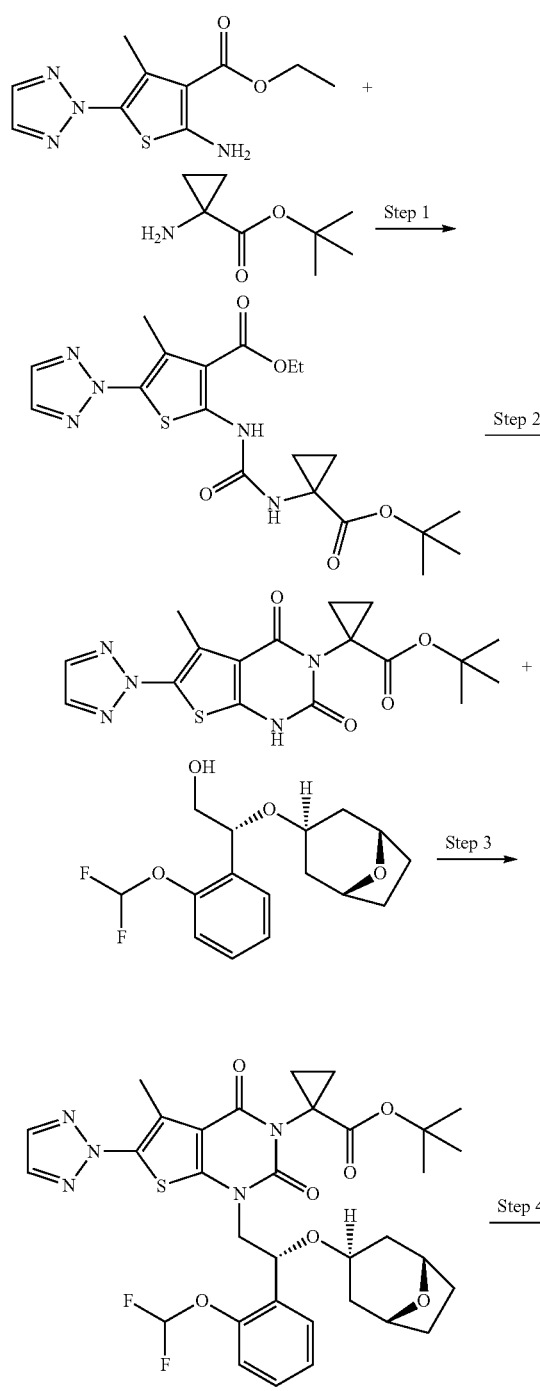

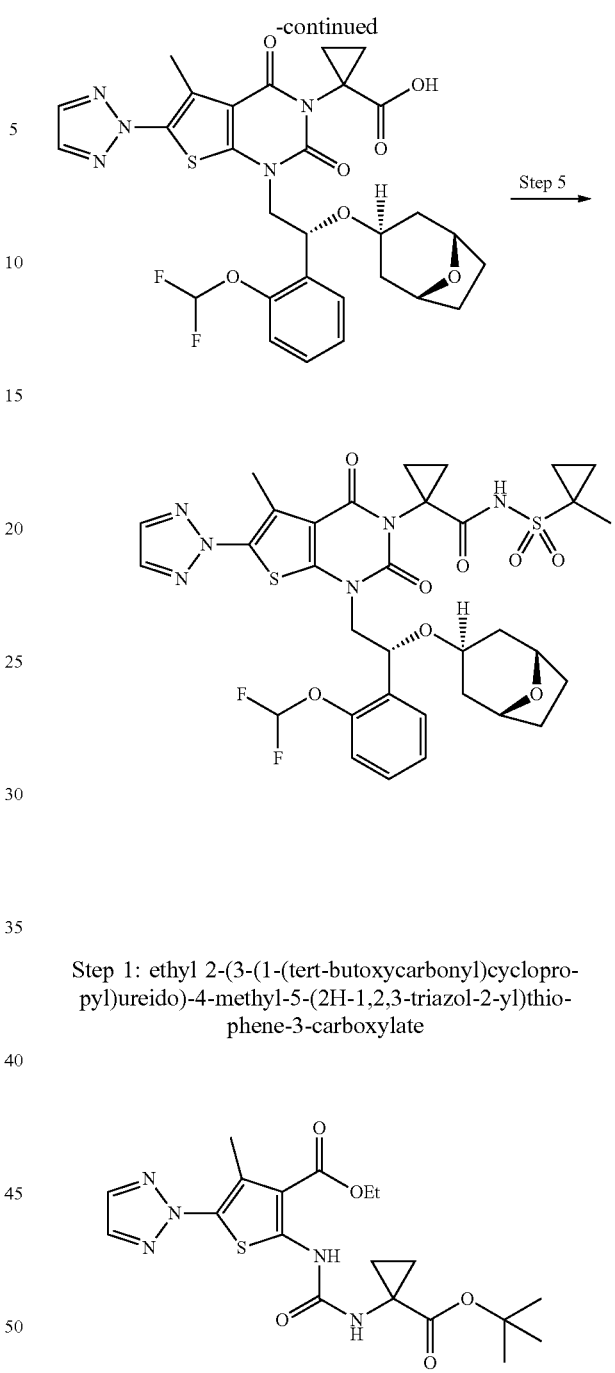

Step 1: ethyl 2-(3-(1-(tert-butoxycarbonyl)cyclopropyl)ureido)-4-methyl-5-(2H-1,2,3-triazol-2-yl)thiophene-3-carboxylate Triphosgene (2 mmol) was added at 0° C. to a mixture of ethyl 2-amino-4-methyl-5-(2H-1,2,3-triazol-2-yl)thiophene-3-carboxylate, prepared according to WO 2017/075056 (6 mmol) in dichloromethane (100 mL), followed by a slow addition of triethylamine (18 mmol). The reaction mixture was stirred for 1 hour at 0° C., then at room temperature for two hours. tert-Butyl 1-aminocyclopropane-1-carboxylate (8 mmol) was added and the reaction mixture was stirred at room temperature overnight. The reaction mixture was filtered to remove solid materials, concentrated and purified by normal phase chromatography (0-100% EtOAc/Hex) to give ethyl 2-(3-(1-(tert-butoxycarbonyl)cyclopropyl)ureido)-4-methyl-5-(2H-1,2,3-triazol-2-yl)thiophene-3-carboxylate. MS (m/z) 435.84 [M+H]$^+$.

Step 2: tert-butyl 1-(5-methyl-2,4-dioxo-6-(2H-1,2,3-triazol-2-yl)-1,4-dihydrothieno[2,3-d]pyrimidin-3(2H)-yl)cyclopropane-1-carboxylate

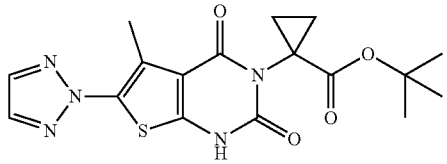 [SMILES: Cc1c(-n2nccn2)sc2[nH]c(=O)n(C3(C(=O)OC(C)(C)C)CC3)c(=O)c12]

A mixture of ethyl 2-(3-(1-(tert-butoxycarbonyl)cyclopropyl)ureido)-4-methyl-5-(2H-1,2,3-triazol-2-yl)thiophene-3-carboxylate (2 mmol), cesium carbonate (9 mmol) in dioxane/tert-butanol mixture (4 mL/4 mL) was stirred at 90° C. for 4 hours. The reaction mixture was concentrated, dissolved in ethyl acetate and washed with 1N HCl solution. Aqueous layer was back extracted with ethyl acetate (2×) and combined organic layers were washed with brine, dried (MgSO₄), filtered and purified by normal phase chromatography (0-100% EtOAc/Hex) to give tert-butyl 1-(5-methyl-2,4-dioxo-6-(2H-1,2,3-triazol-2-yl)-1,4-dihydrothieno[2,3-d]pyrimidin-3(2H)-yl)cyclopropane-1-carboxylate. MS (m/z) 388.35 [M−H]⁻.

Step 3: tert-butyl 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate

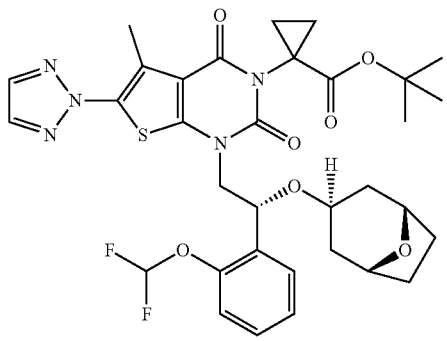 [SMILES: Cc1c(-n2nccn2)sc2c1c(=O)n(C1(C(=O)OC(C)(C)C)CC1)c(=O)n2C[C@H](O[C@@H]1C[C@H]2CC[C@@H](C1)O2)c1ccccc1OC(F)F]

In a vial, triphenylphosphine (0.354 g, 1 mmol) was dissolved in 2-MeTHF (6 mL) and cooled to 0° C. Diisopropyl azodicarboxylate (0.26 mL, 1 mmol) was added and the reaction mixture was stirred at 0° C. for 30 minutes, then stirred at room temperature for an additional 20 minutes to give a suspension.

In a separate flask, tert-butyl 1-(5-methyl-2,4-dioxo-6-(2H-1,2,3-triazol-2-yl)-1,4-dihydrothieno[2,3-d]pyrimidin-3(2H)-yl)cyclopropane-1-carboxylate (0.45 mmol) and (R)-2-(((1R,3s,5S)-8-oxabicyclo[3.2.1]octan-3-yl)oxy)-2-(2-(difluoromethoxy)phenyl)ethan-1-ol (0.45 mmol) were dissolved in 2-MeTHF (3.0 mL). The above mixture was added dropwise, giving a solution that was stirred at room temperature for 14 hours. The reaction mixture was concentrated, dissolved in minimal amount of DCM/Hexane and purified twice by normal phase chromatography (0-40% EtOAC/Hex) to give tert-butyl 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate. MS (m/z) 685.84 [M+H]⁺.

Step 4: 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid

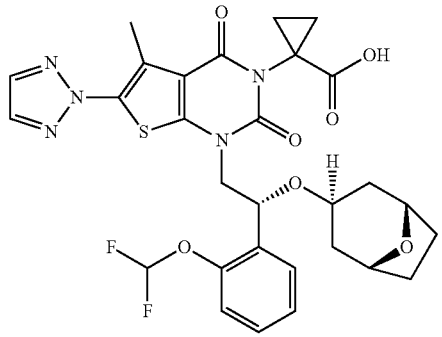 [SMILES: Cc1c(-n2nccn2)sc2c1c(=O)n(C1(C(=O)O)CC1)c(=O)n2C[C@H](O[C@@H]1C[C@H]2CC[C@@H](C1)O2)c1ccccc1OC(F)F]

Trifluoroacetic acid (0.5 mL) was added to a solution of tert-butyl 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3 (2H)-yl)cyclopropane-1-carboxylate (0.102 mmol) in dichloromethane (1 mL). The reaction mixture was stirred for one hour. The reaction mixture was concentrated, dissolved in DMF and purified by HPLC (Gemini, 5-100% ACN/H₂O+0.1% TFA). Product was lyophilized to give 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3 (2H)-yl)cyclopropane-1-carboxylic acid. MS (m/z) 629.90 [M+H]⁺.

Step 5: 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

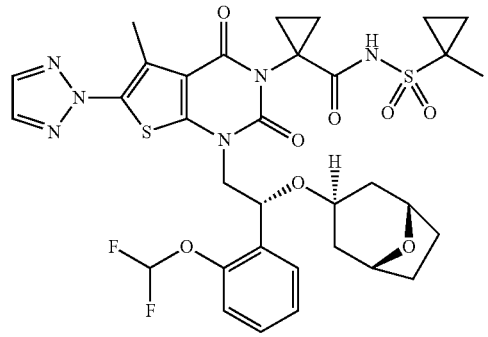 [SMILES: Cc1c(-n2nccn2)sc2c1c(=O)n(C1(C(=O)NS(=O)(=O)C3(C)CC3)CC1)c(=O)n2C[C@H](O[C@@H]1C[C@H]2CC[C@@H](C1)O2)c1ccccc1OC(F)F]

Diisopropylethylamine (14 μL, 0.079 mmol) was added to a solution of 1-(1-((R)-2-(((1R,3s,5S)-8-oxabicyclo[3.2.1]

octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid (0.04 mmol) in DMF (1.0 mL), followed by addition of HATU (0.047 mmol). The resulting solution was stirred at room temperature for 4 hours.

In a separate flask, 1-methylcyclopropane-1-sulfonamide (0.179 mmol) was dissolved in DMF (0.7 mL) and cooled to 0° C. Sodium hydride (60% in mineral oil, 0.159 mmol) was added and reaction mixture was stirred for 35 minutes at 0° C. in an ice bath. The ice bath was removed and stirring continued for 90 minutes. This mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by HPLC (Gemini, 5-100% ACN/H$_2$O+0.1% TFA) to give 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide after lyophilization. MS (m/z) 746.88 [M+H]$^+$. $^1$H NMR (400 MHz, Methanol-d4) δ 7.98 (s, 2H), 7.72-7.50 (m, 1H), 7.50-7.13 (m, 3H), 7.13-6.72 (m, 1H), 5.37 (s, 1H), 4.62 (d, J=20.0 Hz, 1H), 4.36 (d, J=34.9 Hz, 2H), 3.91-3.57 (m, 2H), 2.63 (d, J=10.3 Hz, 3H), 1.99-1.67 (m, 6H), 1.52 (d, J=27.8 Hz, 9H), 1.23-0.96 (m, 2H), 0.79 (m, 2H).

Example 27: 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide Diisopropylethylamine (0.079 mmol) was added to a solution of 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid (0.04 mmol) in DMF (1.0 mL), followed by addition of HATU (0.047 mmol). The resulting solution was stirred at room temperature for 4 hours.

In a separate flask, 2-methylpropane-2-sulfonamide (0.179 mmol) was dissolved in DMF (0.7 mL) and cooled to 0° C. Sodium hydride (60% in mineral oil, 0.159 mmol) was added and the reaction mixture was stirred for 35 minutes at 0° C. in an ice bath. The ice bath was removed and stirring continued for 90 minutes. This mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by HPLC (Gemini, 5-100% ACN/H$_2$O+0.1% TFA) to give 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-(tert-butylsulfonyl)cyclopropane-1-carboxamide after lyophilization. MS (m/z) 748.91 [M+H]$^+$. $^1$H NMR (400 MHz, Methanol-d4) δ 7.97 (d, J=8.4 Hz, 2H), 7.75-7.51 (m, 1H), 7.51-7.14 (m, 3H), 7.14-6.70 (m, 1H), 5.35 (ddd, J=18.0, 7.6, 4.5 Hz, 1H), 4.68-4.45 (m, 1H), 4.36 (d, J=37.2 Hz, 2H), 3.86-3.57 (m, 2H), 2.61 (d, J=17.3 Hz, 3H), 2.13-1.92 (m, 1H), 1.81 (d, J=8.3 Hz, 4H), 1.79-1.62 (m, 2H), 1.62-1.41 (m, 3H), 1.28 (s, 9H), 1.06 (d, J=49.9 Hz, 2H).

Example 28: 1-(1-((R)-2-(((1R,3s,5S)-8-oxabicyclo[3.2.1]octan-3-yl)oxy)-2-(2-(difluoromethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

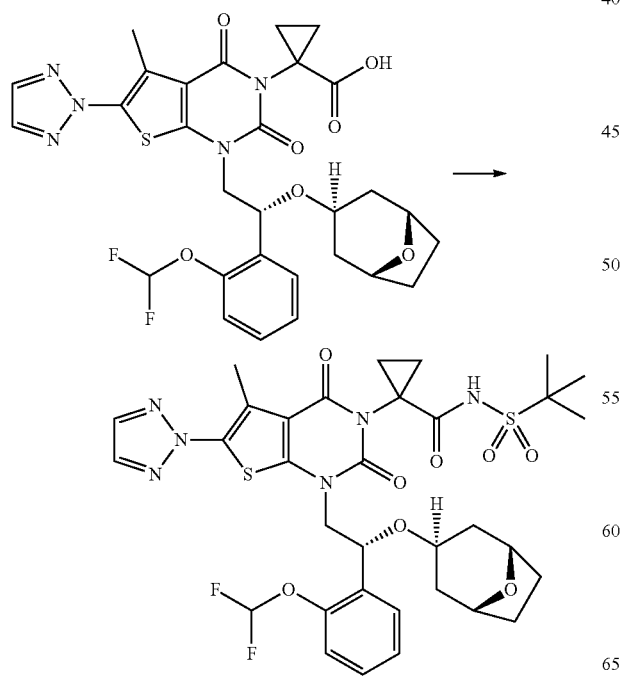

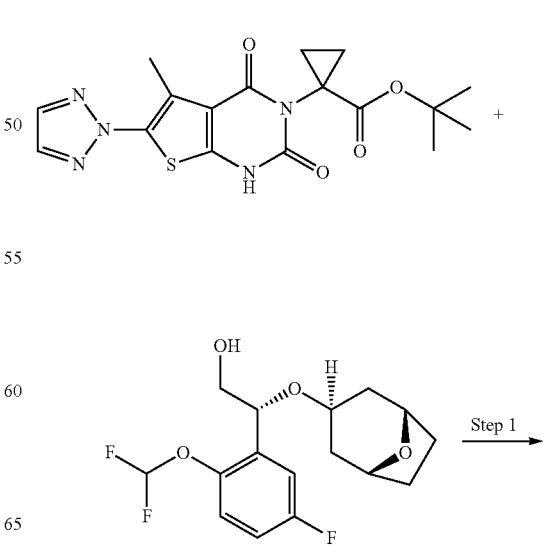

123
-continued

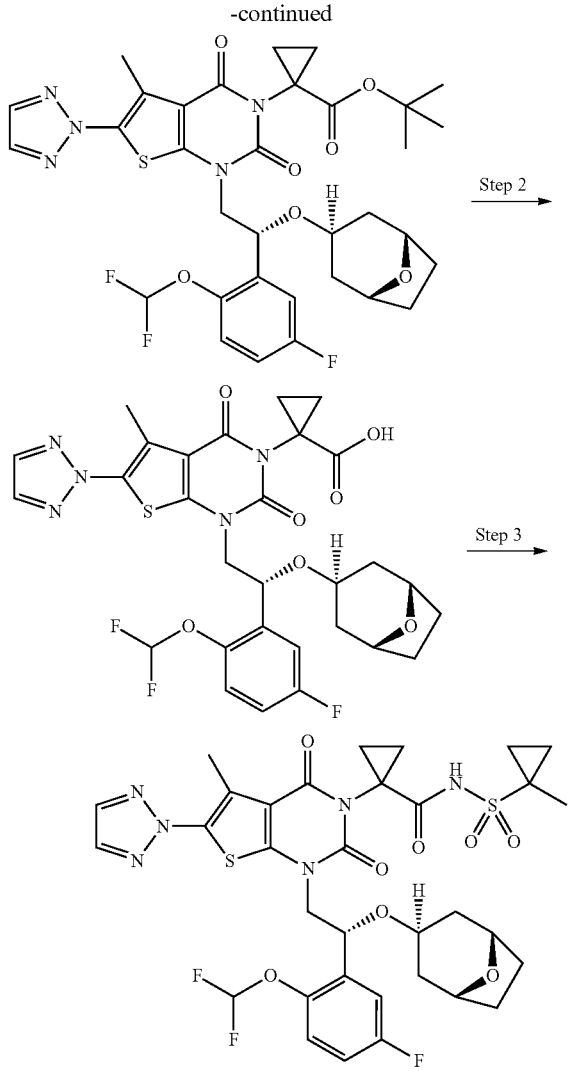

Step 1: tert-butyl 1-(1-((R)-2-(((1R,3s,5S)-8-oxabi-cyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate

124

In a vial, triphenylphosphine (0.27 mmol) was dissolved in 2-MeTHF (2 mL) and cooled to 0° C. Diisopropyl azodicarboxylate (0.27 mmol) was added and the reaction mixture was stirred at 0° C. for 30 minutes, then stirred at room temperature for an additional 20 minutes to give a suspension.

In a separate flask, tert-butyl 1-(5-methyl-2,4-dioxo-6-(2H-1,2,3-triazol-2-yl)-1,4-dihydrothieno[2,3-d]pyrimi-din-3 (2H)-yl)cyclopropane-1-carboxylate (0.09 mmol) and (R)-2-(((1R,3s,5S)-8-oxabicyclo[3.2.1]octan-3-yl)oxy)-2-(2-(difluoromethoxy)-5-fluorophenyl)ethan-1-ol (0.09 mmol) were dissolved in 2-MeTHF (1.0 mL). The above mixture was added dropwise, giving a solution that was stirred at room temperature for 14 hours. The reaction mixture was concentrated, dissolved in minimal amount of DCM/Hex and purified twice by normal phase chromatography (0-40% EtOAC/Hex) gave tert-butyl 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate. MS (m/z) 726.13 [M+Na]+.

Step 2: 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid

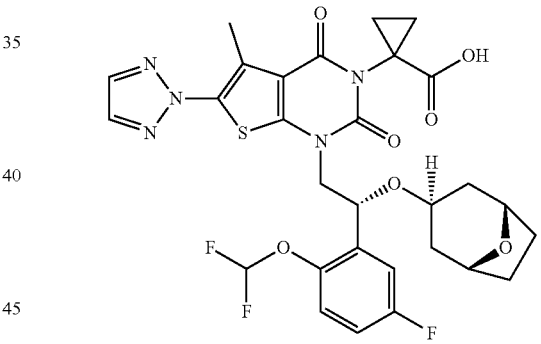

Trifluoroacetic acid (0.5 mL) was added to a solution of tert-butyl 1-(1-((R)-2-(((1R,3 s,5S)-8-oxabicyclo[3.2.1]oc-tan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate (0.023 mmol) in dichloromethane (1 mL). The reaction mixture was stirred for one hour. The reaction mixture was concentrated, dissolved in DMF and purified by HPLC (Gemini, 5-100% ACN/H₂O+0.1% TFA). Product was lyophilized to give 1-(1-((R)-2-(((1R,3s,5S)-8-oxabicy-clo[3.2.1]octan-3-yl)oxy)-2-(2-(difluoromethoxy)-5-fluoro-phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid. MS (m/z) 648.00 [M+H]+.

Step 3: 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

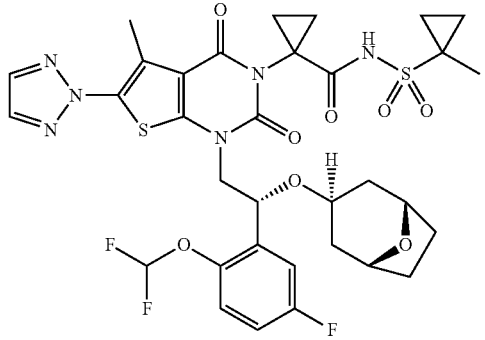 [SMILES: Cc1c(-n2nccn2)sc2c1c(=O)n(C1(C(=O)NS(=O)(=O)C3(C)CC3)CC1)c(=O)n2C[C@H](O[C@@H]1C[C@H]2CC[C@@H](C1)O2)c1cc(F)ccc1OC(F)F]

Diisopropylethylamine (0.018 mmol) was added to a solution of 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid (0.009 mmol) in DMF (1.0 mL), followed by addition of HATU (0.011 mmol). The resulting solution was stirred at room temperature for 4 hours.

In a separate flask, 1-methylcyclopropane-1-sulfonamide (0.041 mmol) was dissolved in DMF (0.7 mL) and cooled to 0° C. Sodium hydride (60% in mineral oil, 0.037 mmol) was added and the reaction mixture was stirred for 35 minutes at 0° C. in an ice bath. The ice bath was removed and stirring continued for 90 minutes. This mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by HPLC (Gemini, 5-100% ACN/H$_2$O+0.1% TFA) to give desired product 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide after lyophilization. MS (m/z) 764.92 [M+H]$^+$. $^1$H NMR (400 MHz, Methanol-d4) δ 7.99 (s, 2H), 7.49-7.12 (m, 3H), 6.92 (t, J=73.5 Hz, 1H), 5.33 (s, 1H), 4.61 (m, 1H), 4.36 (d, J=22.4 Hz, 2H), 3.93-3.56 (m, 2H), 2.64 (s, 3H), 2.11-1.66 (m, 6H), 1.63-1.45 (m, 8H), 1.45-1.11 (m, 3H), 0.91 (d, J=1.9 Hz, 2H).

Example 29: 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)-N-(tert-butylsulfonyl)cyclopropane-1-carboxamide

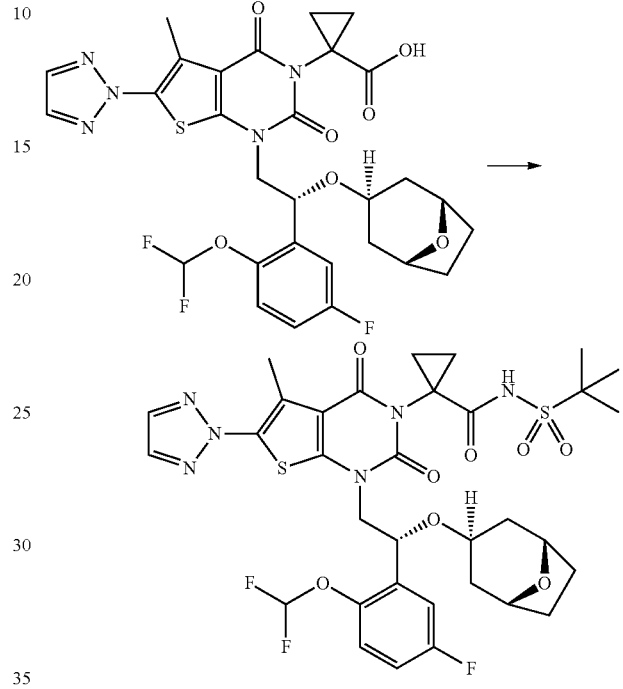

Diisopropylethylamine (0.018 mmol) was added to a solution of 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid (0.009 mmol) in DMF (1.0 mL), followed by an addition of HATU (0.011 mmol). The resulting solution was stirred at room temperature for 4 hours.

In a separate flask, 2-methylpropane-2-sulfonamide (0.041 mmol) was dissolved in DMF (0.7 mL) and cooled to 0° C. Sodium hydride (60% in mineral oil, 0.037 mmol) was added and the reaction mixture was stirred for 35 minutes at 0° C. in an ice bath. The ice bath was removed and stirring continued for 90 minutes. The mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by HPLC (Gemini, 5-100% ACN/H$_2$O+0.1% TFA) to give 1-(1-((R)-2-(((1R,3s,5S)-8-oxabicyclo[3.2.1]octan-3-yl)oxy)-2-(2-(difluoromethoxy)-5-fluorophenyl)ethyl)-5-methyl-2,4-dioxo-6-(2H-1,2,3-triazol-2-yl)-1,4-dihydrothieno[2,3-d]pyrimidin-3 (2H)-yl)-N-(tert-butylsulfonyl)cyclopropane-1-carboxamide after lyophilization. MS (m/z) 766.83 [M+H]$^+$. $^1$H NMR (400 MHz, Methanol-d4) δ 7.99 (s, 2H), 7.20 (d, J=38.0 Hz, 3H), 6.92 (t, J=73.5 Hz, 1H), 5.32 (s, 1H), 4.63 (m, 1H), 4.36 (d, J=21.2 Hz, 2H), 3.79 (d, J=64.0 Hz, 2H), 2.64 (s, 3H), 2.14-1.72 (m, 7H), 1.59 (m, 3H), 1.42 (m, 11H).

127

Example 30: 1-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

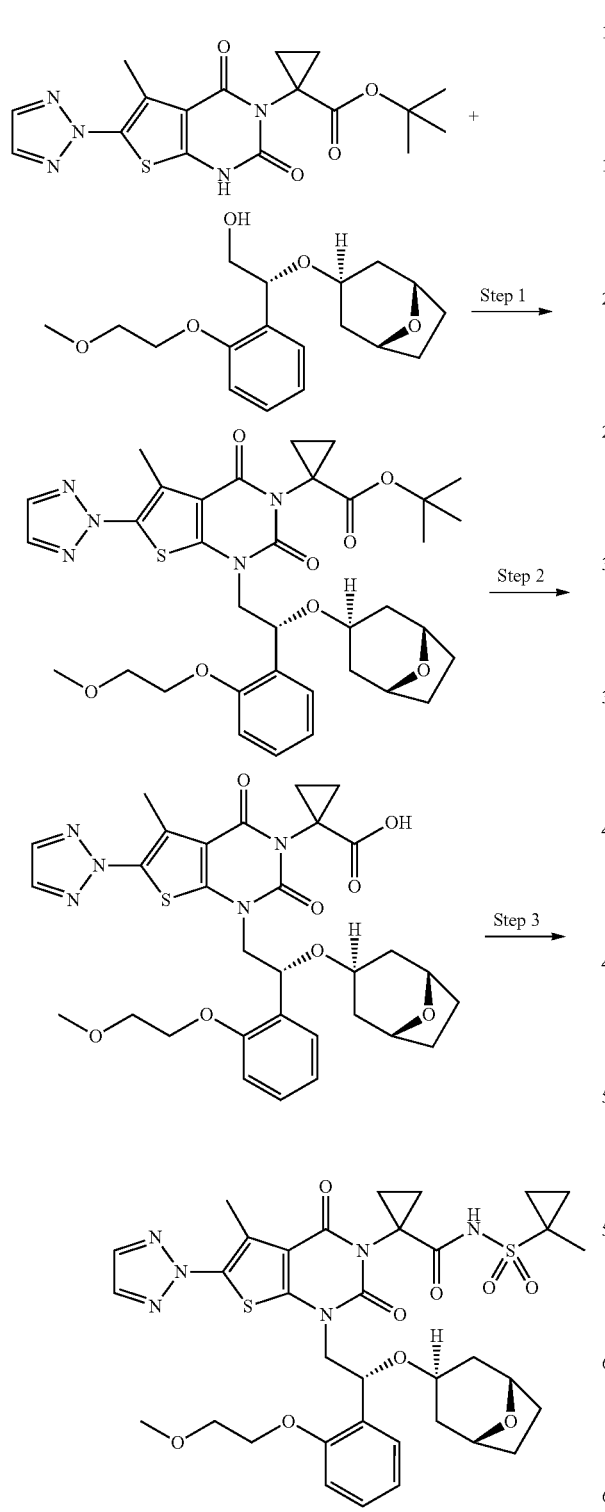

128

Step 1: tert-butyl 1-(1-((R)-2-(((1R,3r,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate

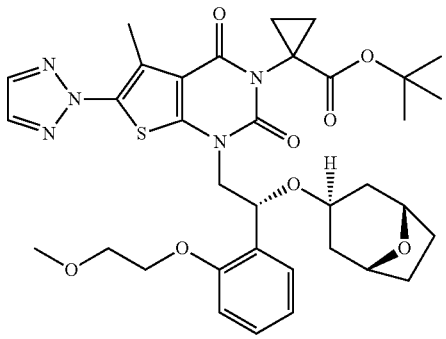 [SMILES: COCCOc1ccccc1[C@H](Cn1c(=O)n(C2(C(=O)OC(C)(C)C)CC2)c(=O)c2c(C)c(-n3nccn3)sc21)O[C@@H]1C[C@H]2CC[C@@H](C1)O2]

tert-Butyl 1-(5-methyl-2,4-dioxo-6-(2H-1,2,3-triazol-2-yl)-1,4-dihydrothieno[2,3-d]pyrimidin-3(2H)-yl)cyclopropane-1-carboxylate (0.169 mmol) and (R)-2-(((1S,5S)-8-oxabicyclo[3.2.1]octan-3-yl)oxy)-2-(2-(2-methoxyethoxy)phenyl)ethan-1-ol (0.264 mmol) were dissolved in THF (2 mL). Diisopropyl azodicarboxylate (0.307 mmol) and triphenylphosphine (0.299 mmol) were added sequentially. The reaction mixture was stirred at room temperature in a sealed tube for 17 hours. The reaction mixture was purified directly using a silica gel column (0-100% EtOAc/Hex) to afford a mixture of N-alkylated and O-alkylated products that was further purified by HPLC (Gemini, 5-100% ACN/$H_2O$+0.1% TFA) and lyophilized from ACN/$H_2O$ to afford tert-butyl 1-(1-((R)-2-(((1R,3r,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylate. MS (m/z) 694.31 $[M+H]^+$.

Step 2: 1-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid

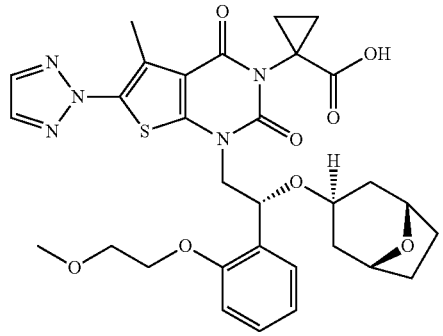 [SMILES: COCCOc1ccccc1[C@H](Cn1c(=O)n(C2(C(=O)O)CC2)c(=O)c2c(C)c(-n3nccn3)sc21)O[C@@H]1C[C@H]2CC[C@@H](C1)O2]

Concentrated sulfuric acid (3 mL) was added to water (3 mL) with vigorous stirring at 0° C., followed by isopropanol (6 mL). tert-Butyl 1-(1-((R)-2-(((1R,3r,5S)-8-oxabicyclo[3.2.1]octan-3-yl)oxy)-2-(2-(2-methoxyethoxy)phenyl)

ethyl)-5-methyl-2,4-dioxo-6-(2H-1,2,3-triazol-2-yl)-1,4-di-hydrothieno[2,3-d]pyrimidin-3(2H)-yl)cyclopropane-1-carboxylate (0.062 mmol) was treated with 2 mL of the above sulfuric acid solution at 0° C. The reaction mixture was allowed to warm to room temperature with stirring and kept at room temperature for 3 hours. The reaction mixture was diluted with water (3 mL) and extracted with EtOAc (3 mL). The organic phase was separated, washed with water and concentrated. The resulting residue was purified by HPLC (Gemini, 5-100% ACN/H$_2$O+0.1% TFA) and lyophilized from ACN/H$_2$O to afford 1-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid. MS (m/z) 636.22 [IVI-1-1]$^-$.

Step 3: 1-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide

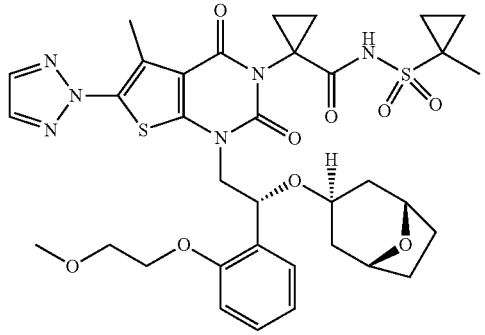 [SMILES: COCCOc1ccccc1[C@H](Cn1c(=O)n(C2(C(=O)NS(=O)(=O)C3(C)CC3)CC2)c(=O)c2c(C)c(-n3nccn3)sc21)O[C@@H]1C[C@H]2CC[C@@H](C1)O2]

1-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)cyclopropane-1-carboxylic acid (6.3 µmol) was dissolved in DMF (0.5 mL) at room temperature under argon. Diisopropylethylamine (12.5 µmol) and HATU (2.9 mg, 7.5 µmol) were added sequentially. The reaction mixture was stirred under argon at room temperature for 17 hours.

In a separate vessel, sodium hydride (60% in mineral oil) (56 µmol) was added at room temperature to a solution of 1-methylcyclopropane-1-sulfonamide (62 µmol) in DMF (0.5 mL). The reaction mixture was stirred for one hour to afford a slurry. The above solution was added dropwise over 5 minutes to this slurry. The resulting reaction mixture was stirred at room temperature for 20 minutes. The reaction mixture was diluted with EtOAc (5 mL) and partitioned between 1N HCl and EtOAc. The organic phase was separated and concentrated. The resulting residue was dissolved in a minimal amount of dichloromethane, and adsorbed onto and purified by preparative TLC (silica gel, 1/1 EtOAc/Heptane) to afford 1-(1-((R)-2-(((1R,3s,5S)-8-oxabicyclo[3.2.1]octan-3-yl)oxy)-2-(2-(2-methoxyethoxy)phenyl)ethyl)-5-methyl-2,4-dioxo-6-(2H-1,2,3-triazol-2-yl)-1,4-dihydrothieno[2,3-d]pyrimidin-3(2H)-yl)-N-((1-methylcyclopropyl)sulfonyl)cyclopropane-1-carboxamide. MS (m/z) 753.81 [M–H]$^-$. $^1$H NMR (400 MHz, Acetonitrile-d3) δ 8.99 (d, J=32.5 Hz, 1H), 7.97 (s, 2H), 7.48 (d, J=27.7 Hz, 1H), 7.32 (ddd, J=8.2, 7.4, 1.8 Hz, 1H), 7.02 (d, J=9.4 Hz, 2H), 5.43-5.29 (m, 1H), 4.66-4.41 (m, 1H), 4.36-4.10 (m, 4H), 4.00-3.47 (m, 4H), 3.41-3.25 (m, 3H), 2.64 (s, 3H), 1.94-1.63 (m, 6H), 1.57-1.34 (m, 6H), 1.48 (s, 3H), 1.33-1.11 (m, 2H), 0.96-0.87 (m, 2H).

Example 31: Preparation of 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-methyl-N-((1-methylcyclopropyl)sulfonyl)propanamide

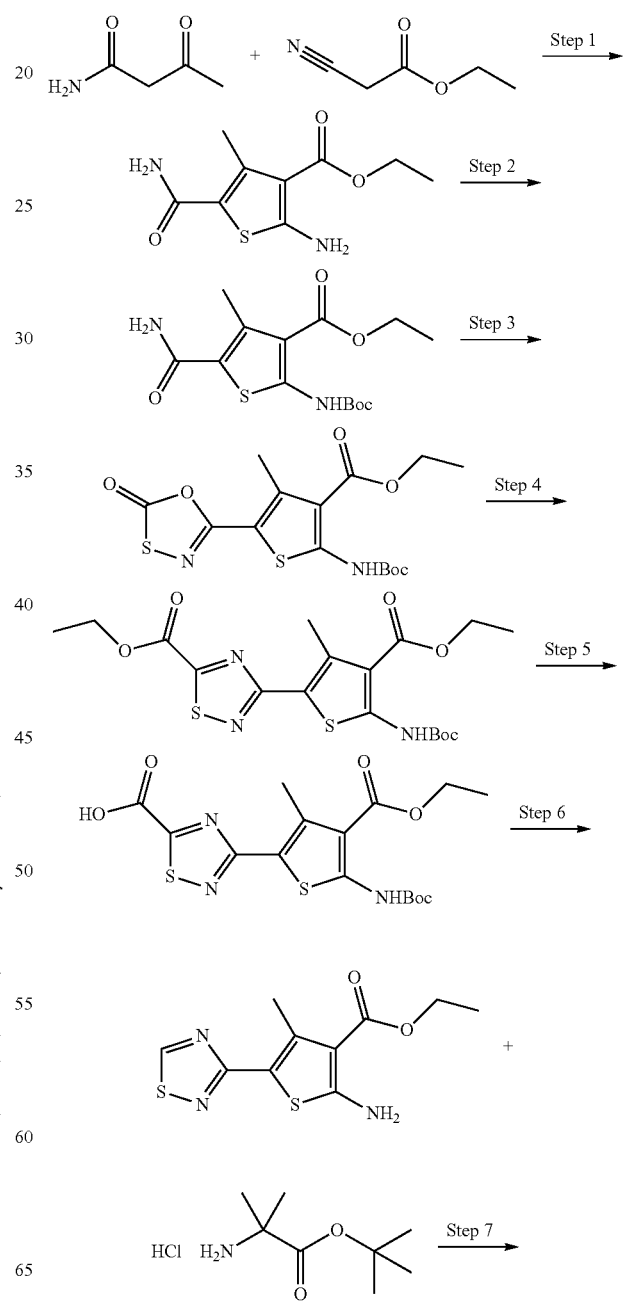

131
-continued

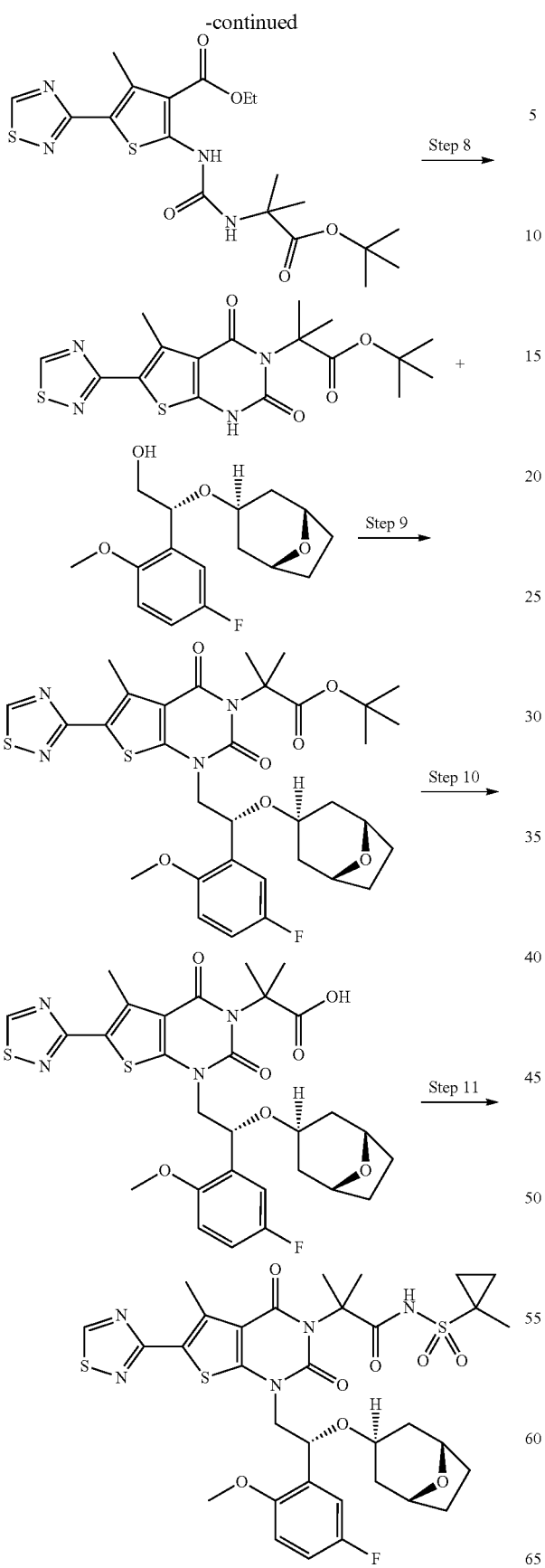

132

Step 1: ethyl 2-amino-5-carbamoyl-4-methylthiophene-3-carboxylate

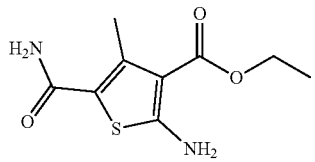

3-Oxobutanamide (499.49 mmol), ethyl 2-cyanoacetate (499.49 mmol), diethylamine (499.06 mmol), ethanol (250 mL), and sulfur (599 mmol) were placed in a 1000-mL round-bottom flask. The resulting solution was stirred for 16 h at 80° C. The reaction mixture was cooled and stored in a refrigerator overnight. The formed solid product was collected, washed with cold EtOH (100 mL) and Et$_2$O (100 mL) to afford ethyl 2-amino-5-carbamoyl-4-methylthiophene-3-carboxylate. MS (m/z): 229.16 [M+H]$^+$.

Step 2: ethyl 2-[[(tert-butoxy)carbonyl]amino]-5-carbamoyl-4-methylthiophene-3-carboxylate

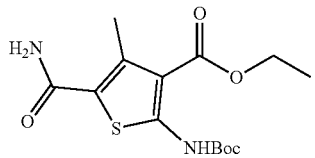 [SMILES: CCOC(=O)c1c(NC(=O)OC(C)(C)C)sc(C(N)=O)c1C]

Ethyl 2-amino-5-carbamoyl-4-methylthiophene-3-carboxylate (175.23 mmol), N,N-dimethylpyridin-4-amine (17.52 mmol), and 1,4-dioxane (1000 mL) were placed in a 2000-mL round-bottom flask. A solution of di-tert-butyl dicarbonate (175.95 mmol) in 1,4-dioxane (40 mL) was added dropwise. The resulting solution was stirred for 48 hours at room temperature. The resulting mixture was concentrated under vacuum. The formed residue was purified on silica gel column (100/1 dichloromethane/methanol) to afford ethyl 2-[[(tert-butoxy)carbonyl]amino]-5-carbamoyl-4-methylthiophene-3-carboxylate. MS (m/z) 329.11 [M+H]$^+$.

Step 3: ethyl 2-[[(tert-butoxy)carbonyl]amino]-4-methyl-5-(2-oxo-2H-1,3,4-oxathiazol-5-yl)thiophene-3-carboxylate

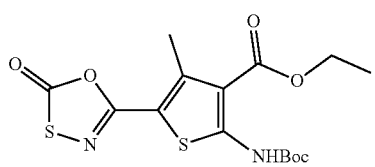 [SMILES: CCOC(=O)c1c(NC(=O)OC(C)(C)C)sc(-c2nsc(=O)o2)c1C]

Ethyl 2-[[(tert-butoxy)carbonyl]amino]-5-carbamoyl-4-methylthiophene-3-carboxylate (51.77 mmol) and tetrahydrofuran (200 mL) were placed in a 500-mL round-bottom flask. Chloro(chlorosulfanyl)methanone (57.26 mmol) was added dropwise to the above solution. The resulting solution was stirred for 1 hour at room temperature. The reaction mixture was concentrated under reduced pressure. The crude product was purified by crystallization from ether (100 mL) to afford ethyl 2-[[(tert-butoxy)carbonyl]amino]-4-methyl-5-(2-oxo-2H-1,3,4-oxathiazol-5-yl)thiophene-3-carboxylate as an off-white solid. MS (m/z) 387.16 [M+H]+.

Step 4: ethyl 3-(5-[[(tert-butoxy)carbonyl]amino]-4-(ethoxycarbonyl)-3-methylthiophen-2-yl)-1,2,4-thiadiazole-5-carboxylate

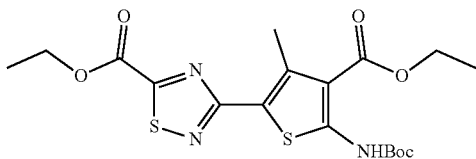 [SMILES: CCOC(=O)c1nc(-c2sc(NC(=O)OC(C)(C)C)c(C(=O)OCC)c2C)ns1]

Ethyl 2-[[(tert-butoxy)carbonyl]amino]-4-methyl-5-(2-oxo-2H-1,3,4-oxathiazol-5-yl)thiophene-3-carboxylate (36.23 mmol, 1.00 equiv), 2-ethoxy-2-oxoacetonitrile (145.33 mmol) and 1,2-dichloroethane (150 mL) were placed in a 500-mL sealed tube. The reaction mixture was irradiated with microwave radiation for 0.5 h at 160° C. The resulting mixture was concentrated under vacuum. The crude product was purified by crystallization from ethanol (50 mL) to afford ethyl 3-(5-[[(tert-butoxy)carbonyl]amino]-4-(ethoxycarbonyl)-3-methylthiophen-2-yl)-1,2,4-thiadiazole-5-carboxylate as a yellow solid. MS (m/z) 442.10 [M+H]+.

Step 5: 3-(5-[[(tert-butoxy)carbonyl]amino]-4-(ethoxycarbonyl)-3-methylthiophen-2-yl)-1,2,4-thiadiazole-5-carboxylic acid

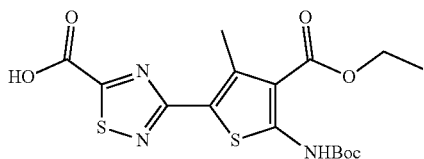 [SMILES: CCOC(=O)c1c(NC(=O)OC(C)(C)C)sc(-c2nsc(C(=O)O)n2)c1C]

Ethyl 3-(5-[[(tert-butoxy)carbonyl]amino]-4-(ethoxycarbonyl)-3-methylthiophen-2-yl)-1,2,4-thiadiazole-5-carboxylate (20.38 mmol), ethanol (200 mL), and sodium hydroxide (2.5 M aq) were placed in a 500-mL round-bottom flask. The resulting solution was stirred for 1 h at room temperature. The resulting mixture of 3-(5-[[(tert-butoxy)carbonyl]amino]-4-(ethoxycarbonyl)-3-methylthiophen-2-yl)-1,2,4-thiadiazole-5-carboxylic acid was used directly in the next step. MS (m/z) 414.07 [M+H]+.

Step 6: ethyl 2-amino-4-methyl-5-(1,2,4-thiadiazol-3-yl)thiophene-3-carboxylate

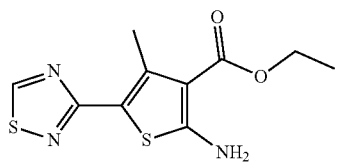 [SMILES: CCOC(=O)c1c(N)sc(-c2ncsn2)c1C]

Concentrated hydrochloric acid (102 mmol) was added to a solution of crude 3-(5-[[(tert-butoxy)carbonyl]amino]-4-(ethoxycarbonyl)-3-methylthiophen-2-yl)-1,2,4-thiadiazole-5-carboxylic acid (20.39 mmol) in ethanol (200 mL). The resulting solution was stirred for 1 hour at 80° C. The resulting mixture was concentrated under vacuum. The resulting solid product was suspended in 100 mL of 15% ammonia and filtered. The crude product was purified on silica gel column (ethyl acetate/petroleum ether (10/90~40/60)) to afford ethyl 2-amino-4-methyl-5-(1,2,4-thiadiazol-3-yl)thiophene-3-carboxylate as a solid. MS (m/z) 270.03 [M+H]+. 41-NMR (300 MHz, CDCl$_3$): δ 9.79 (s, 1H), 6.42 (s, 2H), 4.37 (q, J=7.1 Hz, 2H), 2.89 (s, 3H), 1.42 (t, J=7.1 Hz, 3H).

Step 7: ethyl 2-(3-(1-(tert-butoxy)-2-methyl-1-oxopropan-2-yl)ureido)-4-methyl-5-(1,2,4-thiadiazol-3-yl)thiophene-3-carboxylate

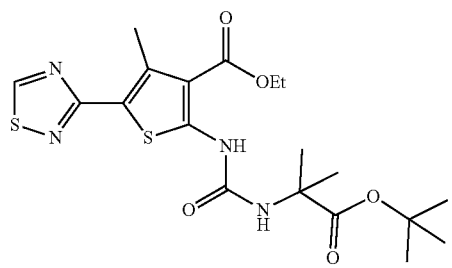 [SMILES: CCOC(=O)c1c(NC(=O)NC(C)(C)C(=O)OC(C)(C)C)sc(-c2ncsn2)c1C]

Triethylamine (11 mmol) was added dropwise to a solution of ethyl 2-amino-4-methyl-5-(1,2,4-thiadiazol-3-yl)thiophene-3-carboxylate (4 mmol) in DCM (5 mL) at 0° C. The reaction mixture was warmed up to room temperature and stirred for 2 hours. tert-Butyl 2-amino-2-methylpropanoate hydrochloride (0.945 g, 5 mmol) was added at room temperature and the resulting reaction mixture was stirred for 17 hours. The reaction mixture was concentrated to dryness, partitioned between NH$_4$Cl/water and EtOAc. The organic phase was separated and concentrated to afford ethyl 2-(3-(1-(tert-butoxy)-2-methyl-1-oxopropan-2-yl)ureido)-4-methyl-5-(1,2,4-thiadiazol-3-yl)thiophene-3-carboxylate. MS (m/z) 453.13 [M−H]−.

Step 8: tert-butyl 2-methyl-2-(5-methyl-2,4-dioxo-6-(1,2,4-thiadiazol-3-yl)-1,4-dihydrothieno[2,3-d]pyrimidin-3(2H)-yl)propanoate

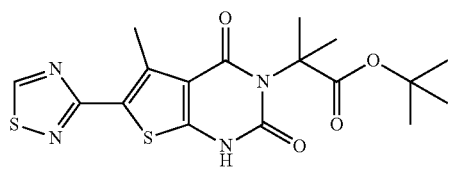 [SMILES: Cc1c(-c2ncsn2)sc2[nH]c(=O)n(C(C)(C)C(=O)OC(C)(C)C)c(=O)c12]

Ethyl 2-(3-(1-(tert-butoxy)-2-methyl-1-oxopropan-2-yl)ureido)-4-methyl-5-(1,2,4-thiadiazol-3-yl)thiophene-3-carboxylate (1 mmol) and NaOtBu (4 mmol) were mixed under argon and t-BuOH (5 mL) was added. The reaction was heated in a sealed tube at 90° C. for 3 hours. The reaction mixture was concentrated to dryness. Residue was partitioned between EtOAc and NH$_4$Cl/water. The organic phase was separated and concentrated. The residue was purified on silica gel column with 0-100% EtOAc/Hex to afford tert-butyl 2-methyl-2-(5-methyl-2,4-dioxo-6-(1,2,4-thiadiazol-3-yl)-1,4-dihydrothieno[2,3-d]pyrimidin-3 (2H)-yl)propanoate. MS (m/z): 407.09 [M−H]⁻.

Step 9: tert-butyl 2-(1-((R)-2-(((1R,3r,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-m ethylpropanoate

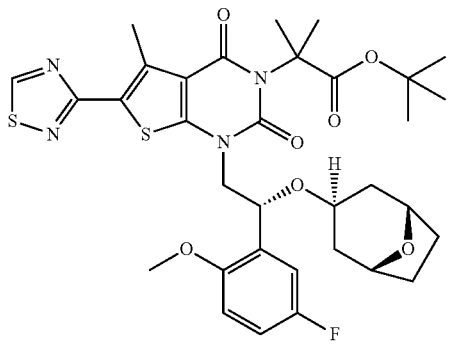 [SMILES: COc1ccc(F)cc1[C@H](Cn1c(=O)n(C(C)(C)C(=O)OC(C)(C)C)c(=O)c2c(C)c(-c3ncsn3)sc21)O[C@@H]1C[C@H]2CC[C@@H](C1)O2]

tert-Butyl 2-methyl-2-(5-methyl-2,4-dioxo-6-(1,2,4-thiadiazol-3-yl)-1,4-dihydrothieno[2,3-d]pyrimidin-3(2H)-yl)propanoate (0.142 mmol) and (R)-2-(((1S,5S)-8-oxabicyclo[3.2.1]octan-3-yl)oxy)-2-(5-fluoro-2-methoxyphenyl)ethan-1-ol (0.202 mmol) were dissolved in THF (2 mL) at room temperature and diisopropyl azodicarboxylate (0.241 mmol) and triphenylphosphine (0.241 mmol) were added sequentially. The reaction mixture was stirred in a sealed tube for 17 hours. The reaction mixture was purified directly on a silica gel column (0-100% EtOAc/Hex) to afford a mixture of N-alkylated and O-alkylated products. The residue was purified with HPLC (Gemini, 5-100% ACN/H₂O+0.1% TFA) and lyophilized from ACN/H₂O to afford tert-butyl 2-(1-((R)-2-(((1R,3r,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-methylpropanoate. MS (m/z) 687.22 [M+H]⁺.

Step 10: 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-methylpropanoic acid

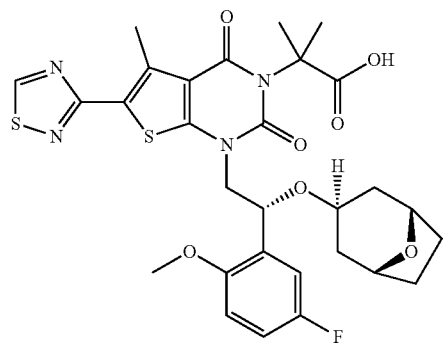 [SMILES: COc1ccc(F)cc1[C@H](Cn1c(=O)n(C(C)(C)C(=O)O)c(=O)c2c(C)c(-c3ncsn3)sc21)O[C@@H]1C[C@H]2CC[C@@H](C1)O2]

Concentrated sulfuric acid (3 mL) was added to water (3 mL) with vigorous stirring at 0° C., followed by isopropanol (6 mL). tert-Butyl 2-(1-((R)-2-(((1R,3r,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-methylpropanoate (0.082 mmol) was treated with the above sulfuric acid solution at 0° C. for 2 hours. The reaction mixture was diluted with water (5 mL) and extracted with EtOAc (5 mL). The organic phase was separated, washed with water and concentrated. The residue was purified by HPLC (Gemini, 5-100% ACN/H₂O+0.1% TFA) and lyophilized from ACN/H₂O to afford 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-methylpropanoic acid. MS (m/z) 629.16 [M−H]⁻.

Step 11: 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-methyl-N-((1-methylcyclopropyl)sulfonyl)propanamide

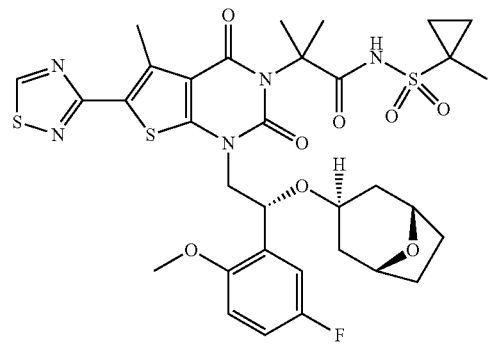 [SMILES: COc1ccc(F)cc1[C@H](Cn1c(=O)n(C(C)(C)C(=O)NS(=O)(=O)C2(C)CC2)c(=O)c2c(C)c(-c3ncsn3)sc21)O[C@@H]1C[C@H]2CC[C@@H](C1)O2]

2-(1-((R)-2-(((1R,3 s,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-methylpropanoic acid (0.079 mmol) was dissolved in DMF (0.5 mL) at room temperature under argon. Diisopropylethylamine (0.238 mmol) and HATU (0.12 mmol) were added sequentially. The reaction mixture was stirred under argon for 17 hours.

In a separate flask, sodium hydride (60% in mineral oil) (0.357 mmol) was added at room temperature to a solution of 1-methylcyclopropane-1-sulfonamide (0.4 mmol) in DMF (0.5 mL). The reaction mixture was stirred for one hour to afford a slurry. The above solution was added dropwise over 5 minutes to this slurry. The resulting reaction mixture was stirred at room temperature for 15 minutes. The reaction mixture was diluted with EtOAc (5 mL) and partitioned between 1N HCl and EtOAc. The organic phase was separated and concentrated. Residue was dissolved in a minimal amount of dichloromethane, and adsorbed onto and purified by preparative TLC (silica gel, 1/1 EtOAc/Heptane) to afford 2-(1-((R)-2-(((1R,3s,5S)-8-oxabicyclo[3.2.1]octan-3-yl)oxy)-2-(5-fluoro-2-methoxyphenyl)ethyl)-5-methyl-2,4-dioxo-6-(1,2,4-thiadiazol-3-yl)-1,4-dihydrothieno[2,3-d]pyrimidin-3(2H)-yl)-2-methyl-N-((1-methylcyclopropyl)sulfonyl)propanamide. MS (m/z) 746.52 [M−H]⁻. ¹H NMR (400 MHz, Acetonitrile-d3) δ 10.07 (s, 1H), 8.81 (s, 1H), 7.27 (dd, J=9.3, 3.2 Hz, 1H), 7.03 (ddd, J=9.0, 8.2, 3.2 Hz, 1H), 6.94 (dd, J=9.0, 4.4 Hz, 1H), 5.35-5.28 (m, 1H), 4.31-4.21 (m, 2H), 4.16 (d, J=13.9 Hz, 1H), 4.03 (d, J=23.3 Hz, 1H), 3.82 (s, 3H), 3.62 (tt, J=10.9, 5.7 Hz, 1H), 2.96 (s, 3H), 1.87-1.66 (m, 3H), 1.79 (s, 3H), 1.76 (s, 3H), 1.60-1.48 (m, 4H), 1.53 (s, 3H), 1.33-1.27 (m, 3H), 0.98-0.86 (m, 2H).

Example 32: Preparation of (S)-2-(1-((R)-2-(((1R, 3s,5S)-8-oxabicyclo[3.2.1]octan-3-yl)oxy)-2-(2-(difluoromethoxy)-5-fluorophenyl)ethyl)-5-methyl-6-(oxazol-2-yl)-2,4-dioxo-1,4-dihydrothieno[2,3-d]pyrimidin-3(2H)-yl)-N-((1-methylcyclopropyl)sulfonyl)propanamide

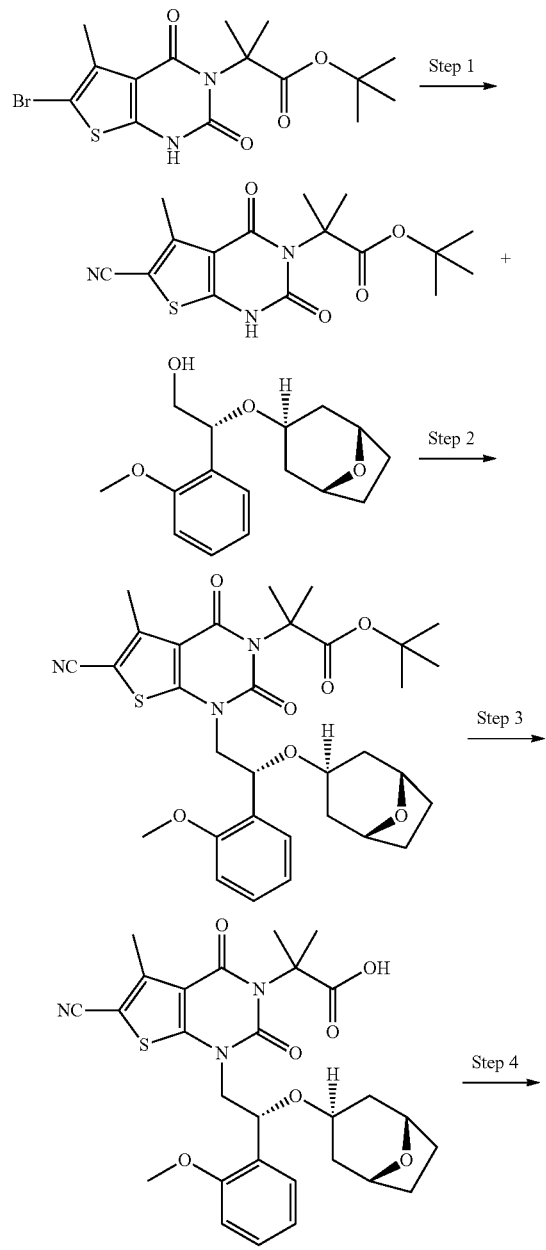

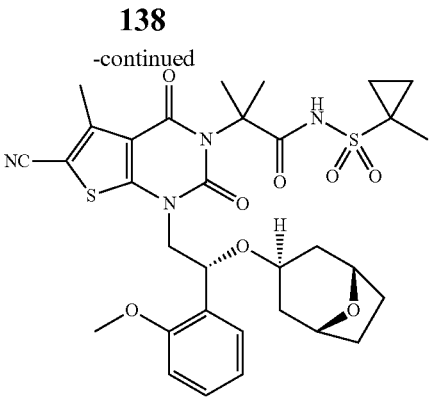

Step 1: tert-butyl 2-(6-cyano-5-methyl-2,4-dioxo-1,4-dihydrothieno[2,3-d]pyrimidin-3(2H)-yl)-2-methylpropanoate

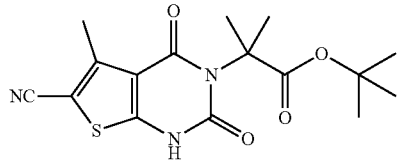 [SMILES: Cc1c(C#N)sc2[nH]c(=O)n(C(C)(C)C(=O)OC(C)(C)C)c(=O)c12]

tert-Butyl 2-(6-bromo-5-methyl-2,4-dioxo-1,4-dihydrothieno[2,3-d]pyrimidin-3(2H)-yl)-2-methylpropanoate (prepared according to WO 2017075056) (500 mg, 1.24 mmol), copper cyanide (2.48 mmol), tetrakis(triphenylphosphine)palladium(0) (0.062 mmol) and zinc powder (0.3 mmol) were charged with NMP (6 mL) in a 20 mL microwave vial. The vial was heated at 100° C. overnight. The reaction mixture was diluted with ethyl acetate and washed with brine. The organic layer was concentrated and purified by normal phase chromatography (0-100% EtOAc/Hex) to give tert-butyl 2-(6-cyano-5-methyl-2,4-dioxo-1,4-dihydrothieno[2,3-d]pyrimidin-3(2H)-yl)-2-methylpropanoate. MS (m/z) 348.19 [M–H]−.

Step 2: tert-butyl 2-(1-((R)-2-(((1R,3s,5S)-8-oxabicyclo[3.2.1]octan-3-yl)oxy)-2-(2-methoxyphenyl)ethyl)-6-cyano-5-methyl-2,4-dioxo-1,4-dihydrothieno[2,3-d]pyrimidin-3(2H)-yl)-2-methylpropanoate

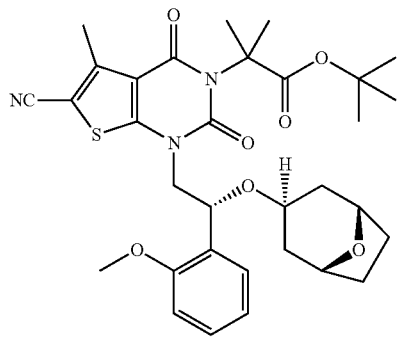 [SMILES: COc1ccccc1[C@H](Cn1c(=O)n(C(C)(C)C(=O)OC(C)(C)C)c(=O)c2c(C)c(C#N)sc21)O[C@@H]1C[C@H]2CC[C@@H](C1)O2]

In a vial, triphenylphosphine (0.318 mmol) was dissolved in 2-MeTHF (6 mL) and cooled to 0° C. Diisopropyl azodicarboxylate (0.318 mmol) was added and the reaction mixture was stirred at 0° C. for 30 minutes, stirred at room temperature for an additional 20 minutes to give a suspension.

In a separate flask, tert-butyl 2-(6-cyano-5-methyl-2,4-dioxo-1,4-dihydrothieno[2,3-d]pyrimidin-3(2H)-yl)-2-methylpropanoate (0.106 mmol) and (R)-2-(((1R,3s,5S)-8-oxabicyclo[3.2.1]octan-3-yl)oxy)-2-(2-methoxyphenyl) ethan-1-ol (0.226 mmol) were dissolved in 2-MeTHF (3.0 mL). The mixture from above was added dropwise, giving a solution that was stirred at room temperature for 14 hours. The reaction mixture was concentrated, dissolved in minimal amount of DCM/Hex and purified twice by normal phase chromatography (0-40% EtOAC/Hex), followed by prep HPLC (Gemini, 5-100% ACN/H$_2$O+0.1% TFA) to give tert-butyl 2-(1-((R)-2-(((1R,3s,5S)-8-oxabicyclo[3.2.1]octan-3-yl)oxy)-2-(2-methoxyphenyl)ethyl)-6-cyano-5-methyl-2,4-dioxo-1,4-dihydrothieno[2,3-d]pyrimidin-3(2H)-yl)-2-methylpropanoate (more polar product). MS (m/z) 609.77 [M+H]$^+$.

Step 3: 2-(1-((R)-2-(((1R,3s,5S)-8-oxabicyclo[3.2.1]octan-3-yl)oxy)-2-(2-methoxyphenyl)ethyl)-6-cyano-5-methyl-2,4-dioxo-1,4-dihydrothieno[2,3-d]pyrimidin-3(2H)-yl)-2-methylpropanoic acid

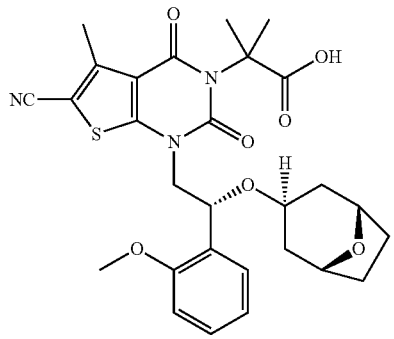 [SMILES: COc1ccccc1[C@H](Cn1c(=O)n(C(C)(C)C(=O)O)c(=O)c2c(C)c(C#N)sc21)O[C@@H]1C[C@H]2CC[C@@H](C1)O2]

Trifluoroacetic acid (0.5 mL) was added to a solution of tert-butyl 2-(1-((R)-2-(((1R,3s,5S)-8-oxabicyclo[3.2.1]octan-3-yl)oxy)-2-(2-methoxyphenyl)ethyl)-6-cyano-5-methyl-2,4-dioxo-1,4-dihydrothieno[2,3-d]pyrimidin-3(2H)-yl)-2-methylpropanoate (0.001 mmol) in dichloromethane (1 mL). The reaction mixture was stirred for 4 hours. The reaction mixture was then concentrated, dissolved in DMF and purified by HPLC (Gemini, 5-100% ACN/H$_2$O+0.1% TFA). Product was lyophilized to give 2-(1-((R)-2-(((1R,3s,5S)-8-oxabicyclo[3.2.1]octan-3-yl) oxy)-2-(2-methoxyphenyl)ethyl)-6-cyano-5-methyl-2,4-dioxo-1,4-dihydrothieno[2,3-d]pyrimidin-3(2H)-yl)-2-methylpropanoic acid. MS (m/z) 552.41 [M-H]$^-$.

Step 4: 2-(1-((R)-2-(((1R,3s,5S)-8-oxabicyclo[3.2.1]octan-3-yl)oxy)-2-(2-methoxyphenyl)ethyl)-6-cyano-5-methyl-2,4-dioxo-1,4-dihydrothieno[2,3-d]pyrimidin-3(2H)-yl)-2-methyl-N-((1-methylcyclopropyl)sulfonyl)propanamide

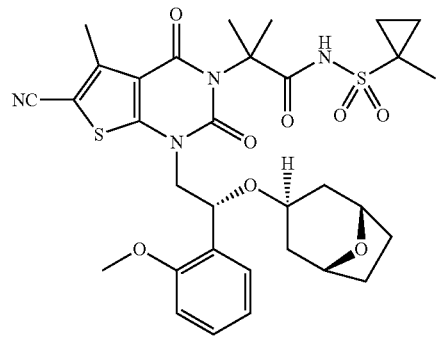 [SMILES: COc1ccccc1[C@H](Cn1c(=O)n(C(C)(C)C(=O)NS(=O)(=O)C2(C)CC2)c(=O)c2c(C)c(C#N)sc21)O[C@@H]1C[C@H]2CC[C@@H](C1)O2]

Diisopropylethylamine (0.058 mmol) was added to a solution of 2-(1-((R)-2-(((1R,3s,5S)-8-oxabicyclo[3.2.1]octan-3-yl)oxy)-2-(2-methoxyphenyl)ethyl)-6-cyano-5-methyl-2,4-dioxo-1,4-dihydrothieno[2,3-d]pyrimidin-3(2H)-yl)-2-methylpropanoic acid (0.029 mmol) in DMF (1.0 mL), followed by addition of HATU (0.035 mmol). The resulting solution was stirred at room temperature for 4 hours.

In a separate flask, 1-methylcyclopropane-1-sulfonamide (0.13 mmol) was dissolved in DMF (0.7 mL) and cooled to 0° C. Sodium hydride (60% in mineral oil, 0.11 mmol) was added and reaction mixture was stirred for 35 minutes at 0° C. in an ice bath. The ice bath was removed and stirring continued for 90 minutes. The resulting mixture was added to the above solution and stirring was continued for 2 hours. The reaction mixture was diluted with ethyl acetate, acidified with 1N HCl and extracted with EtOAc (2×). The combined organic layers were washed with 5% lithium chloride solution (3×), brine, and concentrated under reduced pressure. The obtained crude material was purified by normal phase chromatography (10-100% EtOAc/Hex) to give impure product that was re-purified by HPLC (Gemini, 5-100% ACN/H$_2$O+0.1% TFA) to give 2-(1-((R, 3s,5S)-8-oxabicyclo[3.2.1]octan-3-yl)oxy)-2-(2-m ethoxyphenyl)ethyl)-6-cyano-5-methyl-2,4-dioxo-1,4-dihydrothieno[2,3-d]pyrimidin-3 (2H)-yl)-2-methyl-N-((1-methylcyclopropyl)sulfonyl)propanamide after lyophilization. MS (m/z) 669.67 [M-H]$^-$. $^1$H NMR (400 MHz, Methanol-d4) δ 7.49 (dd, J=7.5, 1.7 Hz, 1H), 7.37-7.25 (m, 1H), 7.04 (t, J=7.6 Hz, 1H), 6.96 (d, J=8.1 Hz, 1H), 5.35 (dd, J=8.1, 5.0 Hz, 1H), 4.34 (d, J=17.5 Hz, 2H), 4.17 (d, J=14.2 Hz, 1H), 4.00 (m, 1H), 3.82 (s, 3H), 3.64 (dq, J=10.9, 5.4 Hz, 1H), 2.62 (s, 3H), 1.82 (m, 2H), 1.79 (m, 7H), 1.76-1.65 (m, 1H), 1.65-1.42 (m, 7H), 1.42-1.24 (m, 2H), 1.00-0.85 (m, 2H).

Example 33: In Vitro De Novo Lipogenesis Assay

De Novo Lipogenesis (DNL) was measured in vitro in HepG2 cells by quantifying the incorporation of $^{13}$C-labeled acetate into palmitic acid.

HepG2 cells were plated in growth medium (DMEM (Corning cat #15-018-CM) supplemented with 10% FBS (HyClone cat #SH30071-03), and 1× penicillin, streptomycin, glutamine (Corning cat #30-009-CI)) at 10,000 cells/ well in a 384-well cell culture-treated plate (Greiner cat #781091). The cells were then incubated overnight at 37° C., 5% $CO_2$. The next day, the cells were washed twice with sterile DPBS (Corning cat #21-031-CM) and the culture medium was changed to fresh growth medium. The compounds of interest were dosed to cells, followed by a 1 hour incubation at 37° C., 5% $CO_2$. $^{13}$C-labeled acetate (Sigma-Aldrich cat #279315-1G) was added to the culture medium at a concentration of 10 mM and the cells were incubated for 24 hours at 37° C., 5% $CO_2$.

In order to analyze the lipid content of the HepG2 cells, the culture medium was removed and the cells were lysed by adding 30 μL of 0.1 M NaOH. After 5 minutes of incubation at room temperature, 15 μL of cell lysate was transferred to a 384-well deep-well plate (Sigma-Aldrich cat #BR701355-48EA) containing 15 μL of 7.3% KOH in ethanol and mixed. This plate was sealed and incubated at 70° C. for 4 hours to hydrolyze the lipids to free fatty acids. 100 μL of acetonitrile was then added and the plate was spun at 3,700 g for 20 minutes to separate the organic and aqueous phases. 50 μL from the top (organic) phase was transferred to a new 384-well plate (NUNC cat #264573) and the samples were analyzed by mass spectrometry using a RapidFire coupled to a QTOF mass spectrometer. The sum of the area under curve (AUC) for palmitate containing 3 to 7 $^{13}$C was normalized with the AUC of oleate and plotted against compound concentration to determine the potency of ACC inhibitors.

To assess the inhibitory potential of the compounds, $EC_{50}$ values were determined for example compounds and are listed below in Table 1 (DNL $EC_{50}$). As indicated in Table 1, the compounds of Examples 1-32 were assessed. A selection of Example compounds were also confirmed to inhibit ACC1 in an enzymatic in vitro assay with nanomolar activity (data not shown). The ACC1 in vitro assay was performed generally as described, e.g., in U.S. Pat. No. 8,969,557.

Example 34: Rat Liver/Plasma Ratio Determination

Liver to plasma (L/P) ratios of certain example compounds were determined in male Sprague-Dawley (SD) rats 2 hours and 24 hours after their administration.

The in vivo phases of the rat L/P ratio determinations for example compounds were conducted at Covance Laboratories (Madison, Wis.) or Charles River Laboratories (Worcester, Wash.). Animals were housed and handled in accordance with the Guide for the Care and Use of Laboratory Animals, Institute of Laboratory Animal Resources. The protocols were reviewed and approved by Institutional Animal Care and Use Committees (IACUC). Male Sprague-Dawley (SD) rats weighing approximately 300 g were fasted overnight prior to dosing and up to 4 hours after dosing. Each example compound was dosed at a single dose at 5 mg/kg or 10 mg/kg orally by gavage to male SD rats (n=3 rats/group). The aqueous formulation contained ethyl alcohol and polyethylene glycol 300. Approximately 100 μL plasma and 0.5 g liver samples were collected from each animal either 2 hours or 24 hours after dosing. The liver samples were homogenized by hard tissue homogenizer probes (Omni International, Kennesaw, Ga.) with 4× extraction buffer. For LC-MS/MS analysis, plasma and liver samples were prepared through protein precipitation extraction and analyzed on a Scitex API 5500 or 6500 LC-MS/MS instrument (Applied Biosystems, Foster City, Calif.). Analyte was eluted on a 1.7 μm 50×2.1 mm Acquity UPLC BEH C18 column (Waters, Milford, Mass.) using mobile phase containing 0.1% formic acid and a linear gradient from 55% to 95% acetonitrile at a flow rate of 800 μL/min. A liver/plasma ratio for each compound was calculated using the liver and plasma concentrations at the corresponding time point (2 hours or 24 hours). Noncompartmental pharmacokinetic parameters were calculated using Phoenix 32 (Pharsight Corporation, Mountain View, Calif.).

To assess the liver loading potential of the compounds, rat liver/plasma ratios (Rat L/P Ratio) values were determined for example compounds and are listed below in Table 1 for 2 hour and 24 hour timepoints (Rat L/P Ratio (2h/24h)). As indicated in Table 1, the compounds of Examples 1-32 were assessed.

TABLE 1

| Example | | DNL $EC_{50}$ (nM) | L/P Ratio (2 h/24 h) |
|---|---|---|---|
| Example 1 | [structure] | 1.0 | 520/1526 |

TABLE 1-continued
| Example | | DNL EC$_{50}$ (nM) | L/P Ratio (2 h/24 h) |
|---|---|---|---|
| Example 2 | 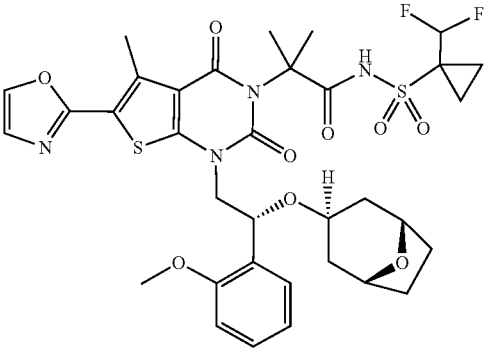 [SMILES: COc1ccccc1[C@H](Cn1c(=O)n(C(C)(C)C(=O)NS(=O)(=O)C2(C(F)F)CC2)c(=O)c2c(C)c(-c3ncco3)sc21)O[C@@H]1C[C@H]2CC[C@@H](C1)O2] | 5.9 | |
| Example 3 | 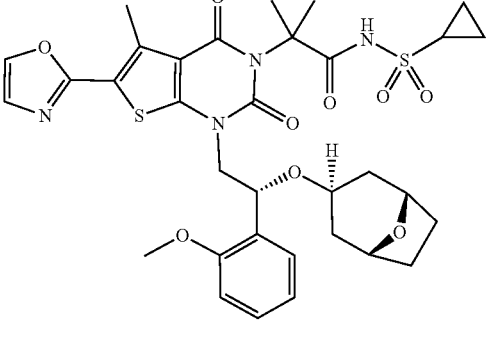 | 1.5 | |
| Example 4 | 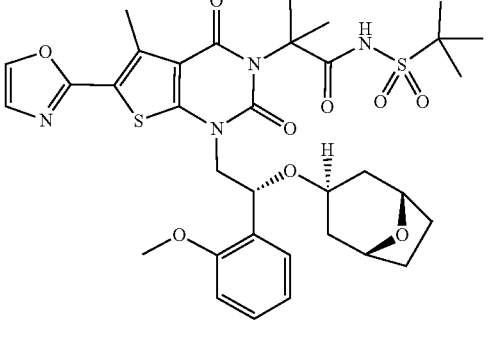 | 1.7 | |
| Example 5 | 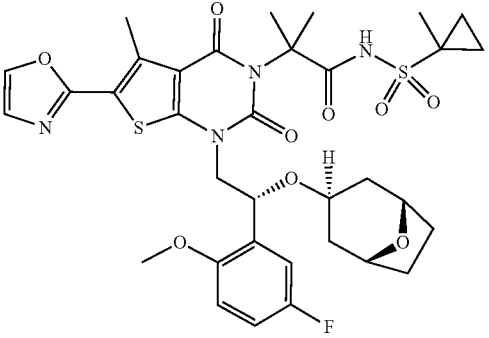 [SMILES: COc1ccc(F)cc1[C@H](Cn1c(=O)n(C(C)(C)C(=O)NS(=O)(=O)C2(C)CC2)c(=O)c2c(C)c(-c3ncco3)sc21)O[C@@H]1C[C@H]2CC[C@@H](C1)O2] | 2.9 | |

TABLE 1-continued

| Example | DNL EC$_{50}$ (nM) | L/P Ratio (2 h/24 h) |
|---|---|---|
| Example 6 | 4.5 | 442/1106 |
| Example 7 | 7.6 | |
| Example 8 | 7.0 | |
| Example 9 | 215.3 | |

TABLE 1-continued

| Example | | DNL EC$_{50}$ (nM) | L/P Ratio (2 h/24 h) |
|---|---|---|---|
| Example 10 | | 48.3 | |
| Example 11 | | 66.2 | |
| Example 12 | | 1.7 | 145/136 |
| Example 13 | | 881.6 | |

TABLE 1-continued
| Example | | DNL EC$_{50}$ (nM) | L/P Ratio (2 h/24 h) |
|---|---|---|---|
| Example 14 | 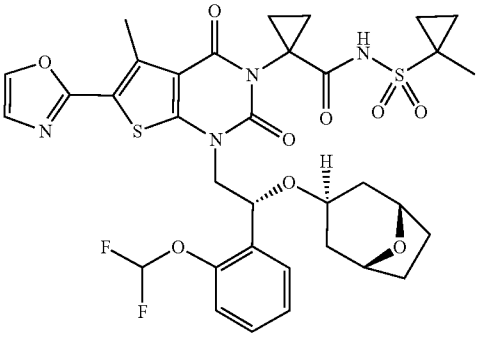 [SMILES: Cc1c(-c2ncco2)sc2c1c(=O)n(C1(C(=O)NS(=O)(=O)C3(C)CC3)CC1)c(=O)n2C[C@H](O[C@@H]1C[C@H]2CC[C@@H](C1)O2)c1ccccc1OC(F)F] | 29.8 | |
| Example 15 | 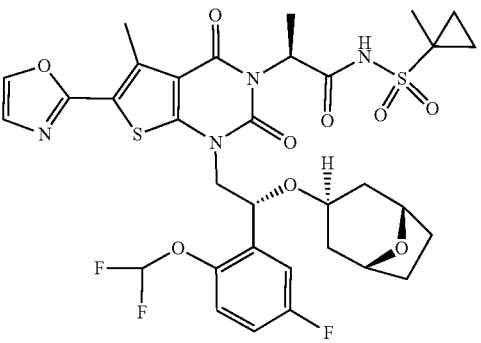 [SMILES: Cc1c(-c2ncco2)sc2c1c(=O)n([C@@H](C)C(=O)NS(=O)(=O)C1(C)CC1)c(=O)n2C[C@H](O[C@@H]1C[C@H]2CC[C@@H](C1)O2)c1cc(F)ccc1OC(F)F] | 2,000.0 | |
| Example 16 | 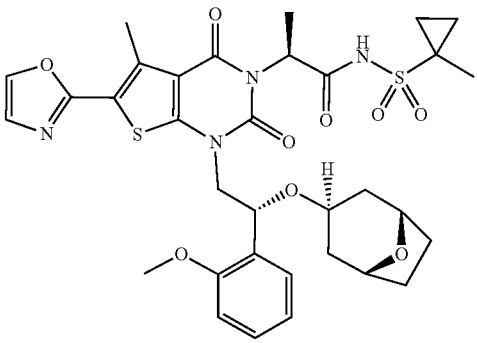 [SMILES: COc1ccccc1[C@H](Cn1c(=O)n([C@@H](C)C(=O)NS(=O)(=O)C2(C)CC2)c(=O)c2c(C)c(-c3ncco3)sc21)O[C@@H]1C[C@H]2CC[C@@H](C1)O2] | 1.9 | |
| Example 17 | 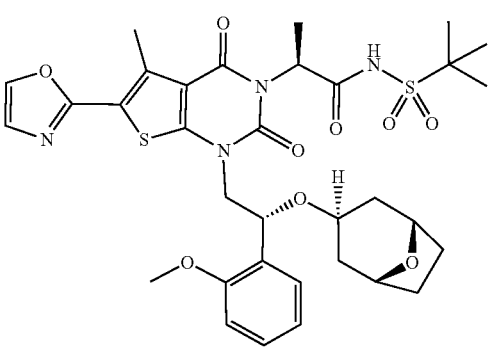 [SMILES: COc1ccccc1[C@H](Cn1c(=O)n([C@@H](C)C(=O)NS(=O)(=O)C(C)(C)C)c(=O)c2c(C)c(-c3ncco3)sc21)O[C@@H]1C[C@H]2CC[C@@H](C1)O2] | 41.1 | |

TABLE 1-continued

| Example | | DNL EC$_{50}$ (nM) | L/P Ratio (2 h/24 h) |
|---|---|---|---|
| Example 18 | | 1.0 | |
| Example 19 | | 1.0 | |
| Example 20 | | 0.3 | 2515/2914 |
| Example 21 | | 29.7 | |

TABLE 1-continued

| Example | DNL EC$_{50}$ (nM) | L/P Ratio (2 h/24 h) |
|---|---|---|
| Example 22 | 915.8 | |
| Example 23 | 267.8 | |
| Example 24 | 24.3 | |
| Example 25 | 1.0 | |

TABLE 1-continued
| Example | | DNL EC$_{50}$ (nM) | L/P Ratio (2 h/24 h) |
|---|---|---|---|
| Example 26 | 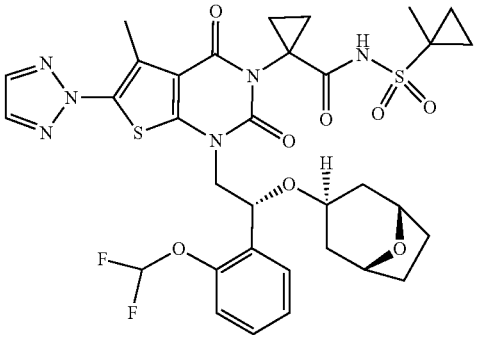 [SMILES: Cc1c(-n2nccn2)sc2c1c(=O)n(C1(C(=O)NS(=O)(=O)C3(C)CC3)CC1)c(=O)n2C[C@H](O[C@@H]1C[C@H]2CC[C@@H](C1)O2)c1ccccc1OC(F)F] | 24.6 | |
| Example 27 | 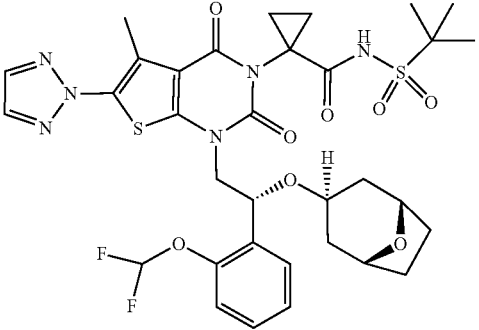 [SMILES: Cc1c(-n2nccn2)sc2c1c(=O)n(C1(C(=O)NS(=O)(=O)C(C)(C)C)CC1)c(=O)n2C[C@H](O[C@@H]1C[C@H]2CC[C@@H](C1)O2)c1ccccc1OC(F)F] | 362.6 | |
| Example 28 | 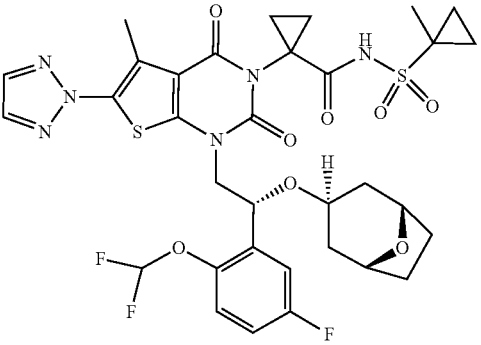 [SMILES: Cc1c(-n2nccn2)sc2c1c(=O)n(C1(C(=O)NS(=O)(=O)C3(C)CC3)CC1)c(=O)n2C[C@H](O[C@@H]1C[C@H]2CC[C@@H](C1)O2)c1cc(F)ccc1OC(F)F] | 0.9 | |
| Example 29 | 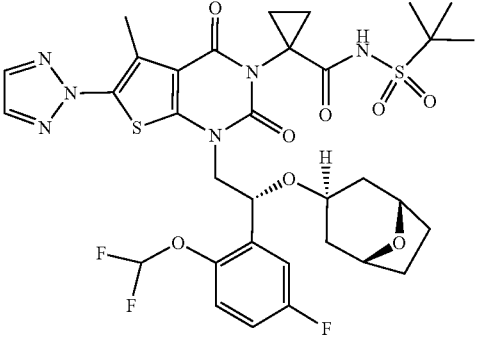 [SMILES: Cc1c(-n2nccn2)sc2c1c(=O)n(C1(C(=O)NS(=O)(=O)C(C)(C)C)CC1)c(=O)n2C[C@H](O[C@@H]1C[C@H]2CC[C@@H](C1)O2)c1cc(F)ccc1OC(F)F] | 10.2 | |

TABLE 1-continued

| Example | | DNL EC$_{50}$ (nM) | L/P Ratio (2 h/24 h) |
|---|---|---|---|
| Example 30 | 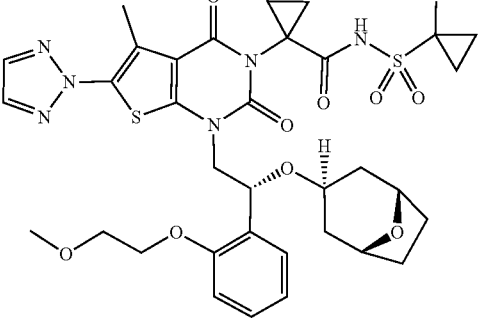 | 33.1 | |
| Example 31 | 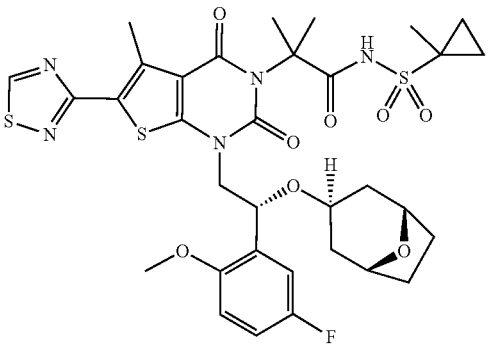 [SMILES: COc1ccc(F)cc1[C@H](Cn1c(=O)n(C(C)(C)C(=O)NS(=O)(=O)C2(C)CC2)c(=O)c2c(C)c(-c3ncsn3)sc21)O[C@@H]1C[C@H]2CC[C@@H](C1)O2] | 1.4 | |
| Example 32 | 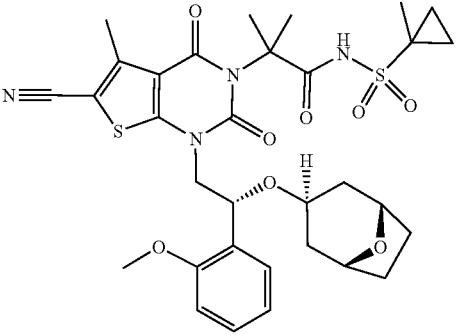 [SMILES: COc1ccccc1[C@H](Cn1c(=O)n(C(C)(C)C(=O)NS(=O)(=O)C2(C)CC2)c(=O)c2c(C)c(C#N)sc21)O[C@@H]1C[C@H]2CC[C@@H](C1)O2] | 9.9 | |

Example 35: In Vivo De Novo Lipogenesis Study

The DNL inhibitory activity of the compound of Example 1 was assessed in vivo as follows.

The studies were performed at Covance Laboratories (Madison, Wis.) in compliance with Institutional Animal Care and Use Committee protocols. Male Sprague Dawley (SD) rats were purchased from Envigo RMS, INC and were acclimatized for 7 days prior to study initiation. Animals were provided ad libitum access to food and water for the duration of the study. On the day of the experiment, animals were randomized into dose groups (n=6 rats/group) based on body weight and received a single p.o dose of vehicle (0.1% Tween 80 in water, pH 7.5-8.0) or a dose range of the compound of Example 1 (0.1 µg/kg-1 mg/kg). 3h post-dose (Example 1), the animals received a single i.p bolus of $^{13}$C-acetate (Perkin Elmer, 32 µCi/animal) and were sacrificed 1h later, and livers were collected for DNL analysis. An approx. 0.75 g piece of liver was saponified at 70° C. for 120 min in 1.5 mL of 2.5M NaOH followed by addition of 2.5 mL of ethanol, vigorous mixing. The samples were allowed to stand overnight after which 4.8 mL of petroleum ether was added to each sample, shaken vigorously and centrifuged at 1000×g for 5 minutes. Resulting petroleum ether layers were removed and discarded. The remaining aqueous layer was acidified with 0.6 mL of 12M HCl and extracted twice with 4.8 mL of petroleum ether. The resulting organic fractions were combined in scintillation vials, the petroleum ether partially evaporated in a hood. Residual ether fractions were dissolved in at least 5 mL of Ultima Gold XR scintillation fluid and analyzed by liquid scintillation counting (LSC). The resulting dpm (disintergrations per million) values were normalized to tissue weight and the data were expressed as a percent of vehicle.

FIG. 1 shows the results of the in vivo DNL study for the compound of Example 1. The effective dose that decreased in vivo DNL by 50% (ED$_{50}$) was determined to be 0.080 µg/kg for the compound of Example 1.

Example 36: Liver Partitioning Study in Cynomolgus Monkeys

To further investigate the liver partitioning properties of the compound of Example 1, the compound was co-administered with rifampicin (RIF, pan-OATP inhibitor) in cynomolgus monkeys in vivo and hepatic uptake experiments were performed in monkey hepatocytes in vitro. In preliminary studies, the systemic blood clearance of the Example 1 compound in monkeys was found to be higher than hepatic blood flow following its intravenous administration. Therefore the coadministration experiments as described below in more detail were conducted to administer Example 1 compound orally (5 mg/kg) in the absence and presence of IV administration of RIF (30 mg/kg). Under these conditions, RIF treatment significantly increased the plasma exposures of Example 1 compound relative to monkeys not treated with RIF (see Table 2). The monkey PK results described in this Example also correlated well with in vitro hepatic uptake results that predicted strong hepatic uptake of Example 1 compound in monkey liver (data not shown).

To assess the OATP (organic anion transporting polypeptides)-mediated liver specific delivery of the Example 1 compound, plasma pharmacokinetics (PK) was evaluated in cynomolgus monkeys. The in-life phase of the cyno PK studies was conducted at Covance Laboratories (Madison, Wis.). Animals were housed and handled in accordance with the Guide for the Care and Use of Laboratory Animals, Institute of Laboratory Animal Resources. The protocols were reviewed and approved by the Institutional Animal Care and Use Committees (IACUC). Male Cynomolgus monkeys weighing approximately 3 kg were used for the in-life portion of the PK studies. The animals were fasted overnight prior to dosing and up to 4 hours after dosing. The animals were administered with the test compound (Example 1) alone or coadministered with 30 mg/kg rifampicin prior to test compound administration at 5 mg/kg via oral gavage (3 monkeys per group). The aqueous formulation contains dimethyl sulfoxide, kolliphor, labrasol and propylene glycol. Approximately 0.5 mL blood samples were collected from each animal and analyzed for test compound (Example 1) concentrations. For LC-MS/MS analysis, plasma samples were prepared through protein precipitation extraction and analyzed on a Sciex API 5500 LC-MS/MS instrument (Applied Biosystems, Foster City, Calif.). Analyte was eluted on a 1.7 μm 50×2.1 mm Acquity UPLC BEH C18 column (Waters, Milford, Mass.) using mobile phases containing 0.1% formic acid and a linear gradient from 60% to 95% acetonitrile at a flow rate of 800 μL/min. Noncompartmental pharmacokinetic parameters were calculated using Phoenix 32 (Pharsight Corporation, Mountain View, Calif.).

Table 2 shows results from the cyno PK study described in this Example.

This Example demonstrates that Example 1 compound is characterized by OATP-mediated hepatic clearance resulting in preferential loading into the target liver tissue. The in vivo and in vitro hepatic uptake assessments in monkey can be applied to predict human PK and clinical dose of the compound of Example 1.

TABLE 2

| Test Compound (Example 1) | No-Pre-treatment | Pretreatment with Rifampicin | Fold-Change |
|---|---|---|---|
| $C_{max}$ (μM) | 162 | 14000 | ↑ 86 |
| AUC (μM · h) | 294 | 48500 | ↑ 165 |
| CL/F (L/h/kg) | 44.9 | 0.15 | ↓ 299 |
| $V_z/F$ (L/kg) | 72.7 | 0.44 | ↓ 165 |

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound of Formula (I),

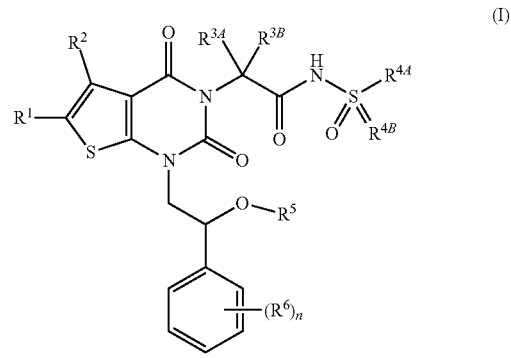

or a pharmaceutically acceptable salt thereof, wherein:

$R^1$ is cyano, halogen, —R, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, —SO$_2$R, or a cyclic group selected from a 4-8 membered monocyclic heterocycle having 1-2 heteroatoms independently selected from nitrogen, oxygen, or sulfur, a 5-6 membered monocyclic heteroaryl having 1-4 heteroatoms independently selected from nitrogen, oxygen, or sulfur, or a 8-10 membered bicyclic heteroaryl having 1-5 heteroatoms independently selected from nitrogen, oxygen, or sulfur, wherein each cyclic group is independently optionally substituted with 1-4 substituents independently selected from halogen, cyano, C$_{1-3}$ alkyl, and C$_{1-3}$ alkoxy;

R$^2$ is hydrogen or C$_{1-4}$ alkyl, optionally substituted with one or more halogen, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$N(R)$_2$, —C(O)R, —C(O)OR, —OC(O)R, —S(O)R, or —SO$_2$R;

each R is independently hydrogen or a group selected from C$_{1-6}$ alkyl, 3-8 membered monocyclic cycloalkyl, phenyl, 8-10 membered bicyclic aryl, 4-8 membered monocyclic heteroaryl having 1-2 heteroatoms independently selected from nitrogen, oxygen, or sulfur, 5-6 membered monocyclic heteroaryl having 1-4 heteroatoms independently selected from nitrogen, oxygen, or sulfur, and 8-10 membered bicyclic heteroaryl having 1-5 heteroatoms independently selected from nitrogen, oxygen, or sulfur, wherein each group is optionally substituted with 1-4 substituents independently selected from halogen, cyano, C$_{1-3}$ alkyl, and C$_{1-3}$ alkoxy;

R$^{3A}$ and R$^{3B}$ are each independently hydrogen or a C$_{1-3}$ alkyl, each optionally substituted with 1 to 3 substituents independently selected from halogen, cyano, C$_{1-3}$ alkyl, or C$_{1-3}$ alkoxy; or R$^{3A}$ and R$^{3B}$ together with the carbon to which they are attached form cyclopropylenyl, cyclobutylenyl, oxetanyl, or tetrahydrofuranyl, each optionally substituted with 1 to 3 substituents independently selected from halogen, cyano, C$_{1-3}$ alkyl, or C$_{1-3}$ alkoxy;

R$^{4A}$ is C$_{1-6}$ alkyl, C$_{1-6}$ alkoxy, C$_{3-6}$ cycloalkyl, C$_{3-6}$ cycloalkoxy, phenyl, or phenoxy, each optionally substituted with 1 to 3 substituents independently selected from halogen, cyano, C$_{1-3}$ alkyl, C$_{1-6}$ alkoxy, C$_{3-6}$ cycloalkyl, or C$_{3-6}$ cycloalkoxy, wherein each C$_{1-3}$ alkyl, C$_{1-6}$ alkoxy, C$_{3-6}$ cycloalkyl, or C$_{3-6}$ cycloalkoxy is optionally substituted with one C$_{1-3}$ alkoxy or 1 to 3 halogens; or R$^{4A}$ is —OR$^{41}$, wherein R$^{41}$ is a 5-6 membered heteroaryl having 1-2 heteroatoms independently selected from nitrogen, oxygen, or sulfur, optionally substituted with 1 to 3 substituents independently selected from halogen, cyano, or C$_{1-3}$ alkyl; or R$^{4A}$ is —N(R$^{42}$)$_2$, wherein each R$^{42}$ is independently selected from hydrogen C$_{1-6}$ alkyl, or C$_{3-6}$ cycloalkyl; or two R$^{42}$ together with the nitrogen to which they are attached form a 4-6 membered heterocycle, optionally substituted with one C$_{1-3}$ alkoxy or 1 to 3 halogens;

R$^{4B}$ is oxo or =NR$^{43}$, wherein R$^{43}$ is selected from C$_{1-6}$ alkyl, C$_{3-6}$ cycloalkyl, C$_{4-6}$ heterocyclyl, C$_{3-6}$ cycloalkoxy, phenyl, 5-6 membered heteroaryl having 1-2 heteroatoms independently selected from nitrogen, oxygen, or sulfur, each optionally substituted with 1 to 3 substituents independently selected from halogen, cyano, or C$_{1-3}$ alkyl;

R$^5$ is a 6-12 membered bridged, fused, or spiro heterocycle having 1 or 2 heteroatoms independently selected from oxygen, sulfur, or nitrogen, wherein the fused, bridged, or spiro heterocycle is optionally substituted with 1 to 4 substituents independently selected from halogen, hydroxyl, oxo, amino, cyano, —OR$^{51}$, —SR$^{54}$, —N(R$^{51}$)$_2$, —N(R$^{51}$)C(O)R$^{51}$, —C(O)N(R$^{51}$)$_2$, —N(R$^{51}$)C(O)N(R$^{51}$)$_2$, —N(R$^{51}$)C(O)OR$^{51}$, —OC(O)N(R$^{51}$)$_2$, —N(R$^{51}$)SO$_2$R$^{51}$, —SO$_2$N(R$^{51}$)$_2$, —C(O)R$^{51}$, —C(O)OR$^{51}$, —OC(O)R$^{51}$, —S(O)R$^{51}$, or —SO$_2$R, C$_{1-3}$ alkyl, or C$_{1-3}$ alkoxy, wherein each R$^{51}$ is independently hydrogen or C$_{1-6}$ alkyl;

R$^6$ is hydrogen, halogen, C$_{1-3}$ alkyl, C$_{1-6}$ alkoxy, C$_{3-6}$ cycloalkyl, or C$_{3-6}$ cycloalkoxy, wherein the C$_{1-3}$ alkyl, C$_{1-6}$ alkoxy, C$_{3-6}$ cycloalkyl, or C$_{3-6}$ cycloalkoxy is optionally substituted with 1 to 3 substituents independently selected from halogen, cyano, C$_{1-3}$ alkyl, or C$_{1-3}$ alkoxy; and n is 1, 2, or 3.

2. The compound or pharmaceutically acceptable salt thereof of claim 1, wherein the compound is of Formula (II),

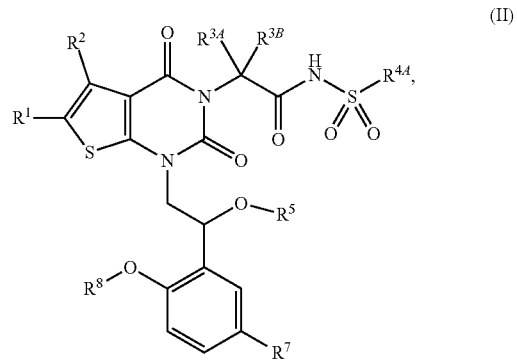

(II)

wherein:

R$^1$ is cyano or a 5 membered heteroaryl having 2 to 3 heteroatoms independently selected from the group consisting of nitrogen, oxygen, and sulfur;

R$^2$ is C$_{1-3}$ alkyl optionally substituted with 1 to 3 F;

R$^{3A}$ and R$^{3B}$ are each independently hydrogen or —CH$_3$, each optionally substituted with 1 to 3 F; or R$^{3A}$ and R$^{3B}$ together with the carbon to which they are attached form cyclopropylenyl or cyclobutylenyl, each optionally substituted with 1 to 3 F;

R$^{4A}$ is C$_{1-6}$ alkyl, C$_{3-6}$ cycloalkyl, phenyl or pyridyl, each optionally substituted with 1 to 3 substituents independently selected from halogen, cyano, or C$_{1-3}$ alkyl, wherein each C$_{1-3}$ alkyl is optionally substituted with one C$_{1-3}$ alkoxy or 1 to 3 halogens;

R$^5$ is an 8-10 membered bridged heterocycloalkyl having one or two oxygens;

R$^7$ is hydrogen or halogen; and

R$^8$ is C$_{1-3}$ alkyl optionally substituted with one —O—CH$_3$ or 1 to 3 halogens.

3. The compound or pharmaceutically acceptable salt thereof of claim 2, wherein the compound is of Formula (IIa),

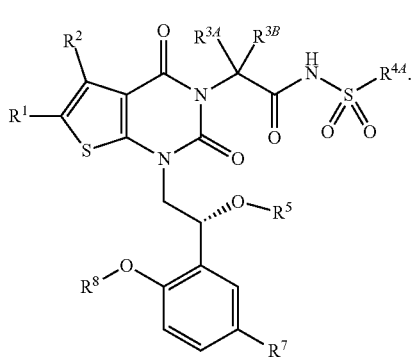

(IIa)

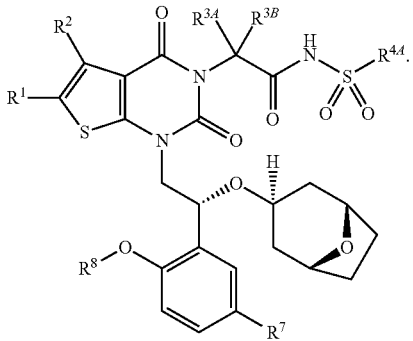

Formula (IIIa)

4. The compound or pharmaceutically acceptable salt thereof of claim 1, wherein the compound is of Formula (III),

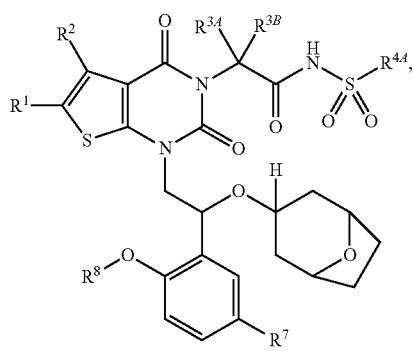

(III)

wherein:

$R^1$ is cyano or a 5 membered heteroaryl having 2 to 3 heteroatoms independently selected from the group consisting of nitrogen, oxygen, and sulfur;

$R^2$ is $C_{1-3}$ alkyl optionally substituted with 1 to 3 F;

$R^{3A}$ and $R^{3B}$ are each independently hydrogen or —CH$_3$ optionally substituted with 1 to 3 F; or $R^{3A}$ and $R^{3B}$ together with the carbon to which they are attached form cyclopropylenyl or cyclobutylenyl, each optionally substituted with 1 to 3 F;

$R^{4A}$ is $C_{1-4}$ alkyl, $C_{3-6}$ cycloalkyl, phenyl or pyridyl, each optionally substituted with 1 to 3 substituents independently selected from halogen, cyano, or $C_{1-3}$ alkyl, wherein each $C_{1-3}$ alkyl is optionally substituted with one $C_{1-3}$ alkoxy or 1 to 3 halogens;

$R^7$ is hydrogen or halogen; and $R^8$ is $C_{1-3}$ alkyl optionally substituted with one —O—CH$_3$ or 1 to 3 halogens.

5. The compound or pharmaceutically acceptable salt thereof of claim 4, wherein the compound is of Formula (IIIa), 6. The compound or pharmaceutically acceptable salt thereof of claim 1, wherein $R^{3A}$ and $R^{3B}$ are each independently hydrogen or —CH$_3$, wherein at least one of $R^{3A}$ and $R^{3B}$ is —CH$_3$.

7. The compound or pharmaceutically acceptable salt thereof of claim 1, wherein $R^{3A}$ and $R^{3B}$ are each —CH$_3$.

8. The compound or pharmaceutically acceptable salt thereof of claim 1, wherein $R^{3A}$ and $R^{3B}$ together with the carbon to which they are attached form cyclopropylenyl or cyclobutylenyl.

9. The compound or pharmaceutically acceptable salt thereof of claim 1, wherein $R^{3A}$ and $R^{3B}$ together with the carbon to which they are attached form cyclopropylenyl.

10. The compound or pharmaceutically acceptable salt thereof of claim 1, wherein $R^{4A}$ is $C_{1-6}$ alkyl.

11. The compound or pharmaceutically acceptable salt thereof of claim 1, wherein $R^{4A}$ is $C_{1-4}$ alkyl.

12. The compound or pharmaceutically acceptable salt thereof of claim 1, wherein $R^{4A}$ is t-butyl.

13. The compound or pharmaceutically acceptable salt thereof of claim 1, wherein $R^{4A}$ is pyridyl.

14. The compound or pharmaceutically acceptable salt thereof of claim 13 wherein $R^{4A}$ is pyrid-2-yl.

15. The compound or pharmaceutically acceptable salt thereof of claim 1, wherein $R^{4A}$ is $C_{3-6}$ cycloalkyl optionally substituted with 1 to 3 substituents independently selected from halogen, cyano, or $C_{1-3}$ alkyl, wherein each $C_{1-3}$ alkyl is optionally substituted with one $C_{1-3}$ alkoxy or 1 to 3 halogens.

16. The compound or pharmaceutically acceptable salt thereof of claim 1, wherein $R^{4A}$ is a $C_{3-6}$ cycloalkyl optionally substituted with one —CH$_3$ or one F, wherein the —CH$_3$ is optionally substituted with one —O—CH$_3$ or 1 to 2 F.

17. The compound or pharmaceutically acceptable salt thereof of claim 1, wherein $R^{4A}$ is

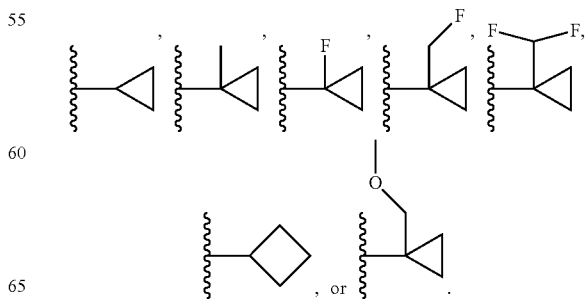

18. The compound or pharmaceutically acceptable salt thereof of claim 1, wherein $R^{4.4}$ is t-butyl,

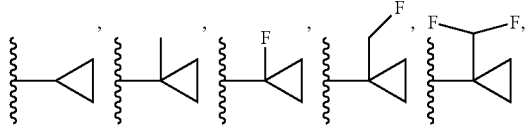

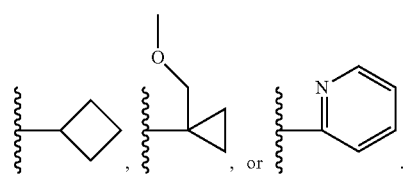

19. The compound or pharmaceutically acceptable salt thereof of claim 1, wherein $R^{4.4}$ is t-butyl,

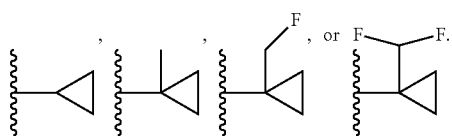

20. The compound or pharmaceutically acceptable salt thereof of claim 1, wherein the compound is of Formula (IV),

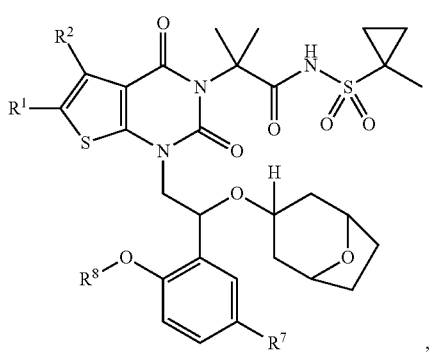

(IV)

wherein:
$R^1$ is cyano or a 5 membered heteroaryl having 2 to 3 heteroatoms independently selected from the group consisting of nitrogen, oxygen, and sulfur;
$R^2$ is $C_{1-3}$ alkyl;
$R^7$ is hydrogen or halogen; and
$R^8$ is $C_{1-3}$ alkyl optionally substituted with one —O—$CH_3$ or 1 to 3 halogens.

21. The compound or pharmaceutically acceptable salt thereof of claim 20, wherein the compound is of Formula (IVa),

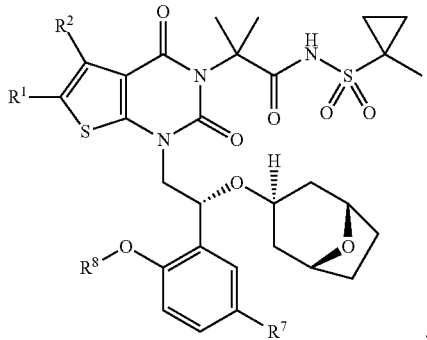

(IVa)

22. The compound or pharmaceutically acceptable salt thereof of claim 1, wherein $R^1$ is cyano.

23. The compound or pharmaceutically acceptable salt thereof of claim 1, wherein $R^1$ is a 5 membered heteroaryl comprising 2 or 3 heteroatoms selected from nitrogen, oxygen, or sulfur.

24. The compound or pharmaceutically acceptable salt thereof of claim 1, wherein $R^1$ is selected from oxazolyl, thiadiazolyl, or trizaolyl.

25. The compound or pharmaceutically acceptable salt thereof of claim 1, wherein $R^1$ is

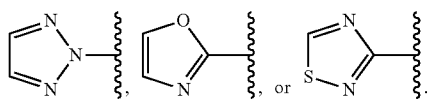

26. The compound or pharmaceutically acceptable salt thereof of claim 1, wherein $R^1$ is

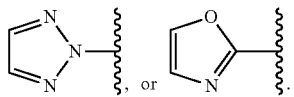

27. The compound or pharmaceutically acceptable salt thereof of claim 1, wherein $R^2$ is —$CH_3$.

28. The compound or pharmaceutically acceptable salt thereof of claim 1, wherein $R^7$ is H or F.

29. The compound or pharmaceutically acceptable salt thereof of claim 1, wherein $R^8$ is —$CH_3$,

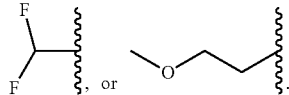

30. The compound or pharmaceutically acceptable salt thereof of claim 1, wherein $R^8$ is —$CH_3$, or

31. A compound selected from the group consisting of:
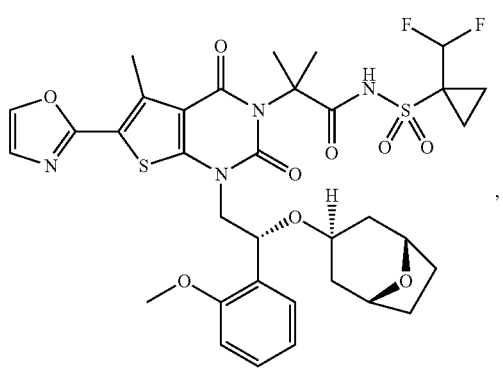
,
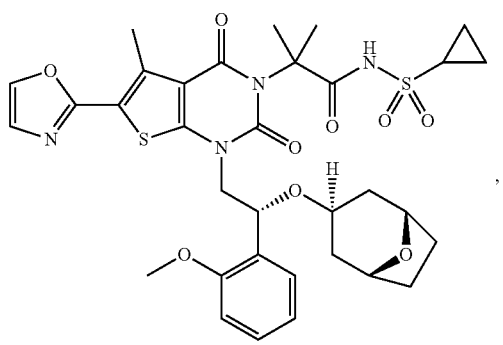
,
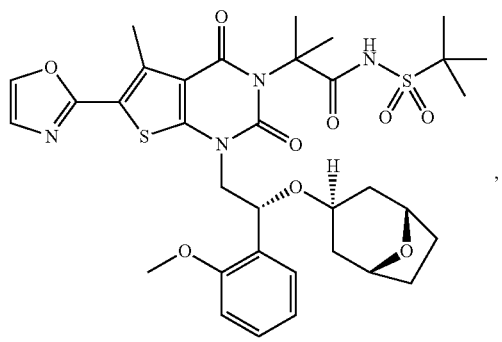
,
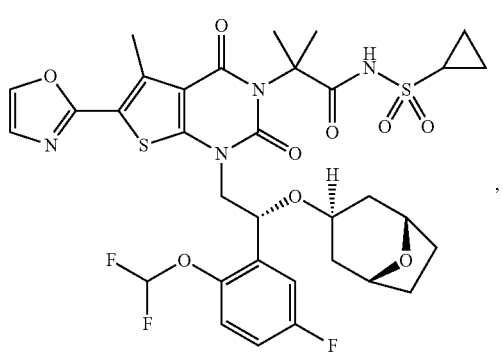
,
-continued
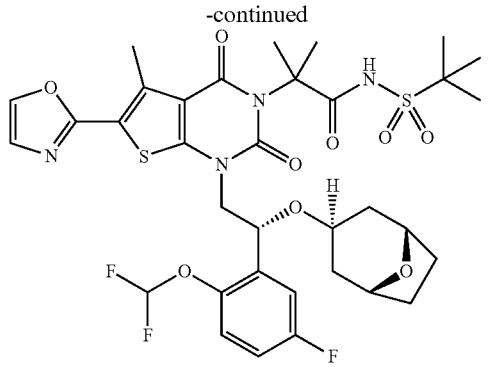
,
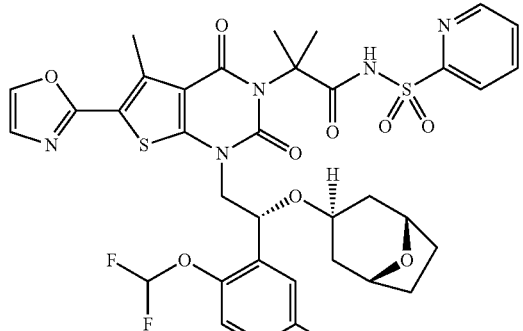
,
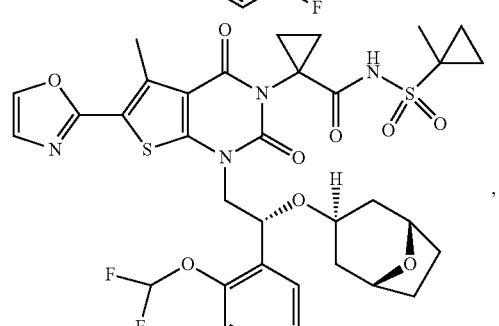
,
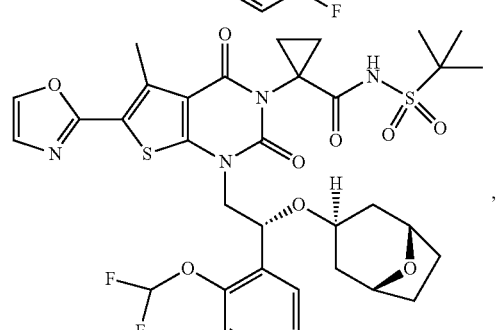
,
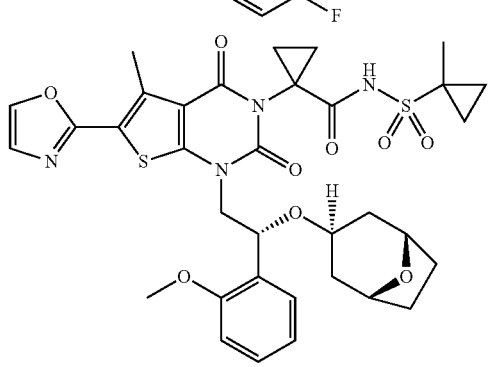
, 169
-continued
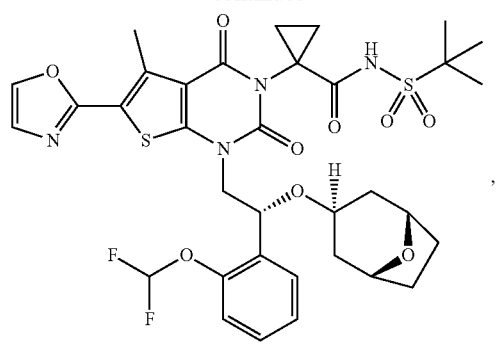
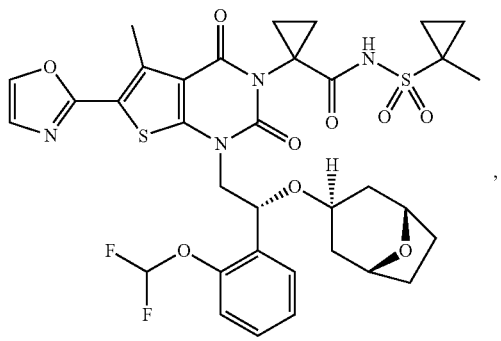
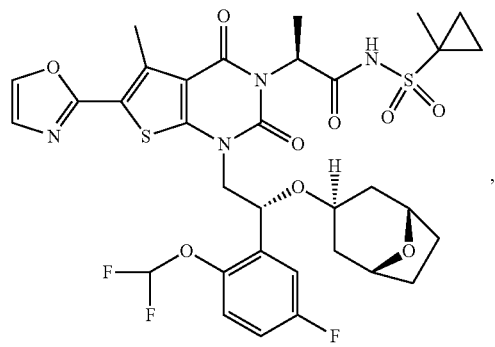
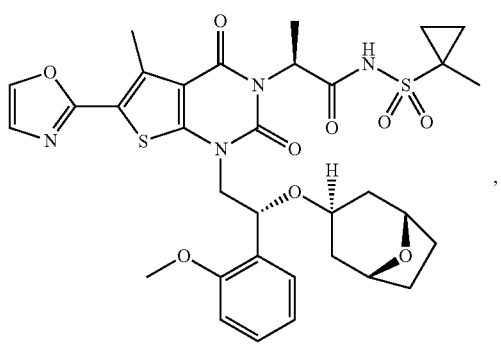
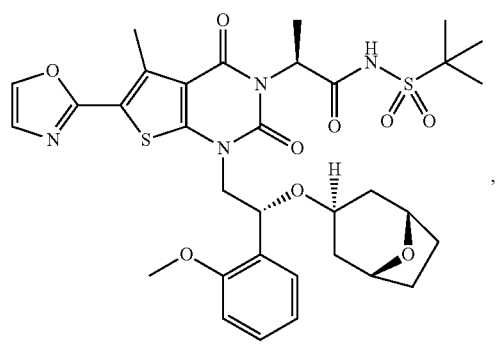 [SMILES: COc1ccccc1[C@H](Cn1c(=O)n(C(C)(C)C(=O)NS(=O)(=O)C2(C)CC2)c(=O)c2c(C)c(-c3ncco3)sc21)O[C@@H]1C[C@H]2CC[C@@H](C1)O2]
170
-continued
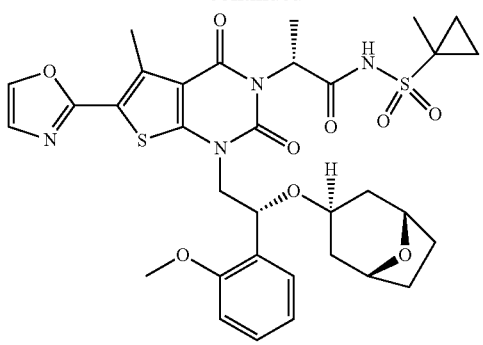
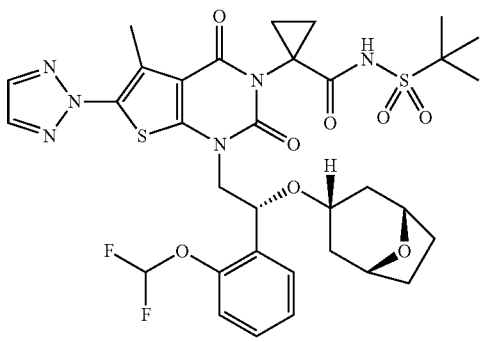
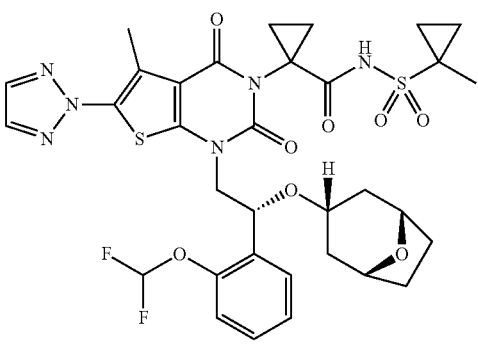
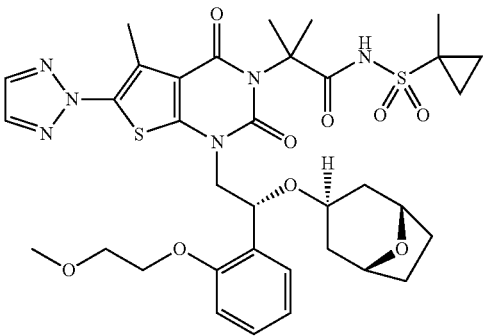
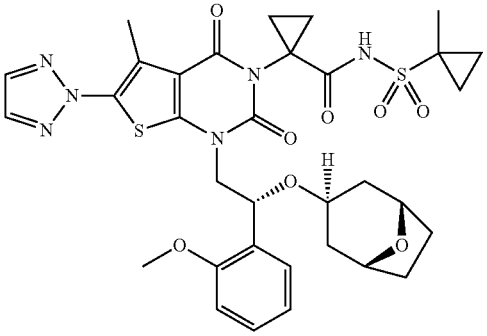

-continued
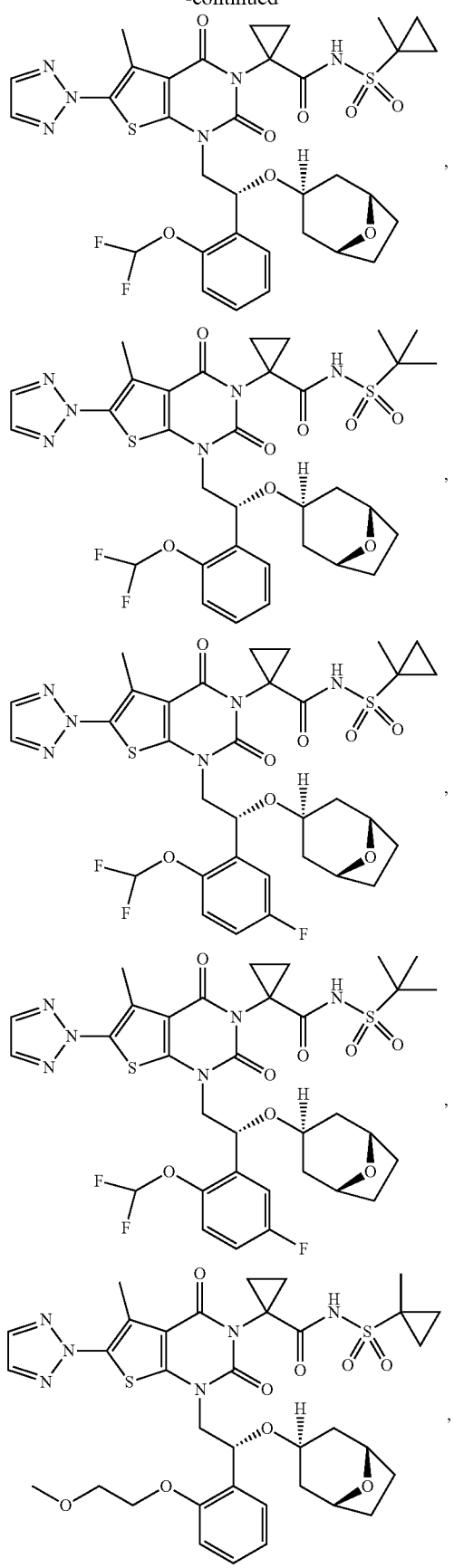
-continued
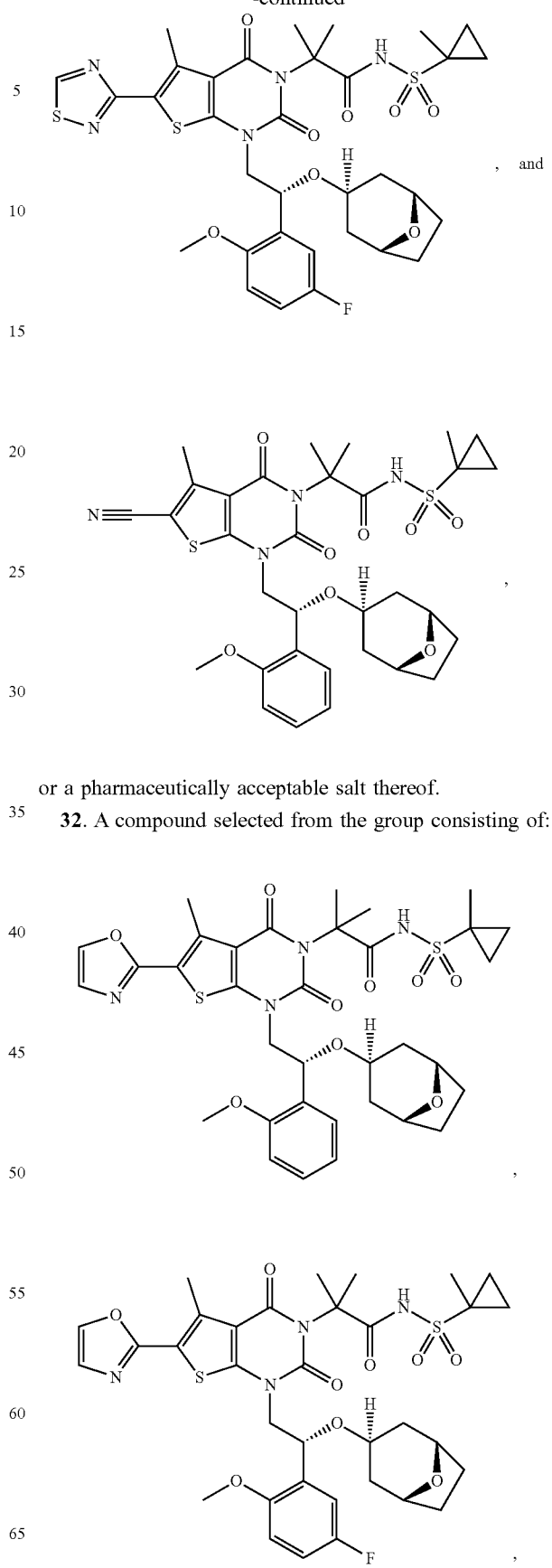
or a pharmaceutically acceptable salt thereof.
32. A compound selected from the group consisting of:

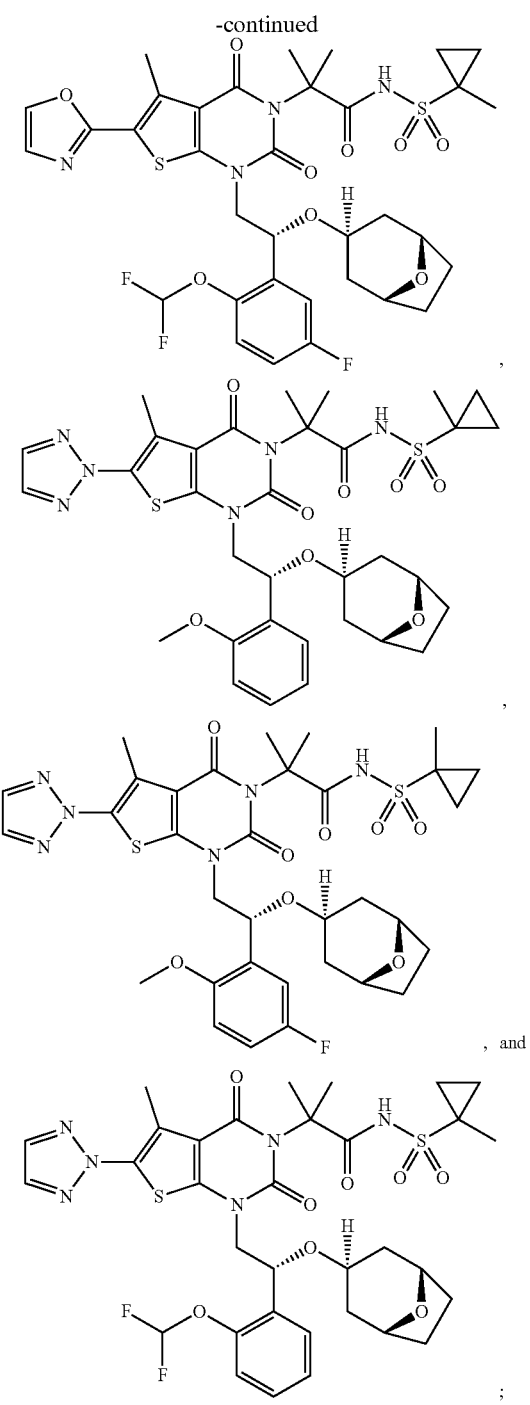

or a pharmaceutically acceptable salt thereof.

33. A compound or pharmaceutically acceptable salt according to claim 1, wherein the compound is 34. A compound or pharmaceutically acceptable salt according to claim 1, wherein the compound is

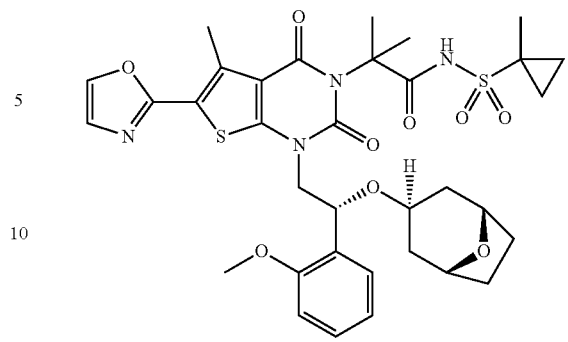

35. A compound or pharmaceutically acceptable salt according to claim 1, wherein the compound is

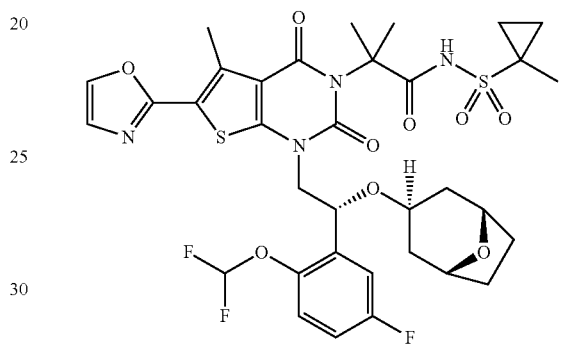

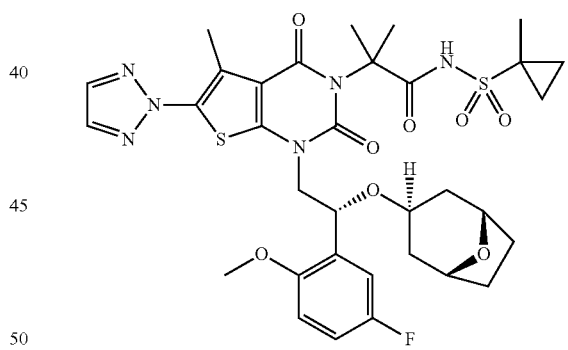

36. A pharmaceutical composition comprising a therapeutically effective amount of a compound of claim 1, or a pharmaceutically acceptable salt thereof, and a pharmaceutically acceptable excipient.

37. A method of treating, stabilizing, or lessening the severity or progression of an ACC mediated disease or condition comprising administering to a patient in need thereof a therapeutically effective amount of a compound of claim 1.

* * * * *